(12) United States Patent
Cayouette et al.

(10) Patent No.: US 12,186,353 B2
(45) Date of Patent: Jan. 7, 2025

(54) METHOD OF REDUCING NEURONAL MICROTUBULE BINDING PROTEIN TAU (TAU) LEVELS

(71) Applicant: ADAERATA, LIMITED PARTNERSHIP, Montréal (CA)

(72) Inventors: Michel Cayouette, Carignan (CA); Marine Lacomme, Montréal (CA)

(73) Assignee: Adaerata, Limited Partnership, Montreal (CA)

( * ) Notice: Subject to any disclaimer, the term of this patent is extended or adjusted under 35 U.S.C. 154(b) by 847 days.

(21) Appl. No.: 17/309,425

(22) PCT Filed: Dec. 5, 2019

(86) PCT No.: PCT/CA2019/051751
§ 371 (c)(1),
(2) Date: May 26, 2021

(87) PCT Pub. No.: WO2020/113338
PCT Pub. Date: Jun. 11, 2020

(65) Prior Publication Data
US 2022/0031778 A1 Feb. 3, 2022

Related U.S. Application Data

(60) Provisional application No. 62/775,520, filed on Dec. 5, 2018.

(51) Int. Cl.
| | | |
|---|---|---|
| *A61K 35/761* | (2015.01) | |
| *A61K 38/17* | (2006.01) | |
| *A61K 45/06* | (2006.01) | |
| *A61P 25/00* | (2006.01) | |
| *A61P 27/02* | (2006.01) | |
| *C07K 14/47* | (2006.01) | |
| *C12N 15/864* | (2006.01) | |

(52) U.S. Cl.
CPC ............ *A61K 35/761* (2013.01); *A61K 45/06* (2013.01); *A61P 25/00* (2018.01); *A61P 27/02* (2018.01); *C07K 14/47* (2013.01); *C12N 15/864* (2013.01); *A61K 38/17* (2013.01)

(58) Field of Classification Search
CPC ........ A61K 35/761; A61P 27/02; A61P 25/00; C07K 14/47
See application file for complete search history.

(56) References Cited

FOREIGN PATENT DOCUMENTS

WO 2020113338 A1 6/2020

OTHER PUBLICATIONS

Kyriazis GA, Wei Z, Vandermey M, Jo DG, Xin O, Mattson MP, Chan SL. Numb endocytic adapter proteins regulate the transport and processing of the amyloid precursor protein in an isoform-dependent manner: implications for Alzheimer disease pathogenesis. J Biol Chem. Sep. 12, 2008;283(37):25492-25502. (Year: 2008).*
Abballe, L., et al., (2018). Numb Isoforms Deregulation in Medulloblastoma and Role of p66 Isoform in Cancer and Neural Stem Cells. Frontiers in Pediatrics, 6(1), 1-10.
Bull, N.D., et al., (2012). Reduced axonal transport and increased excitotoxic retinal ganglion cell degeneration in mice transgenic for human mutant P301S tau. PLoS One 7, e34724.
Chen, T., et al., (2012) The selective mGluR5 agonist CHPG protects against traumatic brain injury in vitro and in vivo via ERK and Akt pathway. Int J Mol Med 29(4) : 630-6.
Chesser, A.S., et al., (2013). Tau clearance mechanisms and their possible role in the pathogenesis of Alzheimer disease. Front Neurol 4, 122.
Chiasseu, M., et al., (2016). Tau Accumulation, Altered Phosphorylation, and Missorting Promote Neurodegeneration in Glaucoma.J Neurosci. May 25, 2016;36(21):5785-98.
De Calignon, A., et al., (2012). Propagation of tau pathology in a model of early Alzheimer's disease. Neuron 73, 685-697.
Dho, S.E., et al., (1999). Characterization of four mammalian numb protein isoforms. Identification of cytoplasmic and membrane-associated variants of the phosphotyrosine binding domain. J Biol Chem 274, 33097-33104.
Dooley, C. M., et al., (2002). "Involvement of numb in vertebrate retinal development: Evidence for multiple roles of numb in neural differentiation and maturation", Journal of Neurobiology, 54(2), 313-325.
Euskirchen, P., et al., (2011). NUMB does not impair growth and differentiation status of experimental gliomas, Experimental Cell Research, Elsevier, Amsterdam, Nl, 317(20), 2864-2873.
Extended European Search Report in the name of Adaerata, Limited Partnership mailed Sep. 8, 2022 in EP19893894.
Flannery, J.G., et al., (1997). Efficient photoreceptor-targeted gene expression in vivo by recombinant adeno-associated virus Proc Natl Acad Sci U S A. 94(13): 6916-6921.
Frederiksen, J., et al., (2012). Tau protein: a possible prognostic factor in optic neuritis and multiple sclerosis. Mult Scler. May 2012;18(5):592-9.

(Continued)

*Primary Examiner* — Janet L Andres
*Assistant Examiner* — Ruixue Wang
(74) *Attorney, Agent, or Firm* — Lavery, de Billy, L.L.P.; Julie Gauvreau

(57) ABSTRACT

There is provided a method of reducing neuronal microtubule binding protein Tau (Tau) levels, promoting neuronal Tau degradation and/or promoting neuronal survival, in a subject in need thereof comprising contacting the subjects neurons with an effective amount of an agent that increases a long phosphotyrosine-binding (PTB) Numb isoform expression and/or activity, whereby neural Tau levels is reduced in the presence of the agent, the neuronal Tau degradation is promoted and/or the neuronal survival is promoted as compared to in the absence thereof. Also provided are methods of stratification based on PTB Numb isoform expression and/or activity of the subjects and compositions and kits for applying the methods.

6 Claims, 67 Drawing Sheets

Specification includes a Sequence Listing.

(56) References Cited

OTHER PUBLICATIONS

Gasparini, L., et al., (2011). Tau inclusions in retinal ganglion cells of human P301S tau transgenic mice: effects on axonal viability. Neurobiol Aging 32, 419-433.

Guillozet, A.L., et al., (2003). Neurofibrillary tangles, amyloid, and memory in aging and mild cognitive impairment. Arch Neurol 60, 729-736.

Guo, L., et al., (2007). Targeting amyloid-beta in glaucoma treatment. Proc Natl Acad Sci U S A 104, 13444-13449.

Gupta, N. et al., (2008). Retinal tau pathology in human glaucomas. Can J Ophthalmol 43, 53-60.

Haider, M. et al., (2011). "Characterization and role of NUMB in the human extravillous trophopblast", Placenta, 32(6), 441-449.

Ittner, L.M., et al., (2010). Dendritic function of tau mediates amyloid-beta toxicity in Alzheimer's disease mouse models. Cell 142, 387-397.

Karaczyn, A., et al. (2010). Two novel human NUMB isoforms provide a potential link between development and cancer. Neural Dev 5, 31.

Kim, K.K., et al., (2013) Rbfox3-regulated alternative splicing of Numb promotes neuronal differentiation during development. J. Cell Biol., 200 (4): 443.

Kyriazis, G.A., et al., (2008). Numb Endocytic Adapter Proteins Regulate the Transport and Processing of the Amyloid Precursor Protein in an Isoform-dependent Manner : Implications for Alzheimer Disease Pathogenesis II, Journal of Biological Chemistry, 283(37), 25492-25502.

Lacomme, M., et al., (2019). "Numb prevents neurodegeneration by regulating intraneuronal Tau levels in an isoform-specific manner", Alzheimer's and Dementia, 15(7), Supplement, p. P643, A poster presentation from the Alzheimer's Association International Conference 2019.

Asagna-Reeves, C.A., et al., (2012). Identification of oligomers at early stages of tau aggregation in Alzheimer's disease. FASEB J 26, 1946-1959.

Lasagna-Reeves, C.A., et al. (2016). Reduction of Nuak1 Decreases Tau and Reverses Phenotypes in a Tauopathy Mouse Model. Neuron 92, 407-418.

Matsuda, T. et al., (2004). Electroporation and RNA interference in the rodent retina in vivo and in vitro. Proc Natl Acad Sci U S A. Jan. 6;101(1): 16-22. Epub Nov. 5, 2003.

McKinnon, S.J. (2003). Glaucoma: ocular Alzheimer's disease? Front Biosci 8, s1140-1156.

Miller, A. D. (1990). Progress Toward Human Gene Therapy. Blood 76:271.

Myeku, N., et al., (2016). Tau-driven 26S proteasome impairment and cognitive dysfunction can be prevented early in disease by activating cAMP-PKA signaling. Nat Med 22, 46-53.

Ning, A., et al., (2008). Amyloid-beta deposits lead to retinal degeneration in a mouse model of Alzheimer disease. Invest Ophthalmol Vis Sci 49, 5136-5143.

Ntelios et al., (2012). "Numb and Alzheimer's disease: the current picture", Frontiers in Neuroscience, 6(4), 1-6.

Oku et al., (2019). Tau Is Involved in Death of Retinal Ganglion Cells of Rats from Optic Nerve Crush.Invest Ophthalmol Vis Sci 60(6):2380-2387.

Pang et al., (2008). Comparative analysis of in vivo and in vitro AAV vector transduction in the neonatal mouse retina: Effects of serotype and site of administration. Vision Research 48(3): 377-385.

Parnell, M., et al., (2012). Ocular manifestations of Alzheimer's disease in animal models. Int J Alzheimers Dis 2012, 786494.

International Search Report in the name of Adaerata, Limited Partnership mailed Feb. 25, 2020 in PCTCA2019051751.

Written Opinion in the name of Adaerata, Limited Partnership mailed Feb. 25, 2020 in PCTCA2019051751.

Perez, S.E., et al., (2009). Beta-amyloid deposition and functional impairment in the retina of the APPswe/PS1DeltaE9 transgenic mouse model of Alzheimer's disease. Invest Ophthalmol Vis Sci 50, 793-800.

Rajendran, D., et al., (2016). Regulation of Numb isoform expression by activated ERK signaling. Oncogene 35, 5202-5213.

Reid, C.A., et al., (2017). Improvement of Photoreceptor Targeting via Intravitreal Delivery in Mouse and Human Retina Using Combinatory rAAV2 Capsid Mutant Vectors. Invest Ophthalmol Vis Sci. 58(14): 6429-6439.

Roberson, E.D., et al., (2007). Reducing endogenous tau ameliorates amyloid beta-induced deficits in an Alzheimer's disease mouse model. Science 316, 750-754.

Roberson, E.D., et al. (2011). Amyloid-beta/Fyn-induced synaptic, network, and cognitive impairments depend on tau levels in multiple mouse models of Alzheimer's disease. J Neurosci 31, 700-711.

Sivak, J.M. (2013). The aging eye: common degenerative mechanisms between the Alzheimer's brain and retinal disease. Invest Ophthalmol Vis Sci 54, 871-880.

Srinivas, S., et al. (2001). Cre reporter strains produced by targeted insertion of EYFP and ECFP into the ROSA26 locus. BMC Developmental Biology 1(4).

Wilson, A., et al. (2007) Normal hemopoiesis and lymphopoiesis in the combined absence of numb and numblike. J Immunol. Jun. 1;178(11):6746-51.

Yang, T., et al. (2016). A small molecule TrkB/TrkC neurotrophin receptor co-activator with distinctive effects on neuronal survival and process outgrowth. Neuropharmacology. 110(Pt A):343-361.

Yoshiyama, Y., et al., (2007). Synapse loss and microglial activation precede tangles in a P301S tauopathy mouse model. Neuron 53, 337-351.

Zhai, H., et al., (2005). Honokiol-induced neurite outgrowth promotion depends on activation of extracellular signal-regulated kinases (ERK1/2). Eur J Pharmacol. 1;516(2):112-7.

Communication pursuant to Article 94(3) EPC issued Jul. 11, 2023 in EP19893894.6 to Adaerata, Limited Partnership.

Chigurupati et al., Evidence for Altered Numb Isoform Levels in Alzheimer's Disease Patients and a Triple Transgenic Mouse Model, Journal of Alzheimer's Disease 24 (2011) 349-361.

* cited by examiner

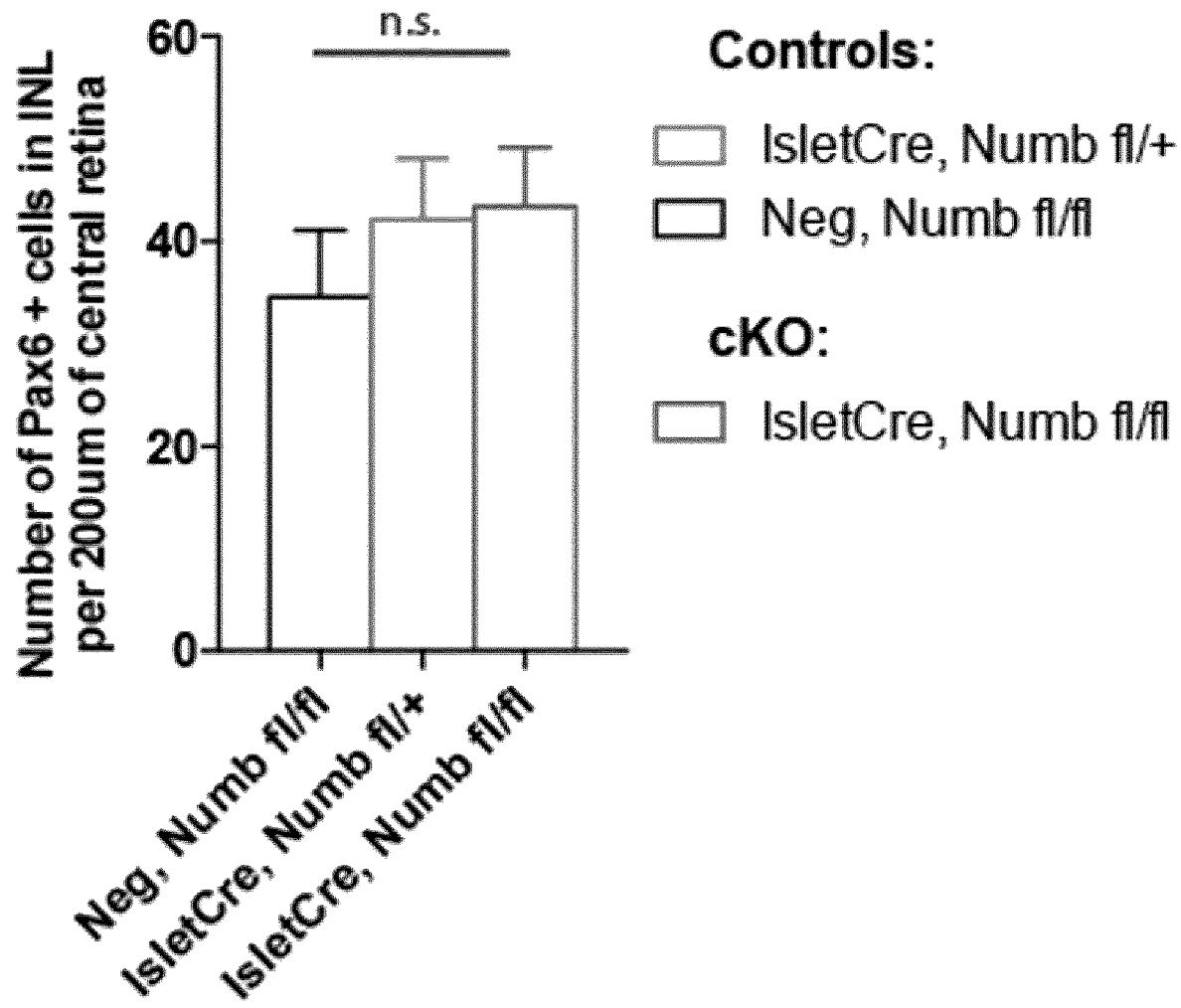

FIG. 16A

\>NP_001005743.1 protein numb homolog isoform 1 [Homo sapiens] (SEQ ID NO: 1)
MNKLRQSFRRKKDVYVPEASRPHQWQTDEEGVRTGKCSFPVKYLGHVEVDESRGMHICEDAVKRLKAERKFFKGFFGKTG
KKAVKAVLWVSADGLRVVDEKTKDLIVDQTIEKVSFCAPDRNFDRAFSYICRDGTTRRWICHCFMAVKDTGERLSHAVGC
AFAACLERKQKREKECGVTATFDASRTTFTREGSFRVTTATEQAEREEIMKQMQDAKKAETDKIVVGSSVAPGNTAPSPS
SPTSPTSDATTSLEMNNPHAIPRRHAPIEQLARQGSFRGFPALSQKMSPFKRQLSLRINELPSTMQRKTDFPIKNAVPEV
EGEAESISSLCSQITNAFSTPEDPFSSAPMTKPVTVVAPQSPTFQANGTDSAFHVLAKPAHTALAPVAMPVRETNPWAHA
PDAANKEIAATCSGTEWGQSSGAASPGLFQAGHRRTPSEADRWLEEVSKSVRAQQPQASAAPLQPVLQPPPPTAISQPAS
PFQGNAFLTSQPVPVGVVPALQPAFVPAQSYPVANGMPYPAPNVPVVGITPSQMVANVFGTAGHPQAAHPHQSPSLVRQQ
TFPHYEASSATTSPFFKPPAQHLNGSAAFNGVDDGRLASADRHTEVPTGTCPVDPFEAQWAALENKSKQRTNPSPTNPFS
SDLQKTFEIEL

FIG. 16B

\>NM_001005743.1 Homo sapiens NUMB, endocytic adaptor protein (NUMB), transcript
variant 1, mRNA(SEQ ID NO: 2)
GTTGTCATGGGGGAGGTGGTGGCGCTTGGTGGCCACTGGCGGCCGAGGTAGAGGCAGTGGCGCTTGAGTTGGTCGGGGGC
AGCGGCAGATTTGAGGCTTAAGCAACTTCTTCCGGGGAAGAGTGCCAGTGCAGCCACTGTTACAATTCAAGATCTTGATC
TATATCCATAGATTGGAATATTGGTGGGCCAGCAATCCTCAGACGCCTCACTTAGGACAAATGAGGAAACTGAGGCTTGG
TGAAGTTACGAAACTTGTCCAAAATCACACAACTTGTAAAGGGCACAGCCAAGATTCAGAGCCAGGCTGTAAAAATTAAA
ATGAACAAATTACGGCAAAGTTTTAGGAGAAAGAAGGATGTTTATGTTCCAGAGGCCAGTCGTCCACATCAGTGGCAGAC
AGATGAAGAAGGCGTTCGCACCGGAAAATGTAGCTTCCCGGTTAAGTACCTTGGCCATGTAGAAGTTGATGAATCAAGAG
GAATGCACATCTGTGAAGATGCTGTAAAAAGATTGAAAGCTGAAAGGAAGTTCTTCAAAGGCTTCTTTGGAAAAACTGGA
AAGAAAGCAGTTAAAGCAGTTCTGTGGGTCTCAGCAGATGGACTCAGAGTTGTGGATGAAAAAACTAAGGACCTCATAGT
TGACCAGACGATAGAGAAAGTTTCTTTCTGTGCCCCAGACAGGAACTTTGATAGAGCCTTTTCTTACATATGCCGTGATG
GCACCACTCGTCGCTGGATCTGTCACTGCTTCATGGCTGTCAAGGACACAGGTGAAAGGTTGAGCCATGCAGTAGGCTGT
GCTTTTGCAGCCTGTTTAGAGCGCAAGCAGAAGCGGGAGAAGGAATGTGGAGTGACTGCTACTTTTGATGCTAGTCGGAC
CACTTTTACAAGAGAAGGATCATTCCGTGTCACAACAGCCACTGAACAAGCAGAAAGAGAGGAGATCATGAAACAAATGC
AAGATGCCAAGAAAGCTGAAACAGATAAGATAGTCGTTGGTTCATCAGTTGCCCCTGGCAACACTGCCCCATCCCCATCC
TCTCCCACCTCTCCTACTTCTGATGCCACGACCTCTCTGGAGATGAACAATCCTCATGCCATCCCACGCCGGCATGCTCC
AATTGAACAGCTTGCTCGCCAAGGCTCTTTCCGAGGTTTTCCTGCTCTTAGCCAGAAGATGTCACCCTTTAAACGCCAAC
TATCCCTACGCATCAATGAGTTGCCTTCCACTATGCAGAGGAAGACTGATTTCCCCATTAAAAATGCAGTGCCAGAAGTA
GAAGGGGAGGCAGAGAGCATCAGCTCCCTGTGCTCACAGATCACCAATGCCTTCAGCACACCTGAGGACCCCTTCTCATC
TGCTCCGATGACCAAACCAGTGACAGTGGTGGCACCACAATCTCCTACCTTCCAAGCTAATGGCACTGACTCAGCCTTCC
ATGTGCTTGCTAAGCCAGCCCATACTGCTCTAGCACCCGTAGCAATGCCTGTGCGTGAAACCAACCCTTGGGCCCATGCC
CCTGATGCTGCTAACAAGGAAATTGCAGCCACATGTTCGGGGACCGAGTGGGGTCAATCTTCTGGTGCTGCCTCTCCAGG
TCTCTTCCAGGCCGGTCATAGACGTACTCCCTCTGAGGCCGACCGATGGTTAGAAGAGGTGTCTAAGAGCGTCCGGGCTC
AGCAGCCCCAGGCCTCAGCTGCTCCTCTGCAGCCAGTTCTCCAGCCTCCTCCACCCACTGCCATCTCCCAGCCAGCATCA
CCTTTCCAAGGGAATGCATTCCTCACCTCTCAGCCTGTGCCAGTGGGTGTGGTCCCAGCCCTGCAACCAGCCTTTGTCCC
TGCCCAGTCCTATCCTGTGGCCAATGGAATGCCCTATCCAGCCCCTAATGTGCCTGTGGTGGGCATCACTCCCTCCCAGA
TGGTGGCCAACGTATTTGGCACTGCAGGCCACCCTCAGGCTGCCCATCCCCATCAGTCACCCAGCCTGGTCAGGCAGCAG
ACATTCCCTCACTACGAGGCAAGCAGTGCTACCACCAGTCCCTTCTTTAAGCCTCCTGCTCAGCACCTCAACGGTTCTGC
AGCTTTCAATGGTGTAGATGATGGCAGGTTGGCCTCAGCAGACAGGCATACAGAGGTTCCTACAGGCACCTGCCCAGTGG
ATCCTTTTGAAGCCCAGTGGGCTGCATTAGAAAATAAGTCCAAGCAGCGTACTAATCCCTCCCCTACCAACCCTTTCTCC
AGTGACTTACAGAAGACGTTTGAAATTGAACTTTAAGCAATCATTATGGCTATGTATCTTGTCCATACCAGACAGGGAGC
AGGGGGTAGCGGTCAAAGGAGCAAAACAGACTTTGTCTCCTGATTAGTACTCTTTTCACTAATCCCAAAGGTCCCAAGGA
ACAAGTCCAGGCCCAGAGTACTGTGAGGGGTGATTTTGAAAGACATGGGAAAAAGCATTCCTAGAGAAAAGCTGCCTTGC
AATTAGGCTAAAGAAGTCAAGGAAATGTTGCTTTCTGTACTCCCTCTTCCCTTACCCCCTTACAAATCTCTGGCAACAGA
GAGGCAAAGTATCTGAACAAGAATCTATATTCCAAGCACATTTACTGAAATGTAAAACACAACAGGAAGCAAAGCAATCT
CCCTTTGTTTTTCAGGCCATTCACCTGCCTCCTGTCAGTAGTGGCCTGTATTAGAGATCAAGAAGAGTGGTTTGTGCTCA
GGCTGGGGAACAGAGAGGCACGCTATGCTGCCAGAATTCCCAGGAGGGCATATCAGCAACTGCCCAGCAGAGCTATATTT
TGGGGGAGAAGTTGAGCTTCCATTTTGAGTAACAGAATAAATATTATATATATCAAAAGCCAAAATCTTTATTTTTATGC
ATTTAGAATATTTTAAATAGTTCTCAGATATTAAGAAGTTGTATGAGTTGTAAGTAATCTTGCCAAAGGTAAAGGGGCTA
GTTGTAAGAAATTGTACATAAGATTGATTTATCATTGATGCCTACTGAAATAAAAAGAGGAAAGGCTGGAAGCTGCAGAC
AGGATCCCTAGCTTGTTTTCTGTCAGTCATTCATTGTAAGTAGCACATTGCAACAACAATCATGCTTATGACCAATACAG
TCACTAGGTTGTAGTTTTTTTAAATAAAGGAAAAGCAGTATTGTCCTGGTTTTAAACCTATGATGGAATTCTAATGTCA
TTATTTTAATGGAATCAATCGAAATATGCTCTATAGAGAATATATCTTTTATATATTGCTGCAGTTTCCTTATGTTAATC
CTTTAACACTAAGGTAACATGACATAATCATACCATAGAAGGGAACACAGGTTACCATATTGGTTTGTAATATGGGTCTT
GGTGGGTTTTGTTTTATCCTTTAAATTTTGTTCCCATGAGTTTTGTGGGGATGGGGATTCTGGTTTTATTAGCTTTGTGT
GTGTCCTCTTCCCCCAAACCCCCTTTTGGTGAGAACATCCCCTTGACAGTTGCAGCCTCTTGACCTCGGATAACAATAAG
AGAGCTCATCTCATTTTTACTTTTGAACGTTGGCCTTACAATCAAATGTAAGTTATATATATTTGTACTGATGAAATTT
ATAATCTGCTTTAACAAAAATAAATGTTCATGGTAGAAGCTTTTAAA

FIG. 17A

\>NP_001307043.1 protein numb homolog isoform 2 [Homo sapiens] (SEQ ID NO: 3)
MNKLRQSFRRKKDVYVPEASRPHQWQTDEEGVRTGKCSFPVKYLGHVEVDESRGMHICEDAVKRLKAERKFFKGFFGKTG
KKAVKAVLWVSADGLRVVDEKTKDLIVDQTIEKVSFCAPDRNFDRAFSYICRDGTTRRWICHCFMAVKDTGERLSHAVGC
AFAACLERKQKREKECGVTATFDASRTTFTREGSFRVTTATEQAEREEIMKQMQDAKKAETDKIVVGSSVAPGNTAPSPS
SPTSPTSDATTSLEMNNPHAIPRRHAPIEQLARQGSFRGFPALSQKMSPFKRQLSLRINELPSTMQRKTDFPIKNAVPEV
EGEAESISSLCSQITNAFSTPEDPFSSAPMTKPVTVVAPQSPTFQGTEWGQSSGAASPGLFQAGHRRTPSEADRWLEEVS
KSVRAQQPQASAAPLQPVLQPPPPTAISQPASPFQGNAFLTSQPVPVGVVPALQPAFVPAQSYPVANGMPYPAPNVPVVG
ITPSQMVANVFGTAGHPQAAHPHQSPSLVRQQTFPHYEASSATTSPFFKPPAQHLNGSAAFNGVDDGRLASADRHTEVPT
GTCPVDPFEAQWAALENKSKQRTNPSPTNPFSSDLQKTFEIEL

FIG. 17B sp|P49757|33-193 PID/PTB Numb Domain (the 11 aa encoded by exon 3 in bold underline) (SEQ ID NO: 4)
RTGKCSFPVKYLGHVEVDESRGMHICEDAVKRLKA<u>ERKFFKGFFGK</u>TGKKAVKAVLWVSADGLRVVDEKTKDLIVDQTIE
KVSFCAPDRNFDRAFSYICRDGTTRRWICHCFMAVKDTGERLSHAVGCAFAACLERKQKREKECGVTATFDASRTTFTRE
G

FIG. 17C

\>NM_001005744.1 Homo sapiens NUMB, endocytic adaptor protein (NUMB), transcript variant 2, mRNA(SEQ ID NO: 5)
GTTGTCATGGGGGAGGTGGTGGCGCTTGGTGGCCACTGGCGGCCGAGGTAGAGGCAGTGGCGCTTGAGTTGGTCGGGGGC
AGCGGCAGATTTGAGGCTTAAGCAACTTCTTCCGGGGAAGAGTGCCAGTGCAGCCACTGTTACAATTCAAGATCTTGATC
TATATCCATAGATTGGAATATTGGTGGGCCAGCAATCCTCAGACGCCTCACTTAGGACAAATGAGGAAACTGAGGCTTGG
TGAAGTTACGAAACTTGTCCAAAATCACACAACTTGTAAAGGGCACAGCCAAGATTCAGAGCCAGGCTGTAAAAATTAAA
ATGAACAAATTACGGCAAAGTTTTAGGAGAAAGAAGGATGTTTATGTTCCAGAGGCCAGTCGTCCACATCAGTGGCAGAC
AGATGAAGAAGGCGTTCGCACCGGAAAATGTAGCTTCCCGGTTAAGTACCTTGGCCATGTAGAAGTTGATGAATCAAGAG
GAATGCACATCTGTGAAGATGCTGTAAAAAGATTGAAAGCTGAAAGGAAGTTCTTCAAAGGCTTCTTTGGAAAAACTGGA
AAGAAAGCAGTTAAAGCAGTTCTGTGGGTCTCAGCAGATGGACTCAGAGTTGTGGATGAAAAAACTAAGGACCTCATAGT
TGACCAGACGATAGAGAAAGTTTCTTTCTGTGCCCCAGACAGGAACTTTGATAGAGCCTTTTCTTACATATGCCGTGATG
GCACCACTCGTCGCTGGATCTGTCACTGCTTCATGGCTGTCAAGGACACAGGTGAAAGGTTGAGCCATGCAGTAGGCTGT
GCTTTTGCAGCCTGTTTAGAGCGCAAGCAGAAGCGGGAGAAGGAATGTGGAGTGACTGCTACTTTTGATGCTAGTCGGAC
CACTTTTACAAGAGAAGGATCATTCCGTGTCACAACAGCCACTGAACAAGCAGAAAGAGAGGAGATCATGAAACAAATGC
AAGATGCCAAGAAAGCTGAAACAGATAAGATAGTCGTTGGTTCATCAGTTGCCCCTGGCAACACTGCCCCATCCCCATCC
TCTCCCACCTCTCCTACTTCTGATGCCACGACCTCTCTGGAGATGAACAATCCTCATGCCATCCCACGCCGGCATGCTCC
AATTGAACAGCTTGCTCGCCAAGGCTCTTTCCGAGGTTTTCCTGCTCTTAGCCAGAAGATGTCACCCTTTAAACGCCAAC
TATCCCTACGCATCAATGAGTTGCCTTCCACTATGCAGAGGAAGACTGATTTCCCCATTAAAAATGCAGTGCCAGAAGTA
GAAGGGGAGGCAGAGAGCATCAGCTCCCTGTGCTCACAGATCACCAATGCCTTCAGCACACCTGAGGACCCCTTCTCATC
TGCTCCGATGACCAAACCAGTGACAGTGGTGGCACCACAATCTCCTACCTTCCAAGGGACCGAGTGGGGTCAATCTTCTG
GTGCTGCCTCTCCAGGTCTCTTCCAGGCCGGTCATAGACGTACTCCCTCTGAGGCCGACCGATGGTTAGAAGAGGTGTCT
AAGAGCGTCCGGGCTCAGCAGCCCCAGGCCTCAGCTGCTCCTCTGCAGCCAGTTCTCCAGCCTCCTCCACCCACTGCCAT
CTCCCAGCCAGCATCACCTTTCCAAGGGAATGCATTCCTCACCTCTCAGCCTGTGCCAGTGGGTGTGGTCCCAGCCCTGC
AACCAGCCTTTGTCCCTGCCCAGTCCTATCCTGTGGCCAATGGAATGCCCTATCCAGCCCCTAATGTGCCTGTGGTGGGC
ATCACTCCCTCCCAGATGGTGGCCAACGTATTTGGCACTGCAGGCCACCCTCAGGCTGCCCATCCCCATCAGTCACCCAG
CCTGGTCAGGCAGCAGACATTCCCTCACTACGAGGCAAGCAGTGCTACCACCAGTCCCTTCTTTAAGCCTCCTGCTCAGC
ACCTCAACGGTTCTGCAGCTTTCAATGGTGTAGATGATGGCAGGTTGGCCTCAGCAGACAGGCATACAGAGGTTCCTACA
GGCACCTGCCCAGTGGATCCTTTTGAAGCCCAGTGGGCTGCATTAGAAAATAAGTCCAAGCAGCGTACTAATCCCTCCCC
TACCAACCCTTTCTCCAGTGACTTACAGAAGACGTTTGAAATTGAACTTTAAGCAATCATTATGGCTATGTATCTTGTCC
ATACCAGACAGGGAGCAGGGGGTAGCGGTCAAAGGAGCAAAACAGACTTTGTCTCCTGATTAGTACTCTTTTCACTAATC
CCAAAGGTCCCAAGGAACAAGTCCAGGCCCAGAGTACTGTGAGGGGTGATTTTGAAAGACATGGGAAAAAGCATTCCTAG
AGAAAAGCTGCCTTGCAATTAGGCTAAAGAAGTCAAGGAAATGTTGCTTTCTGTACTCCCTCTTCCCTTACCCCCTTACA
AATCTCTGGCAACAGAGAGGCAAAGTATCTGAACAAGAATCTATATTCCAAGCACATTTACTGAAATGTAAAACACAACA
GGAAGCAAAGCAATCTCCCTTTGTTTTTCAGGCCATTCACCTGCCTCCTGTCAGTAGTGGCCTGTATTAGAGATCAAGAA
GAGTGGTTTGTGCTCAGGCTGGGGAACAGAGAGGCACGCTATGCTGCCAGAATTCCCAGGAGGGCATATCAGCAACTGCC
CAGCAGAGCTATATTTTGGGGGAGAAGTTGAGCTTCCATTTTGAGTAACAGAATAAATATTATATATATCAAAAGCCAAA
ATCTTTATTTTTATGCATTTAGAATATTTTAAATAGTTCTCAGATATTAAGAAGTTGTATGAGTTGTAAGTAATCTTGCC
AAAGGTAAAGGGCTAGTTGTAAGAAATTGTACATAAGATTGATTTATCATTGATGCCTACTGAAATAAAAAGAGGAAAG
GCTGGAAGCTGCAGACAGGATCCCTAGCTTGTTTTCTGTCAGTCATTCATTGTAAGTAGCACATTGCAACAACAATCATG
CTTATGACCAATACAGTCACTAGGTTGTAGTTTTTTTAAATAAAGGAAAAGCAGTATTGTCCTGGTTTTAAACCTATGA
TGGAATTCTAATGTCATTATTTTAATGGAATCAATCGAAATATGCTCTATAGAGAATATATCTTTTATATATTGCTGCAG
TTTCCTTATGTTAATCCTTTAACACTAAGGTAACATGACATAATCATACCATAGAAGGGAACACAGGTTACCATATTGGT
TTGTAATATGGGTCTTGGTGGGTTTTGTTTTATCCTTTAAATTTTGTTCCCATGAGTTTTGTGGGGATGGGGATTCTGGT

FIG. 17D
TTTATTAGCTTTGTGTGTGTCCTCTTCCCCCAAACCCCCTTTTGGTGAGAACATCCCCTTGACAGTTGCAGCCTCTTGAC
CTCGGATAACAATAAGAGAGCTCATCTCATTTTTACTTTTGAACGTTGGCCTTACAATCAAATGTAAGTTATATATATTT
GTACTGATGAAAATTTATAATCTGCTTTAACAAAAATAAATGTTCATGGTAGAAGCTTTTAAA

FIG. 18A
>NP_003735.3 protein numb homolog isoform 3 [Homo sapiens] (SEQ ID NO:
6)MNKLRQSFRRKKDVYVPEASRPHQWQTDEEGVRTGKCSFPVKYLGHVEVDESRGMHICEDAVKRLKATGKKAVKAVLW
VSADGLRVVDEKTKDLIVDQTIEKVSFCAPDRNFDRAFSYICRDGTTRRWICHCFMAVKDTGERLSHAVGCAFAACLERK
QKREKECGVTATFDASRTTFTREGSFRVTTATEQAEREEIMKQMQDAKKAETDKIVVGSSVAPGNTAPSPSSPTSPTSDA
TTSLEMNNPHAIPRRHAPIEQLARQGSFRGFPALSQKMSPFKRQLSLRINELPSTMQRKTDFPIKNAVPEVEGEAESISS
LCSQITNAFSTPEDPFSSAPMTKPVTVVAPQSPTFQANGTDSAFHVLAKPAHTALAPVAMPVRETNPWAHAPDAANKEIA
ATCSGTEWGQSSGAASPGLFQAGHRRTPSEADRWLEEVSKSVRAQQPQASAAPLQPVLQPPPPTAISQPASPFQGNAFLT
SQPVPVGVVPALQPAFVPAQSYPVANGMPYPAPNVPVVGITPSQMVANVFGTAGHPQAAHPHQSPSLVRQQTFPHYEASS
ATTSPFFKPPAQHLNGSAAFNGVDDGRLASADRHTEVPTGTCPVDPFEAQWAALENKSKQRTNPSPTNPFSSDLQKTFEI
EL

FIG. 18B
>NP_001005745.1 protein numb homolog isoform 4 [Homo sapiens] (SEQ ID NO: 7)
MNKLRQSFRRKKDVYVPEASRPHQWQTDEEGVRTGKCSFPVKYLGHVEVDESRGMHICEDAVKRLKATGKKAVKAVLWVS
ADGLRVVDEKTKDLIVDQTIEKVSFCAPDRNFDRAFSYICRDGTTRRWICHCFMAVKDTGERLSHAVGCAFAACLERKQK
REKECGVTATFDASRTTFTREGSFRVTTATEQAEREEIMKQMQDAKKAETDKIVVGSSVAPGNTAPSPSSPTSPTSDATT
SLEMNNPHAIPRRHAPIEQLARQGSFRGFPALSQKMSPFKRQLSLRINELPSTMQRKTDFPIKNAVPEVEGEAESISSLC
SQITNAFSTPEDPFSSAPMTKPVTVVAPQSPTFQGTEWGQSSGAASPGLFQAGHRRTPSEADRWLEEVSKSVRAQQPQAS
AAPLQPVLQPPPPTAISQPASPFQGNAFLTSQPVPVGVVPALQPAFVPAQSYPVANGMPYPAPNVPVVGITPSQMVANVF
GTAGHPQAAHPHQSPSLVRQQTFPHYEASSATTSPFFKPPAQHLNGSAAFNGVDDGRLASADRHTEVPTGTCPVDPFEAQ
WAALENKSKQRTNPSPTNPFSSDLQKTFEIEL

FIG. 18C
>ABY89092.1 numb isoform 7 [Homo sapiens] (SEQ ID NO: 8)
MNKLRQSFRRKKDVYVPEASRPHQWQTDEEGVRTGKCSFPVKYLGHVEVDESRGMHICEDAVKRLKAERKFFKGFFGKTG
KKAVKAVLWVSADGLRVVDEKTKDLIVDQTIEKVSFCAPDRNFDRAFSYICRDGTTRRWICHCFMAVKDTGERLSHAVGC
AFAACLERKQKREKECGVTATFDASRTTFTREGSFRVTTATEQAEREEIMKQMQDAKKGTEWGQSSGAASPGLFQAGHRR
TPSEADRWLEEVSKSVRAQQPQASAAPLQPVLQPPPPTAISQPASPFQGNAFLTSQPVPVGVVPALQPAFVPAQSYPVAN
GMPYPAPNVPVVGITPSQMVANVFGTAGHPQAAHPHQSPSLVRQQTFPHYEASSATTSPFFKPPAQHLNGSAAFNGVDDG
RLASADRHTEVPTGTCPVDPFEAQWAALENKSKQRTNPSPTNPFSSDLQKTFEIEL

FIG. 18D
>ABY89093.1 numb isoform 8 [Homo sapiens] (SEQ ID NO: 9)
MNKLRQSFRRKKDVYVPEASRPHQWQTDEEGVRTGKCSFPVKYLGHVEVDESRGMHICEDAVKRLKATGKKAVKAVLWVS
ADGLRVVDEKTKDLIVDQTIEKVSFCAPDRNFDRAFSYICRDGTTRRWICHCFMAVKDTGERLSHAVGCAFAACLERKQK
REKECGVTATFDASRTTFTREGSFRVTTATEQAEREEIMKQMQDAKKGTEWGQSSGAASPGLFQAGHRRTPSEADRWLEE
VSKSVRAQQPQASAAPLQPVLQPPPPTAISQPASPFQGNAFLTSQPVPVGVVPALQPAFVPAQSYPVANGMPYPAPNVPV
VGITPSQMVANVFGTAGHPQAAHPHQSPSLVRQQTFPHYEASSATTSPFFKPPAQHLNGSAAFNGVDDGRLASADRHTEV
PTGTCPVDPFEAQWAALENKSKQRTNPSPTNPFSSDLQKTFEIEL

FIG. 19A
CLUSTAL O(1.2.4) multiple sequence alignment

```
numb8      MNKLRQSFRRKKDVYVPEASRPHQWQTDEEGVRTGKCSFPVKYLGHVEVDESRGMHICED
numb7      MNKLRQSFRRKKDVYVPEASRPHQWQTDEEGVRTGKCSFPVKYLGHVEVDESRGMHICED
numb4      MNKLRQSFRRKKDVYVPEASRPHQWQTDEEGVRTGKCSFPVKYLGHVEVDESRGMHICED
numb2      MNKLRQSFRRKKDVYVPEASRPHQWQTDEEGVRTGKCSFPVKYLGHVEVDESRGMHICED
numb1      MNKLRQSFRRKKDVYVPEASRPHQWQTDEEGVRTGKCSFPVKYLGHVEVDESRGMHICED
numb3      MNKLRQSFRRKKDVYVPEASRPHQWQTDEEGVRTGKCSFPVKYLGHVEVDESRGMHICED
           ************************************************************ numb8      AVKRLKA-----------TGKKAVKAVLWVSADGLRVVDEKTKDLIVDQTIEKVSFCAPD
numb7      AVKRLKAERKFFKGFFGKTGKKAVKAVLWVSADGLRVVDEKTKDLIVDQTIEKVSFCAPD
numb4      AVKRLKA-----------TGKKAVKAVLWVSADGLRVVDEKTKDLIVDQTIEKVSFCAPD
numb2      AVKRLKAERKFFKGFFGKTGKKAVKAVLWVSADGLRVVDEKTKDLIVDQTIEKVSFCAPD
numb1      AVKRLKAERKFFKGFFGKTGKKAVKAVLWVSADGLRVVDEKTKDLIVDQTIEKVSFCAPD
numb3      AVKRLKA-----------TGKKAVKAVLWVSADGLRVVDEKTKDLIVDQTIEKVSFCAPD
           *****           **************************************** numb8      RNFDRAFSYICRDGTTRRWICHCFMAVKDTGERLSHAVGCAFAACLERKQKREKECGVTA
numb7      RNFDRAFSYICRDGTTRRWICHCFMAVKDTGERLSHAVGCAFAACLERKQKREKECGVTA
numb4      RNFDRAFSYICRDGTTRRWICHCFMAVKDTGERLSHAVGCAFAACLERKQKREKECGVTA
numb2      RNFDRAFSYICRDGTTRRWICHCFMAVKDTGERLSHAVGCAFAACLERKQKREKECGVTA
numb1      RNFDRAFSYICRDGTTRRWICHCFMAVKDTGERLSHAVGCAFAACLERKQKREKECGVTA
numb3      RNFDRAFSYICRDGTTRRWICHCFMAVKDTGERLSHAVGCAFAACLERKQKREKECGVTA
           ************************************************************ numb8      TFDASRTTFTREGSFRVTTATEQAEREEIMKQMQDAKK----------------------
numb7      TFDASRTTFTREGSFRVTTATEQAEREEIMKQMQDAKK----------------------
numb4      TFDASRTTFTREGSFRVTTATEQAEREEIMKQMQDAKKAETDKIVVGSSVAPGNTAPSPS
numb2      TFDASRTTFTREGSFRVTTATEQAEREEIMKQMQDAKKAETDKIVVGSSVAPGNTAPSPS
numb1      TFDASRTTFTREGSFRVTTATEQAEREEIMKQMQDAKKAETDKIVVGSSVAPGNTAPSPS
numb3      TFDASRTTFTREGSFRVTTATEQAEREEIMKQMQDAKKAETDKIVVGSSVAPGNTAPSPS
           ************************************** numb8      ------------------------------------------------------------
numb7      ------------------------------------------------------------
numb4      SPTSPTSDATTSLEMNNPHAIPRRHAPIEQLARQGSFRGFPALSQKMSPFKRQLSLRINE
numb2      SPTSPTSDATTSLEMNNPHAIPRRHAPIEQLARQGSFRGFPALSQKMSPFKRQLSLRINE
numb1      SPTSPTSDATTSLEMNNPHAIPRRHAPIEQLARQGSFRGFPALSQKMSPFKRQLSLRINE
numb3      SPTSPTSDATTSLEMNNPHAIPRRHAPIEQLARQGSFRGFPALSQKMSPFKRQLSLRINE numb8      ------------------------------------------------------------
numb7      ------------------------------------------------------------
numb4      LPSTMQRKTDFPIKNAVPEVEGEAESISSLCSQITNAFSTPEDPFSSAPMTKPVTVVAPQ
numb2      LPSTMQRKTDFPIKNAVPEVEGEAESISSLCSQITNAFSTPEDPFSSAPMTKPVTVVAPQ
numb1      LPSTMQRKTDFPIKNAVPEVEGEAESISSLCSQITNAFSTPEDPFSSAPMTKPVTVVAPQ
numb3      LPSTMQRKTDFPIKNAVPEVEGEAESISSLCSQITNAFSTPEDPFSSAPMTKPVTVVAPQ
```

FIG. 19B

```
numb8    ------------------------------------------------------GTEWGQS
numb7    ------------------------------------------------------GTEWGQS
numb4    SPTFQ-------------------------------------------------GTEWGQS
numb2    SPTFQ-------------------------------------------------GTEWGQS
numb1    SPTFQANGTDSAFHVLAKPAHTALAPVAMPVRETNPWAHAPDAANKEIAATCSGTEWGQS
numb3    SPTFQANGTDSAFHVLAKPAHTALAPVAMPVRETNPWAHAPDAANKEIAATCSGTEWGQS
                                                               ******* numb8    SGAASPGLFQAGHRRTPSEADRWLEEVSKSVRAQQPQASAAPLQPVLQPPPPTAISQPAS
numb7    SGAASPGLFQAGHRRTPSEADRWLEEVSKSVRAQQPQASAAPLQPVLQPPPPTAISQPAS
numb4    SGAASPGLFQAGHRRTPSEADRWLEEVSKSVRAQQPQASAAPLQPVLQPPPPTAISQPAS
numb2    SGAASPGLFQAGHRRTPSEADRWLEEVSKSVRAQQPQASAAPLQPVLQPPPPTAISQPAS
numb1    SGAASPGLFQAGHRRTPSEADRWLEEVSKSVRAQQPQASAAPLQPVLQPPPPTAISQPAS
numb3    SGAASPGLFQAGHRRTPSEADRWLEEVSKSVRAQQPQASAAPLQPVLQPPPPTAISQPAS
         ************************************************************ numb8    PFQGNAFLTSQPVPVGVVPALQPAFVPAQSYPVANGMPYPAPNVPVVGITPSQMVANVFG
numb7    PFQGNAFLTSQPVPVGVVPALQPAFVPAQSYPVANGMPYPAPNVPVVGITPSQMVANVFG
numb4    PFQGNAFLTSQPVPVGVVPALQPAFVPAQSYPVANGMPYPAPNVPVVGITPSQMVANVFG
numb2    PFQGNAFLTSQPVPVGVVPALQPAFVPAQSYPVANGMPYPAPNVPVVGITPSQMVANVFG
numb1    PFQGNAFLTSQPVPVGVVPALQPAFVPAQSYPVANGMPYPAPNVPVVGITPSQMVANVFG
numb3    PFQGNAFLTSQPVPVGVVPALQPAFVPAQSYPVANGMPYPAPNVPVVGITPSQMVANVFG
         ************************************************************ numb8    TAGHPQAAHPHQSPSLVRQQTFPHYEASSATTSPFFKPPAQHLNGSAAFNGVDDGRLASA
numb7    TAGHPQAAHPHQSPSLVRQQTFPHYEASSATTSPFFKPPAQHLNGSAAFNGVDDGRLASA
numb4    TAGHPQAAHPHQSPSLVRQQTFPHYEASSATTSPFFKPPAQHLNGSAAFNGVDDGRLASA
numb2    TAGHPQAAHPHQSPSLVRQQTFPHYEASSATTSPFFKPPAQHLNGSAAFNGVDDGRLASA
numb1    TAGHPQAAHPHQSPSLVRQQTFPHYEASSATTSPFFKPPAQHLNGSAAFNGVDDGRLASA
numb3    TAGHPQAAHPHQSPSLVRQQTFPHYEASSATTSPFFKPPAQHLNGSAAFNGVDDGRLASA
         ************************************************************ numb8    DRHTEVPTGTCPVDPFEAQWAALENKSKQRTNPSPTNPFSSDLQKTFEIEL
numb7    DRHTEVPTGTCPVDPFEAQWAALENKSKQRTNPSPTNPFSSDLQKTFEIEL
numb4    DRHTEVPTGTCPVDPFEAQWAALENKSKQRTNPSPTNPFSSDLQKTFEIEL
numb2    DRHTEVPTGTCPVDPFEAQWAALENKSKQRTNPSPTNPFSSDLQKTFEIEL
numb1    DRHTEVPTGTCPVDPFEAQWAALENKSKQRTNPSPTNPFSSDLQKTFEIEL
numb3    DRHTEVPTGTCPVDPFEAQWAALENKSKQRTNPSPTNPFSSDLQKTFEIEL
         ***************************************************
```

FIG. 19C

> Consensus of human Numb1-Numb4, Numb7 and Numb8 (SEQ ID NO: 10)
MNKLRQSFRRKKDVYVPEASRPHQWQTDEEGVRTGKCSFPVKYLGHVEVDESRGMHICEDAVKRLKAXXXXXXXXXX
XXTGKKAVKAVLWVSADGLRVVDEKTKDLIVDQTIEKVSFCAPDRNFDRAFSYICRDGTTRRWICHCFMAVKDTGE
RLSHAVGCAFAACLERKQKREKECGVTATFDASRTTFTREGSFRVTTATEQAEREEIMKQMQDAKKXXXXXXXXXX
XXXXXXXXXXXXXXXXXXXXXXXXXXXXXXXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXXXXXXXXXXXXXXXXXXXXXXXXXXXXXXXX
XXXXXXXXXXXXXXXXXXXXXXXXXXXXXXXXXGTEWGQSSGAASPGLFQAGHRRTPSEADRWLEEVSKSVRAQQP
QASAAPLQPVLQPPPPTAISQPASPFQGNAFLTSQPVPVGVVPALQPAFVPAQSYPVANGMPYPAPNVPVVGITPS
QMVANVFGTAGHPQAAHPHQSPSLVRQQTFPHYEASSATTSPFFKPPAQHLNGSAAFNGVDDGRLASADRHTEVPT
GTCPVDPFEAQWAALENKSKQRTNPSPTNPFSSDLQKTFEIEL

FIG. 19D

> Consensus of human Numb1 and Numb2 (SEQ ID NO: 11)
MNKLRQSFRRKKDVYVPEASRPHQWQTDEEGVRTGKCSFPVKYLGHVEVDESRGMHICEDAVKRLKAERKFFKGFFGKTG
KKAVKAVLWVSADGLRVVDEKTKDLIVDQTIEKVSFCAPDRNFDRAFSYICRDGTTRRWICHCFMAVKDTGERLSHAVGC
AFAACLERKQKREKECGVTATFDASRTTFTREGSFRVTTATEQAEREEIMKQMQDAKKAETDKIVVGSSVAPGNTAPSPS
SPTSPTSDATTSLEMNNPHAIPRRHAPIEQLARQGSFRGFPALSQKMSPFKRQLSLRINELPSTMQRKTDFPIKNAVPEV
EGEAESISSLCSQITNAFSTPEDPFSSAPMTKPVTVVAPQSPTFQXXXXXXXXXXXXXXXXXXXXXXXXXXXXXXXXXXX
XXXXXXXXXXXXGTEWGQSSGAASPGLFQAGHRRTPSEADRWLEEVSKSVRAQQPQASAAPLQPVLQPPPPTAISQPAS
PFQGNAFLTSQPVPVGVVPALQPAFVPAQSYPVANGMPYPAPNVPVVGITPSQMVANVFGTAGHPQAAHPHQSPSLVRQQ
TFPHYEASSATTSPFFKPPAQHLNGSAAFNGVDDGRLASADRHTEVPTGTCPVDPFEAQWAALENKSKQRTNPSPTNPFS
SDLQKTFEIEL

FIG. 20A
>sp|P26599|PTBP1_HUMAN Polypyrimidine tract-binding protein 1 OS=Homo sapiens
GN=PTBP1 PE=1 SV=1 (SEQ ID NO: 12)
MDGIVPDIAVGTKRGSDELFSTCVTNGPFIMSSNSASAANGNDSKKFKGDSRSAGVPSRVIHIRKLPIDVTEGEVISLGL
PFGKVTNLLMLKGKNQAFIEMNTEEAANTMVNYYTSVTPVLRGQPIYIQFSNHKELKTDSSPNQARAQAALQAVNSVQSG
NLALAASAAAVDAGMAMAGQSPVLRIIVENLFYPVTLDVLHQIFSKFGTVLKIITFTKNNQFQALLQYADPVSAQHAKLS
LDGQNIYNACCTLRIDFSKLTSLNVKYNNDKSRDYTRPDLPSGDSQPSLDQTMAAAFGLSVPNVHGALAPLAIPSAAAAA
AAAGRIAIPGLAGAGNSVLLVSNLNPERVTPQSLFILFGVYGDVQRVKILFNKKENALVQMADGNQAQLAMSHLNGHKLH
GKPIRITLSKHQNVQLPREGQEDQGLTKDYGNSPLHRFKKPGSKNFQNIFPPSATLHLSNIPPSVSEEDLKVLFSSNGGV
VKGFKFFQKDRKMALIQMGSVEEAVQALIDLHNHDLGENHHLRVSFSKSTI

FIG. 20B
>sp|P26599-2|PTBP1_HUMAN Isoform 2 of Polypyrimidine tract-binding protein 1
OS=Homo sapiens GN=PTBP1 (SEQ ID NO: 13)
MDGIVPDIAVGTKRGSDELFSTCVTNGPFIMSSNSASAANGNDSKKFKGDSRSAGVPSRVIHIRKLPIDVTEGEVISLGL
PFGKVTNLLMLKGKNQAFIEMNTEEAANTMVNYYTSVTPVLRGQPIYIQFSNHKELKTDSSPNQARAQAALQAVNSVQSG
NLALAASAAAVDAGMAMAGQSPVLRIIVENLFYPVTLDVLHQIFSKFGTVLKIITFTKNNQFQALLQYADPVSAQHAKLS
LDGQNIYNACCTLRIDFSKLTSLNVKYNNDKSRDYTRPDLPSGDSQPSLDQTMAAAFASPYAGAGFPPTFAIPQAAGLSV
PNVHGALAPLAIPSAAAAAAAAGRIAIPGLAGAGNSVLLVSNLNPERVTPQSLFILFGVYGDVQRVKILFNKKENALVQM
ADGNQAQLAMSHLNGHKLHGKPIRITLSKHQNVQLPREGQEDQGLTKDYGNSPLHRFKKPGSKNFQNIFPPSATLHLSNI
PPSVSEEDLKVLFSSNGGVVKGFKFFQKDRKMALIQMGSVEEAVQALIDLHNHDLGENHHLRVSFSKSTI

FIG. 20C
>sp|P26599-3|PTBP1_HUMAN Isoform 3 of Polypyrimidine tract-binding protein 1
OS=Homo sapiens GN=PTBP1(SEQ ID NO: 14)
MDGIVPDIAVGTKRGSDELFSTCVTNGPFIMSSNSASAANGNDSKKFKGDSRSAGVPSRVIHIRKLPIDVTEGEVISLGL
PFGKVTNLLMLKGKNQAFIEMNTEEAANTMVNYYTSVTPVLRGQPIYIQFSNHKELKTDSSPNQARAQAALQAVNSVQSG
NLALAASAAAVDAGMAMAGQSPVLRIIVENLFYPVTLDVLHQIFSKFGTVLKIITFTKNNQFQALLQYADPVSAQHAKLS
LDGQNIYNACCTLRIDFSKLTSLNVKYNNDKSRDYTRPDLPSGDSQPSLDQTMAAAFGAPGIISASPYAGAGFPPTFAIP
QAAGLSVPNVHGALAPLAIPSAAAAAAAGRIAIPGLAGAGNSVLLVSNLNPERVTPQSLFILFGVYGDVQRVKILFNKK
ENALVQMADGNQAQLAMSHLNGHKLHGKPIRITLSKHQNVQLPREGQEDQGLTKDYGNSPLHRFKKPGSKNFQNIFPPSA
TLHLSNIPPSVSEEDLKVLFSSNGGVVKGFKFFQKDRKMALIQMGSVEEAVQALIDLHNHDLGENHHLRVSFSKSTI

FIG. 21A
>sp|Q07955|SRSF1_HUMAN Serine/arginine-rich splicing factor 1 OS=Homo sapiens
GN=SRSF1 PE=1 SV=2 (SEQ ID NO: 15)
MSGGGVIRGPAGNNDCRIYVGNLPPDIRTKDIEDVFYKYGAIRDIDLKNRRGGPPFAFVEFEDPRDAEDAVYGRDGYDYD
GYRLRVEFPRSGRGTGRGGGGGGGGAPRGRYGPPSRRSENRVVVSGLPPSGSWQDLKDHMREAGDVCYADVYRDGTGVV
EFVRKEDMTYAVRKLDNTKFRSHEGETAYIRVKVDGPRSPSYGRSRSRSRSRSRSRSNSRSRSYSPRRSRGSPRYSPR
HSRSRSRT

FIG. 21B
>sp|Q07955-2|SRSF1_HUMAN Isoform ASF-2 of Serine/arginine-rich splicing factor 1
OS=Homo sapiens GN=SRSF1(SEQ ID NO: 16)
MSGGGVIRGPAGNNDCRIYVGNLPPDIRTKDIEDVFYKYGAIRDIDLKNRRGGPPFAFVEFEDPRDAEDAVYGRDGYDYD
GYRLRVEFPRSGRGTGRGGGGGGGGAPRGRYGPPSRRSENRVVVSGLPPSGSWQDLKDHMREAGDVCYADVYRDGTGVV
EFVRKEDMTYAVRKLDNTKFRSHEFCLSNREKLPTSGLKLMGPEVQVMEDLDLEAVVVAEAVAEATAGVAVTPQGEAEDH
HAILPVIADLALVHKMIGDTFCRTHVVYSFPLFSTIFSFFNSNCFVQNGLKC

FIG. 21C
>sp|Q07955-3|SRSF1_HUMAN Isoform ASF-3 of Serine/arginine-rich splicing factor 1
OS=Homo sapiens GN=SRSF1(SEQ ID NO: 17)
MSGGGVIRGPAGNNDCRIYVGNLPPDIRTKDIEDVFYKYGAIRDIDLKNRRGGPPFAFVEFEDPRDAEDAVYGRDGYDYD
GYRLRVEFPRSGRGTGRGGGGGGGGAPRGRYGPPSRRSENRVVVSGLPPSGSWQDLKDHMREAGDVCYADVYRDGTGVV
EFVRKEDMTYAVRKLDNTKFRSHEVGYTRILFFDQNWIQWS

FIG. 22A

>NP_058519.3 microtubule-associated protein tau isoform 1 [Homo sapiens] (SEQ ID NO: 18)
MAEPRQEFEVMEDHAGTYGLGDRKDQGGYTMHQDQEGDTDAGLKESPLQTPTEDGSEEPGSETSDAKSTPTAEDVTAPLV
DEGAPGKQAAAQPHTEIPEGTTAEEAGIGDTPSLEDEAAGHVTQEPESGKVVQEGFLREPGPPGLSHQLMSGMPGAPLLP
EGPREATRQPSGTGPEDTEGGRHAPELLKHQLLGDLHQEGPPLKGAGGKERPGSKEEVDEDRDVDESSPQDSPPSKASPA
QDGRPPQTAAREATSIPGFPAEGAIPLPVDFLSKVSTEIPASEPDGPSVGRAKGQDAPLEFTFHVEITPNVQKEQAHSEE
HLGRAAFPGAPGEGPEARGPSLGEDTKEADLPEPSEKQPAAAPRGKPVSRVPQLKARMVSKSKDGTGSDDKKAKTSTRSS
AKTLKNRPCLSPKHPTPGSSDPLIQPSSPAVCPEPPSSPKYVSSVTSRTGSSGAKEMKLKGADGKTKIATPRGAAPPGQK
GQANATRIPAKTPPAPKTPPSSGEPPKSGDRSGYSSPGSPGTPGSRSRTPSLPTPPTREPKKVAVVRTPPKSPSSAKSRL
QTAPVPMPDLKNVKSKIGSTENLKHQPGGGKVQIINKKLDLSNVQSKCGSKDNIKHVPGGGSVQIVYKPVDLSKVTSKCG
SLGNIHHKPGGGQVEVKSEKLDFKDRVQSKIGSLDNITHVPGGGNKKIETHKLTFRENAKAKTDHGAEIVYKSPVVSGDT
SPRHLSNVSSTGSIDMVDSPQLATLADEVSASLAKQGL

FIG. 22B

>NP_005901.2 microtubule-associated protein tau isoform 2 [Homo sapiens] (SEQ ID NO: 19)
MAEPRQEFEVMEDHAGTYGLGDRKDQGGYTMHQDQEGDTDAGLKESPLQTPTEDGSEEPGSETSDAKSTPTAEDVTAPLV
DEGAPGKQAAAQPHTEIPEGTTAEEAGIGDTPSLEDEAAGHVTQARMVSKSKDGTGSDDKKAKGADGKTKIATPRGAAPP
GQKGQANATRIPAKTPPAPKTPPSSGEPPKSGDRSGYSSPGSPGTPGSRSRTPSLPTPPTREPKKVAVVRTPPKSPSSAK
SRLQTAPVPMPDLKNVKSKIGSTENLKHQPGGGKVQIINKKLDLSNVQSKCGSKDNIKHVPGGGSVQIVYKPVDLSKVTS
KCGSLGNIHHKPGGGQVEVKSEKLDFKDRVQSKIGSLDNITHVPGGGNKKIETHKLTFRENAKAKTDHGAEIVYKSPVVS
GDTSPRHLSNVSSTGSIDMVDSPQLATLADEVSASLAKQGL

FIG. 22C

>NP_058518.1 microtubule-associated protein tau isoform 3 [Homo sapiens] (SEQ ID NO: 20)
MAEPRQEFEVMEDHAGTYGLGDRKDQGGYTMHQDQEGDTDAGLKAEEAGIGDTPSLEDEAAGHVTQARMVSKSKDGTGSD
DKKAKGADGKTKIATPRGAAPPGQKGQANATRIPAKTPPAPKTPPSSGEPPKSGDRSGYSSPGSPGTPGSRSRTPSLPTP
PTREPKKVAVVRTPPKSPSSAKSRLQTAPVPMPDLKNVKSKIGSTENLKHQPGGGKVQIINKKLDLSNVQSKCGSKDNIK
HVPGGGSVQIVYKPVDLSKVTSKCGSLGNIHHKPGGGQVEVKSEKLDFKDRVQSKIGSLDNITHVPGGGNKKIETHKLTF
RENAKAKTDHGAEIVYKSPVVSGDTSPRHLSNVSSTGSIDMVDSPQLATLADEVSASLAKQGL

FIG. 22D

>NP_058525.1 microtubule-associated protein tau isoform 4 [Homo sapiens] (SEQ ID NO: 21)
MAEPRQEFEVMEDHAGTYGLGDRKDQGGYTMHQDQEGDTDAGLKAEEAGIGDTPSLEDEAAGHVTQARMVSKSKDGTGSD
DKKAKGADGKTKIATPRGAAPPGQKGQANATRIPAKTPPAPKTPPSSGEPPKSGDRSGYSSPGSPGTPGSRSRTPSLPTP
PTREPKKVAVVRTPPKSPSSAKSRLQTAPVPMPDLKNVKSKIGSTENLKHQPGGGKVQIVYKPVDLSKVTSKCGSLGNIH
HKPGGGQVEVKSEKLDFKDRVQSKIGSLDNITHVPGGGNKKIETHKLTFRENAKAKTDHGAEIVYKSPVVSGDTSPRHLS
NVSSTGSIDMVDSPQLATLADEVSASLAKQGL

FIG. 22E

>NP_001116539.1 microtubule-associated protein tau isoform 5 [Homo sapiens] (SEQ ID NO: 22)
MAEPRQEFEVMEDHAGTYGLGDRKDQGGYTMHQDQEGDTDAGLKESPLQTPTEDGSEEPGSETSDAKSTPTAEAEEAGIG
DTPSLEDEAAGHVTQARMVSKSKDGTGSDDKKAKGADGKTKIATPRGAAPPGQKGQANATRIPAKTPPAPKTPPSSGEPP
KSGDRSGYSSPGSPGTPGSRSRTPSLPTPPTREPKKVAVVRTPPKSPSSAKSRLQTAPVPMPDLKNVKSKIGSTENLKHQ
PGGGKVQIINKKLDLSNVQSKCGSKDNIKHVPGGGSVQIVYKPVDLSKVTSKCGSLGNIHHKPGGGQVEVKSEKLDFKDR
VQSKIGSLDNITHVPGGGNKKIETHKLTFRENAKAKTDHGAEIVYKSPVVSGDTSPRHLSNVSSTGSIDMVDSPQLATLA
DEVSASLAKQGL

FIG. 22F

>NP_001116538.2 microtubule-associated protein tau isoform 6 [Homo sapiens] (SEQ ID NO: 23)
MAEPRQEFEVMEDHAGTYGLGDRKDQGGYTMHQDQEGDTDAGLKESPLQTPTEDGSEEPGSETSDAKSTPTAEDVTAPLV
DEGAPGKQAAAQPHTEIPEGTTAEEAGIGDTPSLEDEAAGHVTQEPESGKVVQEGFLREPGPPGLSHQLMSGMPGAPLLP
EGPREATRQPSGTGPEDTEGGRHAPELLKHQLLGDLHQEGPPLKGAGGKERPGSKEEVDEDRDVDESSPQDSPPSKASPA
QDGRPPQTAAREATSIPGFPAEGAIPLPVDFLSKVSTEIPASEPDGPSVGRAKGQDAPLEFTFHVEITPNVQKEQAHSEE
HLGRAAFPGAPGEGPEARGPSLGEDTKEADLPEPSEKQPAAAPRGKPVSRVPQLKARMVSKSKDGTGSDDKKAKTSTRSS
AKTLKNRPCLSPKHPTPGSSDPLIQPSSPAVCPEPPSSPKYVSSVTSRTGSSGAKEMKLKGADGKTKIATPRGAAPPGQK
GQANATRIPAKTPPAPKTPPSSATKQVQRRPPPAGPRSERGEPPKSGDRSGYSSPGSPGTPGSRSRTPSLPTPPTREPKK
VAVVRTPPKSPSSAKSRLQTAPVPMPDLKNVKSKIGSTENLKHQPGGGKVQIINKKLDLSNVQSKCGSKDNIKHVPGGGS
VQIVYKPVDLSKVTSKCGSLGNIHHKPGGGQVEVKSEKLDFKDRVQSKIGSLDNITHVPGGGNKKIETHKLTFRENAKAK
TDHGAEIVYKSPVVSGDTSPRHLSNVSSTGSIDMVDSPQLATLADEVSASLAKQGL

FIG. 22G

>NP_001190180.1 microtubule-associated protein tau isoform 7 [Homo sapiens] (SEQ ID NO: 24)
MAEPRQEFEVMEDHAGTYGLGDRKDQGGYTMHQDQEGDTDAGLKESPLQTPTEDGSEEPGSETSDAKSTPTAEAEEAGIG
DTPSLEDEAAGHVTQARMVSKSKDGTGSDDKKAKGADGKTKIATPRGAAPPGQKGQANATRIPAKTPPAPKTPPSSGEPP
KSGDRSGYSSPGSPGTPGSRSRTPSLPTPPTREPKKVAVVRTPPKSPSSAKSRLQTAPVPMPDLKNVKSKIGSTENLKHQ
PGGGKVQIVYKPVDLSKVTSKCGSLGNIHHKPGGGQVEVKSEKLDFKDRVQSKIGSLDNITHVPGGGNKKIETHKLTFRE
NAKAKTDHGAEIVYKSPVVSGDTSPRHLSNVSSTGSIDMVDSPQLATLADEVSASLAKQGL

FIG. 22H

>NP_001190181.1 microtubule-associated protein tau isoform 8 [Homo sapiens] (SEQ ID NO: 25)
MAEPRQEFEVMEDHAGTYGLGDRKDQGGYTMHQDQEGDTDAGLKESPLQTPTEDGSEEPGSETSDAKSTPTAEDVTAPLV
DEGAPGKQAAAQPHTEIPEGTTAEEAGIGDTPSLEDEAAGHVTQARMVSKSKDGTGSDDKKAKGADGKTKIATPRGAAPP
GQKGQANATRIPAKTPPAPKTPPSSGEPPKSGDRSGYSSPGSPGTPGSRSRTPSLPTPPTREPKKVAVVRTPPKSPSSAK
SRLQTAPVPMPDLKNVKSKIGSTENLKHQPGGGKVQIVYKPVDLSKVTSKCGSLGNIHHKPGGGQVEVKSEKLDFKDRVQ
SKIGSLDNITHVPGGGNKKIETHKLTFRENAKAKTDHGAEIVYKSPVVSGDTSPRHLSNVSSTGSIDMVDSPQLATLADE
VSASLAKQGL

FIG. 23A

>sp|Q9BWF3|RBM4_HUMAN RNA-binding protein 4 OS=Homo sapiens OX=9606 GN=RBM4 PE=1 SV=1 (SEQ ID NO: 26)
MVKLFIGNLPREATEQEIRSLFEQYGKVLECDIIKNYGFVHIEDKTAAEDAIRNLHHYKLHGVNINVEASKNKSKTSTKL
HVGNISPTCTNKELRAKFEEYGPVIECDIVKDYAFVHMERAEDAVEAIRGLDNTEFQGKRMHVQLSTSRLRTAPGMGDQS
GCYRCGKEGHWSKECPIDRSGRVADLTEQYNEQYGAVRTPYTMSYGDSLYYNNAYGALDAYYKRCRAARSYEAVAAAAAS
VYNYAEQTLSQLPQVQNTAMASHLTSTSLDPYDRHLLPTSGAAATAAAAAAAAAAVTAASTSYYGRDRSPLRRATAPVPT
VGEGYGYGHESELSQASAAARNSLYDMARYEREQYADRARYSAF

FIG. 23B

>sp|Q9BWF3-2|RBM4_HUMAN Isoform 2 of RNA-binding protein 4 OS=Homo sapiens OX=9606 GN=RBM4 (SEQ ID NO: 27)
MVKLFIGNLPREATEQEIRSLFEQYGKVLECDIIKNYGFVHIEDKTAAEDAIRNLHHYKLHGVNINVEASKNKSKTSTKL
HVGNISPTCTNKELRAKFEEYGPVIECDIVKDYAFVHMERAEDAVEAIRGLDNTEFQGEPPSLGRGLNTRLCAENGWISK
RRGLVKITAVGWLVMKK

FIG. 23C

>sp|Q9BWF3-3|RBM4_HUMAN Isoform 3 of RNA-binding protein 4 OS=Homo sapiens OX=9606 GN=RBM4 (SEQ ID NO: 28)
MVKLFIGNLPREATEQEIRSLFEQYGKVLECDIIKNYGFVHIEDKTAAEDAIRNLHHYKLHGVNINVEASKNKSKTSTKL
HVGNISPTCTNKELRAKFEEYGPVIECDIVKDYAFVHMERAEDAVEAIRGLDNTEFQGGMCVG

FIG. 23D

\>sp|Q9BWF3-4|RBM4_HUMAN Isoform 4 of RNA-binding protein 4 OS=Homo sapiens
OX=9606 GN=RBM4   (SEQ ID NO: 29)
MVKLFIGNLPREATEQEIRSLFEQYGKVLECDIIKNYGFVHIEDKTAAEDAIRNLHHYKLHGVNINVEASKNKSKTSTKL
HVGNISPTCTNKELRAKFEEYGPVIECDIVKDYAFVHMERAEDAVEAIRGLDNTEFQGKITPVTEGYCCCNKGHTYIFKN
CNLILESRKSRRC

METHOD OF REDUCING NEURONAL MICROTUBULE BINDING PROTEIN TAU (TAU) LEVELS

CROSS REFERENCE TO RELATED APPLICATIONS

This application is a National Entry Application of PCT application Serial No PCT/CA2019/051751 filed on Dec. 5, 2019 and published in English under PCT Article 21 (2), which itself claims benefit of U.S. provisional application Ser. No. 62/775,520, filed on Dec. 5, 2018. All documents above are incorporated herein in their entirety by reference.

STATEMENT REGARDING FEDERALLY SPONSORED RESEARCH OR DEVELOPMENT

N.A.

FIELD OF THE INVENTION

The present invention relates to a method of reducing neuronal microtubule binding protein Tau (Tau) levels. More specifically, the present invention is concerned with such a method using an agent that increases a long Numb isoform expression and/or activity in a subject having a pathology caused by elevated levels of Tau such as a tauopathy (e.g., Alzheimer's disease), or a Tau-associated optic neuropathy (e.g., glaucoma).

REFERENCE TO SEQUENCE LISTING

Pursuant to 37 C.F.R. 1.821 (c), a sequence listing is submitted herewith as an ASCII compliant text file named Sequence listing 12810-782_ST25, that was created on May 18, 2021 and having a size of 112 kilobytes. The content of the aforementioned file named Sequence listing 12810-782_ST25 is hereby incorporated by reference in its entirety.

BACKGROUND OF THE INVENTION

Tauopathy

Tauopathies are a class of neurodegenerative diseases characterized by the accumulation of toxic forms (often misfolded) of the microtubule-binding protein Tau. The spectrum of diseases associated with pathologic Tau accumulation is large and includes Alzheimer's disease, Pick disease, progressive supranuclear palsy, corticobasal degeneration, argyrophilic grain disease, globular glial tauopathies, primary age-related tauopathy, neurofibrillary tangle dementia, chronic traumatic encephalopathy, and age-related tau astrogliopathy. Various clinical symptoms are associated with tauopathies, such as frontotemporal dementia, corticobasal syndrome, Richardson syndrome, parkinsonism, pure akinesia with gait freezing and, less frequently, motor neuron symptoms or cerebellar ataxia.

Alzheimer's Disease

Alzheimer's disease (AD) is the most common form of dementia, affecting millions of people worldwide. Neuronal cell (neurons) death, synaptic loss, amyloid plaques, and neurofibrillary tangles (NFTs) are the main neuropathological features of the disease. In recent years, increasing evidence have suggested that the intraneuronal accumulation of the microtubule binding protein Tau (Tau) is an important toxic insult leading to neurodegeneration in AD, suggesting that deficits in the pathways that remove pathological forms of Tau in neurons might play a key part in AD. And conversely, mechanisms that could promote the degradation of Tau in neurons might constitute an interesting therapeutic approach.

Tau is a highly soluble microtubule-binding protein that stabilizes axonal microtubules. In AD, however, toxic species of Tau accumulate in neurons to form insoluble fibrillar structures called neurofibrillary tangles (NFTs), which are defining hallmarks of the AD brain. In recent years, the conceptual framework of AD pathogenesis has evolved to suggest that the soluble pathological forms of Tau might be the toxic entities leading to neurodegeneration, rather than the NFTs, largely because synaptic loss and microglia activation appear before any NFTs can be detected (de Calignon et al., 2012; Lasagna-Reeves et al., 2012; Yoshiyama et al., 2007). While many studies have proposed a role for the various modified forms of Tau such as hyperphosphorylation, acetylation, ubiquitination, or truncation in AD pathogenesis, it remains unclear which exact form(s) actually compromise(s) neuronal function (Chesser et al., 2013). Reducing Tau levels in neurons attenuates neuronal dysfunction in mouse model of AD (Ittner et al., 2010; Roberson et al., 2011; Roberson et al., 2007), and the extent of Tau accumulation correlates with cognitive decline in human patients (Guillozet et al., 2003). Recent studies have also shown that lowering the levels of Tau improve cognitive function in mouse models of tauopathy (Lasagna-Reeves et al., 2016; Myeku et al., 2016). It is therefore likely that deficits in pathways that selectively remove pathological forms of Tau could play a pivotal role in AD. Consequently, a better understanding of the degradation pathways regulating Tau levels in neurons is an important step towards the development of therapies.

Tau-Associated Optic Neuropathies

Certain optic neuropathies are associated with an elevation of Tau (Tau-associated optic neuropathies). Various studies have shown that optic neuropathy, retinal ganglion cell (RGC) loss, and visual impairment are clinical features of patients with AD (Parnell et al., 2012; Sivak, 2013), showing that AD leads to both brain and retinal pathologies. Interestingly, R-amyloid (AR) deposits in AD mouse models overexpressing mutant human APP and presenilin 1 lead to retinal degeneration (Ning et al., 2008; Perez et al., 2009), and apoptosis of RGCs in animal models of glaucoma is associated with increased production of AR (McKinnon, 2003). Interestingly, RGC degeneration in glaucoma models can be reversed by inhibition of AR formation and aggregation (Guo et al., 2007). Pathogenic Tau can also trigger retinal degeneration, as elevated phosphorylated Tau is observed in the optic nerve of glaucoma patients (Gupta et al., 2008), and Tau overexpression in RGCs triggers cell death (Bull et al., 2012; Gasparini et al., 2011). Together, these results indicate that retinal neurons are susceptible to AR- and Tau-mediated neurodegeneration, much like brain neurons in AD. The retina is the only part of the CNS that can be directly examined using simple non-invasive methods even in unanesthetized subjects, it is easily accessible for in vivo cellular or genetic manipulations, and it is not essential for survival, making it a prime model to study mechanisms of neurodegeneration.

The present description refers to a number of documents, the content of which is herein incorporated by reference in their entirety.

SUMMARY OF THE INVENTION

More specifically, in accordance with the present invention, there are provided the following items and items':

Item 1. A method of reducing neuronal microtubule binding protein Tau (Tau) levels, promoting neuronal Tau degradation and/or promoting neuronal survival, in a subject in need thereof comprising contacting the subject's neurons with an effective amount of an agent that increases a long phosphotyrosine-binding (PTB) Numb isoform expression and/or activity.

Item 2. The method of item 1, wherein the long PTB Numb isoform is Numb-72 or Numb-66.

Item 3. The method of item 1, wherein the long PTB Numb isoform is Numb-72.

Item 4. The method of any one of items 1 to 3, wherein the neurons are retinal neurons.

Item 5. The method of any one of items 1 to 4, wherein the subject has a tauopathy or a Tau-associated optic neuropathy.

Item 6. The method of item 6, wherein the subject has a Tau-associated optic neuropathy.

Item 7. The method of any one of items 1 to 6, wherein the reducing is performed by administration of the long PTB Numb isoform in a gene delivery vector.

Item 8. The method of item 7, wherein the gene delivery vector is a viral vector.

Item 9. The method of item 8, wherein the viral vector is an adeno-associated vector (AAV), Item 10. A method for stratifying a subject having a pathological condition associated with toxic intraneuronal Tau accumulation, comprising detecting a long phosphotyrosine-binding (PTB) Numb isoform expression and/or activity in the subject's neurons, wherein said detecting enables the stratification of the subject, preferably wherein when a reduced long PTB Numb isoform expression and/or activity is detected as compared to a reference long PTB Numb isoform expression and/or activity, the subject is included in a clinical trial for an agent that increases the long PTB Numb isoform expression and/or activity.

Item 11. The method of item 10, wherein the pathological condition associated with intraneuronal Tau accumulation is a tauopathy or a Tau-associated optic neuropathy.

Item 12. The method of item 11, wherein the tauopathy is Alzheimer's disease.

Item 13. A composition comprising (a) an agent that increases neuronal long phosphotyrosine-binding (PTB) Numb isoform expression and/or activity; and (b) (i) a pharmaceutically acceptable carrier; (ii) at least one further therapeutic agent; or (iii) a combination of (i) and (ii).

Item 14. The composition of item 13, comprising at least one further therapeutic agent.

Item 15. The composition of item 14, wherein the at least one further therapeutic agent comprises an acetylcholinesterase inhibitor.

Item 16. A kit or package comprising (a) an agent that increases neuronal long phosphotyrosine-binding (PTB) Numb isoform expression and/or activity; and (b) (i) instructions to use the agent to treat a pathological condition associated with intraneuronal Tau accumulation; (ii) at least one further therapeutic agent; or (iii) a combination of (i) and (ii).

Item 17. The kit or package of item 16, comprising at least one further therapeutic agent.

Item 18. The kit or package of item 17, wherein the at least one further therapeutic agent comprises an acetylcholinesterase inhibitor.

Item 19. A kit or package comprising (a) a reagent for determining a long phosphotyrosine-binding (PTB) Numb isoform expression and/or activity; and (b) (i) a reagent for determining Tau expression and/or activity; (ii) instructions for the prognosis and/or diagnosis of pathological condition associated with intraneuronal Tau accumulation; or (iii) a combination of (i) and (ii).

Item' 1. A method of reducing neuronal microtubule binding protein Tau (Tau) levels, promoting neuronal Tau degradation and/or promoting neuronal survival, in a subject in need thereof comprising contacting the subject's neurons with an effective amount of an agent that increases a long phosphotyrosine-binding (PTB) Numb isoform expression and/or activity, whereby neural Tau levels is reduced in the presence of the agent, the neuronal Tau degradation is promoted and/or the neuronal survival is promoted as compared to in the absence thereof.

Item' 2. The method of item' 1, wherein the long PTB Numb isoform is Numb-72 or Numb-66.

Item' 3. The method of item' 1, wherein the long PTB Numb isoform is Numb-72.

Item' 4. The method of any one of item's 1 to 3, wherein the neurons are retinal neurons.

Item' 5. The method of any one of item's 1 to 4, wherein the subject has a tauopathy or a Tau-associated optic neuropathy.

Item' 6. The method of item' 5, wherein the subject has a Tau-associated optic neuropathy.

Item' 7. The method of any one of item's 1 to 3, wherein the neurons are motoneurons.

Item' 8. The method of item' 7, wherein the subject has a paralysis.

Item' 9. The method of any one of item's 1 to 8, wherein the reducing is performed by administration of the long PTB Numb isoform in a gene delivery vector.

Item' 10. The method of item' 9, wherein the gene delivery vector is a viral vector.

Item' 11. The method of item'10, wherein the viral vector is an adeno-associated vector (AAV).

Item' 12. The method of item' 11, wherein the AAV of serotype 2.

Item' 13. A method for stratifying a subject having a pathological condition associated with toxic intraneuronal Tau accumulation, comprising detecting a long phosphotyrosine-binding (PTB) Numb isoform expression and/or activity in the subject's neurons, wherein said detecting enables the stratification of the subject, preferably wherein when a reduced long PTB Numb isoform expression and/or activity is detected as compared to a reference long PTB Numb isoform expression and/or activity, the subject is included in a clinical trial for an agent that increases the long PTB Numb isoform expression and/or activity.

Item' 14. The method of item' 13, wherein the pathological condition associated with intraneuronal Tau accumulation is a tauopathy, a Tau-associated optic neuropathy or a motor deficit.

Item' 15. The method of item' 14, wherein the tauopathy is Alzheimer's disease.

Item' 16. A composition comprising (a) an agent that increases neuronal long phosphotyrosine-binding (PTB) Numb isoform expression and/or activity; and (b) (i) a pharmaceutically acceptable carrier; (ii) at least one further therapeutic agent; or (iii) a combination of (i) and (ii).

Item' 17. The composition of item' 16, comprising at least one further therapeutic agent.

Item' 18. The composition of item' 17, wherein the at least one further therapeutic agent comprises an acetylcholinesterase inhibitor.

Item' 19. A kit or package comprising (a) an agent that increases neuronal long phosphotyrosine-binding (PTB) Numb isoform expression and/or activity; and (b) (i) instructions to use the agent to treat a pathological condition associated with intraneuronal Tau accumulation; (ii) at least one further therapeutic agent; or (iii) a combination of (i) and (ii).

Item' 20. The kit or package of item' 19, comprising at least one further therapeutic agent.

Item' 21. The kit or package of item' 20, wherein the at least one further therapeutic agent comprises an acetylcholinesterase inhibitor.

Item' 22. A kit or package comprising (a) a reagent for determining a long phosphotyrosine-binding (PTB) Numb isoform expression and/or activity; and (b) (i) a reagent for determining Tau expression and/or activity; (ii) instructions for the prognosis and/or diagnosis of pathological condition associated with intraneuronal Tau accumulation; or (iii) a combination of (i) and (ii).

There is also provided a use of an agent that increases a long phosphotyrosine-binding (PTB) Numb isoform expression and/or activity, for reducing neuronal microtubule binding protein Tau (Tau) levels, promoting neuronal Tau degradation and/or promoting neuronal survival, in a subject in need thereof.

There is also provided a use of an agent that increases a long phosphotyrosine-binding (PTB) Numb isoform expression and/or activity, for the preparation of a medicament for reducing neuronal microtubule binding protein Tau (Tau) levels, promoting neuronal Tau degradation and/or promoting neuronal survival, in a subject in need thereof.

There is also provided an agent that increases a long phosphotyrosine-binding (PTB) Numb isoform expression and/or activity, for use in the reduction of neuronal microtubule binding protein Tau (Tau) levels, promotion of neuronal Tau degradation and/or promotion of neuronal survival, in a subject in need thereof.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1A: Numb immunostaining (visible in ganglion cell layer (GCL)) in adult retinal section at 5-month-old, showing Numb expression in retinal ganglion cells (RGCs), indicated by arrows. Dapi (4',6-diamidino-2-phenylindole), is a fluorescent stain that binds strongly to adenine-thymine rich regions in DNA and is used here as a marker of cell nuclei. FIG. 1B: Numb immunostaining (visible in GCL layer) in primary retinal cell culture prepared from postnatal day 8 (P8) retina and cultured for 14 days. Neurofilament 165 (NF165 visible as string) is a specific marker of RGCs neurofilament, showing that Numb is expressed in cell body and neurites of the RGCs. INL: inner nuclear layer. GCL: ganglion cell layer.

FIG. 2A. A diagram illustrating the breeding scheme to generate Numb cKO (conditional knock-out) in RGCs using the Cre/loxP system. The Islet1-Cre mouse line (Srinivas et al., BMC Dev. Biol., 2001) is crossed with a mouse line in which exon 1 of the numb gene is flanked by loxP sites (Wilson et al., 2007). The animals are produced on a Numb-like (NbL) null background to avoid compensation of Numb inactivation by NbL. The Rosa-TdTomato mouse is used as a Cre reporter. FIG. 2B. Recombination pattern in the retina using the Islet1-Cre mouse at different stages of retina development. TdTomato was detected on retinal section in developing RGCs from E14.5 (arrowheads), and bipolar cells in the adult retina (asterisk). FIGS. 2C-F. Immunostaining for CHX10, a transcription factor specifically expressed in bipolar cells, Pax6, a transcription factor expressed in amacrine cells and Brn3b, a transcription factor specifically expressed in RGCs, was performed on retinal section at 5-month-old in controls (Islet Cre+; Numb fl/+ are shown on the images)) and cKO (Islet Cre+; Numb fl/fl) mice. The fl/+ refer to one floxed allele and one wildtype allele of Numb: these animals are Numb heterozygotes when Cre is present and used as controls, whereas the fl/fl have both alleles of Numb floxed: they are Numb homozygotes knockout when Cre is present (cKO). For all the markers the numbers of positive cells were counted on a 200 um stretch of retina. The number of bipolar, amacrine and RGCs were unchanged at 5-month-old. Mean±SEM, n=4 animals/genotype/time point. Anova test n.s: not significant.

FIG. 3A, left panels (DiI In vivo incorporation). DiI diffusion into RGCs axons of control and cKO in retinal flat mount at 5-month-old. An increase of bleb, a marker of neurodegeneration, was observed in cKO, arrowheads point to blebbing. FIG. 3A, right panels (AAVEGFP2 injections). AAVEGFP (adeno-associated viral vector enhanced green fluorescent protein) type 2 injection in control and cKO retina for 7 days at 5-month-old. Brn3b staining was performed on retinal flat mount, green fluorescent protein (GFP) reflects the AAVEGFP injection, blebs (arrowheads) can be observed in vivo. FIG. 3B. Primary retinal cultures were performed at P8 and analysed 14 days later. By using a combination of TdTomato report and NF165 immunostaining, neuronal morphology was analysed in control and cKO RGCs. An increase of blebs (arrowheads) was observed in cKO RGCs.

FIGS. 3C-F. Primary retinal cultures were performed at P8 and analysed 14 days later. Quantification of axon length, branching number and relative number of axonal blebs in control (Islet Cre+; Numb fl/+) and cKO (Islet Cre+; Numb fl/fl) RGC neurites. Control numbers were normalized to 1. Error bars represent SEM, ** $p \leq 0.001$; n.s. non-significant Student's t test. This experiment indicates that before any cell loss could be detected, axonal blebbing was increased in Numb cKO RGCs both in vitro and in vivo. FIG. 3G. Primary retinal cultures were performed at P8 and analysed 14 days later. Immunostaining for phosphoTau (AT8 antibody) on cKO RGCs TdTomato+. The second, third and last panels of FIG. 3G constitute a magnification of the boxed area of FIG. 3G, left panel. Axonal blebs contained phosphorylated Tau (arrowheads), suggesting a connection between the loss of Numb and the formation of toxic forms of Tau.

FIG. 4A. Detection of Tau levels by western blot in optic nerve extracts from 5-month-old control and cKO mice. GAPDH level was used to normalise. Acetylated Tubulin shows that microtubule integrity was not changed in Numb cDKO. FIG. 4B. Quantification of relative levels of Tau. Error bar represents SEM, * $p \leq 0.05$; Student's t test, n=7 CTL and 7 cKO. FIG. 4C. Detection of monomers and oligomers form of Tau levels using T22, tau oligomeric antibody, by western blot in optic nerve extracts from adult 5-month-old of control and cKO mice, confirmed the appearance of Tau monomeric at 50 KDa and oligomeric complex form of Tau above 50 kDa in absence of Numb. FIG. 4D. Quantification of relative levels of monomers and oligomers of Tau. Error bar represents SEM, *$p \leq 0.05$; Student's t test, n=7 CTL and 8 cKO. FIG. 4E. Primary retinal cultures were performed at P8 and cells were transfected using Amaxa™ electroporator and analysed 14 days later. Cells GFP and NF165 positive were analysed in control and cKO cells. Images represent an hi-magnification view of RGC axons stained for NF165. Arrowheads indicate blebbing. FIG. 4F. Quantification of relative number of axonal blebs after GFP or Tau::GFP transfection in RGCs. Error bars represent SEM, * $p \leq 0.05$; Student's t test. FIG. 4G. Quantification of relative number of axonal blebs after GFP, Tau::GFP or 3 human mutated forms of Tau, transfection in RGCs using Amaxa™ electroporator. Error bars represent SEM, * $p \leq 0.05$; Anova test.

FIG. 5A. Immunostaining for Brn3b on retina flat mounts in control and cKO 5-month-old mice 3 days after injection of saline (left panels, FIG. 5A) or NMDA (10 mM; right panels FIG. 5A). Images were taken in the ganglion cell layer. FIGS. 5B and C. Quantification of the number of Brn3b+RGCs per mm² in control and cKO mice 3 days after intravitreal injection of saline (FIG. 5B) or NMDA (FIG. 5C). Error bars represent SEM, * $p \leq 0.05$, n.s. non-significant; Student's t test.

FIG. 6A. Schematic of 4 Numb isoforms, differing with the presence or the absence of an insertion (arrowhead) in PTB domain arrowhead, and the presence or the absence of an insertion in the proline-rich region (PRR). FIG. 6B. Coimmunoprecipitation of Tau and 4 isoforms of Numb in HEK293 cells. Each Numb isoform was transfected in HEK293T cells together with a flag-tagged version of Tau and immunoprecipitation was perform 24 hours later with a flag antibody and blotted for Numb. This experiment revealed that Tau interacts with the 4 isoforms of Numb. FIG. 6C. Detection of Tau::GFP level in presence of 4 isoforms of Numb by western blot in HEK293. All the Numb isoforms were transfected with a Tau::GFP fusion protein in HEK293T cells and the levels of Tau::GFP was analysed by western blot 48 hours after transfection. FIG. 6D. Schematic representation of DNA construct of a human-medulloblastoma-derived cell line (DAOY) expressing human Tau fused with EGFP (Lasagna-Reeves et al., 2016). Additionally, this cell line expresses DsRed upstream of an internal ribosomal entry site (IRES), which is translated independently of the Tau-GFP protein. DsRed-IRES-Tau::EGFP expressing cells were used to assess the abundance of Tau by monitoring the Tau-GFP to DsRed fluorescence ratio. FIG. 6E. DsRed and Tau::EGF expression in Daoy cells, transfected with Myc only construct. FIGS. 6F-J. Fluorescence-activated cell sorting (FACs) analysis of the 4 Numb isoforms affected 3 days after transfection on ratio DsRed versus DsRed and GFP-positives cells compared to the control (Myc-Tag).

FIG. 7A Stable inducible cell line HEK293 that express a Tau::GFP fusion protein was transfected with Control Myc or Numb72::Myc, and the Tau::GFP expression was activated by adding Doxycycline 6 h later. The cells were fixed 48 h later and stained for Myc. FIG. 7B. The mean intensity (±SEM) of intracellular Tau::GFP fluorescence in transfected cells was quantified. Cells were treated with vehicle, MG132 (a proteasome inhibitor, 25 uM) or Chloroquine (a lysosome inhibitor, 25 uM) for 4 h before fixation and Myc staining. Quantification represents mean intensity +/− SEM, *$p \leq 0.01$; Anova 1-way test.

FIG. 8A. Detection of LC3 levels, a marker of autophagy, by western blot in optic nerve extracts from 5-month-old control and cKO mice. A cytosolic form of LC3 (LC3-I) was conjugated to phosphatidylethanolamine to form LC3-phosphatidylethanolamine conjugate (LC3-II), was recruited to autophagosomal membranes. Lysosomal turnover of the autophagosomal marker LC3-11 therefore reflects autophagic activity. FIG. 8B The ratio LC311/LC31 was measured to evaluate autophagy. Quantification of LC3 levels error bar represents SEM, n.s non-significant; Student's t test, n=3 CTL and 5 cKO.

FIG. 9A. Dot blot of monomeric Tau levels (5A6) and oligomer of Tau (T22) in the media of HEK293T stable inducible cells line expressing Tau transfected with either GFP (Control) or Numb72. Tau expression was activated by adding Doxycycline 6 h after transfection and the media collected 24 h later for Dot-blot. FIG. 9B. Quantification of extracellular Tau levels; data are mean±SEM, n.s non-significant; *p<0.05. Student's t test, n=6 for Tau5A6 and n=4 for T22.

FIG. 10A. Primary retinal cultures were performed at P8 and cells were transfected using an Amaxa™ electroporator and analysed 14 days later. Cells GFP and NF165 positive were analysed in B6129J mouse line (Control) and triple transgenic mice (3×TGAD) expressing three mutations associated with familial Alzheimer's disease (APP Swedish, MAPT P301L, and PSEN1 M146V) after transfection of GFP or Numb-72 IRES::GFP. An increase in number of blebs (indicated by arrowheads), was observed in transgenic neuron compare to control but reversed when Numb-72 was overexpressed. FIGS. 10B-D. Quantification of relative number of axonal blebs (FIG. 10B); axon (neurites) length (FIG. 10C) and branching number (FIG. 10D) in Control (B6129J) and 3×TGAD RGC axons was performed. Control numbers were normalized to 1. Error bars represent SEM, ** p≤0.001; n.s. non-significant; Anova 2 way for blebs and Student's t test for length and branching. FIG. 10E Primary retinal culture was performed at P8 and cells were transfected using an Amaxa™ electroporator and analysed 14 days later. Cells GFP and NF165 positive were analysed in C57b6 mouse line (Control) and P301S Tau mutant (TauP301S) (model of tauopathy) after transfection of GFP or Numb-72 IRES::GFP. An increase in the number of blebs was observed in transgenic neuron compared to control but reversed when Numb-72 was overexpressed. FIGS. 10F-H. Quantification of relative number of axonal blebs (FIG. 10F); axon (neurites) length (FIG. 10G) and branching number (FIG. 7H) in Control (C57b6) (Control, FIGS. 10F-H) and TauP301S (FIGS. 10F-H) RGC axons was performed. Control numbers were normalized to 1. Error bars represent SEM, * p≤0.05; n.s. non-significant Anova 2 way for blebs and Student's t test for length and branching.

FIG. 11A. Immunostaining for Brn3b (labelling RGCs) of retina flat mounts from wild type mice, 7 weeks after intravitreal injections of AAVGFP (adeno-associated viral vector enhanced green fluorescent protein) type 2 in 5 months-old animals (top panel). Immunostaining for Numb and Brn3b of retina flat mounts from wild type mice, 7 weeks after intravitreal injections of AAVNumb72 type 2 in 5 months-old animals (bottom panel). FIG. 11B: Immunostaining for Brn3b of retina flat mounts from B6129J mouse line (Control) and triple transgenic mice (3×TGAD), 7 weeks after intravitreal injections of AAVGFP type 2 or AAVNumb72 type 2 in 5 months-old animals. Three days (72 h) prior to sacrifice, all animals received an intravitreal injection of sublethal doses of NMDA (10 nM). Images were taken in the ganglion cell layer. FIG. 11C. Quantification of number of Brn3b RGC per $mm^2$ in control and 3×TGAD after AAVGFP+NMDA or AAVNumb72+NMDA injection. Error bars represent SEM, n.s=not significant, **p≤0.01; Anova 2-way test.

FIG. 12A. Immunostaining for Brn3b of retina flat mounts from C57b6 mouse line (Control) and transgenic mutant human Tau mouse line (TauP301S), 7 weeks after intravitreal injections of AAVGFP type 2 or AAVNumb72 type 2 in 5 months-old animals. Three days (72 h) prior to sacrifice, all animals received an intravitreal injection of sublethal doses of NMDA (10 nM). Images were taken in the ganglion cell layer. FIG. 12B. Quantification of number of Brn3b RGC per $mm^2$ in control and TauP301S after AAVGFP+NMDA or AAVNumb72+NMDA injection. Error bars represent SEM, n.s=not significant, *p≤0.05; Anova 2-way test.

FIG. 13A: Diagram of mouse crossing, cKO mice for Numb are crossed with transgenic mutant human Tau mouse line (TauP301S), a mouse model of tauopathy. FIG. 13B: Immunostaining for Brn3b of retina flat mounts at 8-month-old from Ilset1Cre, Numbflox, TauP301S mouse line. 3 different controls were used (Islet Cre Negative (Neg), Numb fl/fl, TauP301S transgene negative (TauP301S Tg−) top left panel; Islet Cre+(IsletCre), Numb fl/fl, TauP301S Tg−, top right panel; and IsletCre Neg (Neg), Numb fl/fl, TauP301S transgene positive (TauP301S Tg+), bottom left panel; and one cKO/TauP301S transgene positive (Islet Cre+(IsletCre), Numb fl/fl, TauP301S Tg+), bottom right panel.

FIG. 14A Top images: Representative picture of 260 days-old transgenic TauP301S mouse (not paralysed) next to a representative picture of an Islet Cre+; Numb fl/fl, TauP301S at the same age (showed obvious signs of paralysis). Arrow points to spinal cord defects in the lumbar region (top picture). FIG. 14A: Bottom images: Representative pictures of: a TauP301S mouse with a normal hind-limb reflex at 260 days when suspended by the tail and an Islet Cre+; Numb fl/fl, TauP301S mouse with a complete absence of extension reflex in both hindlimbs. FIG. 14B Graph depicting the time of paralysis onset in the lumbar region in TauP301S and Islet Cre+; Numb fl/fl, TauP301S mice, Matel-Cox test p=0.02, n=21 TauP301S and n=8 Islet Cre+; Numb fl/fl, TauP301S.

FIG. 15A: Diagram of the construct used to generate a Cre-inducible Numb72 transgenic mouse line. FIG. 15B: Flat mounts of retinas stained for GFP and Numb 4 weeks after intravitreal injection of an AAVCRE vector. GFP and Numb are overexpressed in infected cells. Images were taken in the ganglion cell layer (GCL) at 40× and 63×.

FIGS. 16A-B: human Numb1 (Numb-72) amino acid sequence (SEQ ID NO: 1) (FIG. 16A); and human Numb1 nucleic acid sequence (SEQ ID NO: 2) (FIG. 16B).

FIGS. 17A-D: human Numb2 (Numb-66) amino acid sequence (SEQ ID NO: 3); and human Numb1 nucleic acid sequence (SEQ ID NO: 5) (FIGS. 17A and C-D); and the PTB Numb domain with bolded and underlined exon 3 encoded domain (FIG. 17B) (SEQ ID NO: 4).

FIG. 18A-D: amino acid sequences of Numb3 (Numb-71) (SEQ ID NO: 6), Numb4 (Numb-65) (SEQ ID NO: 7), Numb7 (SEQ ID NO:8 and Numb8 (SEQ ID NO: 9).

FIGS. 19A-D: FIGS. 19A-B: Alignment of amino acid sequences of human Numb isoforms 1-4, 7 and 8 (SEQ ID NOs: 1, 3 and 6-9); FIG. 19C a consensus sequence thereof (SEQ ID NO: 10); and FIG. 19D: consensus of human Numb1 and Numb2 (SEQ ID NO: 11).

FIGS. 20A-C: amino acid sequences for human polypyrimidine tract binding protein 1 (PTBP1) isoforms 1 (SEQ ID NO: 12), 2 (SEQ ID NO: 13), and 3 (SEQ ID NO: 14).

FIGS. 21A-C: amino acid sequences for human serine and arginine rich splicing factor 1 (ASF/SF2) isoforms 1 (SEQ ID NO: 15), 2 (SEQ ID NO: 16), and 3 (SEQ ID NO: 17).

FIGS. 22A-H: amino acid sequences for human Tau isoforms 1 (SEQ ID NO: 18), 2 (SEQ ID NO: 19), 3 (SEQ ID NO: 20), 4 (SEQ ID NO: 21), 5 (SEQ ID NO: 22), 6 (SEQ ID NO: 23), 7 (SEQ ID NO: 24), and 8 (SEQ ID NO: 25).

FIGS. 23A-D: amino acid sequences for human RNA-binding motif protein 4 (RBM4) isoform 1 (SEQ ID NO: 26), 2 (SEQ ID NO: 27), 3 (SEQ ID NO: 28), and 4 (SEQ ID NO: 29).

DESCRIPTION OF ILLUSTRATIVE EMBODIMENTS

Definitions

Figure 1A:
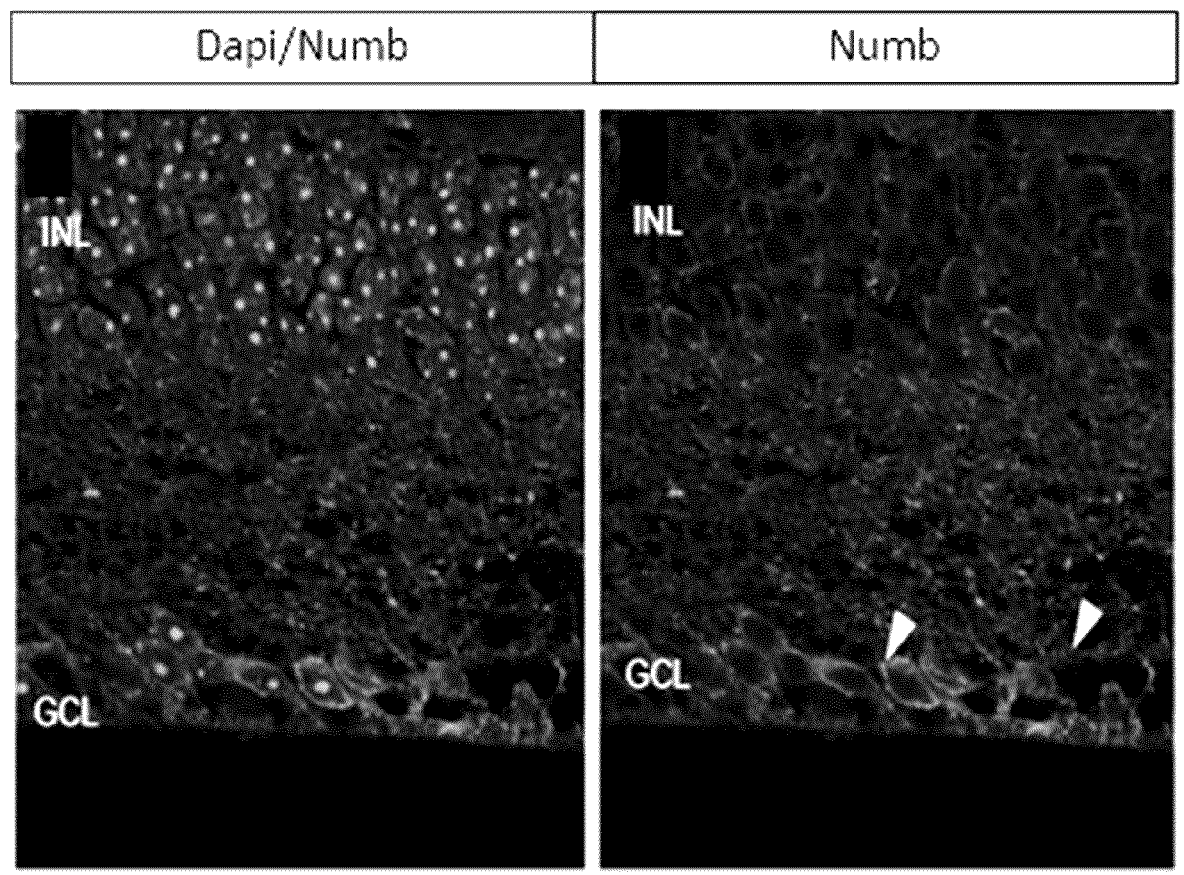
FIGS. 1A-B: Numb is highly expressed in retinal ganglion cells.

Numb is an endocytic adaptor protein containing a proline rich region (PRR) that can be short (e.g., 65 or 66 kDa) or long (71 or 72 kDa) (called herein "Numb-65, Numb-66, Numb-71 and Numb-72, respectively) and a phosphotyrosine-binding (PTB) domain that can be short (Numb-65 and Numb-71) or long (Numb-66 and Numb-72) depending on the isoform (Dho et al., 1999; Karaczyn et al., 2010). In vertebrates, four protein isoforms of Numb are produced through alternative splicing (AS) of two cassette exons, namely exons 3 (E3) and 9 (E9). AS of E9 produces E9-included (p72/p71) and -excluded (p66/p65) protein products, whereas AS of E3 produces E3-included (p72/p66) and excluded (p71/p65) proteins. Expression of Numb isoforms is developmentally regulated, with E9-included products usually expressed in proliferating progenitors, whereas E9-excluded isoforms are dominantly expressed in postmitotic differentiated cells. In humans, the 65 kDA (Numb-65), 66 kDa (Numb-66), 71 kDa (Numb-71) and 72 kDa (Numb-72) correspond respectively to the isoforms 4 (e.g., accession number NP_001005745.1 or AAD54282.1, 592aa), 2 (e.g., accession number NP_001307043.1 or NP_001005744.1 or AAD54280.1, 603aa), 3 (e.g., accession number NP_003735.3 or AAD54281.1, 640aa) and 1 (e.g., accession number NP_001005743.1 or AAD54279.1, 651aa) of Numb. Human Numb isoforms also include isoforms 7 (accession no. ABY89092.1, 456aa) and 8 (accession no. ABY89093.1, 445aa). Without being so limited, an illustrative amino acid sequence of human Numb1 (Numb-72) is depicted in FIG. 16A and the corresponding illustrative nucleotide sequence of human Numb1 (Numb-72) is depicted in FIG. 16B (NM_001005743.1).

Alternative splicing, or differential splicing, is a regulated process during gene expression that results in a single gene coding for multiple proteins. In this process, particular exons of a gene may be included within or excluded from the final processed messenger RNA (mRNA) produced from that gene. Consequently, the proteins translated from alternatively spliced mRNAs will contain differences in their amino acid sequences and, often, in their biological functions. There are numerous modes of alternative splicing observed, of which the most common is exon skipping. In this mode, a particular exon may be included in mRNAs under some conditions or in particular tissues and omitted from the mRNA in others. The production of alternatively spliced mRNAs is regulated by a system of trans-acting proteins that bind to cis-acting sites on the primary transcript itself. Trans-acting proteins include splicing activators that promote the usage of a particular splice site, and splicing repressors that reduce the usage of a particular site. There are two major types of cis-acting RNA sequence elements present in pre-mRNAs and they have corresponding trans-acting RNA-binding proteins. Splicing silencers are sites to which splicing repressor proteins bind, reducing the probability that a nearby site will be used as a splice junction. These can be located in the intron itself (intronic splicing silencers, ISS) or in a neighboring exon (exonic splicing silencers, ESS). They vary in sequence, as well as in the types of proteins that bind to them. The majority of splicing repressors are heterogeneous nuclear ribonucleoproteins (hnRNPs) such as hnRNPA1 and polypyrimidine tract binding protein (PTB). Splicing enhancers are sites to which splicing activator proteins bind, increasing the probability that a nearby site will be used as a splice junction. These also may occur in the intron (intronic splicing enhancers, ISE) or exon (exonic splicing enhancers, ESE). Most of the splicing activator proteins that bind to ISEs and ESEs are members of the Serine/Arginine (SR) protein family. Such proteins contain RNA recognition motifs and arginine and serine-rich (RS) domains.

Antisense Oligonucleotides (ASO, AON) can be used to modulate alternative splicing. ASOs are short oligonucleotides, typically 15-25 bases in length, which are the reverse complement sequence of a specific RNA transcript target region. ASOs function by forming Watson-Crick base-pairs with the target RNA. ASO binding to a target RNA sterically blocks access of splicing factors to the RNA sequence at the target site. ASOs targeted to a splicing enhancer or silencer can prevent binding of transacting regulatory splicing factors at the target site and effectively block or promote splicing. The sequence specificity of ASOs allows them to bind precisely to endogenous RNAs and, importantly, their fidelity allows targeting of distinct RNA isoforms. In addition to their specificity, ASOs have many other features that make them an ideal therapeutic tool. For example, ASOs are relatively non-invasive in that they do not alter the genome directly and improvements in chemistries have been developed to improve the utility of ASOs as a therapeutic drug.

Some RNA binding proteins can block or promote the inclusion of specific exons by binding the same sequence at different regions of the pre-mRNA. For example, Rbfox protein can function as an activator and a repressor of alternative splicing depending on its binding location on pre-mRNA relative to the regulated exon. For instance, Rbfox proteins enhance exon inclusion by binding to the (U)GCAUG element that lies downstream of the alternative Numb E9, whereas they repress inclusion by binding to the same element upstream of the alternative Numb E9 (Kim et al., 2013). An ASO targeting the upstream intronic (UG-CAUG) site of Numb E9 is expected to have the effect of promoting exon 9 inclusion.

As used herein the term "long PTB Numb isoform" refers to a Numb isoform comprising a PTB form including the sequence ERKFFKGFFGK (SEQ ID NO: 30) encoded by exon 3 (see e.g., FIGS. 16A, 17A and 17B). Of note, this fragment is identical in human and mice orthologs. Without being so limited, long PTB Numb isoforms includes Numb-66 and Numb-72.

Long PTB Numb isoform gene or nucleic acid (such as Numb-72 and Numb-66 gene or nucleic acid) refers to nucleic acid (e.g., genomic DNA, cDNA, RNA) encoding a long PTB Numb isoform polypeptide. The description of the various aspects and embodiments of the invention is provided with reference to exemplary long PTB Numb isoform nucleic acid sequences and amino acid sequence (e.g., as shown in FIGS. 16A-B and 17A and C). Such reference is meant to be exemplary only and the various aspects and embodiments of the invention are also directed to other long PTB Numb isoform nucleic acids and polypeptides (also referred to long PTB Numb isoform gene expression products), such as long PTB Numb isoform nucleic acid or polypeptide mutants/variants, long PTB Numb isoform variants from species to species or subject to subject. Consensuses derived from the alignments of certain Numb variants are also encompassed by the present invention (see e.g., SEQ ID NOs: 10-11). In specific embodiments of the consensus, each X in the consensus sequence is defined as being any amino acid, or absent when this position is absent in one or more of Numb Homo sapiens isoforms, variants or orthologues. In specific embodiment of the consensus, each X in the consensus sequences is defined as being any amino acid that constitutes a conserved or semi-conserved substitution of any of the amino acid in the corresponding position in the orthologues presented in the alignment, or absent when this position is absent in one or more of the orthologues presented in the alignment. Conservative substitutions are denoted by the symbol ":" and semi-conservative substitutions are denoted by the symbol ".". In another embodiment, each X refers to any amino acid belonging to the same class as any of the amino acid residues in the corresponding position in the orthologues presented in the alignment, or absent when this position is absent in one or more of the orthologues presented in the alignment. In another embodiment, each X refers to any amino acid in the corresponding position of the orthologues presented in the alignment, or absent when this position is absent in one or more of the orthologues presented in the alignment. The Table below indicates which amino acid belongs to each amino acid class.

| Class | Name of the amino acids |
|---|---|
| Aliphatic | Glycine, Alanine, Valine, Leucine, Isoleucine |
| Hydroxyl or Sulfur/Selenium-containing | Serine, Cysteine, Selenocysteine, Threonine, Methionine |
| Cyclic | Proline |
| Aromatic | Phenylalanine, Tyrosine, Tryptophan |
| Basic | Histidine, Lysine, Arginine |
| Acidic and their Amide | Aspartate, Glutamate, Asparagine, Glutamine |

As used herein the term "Tau", unless more specifically identified, refers to all forms of tau including toxic forms of Tau (e.g., phosphorylated tau, and oligomeric tau; without being so limited, the phosphorylated form is believed to lead to oligomeric tau).

Protein Expression

As used herein the terms "long PTB Numb isoform level" (e.g., "Numb-72 expression level"; "Numb-72 expression", "Numb-66 expression level"; "Numb-66 expression"), or "Tau expression level" or "Tau expression", refer to the measurement in a cell or a tissue of a long PTB Numb isoform level or Tau gene product, respectively. Long PTB Numb isoform levels and TAU expression levels could be evaluated at the polypeptide and/or nucleic acid levels (e.g., DNA or RNA) using any standard methods known in the art. The nucleic acid sequence of a nucleic acid molecule in a sample can be detected by any suitable method or technique of measuring or detecting gene sequence or expression. Such methods include, but are not limited to, polymerase chain reaction (PCR), reverse transcriptase-PCR (RT-PCR), in situ PCR, SAGE, quantitative PCR (q-PCR), in situ hybridization, Southern blot, Northern blot, sequence analysis, microarray analysis, detection of a reporter gene, or other DNA/RNA hybridization platforms. For RNA expression, preferred methods include, but are not limited to: extraction of cellular mRNA and Northern blotting using labeled probes that hybridize to transcripts encoding all or part of one or more of the genes of this invention; amplification of mRNA expressed from one or more of the genes of this invention using gene-specific primers, polymerase chain reaction (PCR), quantitative PCR (q-PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding all or part of the genes of this invention, arrayed on any of a variety of surfaces; in situ hybridization; and detection of a reporter gene.

In the context of this invention, "hybridization" means hydrogen bonding between complementary nucleoside or nucleotide bases. The terms "specifically hybridizable" and "complementary" are the terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound (e.g., ASO) is specifically hybridizable when binding of the compound to the target DNA or RNA molecule interferes with the normal function of the target DNA or RNA to cause e.g., a loss of utility or affect splicing, and there is a sufficient degree of complementarity to avoid non-specific binding of the antisense compound (e.g., ASO) to non-target sequences under conditions in which specific binding is desired, i.e., under physiological conditions in the case of in vivo assays or therapeutic treatment, and in the case of in vitro assays, under conditions in which the assays are performed. Such conditions may comprise, for example, 400 mM NaCl, 40 mM PIPES pH 6.4, 1 mM EDTA, at 50 to 70° C. for 12 to 16 hours, followed by washing. The skilled person will be able to determine the set of conditions most appropriate for a test of complementarity of two sequences in accordance with the ultimate application of the hybridized nucleotides.

Methods to measure protein expression levels of selected genes of this invention, include, but are not limited to: western blot, tissue microarray, immunoblot, enzyme-linked immunosorbent assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microscopy, fluorescence activated cell sorting (FACS), flow cytometry, and assays based on a property of the protein including but not limited to DNA binding, ligand binding, or interaction with other protein partners. In a further embodiment, the long PTB Numb isoform level and/or Tau expression level is measured by immunohistochemical staining, and the percentage and/or the intensity of immunostaining of immunoreactive cells in the sample is determined.

In an embodiment, the level of a long PTB Numb isoform and/or Tau polypeptide is determined using an anti-long PTB Numb isoform or an anti-Tau antibody. By "long PTB Numb isoform antibody" and "anti-long PTB Numb isoform" or "Tau antibody" and "anti-Tau", in the present context is meant to refer to an antibody capable of detecting (i.e. binding to) a long PTB Numb isoform protein or a long PTB Numb isoform protein fragment (e.g., the PTB fragment ERKFFKGFFGK (SEQ ID NO: 30)) or a Tau protein or a Tau protein fragment, respectively.

Without being limited, long PTB Numb isoform antibodies (which can be used for detection) include those listed in Table I below, Tau antibodies include those listed in Table II below. Other antibodies can be found on the Biocompare™ webpage.

TABLE I

Examples of available long PTB Numb isoform antibodies

| Company | Name/catalog number | Type |
| --- | --- | --- |
| Millipore Sigma | 07-144 | Rabbit polyclonal Numb-72 |
| Developmental and Stem Cell Institute of West China Second University Hospital | | Rabbit polyclonal Numb-72 |

TABLE II

Examples of available Tau antibodies.

| Company | Name/catalog number | Type |
| --- | --- | --- |
| Millipore Sigma | MAB2241 | monoclonal |
| BosterBio | M00097 | monoclonal |
| Atlas Antibodies | HPA048895 | monoclonal |
| LifeSpan Biosciences | LS-B1223 | polyclonal |

Methods for normalizing the level of expression of a gene are well known in the art. For example, the expression level of a gene of the present invention can be normalized on the basis of the relative ratio of the mRNA level of this gene to the mRNA level of a housekeeping gene, or the relative ratio of the protein level of the protein encoded by this gene to the protein level of the housekeeping protein, so that variations in the sample extraction efficiency among cells or tissues are reduced in the evaluation of the gene expression level. A "housekeeping gene" is a gene the expression of which is substantially the same from sample to sample or from tissue to tissue, or one that is relatively refractory to change in response to external stimuli. A housekeeping gene can be any RNA molecule other than that encoded by the gene of interest that will allow normalization of sample RNA or any other marker that can be used to normalize for the amount of total RNA added to each reaction. For example, the GAPDH gene, the G6PD gene, the actin gene, ribosomal RNA, 3664 RNA, PGK1, RPLP0, or the like, may be used as a housekeeping gene.

Methods for calibrating the level of expression of a gene are well known in the art. For example, the expression of a gene can be calibrated using reference samples, which are commercially available. Examples of reference samples include but are not limited to: Stratagene™ QPCR Human Reference Total RNA, Clontech™ Universal Reference Total RNA, and XpressRef™ Universal Reference Total RNA.

In an embodiment, the above-mentioned methods comprise determining the level of a long PTB Numb isoform and/or Tau protein and/or nucleic acid (e.g., nucleic acids or encoded proteins as shown in in FIGS. 16A-B, 17A and C, 18C-D, 19A-D. and 22A-H) in the sample. In another embodiment, the above-mentioned method comprises determining the level of a long PTB Numb isoform and/or Tau polypeptide (e.g., polypeptides as shown in FIGS. 16A-B, FIGS. 17A and C, 18C-D, 19A-D and 22A-H) in the sample.

Nucleic Acids and Host Cells

The present invention also relates to nucleic acids comprising nucleotide sequences encoding the above-mentioned agent (e.g., a long PTB Numb isoform). The nucleic acid may be codon-optimized. The nucleic acid can be a DNA or an RNA. The nucleic acid sequence can be deduced by the skilled artisan on the basis of the disclosed amino acid sequences.

The present invention also encompasses vectors (e.g., plasmids, viral vector) comprising the above-mentioned nucleic acids. The vectors can be of any type suitable, e.g., for expression of said polypeptides or propagation of genes encoding said polypeptides in a particular organism. The organism may be of eukaryotic or prokaryotic origin. The specific choice of vector depends on the host organism and is known to a person skilled in the art. In an embodiment, the vector comprises transcriptional regulatory sequences (e.g., a CAG promoter) or a promoter operably-linked (see definition of "operably-linked" above) to a nucleic acid comprising a sequence encoding one or more of the above-mentioned agents (e.g., a long PTB Numb isoform) of the invention. A first nucleic acid sequence is "operably-linked" with a second nucleic acid sequence when the first nucleic acid sequence is placed in a functional relationship with the second nucleic acid sequence. For instance, a promoter (e.g., CAG) is operably-linked to a coding sequence if the promoter affects the transcription or expression of the coding sequence. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous.

"Transcriptional regulatory sequences" or "transcriptional regulatory elements" are generic terms that refer to DNA sequences, such as initiation and termination signals, enhancers, and promoters, splicing signals, polyadenylation signals, etc., which induce or control transcription of protein coding sequences with which they are operably-linked. For instance, the CAG promoter is a strong non-specific synthetic promoter frequently used to drive high levels of gene expression in mammalian expression vectors containing (A) the cytomegalovirus (CMV) early enhancer element, (B) the promoter, the first exon and the first intron of chicken beta-actin gene, and (C) the splice acceptor of the rabbit beta-globin gene.

A recombinant expression vector comprising a nucleic acid sequence of the present invention may be introduced into a cell, e.g., a host cell (such as a neuron), which may include a living cell capable of expressing the protein coding region from the defined recombinant expression vector. Accordingly, the present invention also relates to cells (host cells) comprising the nucleic acid and/or vector as described above. The suitable host cell may be any cell of eukaryotic or prokaryotic (bacterial) origin that is suitable, e.g., for expression of or propagation of genes/nucleic acids encoding said above-mentioned agents (e.g., a long PTB Numb isoform). The eukaryotic cell line may be of mammalian, of yeast, or invertebrate origin. The specific choice of cell line is known to a person skilled in the art. Choice of bacterial strains will depend on the task at hand and is commonly known to a person skilled in the art. The terms "host cell" and "recombinant host cell" are used interchangeably herein. Such terms refer not only to the particular subject cell, but also to the progeny or potential progeny of such a cell. Because certain modifications may occur in succeeding generations due to either mutation or environmental influences, such progeny may not, in fact, be identical to the parent cell, but are still included within the scope of the term as used herein.

Vectors can be introduced into cells via conventional transformation or transfection techniques. The terms "transformation" and "transfection" refer to techniques for introducing foreign nucleic acid into a host cell (such as a neuron), including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), Sambrook and Russell (supra) and other laboratory manuals. Methods for introducing nucleic acids into mammalian cells in vivo are also known and may be used to deliver the vector DNA of the invention to a subject for gene therapy.

The above-mentioned nucleic acid or vector may be delivered to cells in vivo (to induce the expression of the above-mentioned agents (e.g., a long PTB Numb isoform) using methods well known in the art such as direct injection of DNA, receptor-mediated DNA uptake, viral-mediated transfection or non-viral transfection and lipid based transfection, all of which may involve the use of gene therapy vectors. Direct injection has been used to introduce naked DNA into cells in vivo. A delivery apparatus (e.g., a "gene gun") for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor. Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes.

Defective retroviruses are well characterized for use as gene therapy vectors (for a review see Miller, A. D. (1990) *Blood* 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include psiCrip, psiCre, psi2 and psiAm. Retroviruses have been used to introduce a variety of genes into many different cell types, including epithelial cells, endothelial cells, lymphocytes, myoblasts, hepatocytes, and bone marrow cells, in vitro and/or in vivo.

For use as a gene therapy vector, the genome of an adenovirus may be manipulated so that it encodes and expresses a nucleic acid of the invention (e.g., a nucleic acid encoding one of the above-mentioned agents (e.g., a long PTB Numb isoform)), but is inactivated in terms of its ability to replicate in a normal lytic viral life cycle. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles (e.g., viral vectors) and can be used to infect a wide variety of cell types, including neurons, RGCs, airway epithelium, endothelial cells, hepatocytes, and muscle cells.

Adeno-associated virus (AAV) may be used as a gene delivery vector for delivery of DNA for gene therapy purposes (e.g., adeno-associated viral (AAV) vector expressing a long PTB Numb isoform). AAV is a naturally occurring defective virus that requires another virus, such as an adenovirus or a herpes virus, as a helper virus for efficient replication and a productive life cycle. AAV may be used to integrate DNA into non-dividing cells. Lentiviral gene therapy vectors may also be adapted for use in the invention. Alphavirus vectors such as Semliki Forest virus-based vectors and Sindbis virus-based vectors and the like can also be used.

Delivery

As seen herein, the long PTB Numb isoform of the instant disclosure can be delivered to target cells through the use of a nucleic acid encoding the isoform (e.g., viral vector). It can also be directly delivered as a purified (recombinant) protein. In particular, nanoparticles or peptide-based technologies can be used. In particular, for intraocular delivery, and without being so limited, membrane permeabilizing amphiphilic peptide of Feldan Therapeutics could be used.

Long PTB Numb Isoform Activity

As used herein the terms "long PTB Numb isoform activity" and "long PTB Numb isoform function" (such as "Numb-72 activity" and "Numb-72 function", "Numb-66 activity" and "Numb-66 function") are used interchangeably and refer to detectable (direct or indirect) enzymatic, biochemical or cellular activity attributable to a long PTB Numb isoform (e.g., increasing neuronal survival (see e.g., Examples 3, 6 and 13), preventing neurodegeneration (e.g., Example 14), including in stress condition such as aging (Examples 3, 6 and 13) and/or excitotoxicity (see e.g., Examples 6 and 13), preventing motor deficit (e.g., Example 15), decreasing intracellular (neuronal) Tau (e.g., oligomeric) levels (e.g., in RGCs) (see e.g., Examples 4 and 8), reducing Tau (e.g., pTau)-containing axonal blebbing (see e.g., Examples 3 and 5), interaction with Tau (see e.g., Example 7), stimulating secretion of monomeric Tau (see e.g., Example 11), and promoting intraneuronal Tau degradation (e.g., in brain tissue) (see e.g., Example 12). Long PTB Numb isoforms activity could also be indirectly measured by evaluating the level of expression of the long PTB Numb isoform, or a fragment thereof, in cells as well as in biological samples (e.g., tissue, organ, fluid).

Modulation of Long PTB Numb Isoform Expression or Activity

The modulation of long PTB Numb isoform expression and/or activity (e.g., Numb-72 and/or Numb-66 expression and/or activity) could be achieved directly or indirectly by various mechanisms, which among others could act at the level of (i) transcription, for example by activating promoter or enhancer elements and thereby increasing their messenger RNA expression (e.g., by cytokine stimulation, etc.), (ii) splicing, for example by inhibiting expression or activity of a splicing regulator that promotes Numb exon 3 exclusion, or by activating a splicing regulator that enhance exon 3 inclusion, (iii) translation, (iv) post-translational modifications, e.g., glycosylation, sulfation, phosphorylation, ubiquitination (e.g., polyubiquitinylation and proteasomal degradation), (v) cellular localization (e.g., cytoplasmic versus nuclear localization), and (vi) protein-protein interaction. These regulatory processes occur through different molecular interactions that could be modulated using a variety of compounds or modulators.

In the context of the present invention, a "compound" is a molecule such as, without being so limited, a dsRNA (e.g., siRNA), antisense molecule (ASO), protein, peptide, small molecule, antibody, etc.

Agent that Increases Long PTB Numb Isoform Expression and/or Activity

As used herein an "agent that increases a long PTB Numb isoform expression and/or activity" (e.g., "agent that increases Numb-72 or Numb-66 expression and/or activity"), such as agents that promote a long PTB Numb isoform expression and/or activity in neurons, refers to any compound or composition that directly or indirectly increases at least one long PTB Numb isoform expression and/or activity (e.g., Numb-72 or Numb-66 expression and/or activity). It includes molecules such as, without being so limited, nucleic acids encoding a long PTB Numb isoform expression product (such as human Numb-72 (Numb1) nucleic acid (see e.g., NM_001005743.1 shown in FIG. 16B) or human Numb-66 (Numb2) nucleic acid (e.g., NM_001005744.1 shown in FIG. 17C)); a long PTB Numb isoform polypeptide or a fragment thereof having a long PTB Numb isoform activity, such as human Numb-72 (e.g., NP_001005743.1 shown in FIG. 16A) or a fragment thereof having Numb-72 activity; or human Numb-66 polypeptide (see e.g., NP_001307043.1 shown in FIG. 17A) or a fragment thereof having Numb-66 activity; a long PTB Numb polypeptide of sequence SEQ ID NO: 10 or 11; an agent which increases the level of a long PTB Numb isoform (e.g., nucleic acid encoding for Numb-66 or Numb-72, e.g., FIGS. 16B and 17C) by acting on splicing; an agent promoting the Numb exon 3 inclusion by activating an RNA binding protein that enhances exon 3 inclusion such as RNA-binding motif protein 4 (RBM4) (see e.g., FIGS. 23A-D and SEQ ID NOs: 26-29) that promotes inclusion of exon 3 of Numb but excludes exon 9 (Tarn et al. 2016); an agent such as an antisense oligonucleotide (ASO) that blocks the recognition of sequences required for Numb exon 3 exclusion; an agent such as a siRNA targeting a gene coding for a splicing regulator promoting the exclusion of Numb exon 3; an agent promoting the Numb exon 9 inclusion by activating an RNA binding protein that enhances exon 9 inclusion such as but not limited to RNA-binding protein 6 (RBM6) (e.g., P78332-1 (isoform 1); P78332-3 (isoform 2) and P78332-3 (isoform 3)); RNA-binding protein 5 (RBM5) (e.g., P52756-1 (isoform 1), P52756-2 (isoform 2), P52756-3 (isoform 3), P52756-4 (isoform 4), and P52756-5 (isoform 5)); PTBP1 (Rajendran et al., 2016) (see illustrative human amino acid sequences in FIGS. 20A-C and SEQ ID NOs: 12-14); Mitogen-activated protein kinase (MAPK)/extracellular signal-regulated kinase (ERK) (Rajendran et al., 2016), agonists to MAPK/ERK (such as Honokiol (Zhai et al. 2005), CHPG sodium salt (Tao Chen et al. 2012), LM22B-10 (Yang T, et al. Neuropharmacology. 2016)); an agent such as an antisense oligonucleotide (ASO) that blocks the recognition of sequences required for Numb exon 9 exclusion, such as an ASO targeting upstream intronic UGCAUG (see above); an agent such as a siRNA targeting a gene coding for a splicing regulator promoting the exclusion of Numb exon 9, such as an siRNA targeting upstream intronic UGCAUG; an exon 9 splicing factor inhibitor, such as a serine and arginine rich splicing factor 1 (ASF/SF2) inhibitor (see e.g., FIGS. 21A-C for ASF/SF2 isoforms 1-3 sequences); a polypyrimidine Tract Binding Protein 1 (PTBP1) inhibitor (see e.g., FIGS. 20A-C for PTB1 isoforms 1-3 sequences); an RNA binding motif protein 6 (RBM6) inhibitor; an RNA binding motif protein (RBM10) inhibitor; or an RNA-binding FOX3 (RBFOX3) inhibitor.

More particularly, agents of the present invention include nucleic acid encoding Numb-72 or Numb-66 and agents which increase the level of RNAs encoding for Numb-66 or Numb-72 isoforms by modulating splicing to increase Numb exon 3 inclusion; small RNA molecules (e.g., antisense oligonucleotides (AOS) and siRNAs); peptides; small molecules; antibodies, etc. Candidate compounds are tested using a variety of methods and assays.

Agents that increase a long PTB Numb isoform expression and/or activity (e.g., Numb-72 and/or Numb-66 expression and/or activity) can be used to target (e.g., tau expressing) neurons (e.g., RGCs, brain neurons, spinal cord, motoneurons) using e.g., viral vectors (e.g., adenoviruses, lentivirus, AAVs (see Example 13)) or other gene/protein delivery and thereby force a long PTB Numb isoform expression (e.g., Numb-72 expression) on the neurons. Such neurons may thereafter benefit from treatments described herein.

Cell targets of the agents of the present invention are neurons. Without being so limited, such cells include neurons of the central nervous system such as brain neurons, retinal neurons (RGCs) and spinal cord neurons.

Screening Assays

Given the correlation between long PTB Numb isoforms expression/activity (e.g., Numb-72 and/or Numb-66 expression/activity) on intraneuronal Tau levels or degradation, compounds which are capable of increasing a long PTB Numb isoform (e.g., Numb-72 and/or Numb-66 expression and/or activity) may be used for the prevention and/or treatment of a pathological condition associated with intraneuronal Tau accumulation.

Screening for Agents that Increase Long PTB Numb Isoforms Expression and/or Activity Therefore, the invention further relates to screening methods using a long PTB Numb isoform positive cells for the identification and characterization of compounds capable of increasing a long PTB Numb isoform activity and/or expression which may be used for the prevention and/or treatment of a pathological condition associated with intraneuronal Tau accumulation.

The present invention also provides a method (e.g., an in vitro method) for determining whether a test compound is useful for the prevention and/or treatment of a pathological condition associated with intraneuronal Tau accumulation, said method comprising: (a) contacting said test compound with a (neuronal) cell expressing a long PTB Numb isoform and Tau; and (b) determining the intraneuronal Tau levels, degradation and/or neuronal survival, in the presence or absence of said test compound (and eventually in the presence of NMDA); wherein a decrease in the Tau levels and/or degradation and/or an increase in the Tau survival in the presence of said test compound relative to the absence thereof is indicative that said test compound may be used for the prevention and/or treatment of a pathological condition associated with intraneuronal Tau accumulation (e.g., tauopathy and/or Tau-associated optic neuropathy).

The present invention also provides a method (e.g., an in vitro method) for determining whether a test compound is useful for the prevention and/or treatment of a pathological condition associated with intraneuronal Tau accumulation, said method comprising: (a) contacting said test compound with a (neuronal) cell expressing a long PTB Numb isoform (e.g., Numb-72); and (b) determining the a long PTB Numb isoform levels in the presence or absence of said test compound; wherein an increase in the long PTB Numb isoform levels in the presence of said test compound relative to the absence thereof is indicative that said test compound may be used for the prevention and/or treatment of a pathological condition associated with intraneuronal Tau accumulation (e.g., tauopathy and/or Tau-associated optic neuropathy).

The present invention also provides a method (e.g., an in vivo method in an animal model) for determining whether a test vector (e.g., AAV vector) expressing a long PTB Numb isoform (e.g., Numb-72) or a fragment thereof having a long PTB Numb isoform activity (e.g., Numb-72 activity) is useful for the prevention and/or treatment of a pathological condition associated with intraneuronal Tau accumulation, said method comprising: (a) expressing said long PTB Numb isoform or fragment thereof in a (neuronal) cell expressing Tau; and (b) determining the intraneuronal Tau levels, degradation and/or neuronal survival, in the presence or absence of said long PTB Numb isoform or fragment thereof; wherein a decrease in the Tau levels and/or degradation and/or an increase in the neuronal survival in the presence of said long PTB Numb isoform or fragment thereof relative to the absence thereof is indicative that said test viral vector expressing said long PTB Numb isoform or fragment thereof may be used for the prevention and/or treatment of a pathological condition associated with intraneuronal Tau accumulation (e.g., tauopathy and/or Tau-associated optic neuropathy). (see e.g., Example 13)

The present invention also provides a method (e.g., an in vitro method) for determining whether a test compound is useful for the prevention and/or treatment of a pathological condition associated with intraneuronal Tau accumulation, said method comprising: (a) contacting said test compound with a long PTB Numb isoform polypeptide, or a fragment thereof having a long PTB Numb isoform activity; and (b) determining the expression and/or activity of the long PTB Numb isoform polypeptide or fragment thereof, in the presence or absence of said test compound; wherein an increase in the expression and/or activity of the long PTB Numb isoform in the presence of said test compound relative to the absence thereof is indicative that said test compound may be used for the prevention and/or treatment of a pathological condition associated with intraneuronal Tau accumulation.

The present invention also provides a method (e.g., an in vitro method) for determining whether a test compound is useful for the prevention and/or treatment of a pathological condition associated with intraneuronal Tau accumulation (e.g., tauopathy, Tau-associated optic neuropathy), said method comprising: (a) contacting said test compound with a cell comprising a first nucleic acid comprising a transcriptionally regulatory element normally associated with a long PTB Numb isoform gene, operably linked to a second nucleic acid comprising a reporter gene encoding a reporter protein; and (b) determining whether the reporter gene expression and/or reporter protein activity is increased in the presence of said test compound; wherein said increase in reporter gene expression and/or reporter protein activity is indicative that said test compound may be used for prevention and/or treatment of a pathological condition associated with intraneuronal Tau accumulation.

The present invention also provides a method (e.g., an in vitro method) for identifying an agent (e.g., an agent that promotes the Numb exon 3 inclusion) is useful for the prevention and/or treatment of a pathological condition associated with intraneuronal Tau accumulation (e.g., tauopathy, Tau-associated optic neuropathy), said method comprising: (a) contacting said test compound with a cell comprising a first nucleic acid comprising Numb exon 3, its upstream and downstream flanking introns, and constitutive exons 2 and 4, wherein the Numb exon 3 is operably linked to a second nucleic acid comprising a reporter gene encoding a reporter protein (e.g., fluorescent reporter), so that the presence of exon 3 is revealed by the reporter protein; and (b) determining whether the reporter gene expression and/or reporter protein activity is increased (e.g., fluorescence) in the presence of said test compound; wherein said increase in reporter gene expression and/or reporter protein activity is indicative that said test compound may be used for prevention and/or treatment of a pathological condition associated with intraneuronal Tau accumulation.

The above-mentioned methods may be employed either with a single test compound or a plurality or library (e.g., a combinatorial library) of test compounds. In the latter case, synergistic effects provided by combinations of compounds may also be identified and characterized. The above-mentioned compounds may be used for prevention and/or treatment of a pathological condition associated with intraneuronal Tau accumulation or may be used as lead compounds for the development and testing of additional compounds having improved specificity, efficacy and/or pharmacological (e.g., pharmacokinetic) properties. In an embodiment, the compound may be a prodrug which is altered into its active form at the appropriate site of action, (e.g., neurons). In certain embodiments, one or a plurality of the steps of the screening/testing methods of the invention may be automated.

Such assay systems may comprise a variety of means to enable and optimize useful assay conditions. Such means may include but are not limited to: suitable buffer solutions, for example, for the control of pH and ionic strength and to provide any necessary components for optimal long PTB Numb isoform (e.g., Numb-72) activity and stability, temperature control means for long PTB Numb isoform activity and or stability, and detection means to enable the detection of a long PTB Numb isoform activity reaction product. A variety of such detection means may be used, including but not limited to one or a combination of the following: radiolabeling (e.g., $^{32}$P, $^{14}$C, $^{3}$H), antibody-based detection, fluorescence, chemiluminescence, spectroscopic methods (e.g., generation of a product with altered spectroscopic properties), various reporter enzymes or proteins (e.g., horseradish peroxidase, green fluorescent protein), specific binding reagents (e.g., biotin/(strept)avidin), and others.

The assay may be carried out in vitro utilizing a source of long PTB Numb isoform (e.g., Numb-72) which may comprise naturally an isolated or recombinantly produced long PTB Numb isoform, in preparations ranging from crude to pure. Recombinant long PTB Numb isoform (e.g., Numb-72) may be produced in a number of prokaryotic or eukaryotic expression systems, which are well known in the art. Such assays may be performed in an array format.

As noted above, the invention further relates to methods for the identification and characterization of compounds capable of modulating long PTB Numb isoform (e.g., Numb-72) gene expression. Such a method may comprise assaying long PTB Numb isoform (e.g., Numb-72) gene expression in the presence versus the absence of a test compound. Such gene expression may be measured by detection of the corresponding RNA or protein, or via the use of a suitable reporter construct comprising one or more transcriptional regulatory element(s) normally associated with a long PTB Numb isoform (e.g., Numb-72) gene, operably-linked to a reporter gene.

See above for definitions of "operably-linked" and "Transcriptional regulatory element". The expression of a reporter gene may be measured on the transcriptional or translational level, e.g., by the amount of RNA or protein produced. RNA may be detected by for example Northern analysis or by the reverse transcriptase-polymerase chain reaction (RT-PCR) method (see for example Sambrook et al. (1989) Molecular Cloning: A Laboratory Manual ($2^{nd}$ edition), Cold Spring Harbor Laboratory Press, Cold Spring Harbor, N.Y., USA).

Protein levels may be detected either directly using affinity reagents (e.g., an antibody or fragment thereof (for methods, see for example Harlow, E. and Lane, D (1988) Antibodies: A Laboratory Manual, Cold Spring Harbor Laboratory Press, Cold Spring Harbor, N.Y.); a ligand which binds the protein) or by other properties (e.g., fluorescence in the case of green fluorescent protein) or by measurement of the protein's activity, which may entail enzymatic activity to produce a detectable product (e.g., with altered spectroscopic properties) or a detectable phenotype (e.g., alterations in cell growth/function). Suitable reporter genes include but are not limited to chloramphenicol acetyltransferase, beta-D galactosidase, luciferase, or green fluorescent protein (GFP or EGFP).

Long PTB Numb isoform (e.g., Numb-72) expression levels could be determined using any standard methods known in the art. Non-limiting examples of such methods include western blot, immunoblot, enzyme-linked immunosorbent assay (ELISA), radioimmunoassay (RIA), immunoprecipitation, immunocytochemistry, immunohistochemistry, as well as methods to determine mRNA levels such as RT-PCR and northern analysis, real-time PCR, PCR, in situ hybridization and so on.

In another aspect, the present invention provides an agent that increases long PTB Numb isoform (e.g., Numb-72) expression or activity identified by the above-noted screening method.

Pathological Condition Associated with Intraneuronal Tau Accumulation

As used herein, the term "pathological condition associated with intraneuronal Tau accumulation" refers to tauopathies and Tau-associated optic neuropathies.

As used herein the term "tauopathy" refers to neurodegenerative diseases associated with the pathological aggregation of tau protein in neurofibrillary or gliofibrillary tangles in the human brain and eyes. Without being so limited, tauopathies include Alzheimer's disease, primary age-related tauopathy (PART), chronic traumatic encephalopathy, including dementia pugilistica, progressive supranuclear palsy, corticobasal degeneration, frontotemporal dementia, parkinsonism linked to chromosome 17, Lytico-Bodig disease (Parkinson-dementia complex of Guam), ganglioglioma, gangliocytoma, meningioangiomatosis, postencephalitic parkinsonism, subacute sclerosing panencephalitis, lead encephalopathy, tuberous sclerosis, pantothenate kinase-associated neurodegeneration, and lipofuscinosis.

As used herein the term "Tau-associated optic neuropathy" refers to diseases characterized by damages in the optic nerve associated to an elevated level of tau which then causes degeneration of retinal ganglion cells such as but no limited to glaucoma (Chiasseu, 2016), optic neuritis (Frederiksen et al. 2012) and compressive optic neuropathy (Oku et al. 2019).

As used herein the term "motor deficit" refers to motor nerves degeneration leading to paralysis and/or muscles atrophy.

Treatment and Prevention

The terms "treat/treating/treatment" and "prevent/preventing/prevention" as used herein, refers to eliciting the desired biological response, i.e., a therapeutic and prophylactic effect, respectively. In accordance with the subject invention, the therapeutic effect comprises one or more of a decrease/reduction in the severity of the pathological condition associated with intraneuronal Tau accumulation (e.g., tauopathy (e.g., reduced memory loss), Tau-associated optic neuropathy (reduced visual impairment), motor deficit, a decrease/reduction in at least one symptom or disease-related effect (e.g., a reduction of intraneuronal Tau levels, an increase of intraneuronal Tau degradation, an increase of neuron survival), an amelioration of at least one symptom or disease-related effect, and an increased survival time of the affected host animal, following administration of the at least one agent that increases a long PTB Numb isoform expression or activity, or of a composition comprising the agent. In accordance with the invention, a prophylactic effect may comprise a complete or partial avoidance/inhibition of the pathological condition associated with intraneuronal Tau accumulation, and an increased survival time of the affected host animal, following administration of the at least one agent that increases a long PTB Numb isoform expression or activity or of a composition comprising the agent.

As such, a "therapeutically effective" or "prophylactically effective" amount of agent affecting a long PTB Numb isoform expression and/or activity (e.g., Tau intraneuronal levels or degradation or neuron survival), or a combination of such agents, may be administered to an animal, in the context of the methods of treatment and prevention, respectively, described herein.

Types of Samples from the Subject and of Control Samples

As used herein, the term "organism" refers to a living thing which, in at least some form, is capable of responding to stimuli, reproduction, growth or development, or maintenance of homeostasis as a stable whole (e.g., an animal). The organism may be composed of many cells which may be grouped into specialized tissues or organs.

"Sample" or "biological sample" refers to any solid or liquid sample isolated from a live being. In a particular embodiment, it refers to any solid (e.g., tissue sample) or liquid sample isolated from an animal (e.g., human), such as a biopsy material (e.g., solid tissue sample), blood (e.g., plasma, serum or whole blood), saliva, synovial fluid, urine, amniotic fluid and cerebrospinal fluid. Such sample may be, for example, fresh, fixed (e.g., formalin-, alcohol- or acetone-fixed), paraffin-embedded or frozen prior to analysis of a long PTB Numb isoform expression level or Tau expression level. In an embodiment, the above-mentioned sample is obtained from a subject having a pathological condition associated with intraneuronal Tau accumulation.

As used herein, the term "tissue" or "tissue sample" refers to a group of cells, not necessarily identical, but from the same origin, that together carry out a specific function. A tissue is a cellular organizational level intermediate between cells and a complete organism. Organs are formed by the functional grouping together of multiple tissues. Examples of tissues include neuronal, retinal and nervous tissues. Other examples of biological tissues include blood cells populations (e.g., B or T lymphocytes populations), breast, skin, lung or colon tissues.

Similarly, the expression "reference gene expression and/or activity of a gene" refers to the expression and/or activity of that gene used as a control for the measure performed in a sample from a subject. "Reference gene sample" as used herein refers to a sample comprising a reference expression and/or activity of a gene.

More particularly, the expression "reference long PTB Numb isoform expression and/or activity" and "reference Tau expression and/or activity" refers to the long PTB Numb isoform and Tau expression and/or activity, respectively, used as a control for the measure performed in a sample from a subject. "Reference long PTB Numb isoform sample" and "reference Tau sample" as used herein refer to a sample comprising a "reference long PTB Numb isoform expression and/or activity" and "reference Tau expression and/or activity", respectively.

Depending on the type of assay performed, the reference long PTB Numb isoform (e.g., Numb-72) expression and/or activity and reference Tau expression can be selected from an established standard, a corresponding long PTB Numb isoform and Tau expression and/or activity, respectively, determined in the subject (in a sample from the subject) at an earlier time; a corresponding long PTB Numb isoform and Tau expression and/or activity, respectively, determined in one or more control subject(s) known to not being predisposed to a pathological condition associated with intraneuronal Tau accumulation, known to not having a pathological condition associated with intraneuronal Tau accumulation (in specific embodiments, a tauopathy such as AD; or a Tau-associated optic neuropathy) or known to have a good prognosis; or determined in one or more control subject(s) known to have a predisposition to a pathological condition associated with intraneuronal Tau accumulation, known to have a pathological condition associated with intraneuronal Tau accumulation or known to have a poor prognosis. In another embodiment, the reference long PTB Numb isoform expression and/or activity and reference Tau expression and/or activity is the average or median value obtained following determination of long PTB Numb isoform and Tau expression or activity, respectively, in a plurality of samples (e.g., samples obtained from several healthy subjects or samples obtained from several subjects having a pathological condition associated with intraneuronal Tau accumulation (e.g., tauopathy or Tau-associated optic neuropathy)).

"Corresponding normal tissue" or "corresponding tissue" as used herein refers to a reference sample obtained from the same tissue as that obtained from a subject. Corresponding tissues between organisms (e.g., human subjects) are thus tissues derived from the same origin (e.g., two B lymphocyte populations).

Measurement of a Long PTB Numb Isoform, and Tau in a Sample

The present invention encompasses methods comprising detecting the presence of long PTB Numb isoform (e.g., Numb-72) and optionally Tau activity and/or expression in a subject sample. In a specific embodiment, the present invention encompasses detecting the presence of long PTB Numb isoform and optionally Tau activity and/or expression in a subject sample. In another specific embodiment, the present invention encompasses detecting the presence of long PTB Numb isoform activity and/or expression in a subject sample.

In another embodiment, the present invention encompasses methods comprising determining whether a long PTB Numb isoform and optionally Tau expression and/or activity in a subject sample is substantially similar to that of a reference expression and/or activity. In a specific embodiment, the present invention encompasses determining whether a long PTB Numb isoform activity and/or expression in a subject sample is substantially similar to that of a reference expression and/or activity.

In another embodiment, the present invention encompasses methods comprising determining whether a long PTB Numb isoform activity and/or expression in a subject sample is higher than a reference expression and/or activity.

In cases where the reference long PTB Numb isoform sample and reference Tau samples are from the subject at an earlier time; from subject(s) known not to being predisposed to a pathological condition associated with intraneuronal Tau accumulation, known not to have an pathological condition associated with intraneuronal Tau accumulation, or known to have a good prognosis, (1) a decreased long PTB Numb isoform (e.g., Numb-72); and optionally (i) increased Tau expression and/or activity, respectively in the sample from the subject relative to the reference long PTB Numb isoform and Tau expression and/or activity, respectively, is indicative that the subject would likely benefit from an agent that increases long PTB Numb isoform expression or activity, while a comparable or lower expression or activity in a sample from the subject relative to the reference expression and/or activity is indicative that the subject would likely not benefit from an agent that increase long PTB Numb isoform expression or activity.

In cases where the reference long PTB Numb isoform sample is from subject(s) known to have a pathological condition associated with intraneuronal Tau accumulation, known to have a pathological condition associated with intraneuronal Tau accumulation or known to have a poor prognosis, (1) a comparable or a decreased long PTB Numb isoform and eventually (i) a comparable or an increased Tau expression and/or activity, respectively in the sample from the subject relative to the reference long PTB Numb isoform and reference Tau expression and/or activity, respectively, is indicative that the subject would likely benefit from an agent that increases long PTB Numb isoform expression or activity, while a higher long PTB Numb isoform expression or activity in a sample from the subject relative to the reference expression and/or activity is indicative that the subject would likely not benefit from an agent that increases long PTB Numb isoform expression or activity.

As used herein, a "higher" or "increased" level of expression and/or activity of a long PTB Numb isoform (e.g., Numb-72 and/or Numb-66 expression and/or activity) refers to levels of expression or activity in a sample (i.e. sample from the subject) which exceeds with statistical significance that in the reference sample (e.g., an average corresponding level of expression or activity a healthy subject or of a population of healthy subjects, or when available, the normal counterpart of the affected or pathological tissue) measured through direct (e.g., Anti-long PTB Numb isoform antibody, Anti-Tau antibody, quantitative PCR) or indirect methods. The increased level of expression and/or activity refers to level of expression and/or activity in a sample (i.e. sample from the subject) which is at least 10% higher, in another embodiment at least 15% higher, in another embodiment at least 20% higher, in another embodiment at least 25%, in another embodiment at least 30% higher, in a further embodiment at least 40% higher; in a further embodiment at least 50% higher, in a further embodiment at least 60% higher, in a further embodiment of at least 70% higher, in a further embodiment of at least 80% higher, in a further embodiment of at least 90% higher, in a further embodiment at least 100% higher (i.e. 2-fold), in a further embodiment at least 200% higher (i.e. 3-fold), in a further embodiment at least 300% higher (i.e. 4-fold), relative to the reference expression and/or activity.

As used herein, a "substantially similar level" refers to a difference in the level of expression or activity between the level determined in a first sample (e.g., sample from the subject) and the reference expression and/or activity which is less than about 10%; in a further embodiment, 5% or less, in a further embodiment, 2% or less.

Methods for measuring a long PTB Numb isoform and Tau expression and/or activity are well known. See in particular under title "Protein expression" above and Examples herein.

Subjects Stratification Methods

The methods of the present invention may also be used for classifying or stratifying a subject into subgroups based on a long PTB Numb isoform and/or Tau expression and/or activity enabling a better characterization of the subject disease and a better selection of treatment. It may further be used to determine whether a subject should be included in a clinical trial testing an agent that increases a long PTB Numb isoform expression or activity, depending on the subgroup to which the subject belongs. If a subject belongs to the subgroup of subjects having Tau positive neurons, he would likely be a good candidate for inclusion in a clinical trial testing an agent that increases a long PTB Numb isoform expression or activity (i.e. the subject is likely responsive to such an agent).

In one aspect, the present invention provides a method for stratifying a subject, said method comprising: (a) detecting/determining the expression and/or activity of a long PTB Numb isoform in a sample from the subject, and optionally (b) comparing said expression and/or activity to a reference expression and/or activity; and (c) stratifying said subject based on said detection and/or said comparison in a subgroup. In a specific embodiment, the method further comprises detecting/determining the expression and/or activity of Tau.

The invention provides a method for stratifying a subject based on the expression and/or activity of such biomarkers as determined in a tissue sample (e.g., a biopsy) from the subject using the assays/methods described herein.

Combination of Therapies

In an embodiment, the above-mentioned prevention/treatment comprises the use/administration of more than one (i.e. a combination of) therapies (e.g., active/therapeutic agent (e.g., an agent capable of preventing and/or treating a pathological condition associated with intraneuronal Tau accumulation)). The combination of prophylactic/therapeutic agents and/or compositions of the present invention may be administered or co-administered (e.g., consecutively, simultaneously, at different times) in any conventional dosage form. Co-administration in the context of the present invention refers to the administration of more than one prophylactic or therapeutic agent in the course of a coordinated treatment to achieve an improved clinical outcome. Such co-administration may also be coextensive, that is, occurring during overlapping periods of time. For example, a first agent may be administered to a subject before, concomitantly, before and after, or after a second active agent is administered. The agents may in an embodiment be combined/formulated in a single composition and thus administered at the same time. In an embodiment, the one or more active agent(s) of the present invention may be used/administered in combination with one or more agent(s) currently used to prevent or treat the pathological condition associated with intraneuronal Tau accumulation (e.g., an acetylcholinesterase inhibitor). Acetylcholinesterase inhibitors inhibit the acetylcholinesterase enzyme from breaking down acetylcholine, thereby increasing both the level and duration of action of the neurotransmitter acetylcholine. They are known to treat certain tauopathies and Tau-associated optic neuropathies. Known acetylcholinesterase inhibitor include Acotiamide, Aldicarb, Alpha-Pinene, Ambenonium, Bendiocarb, Bufencarb, Cadusafos, Caffeine, Carbamates, Carbaryl, Carbendazim, Carbetamide, Carbofuran, Carbosulfan, Chlorbufam, Chloropropham, Chlorpyrifos, Coumarins, Cyclosarin, Demecarium, Diazinon, Dichlorvos, Diisopropyl fluorophosphate, Dimethoate, Donepezil, Echothiophate, Edrophonium, Ethiofencarb, Formetanate, Galantamine, Huperzine A, Lactucopicrin, Ladostigil, Malathion, Methiocarb, Methomyl, Metrifonate, Neostigmine, Onchidal, Organophos, Oxamyl, Parathion, Phenanthrene derivatives, Phenmedipham, Physostigmine, Pinmicarb, Piperidines, Pirimicarb, Propamocarb, Propham, Propoxur, Pyridostigmine, Rivastigmine, Rosmarinic acid, Sarin, Soman, Tabun, Tacrine, also known as tetrahydroaminoacridine (THA'), Ungeremine, VE, VG, VM, and VX.

In one embodiment, the prevention and/or treatment of a pathological condition associated with intraneuronal Tau accumulation with an agent that increase a long PTB Numb isoform expression or activity is combined with at least one other active agent known to prevent and/or treat that pathological condition (e.g., acetylcholinesterase inhibitor).

Dosage

The amount of the agent or pharmaceutical composition which is effective in the prevention and/or treatment of a particular disease, disorder or condition (e.g., pathological condition associated with intraneuronal Tau accumulation) will depend on the nature and severity of the disease, the chosen prophylactic/therapeutic regimen (i.e., compound, DNA construct, protein, cells), systemic administration versus localized delivery, the target site of action, the patient's body weight, the patient's general health, the patient's sex, special diets followed by the patient, concurrent medications being used (drug interaction), the administration route, time of administration, and other factors that will be recognized and will be ascertainable with routine experimentation by those skilled in the art. The dosage will be adapted by the clinician in accordance with conventional factors such as the extent of the disease and different parameters from the patient. Typically, 0.001 to 1000 mg/kg of body weight/of subject per day will be administered to the subject. In an embodiment, a daily dose range of about 0.01 mg/kg to about 500 mg/kg, in a further embodiment of about 0.1 mg/kg to about 200 mg/kg, in a further embodiment of about 1 mg/kg to about 100 mg/kg, in a further embodiment of about 10 mg/kg to about 50 mg/kg, may be used. The dose administered to a subject, in the context of the present invention should be sufficient to produce a beneficial prophylactic and/or therapeutic response in the patient over time. The size of the dose will also be determined by the existence, nature, and extent of any adverse side-effects that accompany the administration. Effective doses may be extrapolated from dose response curves derived from in vitro or animal model test systems. For example, in order to obtain an effective mg/kg dose for humans based on data generated from rat studies, the effective mg/kg dosage in rat may be divided by six.

Adjustment of Dose of Agents of the Present Invention

In one embodiment of the present invention, the dose of the at least one agent administered to increase a long PTB Numb isoform expression and/or activity, is adjusted to the level of the long PTB Numb isoform in the sample (e.g., neuronal tissue).

In another aspect, the present invention provides a method for adjusting a treatment, for example the dose of an agent, to administer to a subject. Such method comprising: (a) determining the expression and/or activity of a long PTB Numb isoform (and/or Tau) in a sample from said subject; (b) comparing said expression and/or activity to a reference expression and/or activity of the long PTB Numb isoform (and/or Tau), determined in a biological sample obtained from said subject at an earlier time (e.g., at the start of treatment); wherein an increase in said long PTB Numb isoform expression and/or activity relative in the sample compared to the expression and/or activity of the long PTB Numb isoform (and/or a decrease in said Tau intraneuronal levels in the sample compared to the expression and/or activity of Tau intraneuronal levels) determined in the biological sample obtained from said subject at an earlier time (at the start of treatment) is indicative that the dose of the at least one administered agent is appropriate whereas a similar level or a decrease of a long PTB Numb isoform expression and/or activity (and/or an increase in said Tau intraneuronal levels) over time is indicative that the dose of the at least one agent administered to the subject should be increased.

Pharmaceutical Composition

The invention also provides a pharmaceutical composition (medicament) comprising at least one agent of the invention (e.g., a Numb-72) (alone or in combination with another agent—see combined treatment above), and a pharmaceutically acceptable carrier (e.g. diluent, solvent, excipient, salt or adjuvant). Such carriers include, for example, saline, buffered saline, dextrose, water, glycerol, ethanol, and combinations thereof. In a specific embodiment, the pharmaceutically acceptable carrier is appropriate for targeting neurons. The pharmaceutical composition may be adapted for the desired route of administration (e.g., intraocular (e.g., intravitreal), oral, sublingual, nasal, parenteral, intravenous, intramuscular, intra-peritoneal, aerosol). In some embodiments, gene therapy is utilized to deliver therapeutic molecules (e.g., a long PTB Numb isoform) to the subject. See also section Nucleic acids and hosts above.

Kit or Package

The present invention also provides a kit or package comprising the above-mentioned agent or pharmaceutical compositions. Such kit may further comprise, for example, instructions for the prevention and/or treatment of pathological condition associated with intraneuronal Tau accumulation (e.g., tauopathy or Tau-associated optic neuropathy), containers, devices for administering the agent/composition, etc.

The present invention also provides a kit or package comprising a reagent useful for determining a long PTB Numb isoform (e.g., Numb-72) and/or Tau expression and/or activity (e.g., a ligand that specifically binds to any long PTB Numb isoform and/or Tau polypeptide such as an anti-long PTB Numb isoform or anti-Tau antibody, or a ligand that specifically binds a long PTB Numb isoform and/or Tau nucleic acid such as an oligonucleotide). Such kit may further comprise, for example, instructions for the prognosis and/or diagnosis of the pathology, control samples, containers, reagents useful for performing the methods (e.g., buffers, enzymes), etc.

As used herein the term "subject" is meant to refer to any animal, such as a mammal including human, mice, rat, dog, cat, pig, cow, monkey, horse, etc. In a particular embodiment, it refers to a human.

A "subject in need thereof" or a "patient" in the context of the present invention is intended to include any subject that will benefit or that is likely to benefit from the increase in the expression and/or activity of a long PTB Numb isoform or decrease of the intraneuronal levels of Tau. In an embodiment, the subject in need thereof is a subject diagnosed as having a pathological condition associated with intraneuronal Tau accumulation.

As used herein, the term "a" or "the" means "at least one".

Although the present invention has been described hereinabove by way of specific embodiments thereof, it can be modified, without departing from the spirit and nature of the subject invention as defined in the appended claims.

The present invention is illustrated in further details by the following non-limiting examples.

Example 1: Materials and Methods

Animals

All animal work was carried in accordance with the Canadian Council on Animal Care guidelines. The Islet1-Cre mouse line (Srinivas et al., 2001) and numb floxed (Wilson et al., 2007) mouse lines were used to generate cKO. Both heterozygotes and Cre-negative animals were used as controls in this study and referred to as "control" throughout the text and figures. Female triple transgenic (3×TgAD) homozygote mice harbouring the $APP_{SWE}$, $PS1_{M146X}$ and $Tau_{P301L}$ transgenes and associated controls (B6129) were imported from Jackson laboratory. Transgenic TauP301S mice (PS19) expressing human Tau-P301S (1N4R), associated controls (C57B6) were imported from Jackson laboratory. We generated Islet1-Cre, Numbflox/flox, TauP301S by crossing the 2 line together. TauP301S allele is heterozygote in all the lines.

Histology, Immunohistochemistry, and Electron Microscopy

Para formaldehyde (PFA) was used as a fixative for all histology and immunohistochemistry. Eyes were enucleated and fixed by immersion in freshly prepared 4% paraformaldehyde in phosphate-buffered saline solution (PBS) for overnight (0/N) at 4° C., cryoprotected in sucrose 20% overnight, and cryosectioned at 14 um. For retina flat mounts, mice were enucleated after euthanasia, and eyes fixed for 2 h in 4% PFA before PBS wash (3 times 10 minutes) and dissected to isolate neural retina from the eye cup. Sections and flat mounts were pre-incubated for 1 h in blocking and permeabilization solution (1% BSA in 0.4% Triton) and then incubated overnight at 4° C. with the primary antibodies. Primary antibodies used in this study: Brn3b, Chx10, Pax6, Numb, NF165, ATB.

RGCs Culture

Retinal tissues were isolated from eyeballs of postnatal day 7 (P7) mice, cut in small pieces and incubated in PBS containing 5 mg/ml of papain, 0.24 mg/ml of L-cysteine, 0.5 mmol/l of EDTA, and 10 U/ml of DNase I for 2×3 min. The reaction was stopped by adding Lo-Ovo solution in PBS, and 10 U/ml of DNase I. The retinal cells were mechanically dissociated by gentle pipetting and collected as a suspension. Procedures were conducted at room temperature in a laminar flow hood. After centrifugation at 1000 rpm for 11 min, cells were resuspended in RGCs media and plate on glass coverslips at 50'000 cells/coverslips on a 24 wells plate and incubated at 37° C.; 8% CO2 for 2 weeks, half media was changed every 3 days. The glass coverslips were incubated the day before with poly-D-lysine (PDL 10 ug/ml) for 1 h and laminin for the entire night. RGCs media is Neurobasal medium supplement with Sato solution, B27 supplement for Primary Neurons (Invitrogen cat #17504044), Penicillin/Streptavidin, Sodium Pyruvate, GlutaMAX™, N-Acetyl-Cysteine (NAC), T3 (Triiodo-Thyronine), Insulin and growth factor, BDNF and CNTF.

Transfections and Constructs

Daoy, and COS-7 cells were transfected using Lipofectamine or Jet Prime with the following constructs: Rab5:: DsRed (Addgene plasmid Plasmid #13050), Myc, Numb65:: Myc, Numb66::Myc, Numb71::Myc, Numb72::Myc. HEK293T cells were transfected with Jet Prime using the following constructs Tau::Flag, Tau::GFP, Numb65, Numb66, Numb71 and Numb72.

Quantification

RGCs survival was assessed by counting Brn3b-positive cells on retina flat mounts the within four square (212 um×212 um) areas around the optic nerve disc, and averaging this number per retina and calculate with the area by multiplied by the total area of square. Cell type quantification in retinal section were made by averaging the total number of positive cells for specific markers in a 200 pm region of the central and peripheral retina on 4 different retinal sections per animal.

Statistical Analysis

Data analysis and statistics were performed using Prism 6 by two-way analysis of variance, one-way analysis of variance (ANOVA) followed by a Bonferroni or Tukey post hoc tests, or by a Student's t-test as indicated in the legends.

Intraocular Injection

Saline, NMDA, siTau and AAVs were injected in adult eyes according to a modified procedure previously described (Matsuda and Cepko, 2004). The titer of the AAV vectors used was 5.50E+13 vg/ml for GFP and 1.63E+14 vg/ml for Numb72 and the serotype was AAV2. The procedures for construction and purification of adenoviral vectors and intraocular injections were described previously (Flannery et al., 1997). The volume of the injection was maintained at 2 μl per eye in the vitreous. Animals were injected with AAV-Numb72 into one eye and received a control injection of vehicle or AAV-GFP into the contra-lateral eye. Eyes were collected 7 weeks after intra-vitreous injections for AAV and after 3 days for NMDA, Saline or siTau injections. After sacrifice, eyes were fixed and neural retina isolated for immunostaining on flat mounts, as described above.

Protein Extraction, Immunoblotting, and Immunoprecipitation

Cells were harvested, and lysed in a NP-40 buffer (50 mm TRIS, pH 8.0, 150 mm NaCl, 1.0% NP-40 with Complete Protease Inhibitor Cocktail (Roche)). For immunoblotting, 40 μg of protein samples for in vivo blot and 10 ug for in vitro blot were loaded on a 10% acrylamide SDS-PAGE gels for separation by electrophoresis migration and then transferred onto PVDF membranes using transblot machine (Millipore). The membranes were blocked with 5% milk in Tris-Buffered saline solution with Teen (TBST, Tris-HCL concentration, NaCl concentration, pH 8.0, 0.1% Tween™). Immunoblotting with the primary antibody was performed at 4° C. overnight in 0.5% dry milk in TBST. The primary antibody was detected with an HRP-conjugated goat anti-rabbit (1:10,000; Jackson Immunoresearch) in 0.5% dry milk in TBST. HRP activity on the membrane was visualized with the ECL kit (GE Life Science).

For immunoprecipitation (IP), Dynabeads Magnetic Beads (Dynabeads Protein G, Invitrogen) were used according to manufacturer's specification. Briefly, 40 μl of beads were incubated with primary antibody for 1 h at 4° C. 1 mg of cell lysate was incubated with the bead-antibody mixture in Iph Buffer (50 mm Tris pH 8.0, 150 mm NaCl, 5 mm EDTA, 0.1% NP-40) overnight at 4° C. The beads were separated using a magnet (MagnaBind, Pierce) and washed in Iph Buffer. The beads were then boiled in 2× Laemmli buffer at 95° C. for 10 min and the supernatant was used for immunoblotting as described above.

Example 2: Numb is Highly Expressed in Retinal Ganglion Cells

Figure 1B:
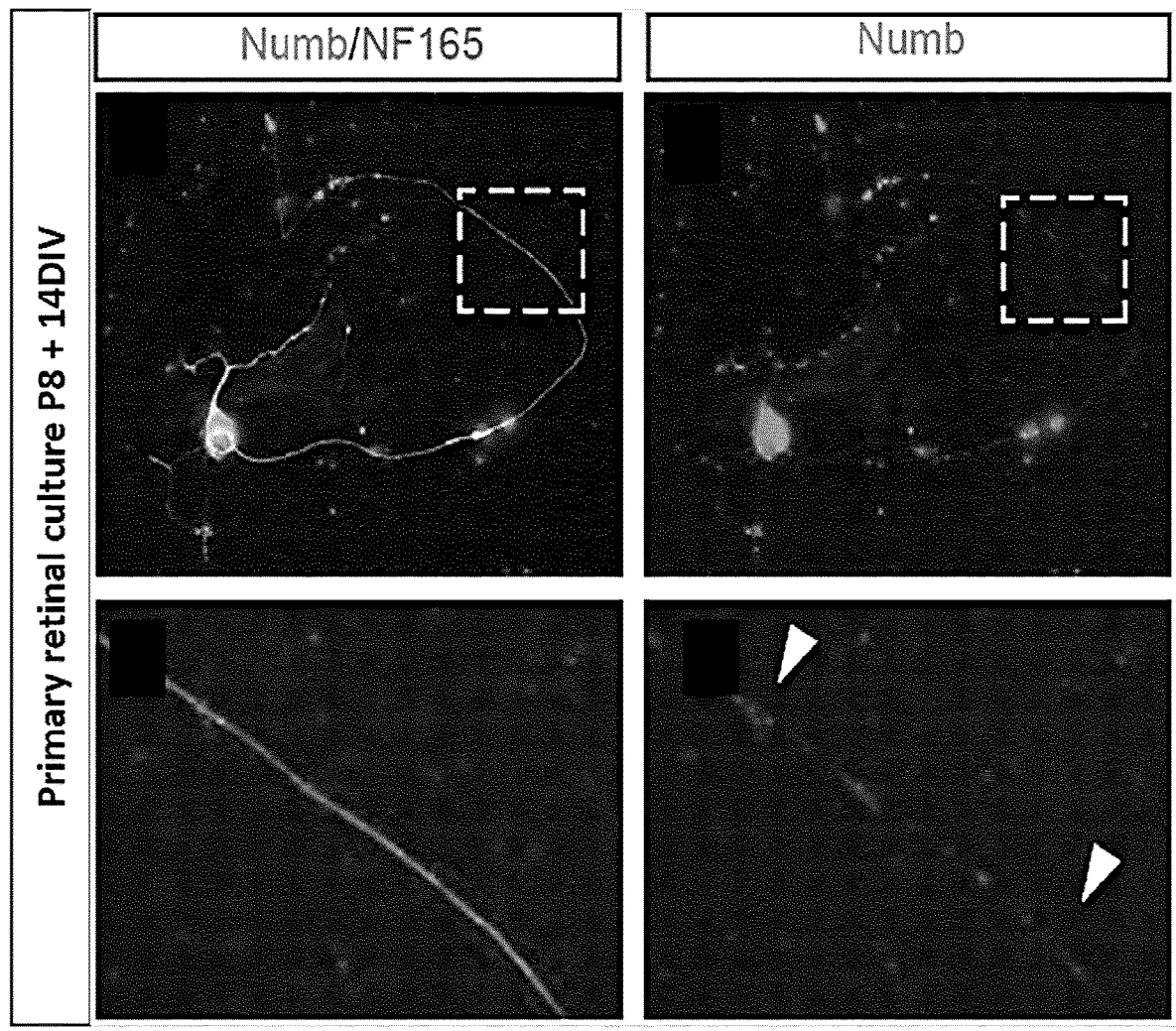

The inventors have found that Numb is expressed in the retina, and more strongly in retinal ganglion cells (RGCs), both in vivo and in cultured primary cells (FIGS. 1A-B). More particularly, FIG. 1A shows Numb immunostaining (shown in ganglion cell line (GCL)) in adult retinal section at 5-month-old, showing that Numb is expressed in retinal ganglion cells. FIG. 1B shows Numb immunostaining (shown as dots and/or boxed in the FIG.) in primary retinal cell culture prepared from P8 retina and cultured for 14 days. Neurofilament 165 (NF165 shown as line) is a specific marker of RGCs neurofilament, showing that Numb is expressed in cell body and neurites of the RGCs. Arrow indicates Numb presence in neurites.

Figure 2A:
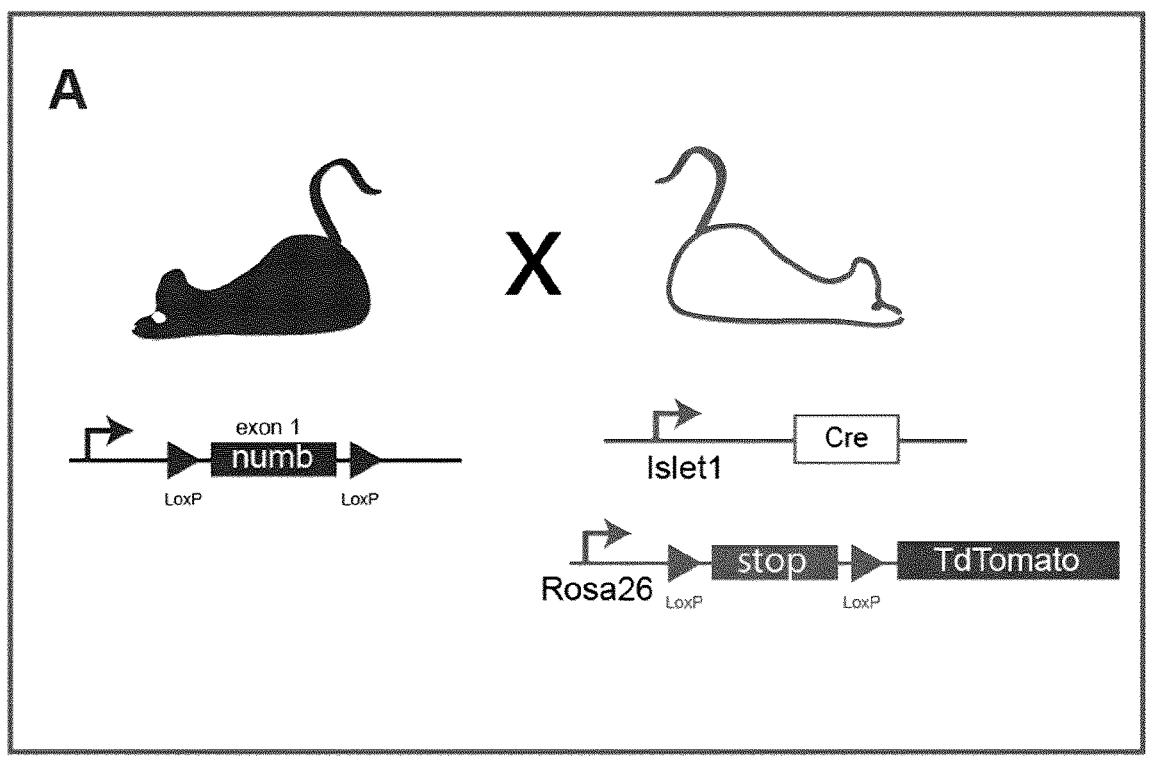
FIGS. 2A-D: Numb is essential for long-term survival of RGCs.
Figure 2B:
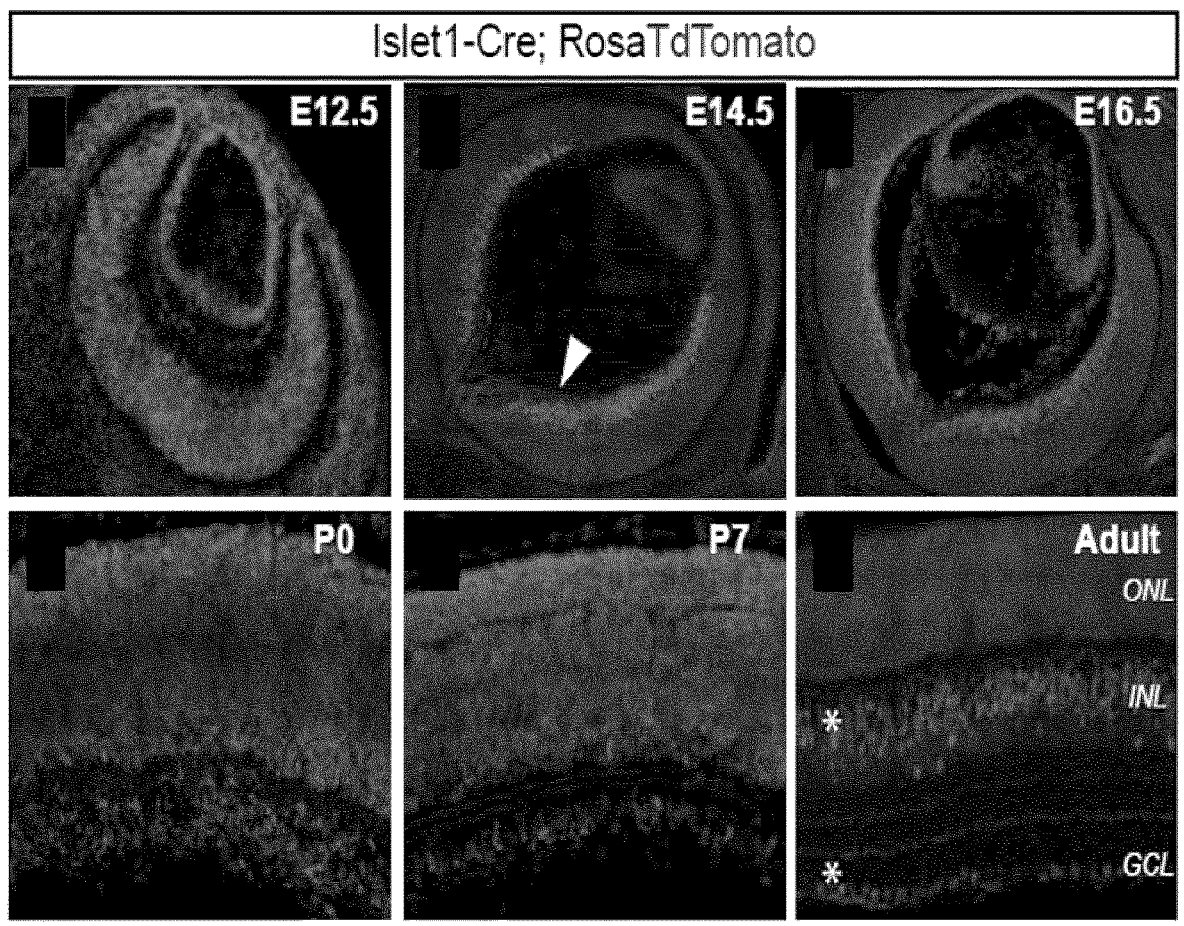
Figure 2C:
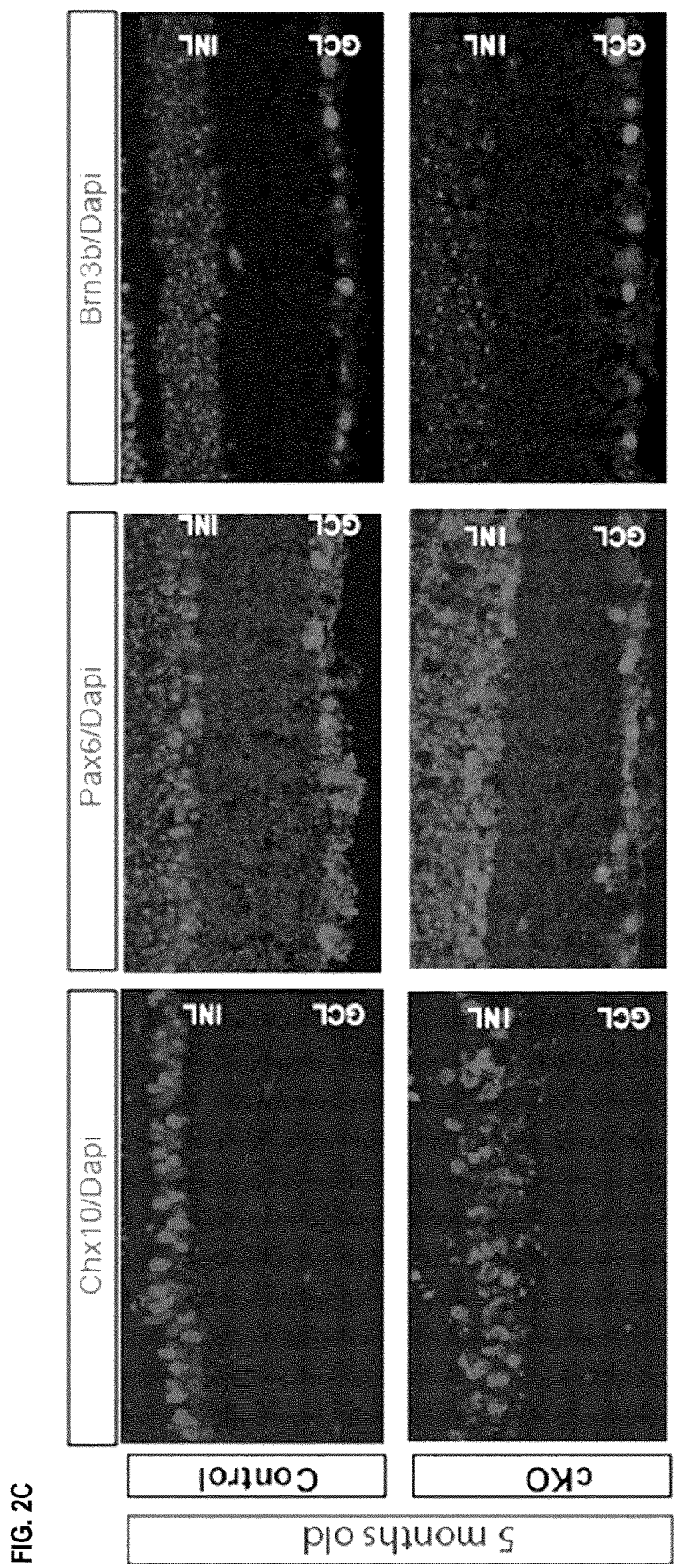
Figure 2D:
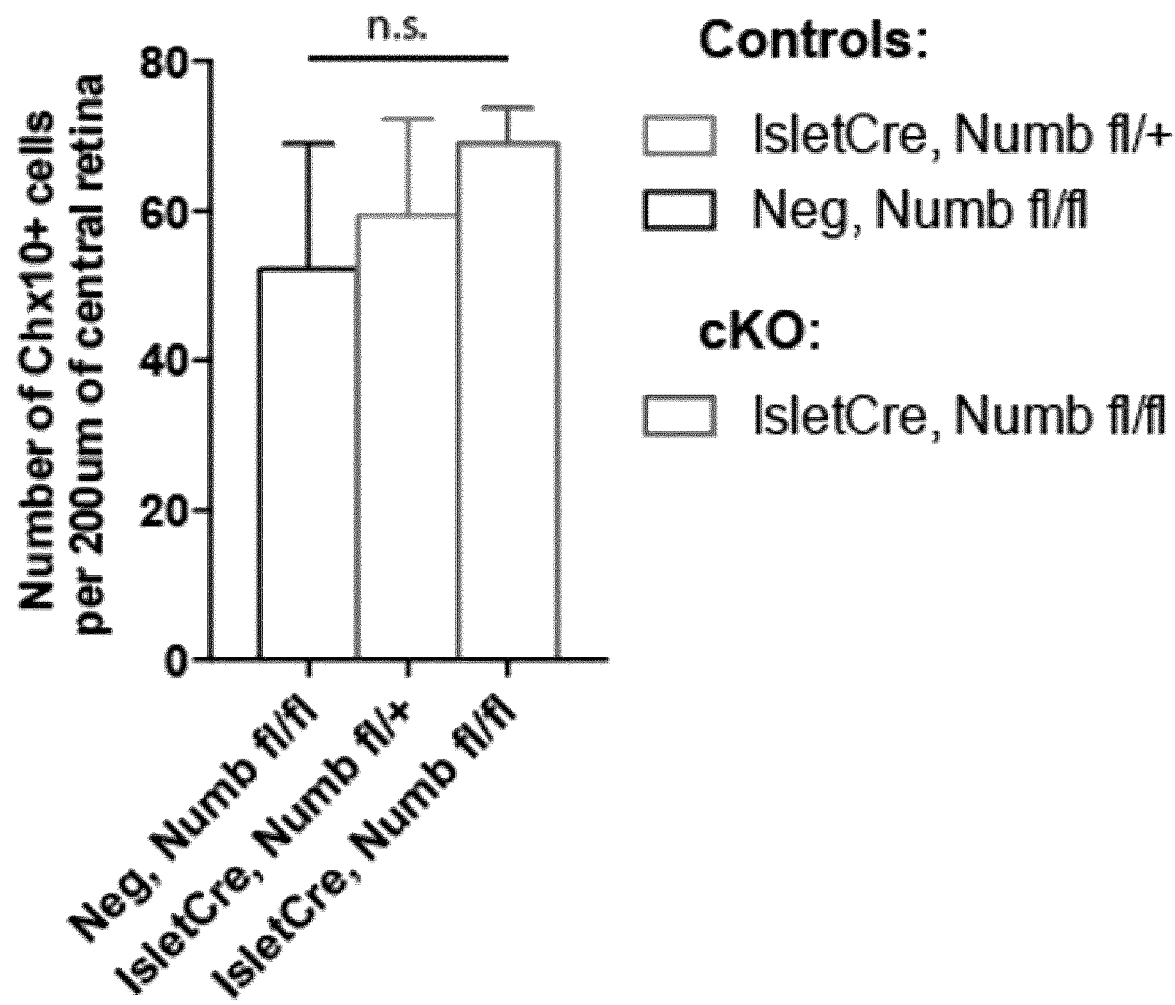
Figure 2F:
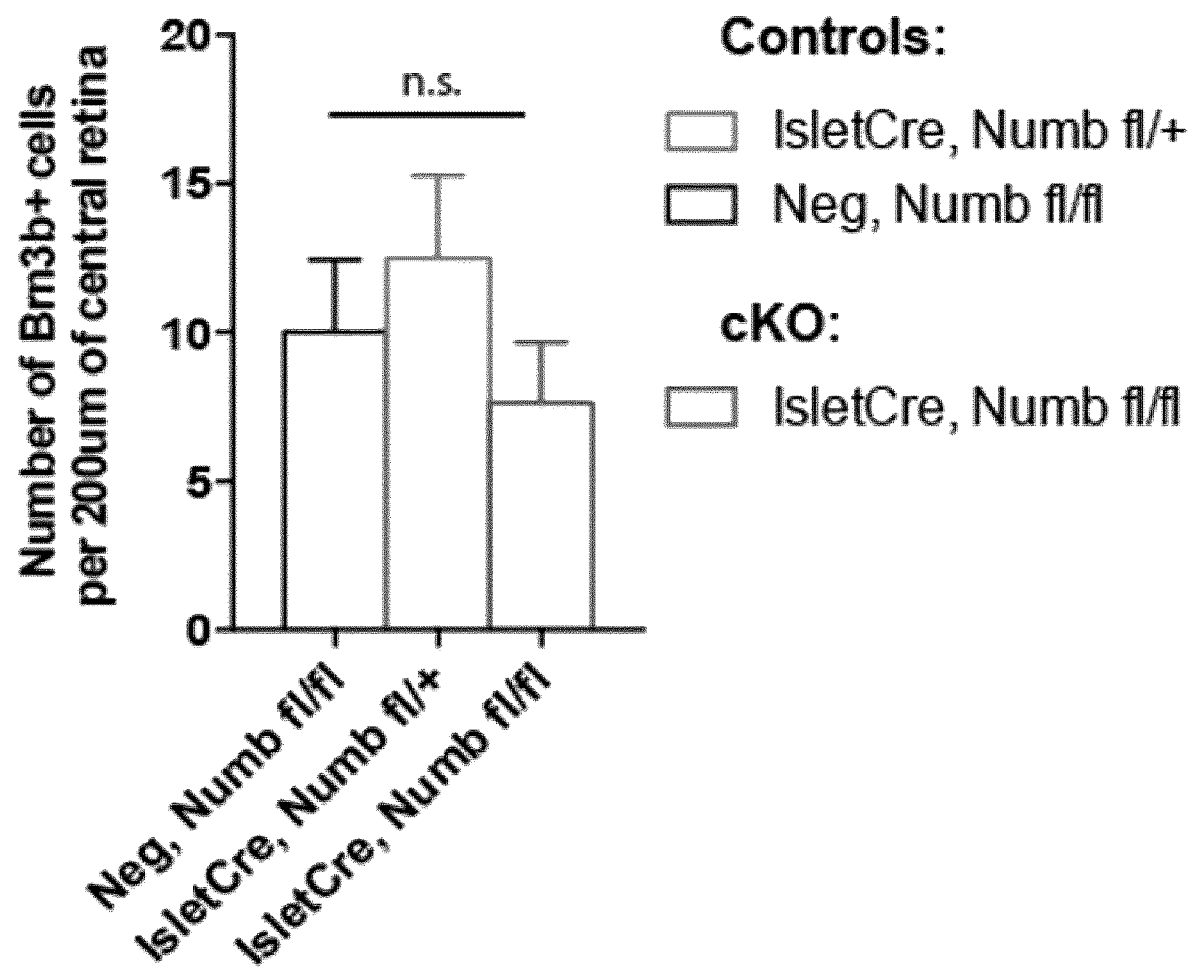

Example 3: Numb is Essential for Long-Term Neuron Survival, and to Maintain Axonal Homeostasis In Vivo and in Culture The inventors generated a conditional knockout (cKO) mouse of Numb in RGCs using the Cre/loxP system. To do this, they crossed the Islet1-Cre mouse line (Srinivas et al., BMC Dev. Biol., 2001) with a mouse line in which exon 1 of the numb gene is flanked by loxP sites (Wilson et al., J. Immunol., 2007). These mice were also null for Numblike, a Numb homolog known to compensate for Numb loss of function and contained a Rosa-TdTomato reporter of Cre activity (FIG. 2A). Examination of the TdTomato reporter expression in the retina showed Cre-mediated recombination in RGCs as early as embryonic day 14.5 (E14.5) and bipolar cells in the adult retina (FIG. 2B).

The retinal sections were immunostaining at 5-month-old and 20-month-old mice in controls (Islet Cre+; Numb fl/+ shown on the images) and cKO (Islet Cre+; Numb fl/fl) mice for CHX10, a transcription factor specifically expressed in bipolar cells, Pax6, a transcription factor expressed in amacrine cells and Brn3b, a transcription factor specifically expressed in RGCs. The fl/+ refer to one floxed allele and one wildtype allele of Numb: these animals are Numb heterozygotes when Cre is present and used as controls, whereas the fl/fl have both alleles of Numb floxed: they are Numb homozygotes knockout when Cre is present (cKO). For all the markers the numbers of positive cells were counted on a 200 um stretch of retina.

The number of bipolar, amacrine and RGCs were unchanged at 5-month-old (FIGS. 2C-F). The number of bipolar and amacrine cells were unchanged at 20-month-old (FIGS. 2G-1), indicating that the loss of Numb does not affect bipolar and amacrine cells survival at long term, whereas around 50% loss of RGCs in 20-month-old mice and around 25% loss of RGCs in 8-month-old mice was observed, indicating that Numb function is essential for long-term survival of RGCs (FIGS. 2G, J-L).

Figure 2G:
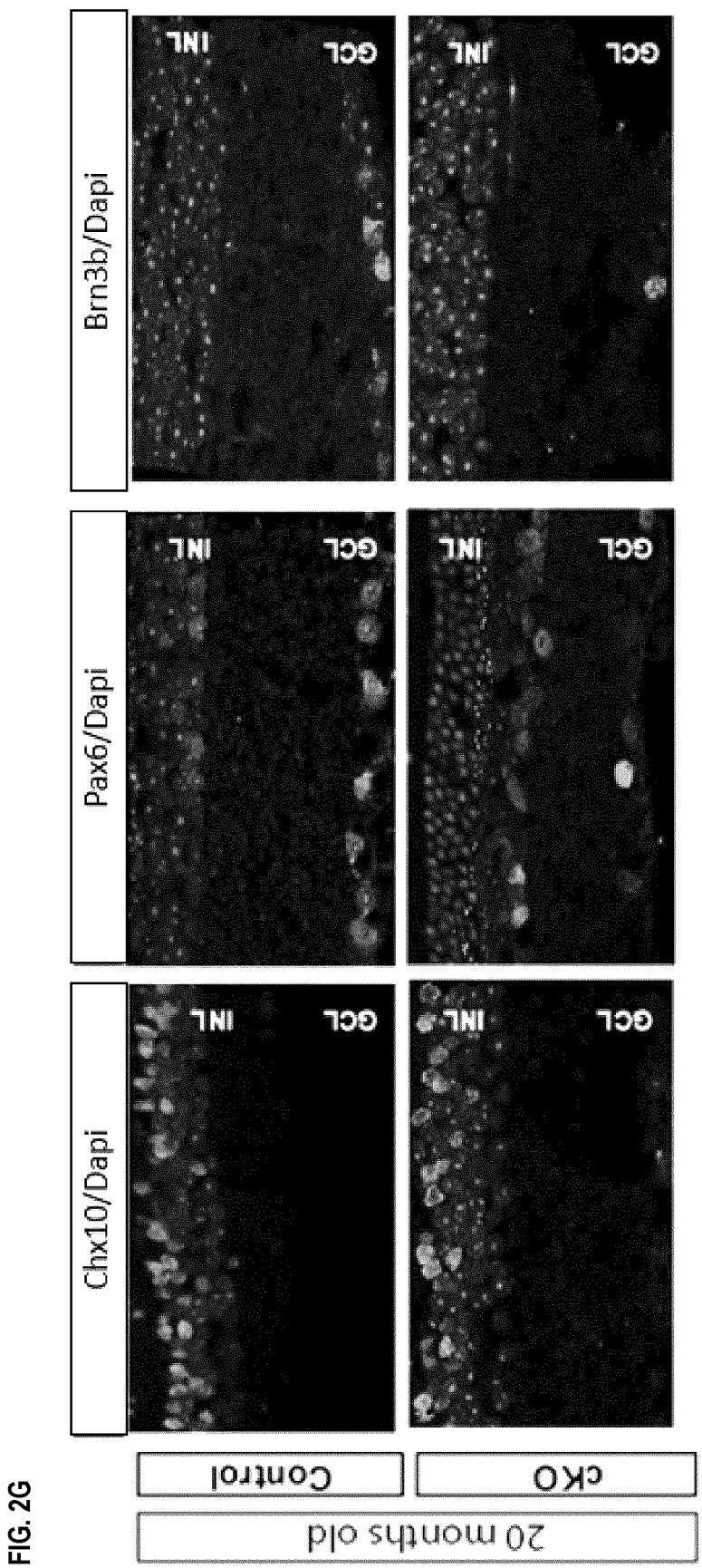
FIGS. 2G-J. Immunostaining for CHX10, Pax6, and Brn3b was performed on retinal section at 20-month-old in controls (Islet Cre+; Numb fl/+ are shown on these images) and cKO (Islet Cre+; Numb fl/fl) mice. For all the markers the numbers of positive cells were counted on a 200 um stretch of retina. The number of bipolar and amacrine cells were unchanged at 20-month-old, indicating that the lost of Numb does not affect bipolar and amacrine cells survival at long term, whereas a 50% loss of RGCs in 20-month-old mice was observed, indicating that Numb function is essential for long-term survival of RGCs. Mean±SEM, n=4 animals/genotype/time point. Anova test n.s: not significant, **p≤0.01.
Figure 2H:
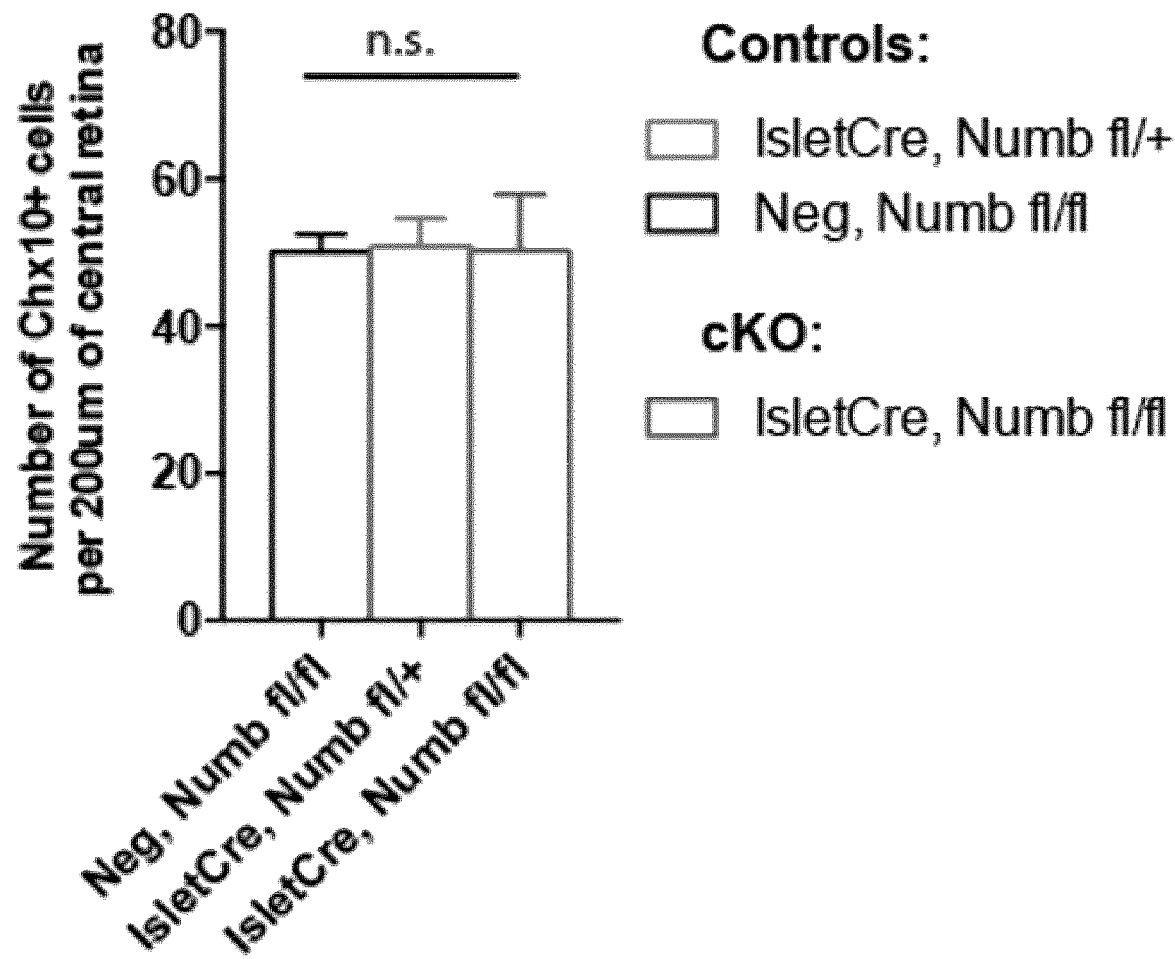
Figure 2I:
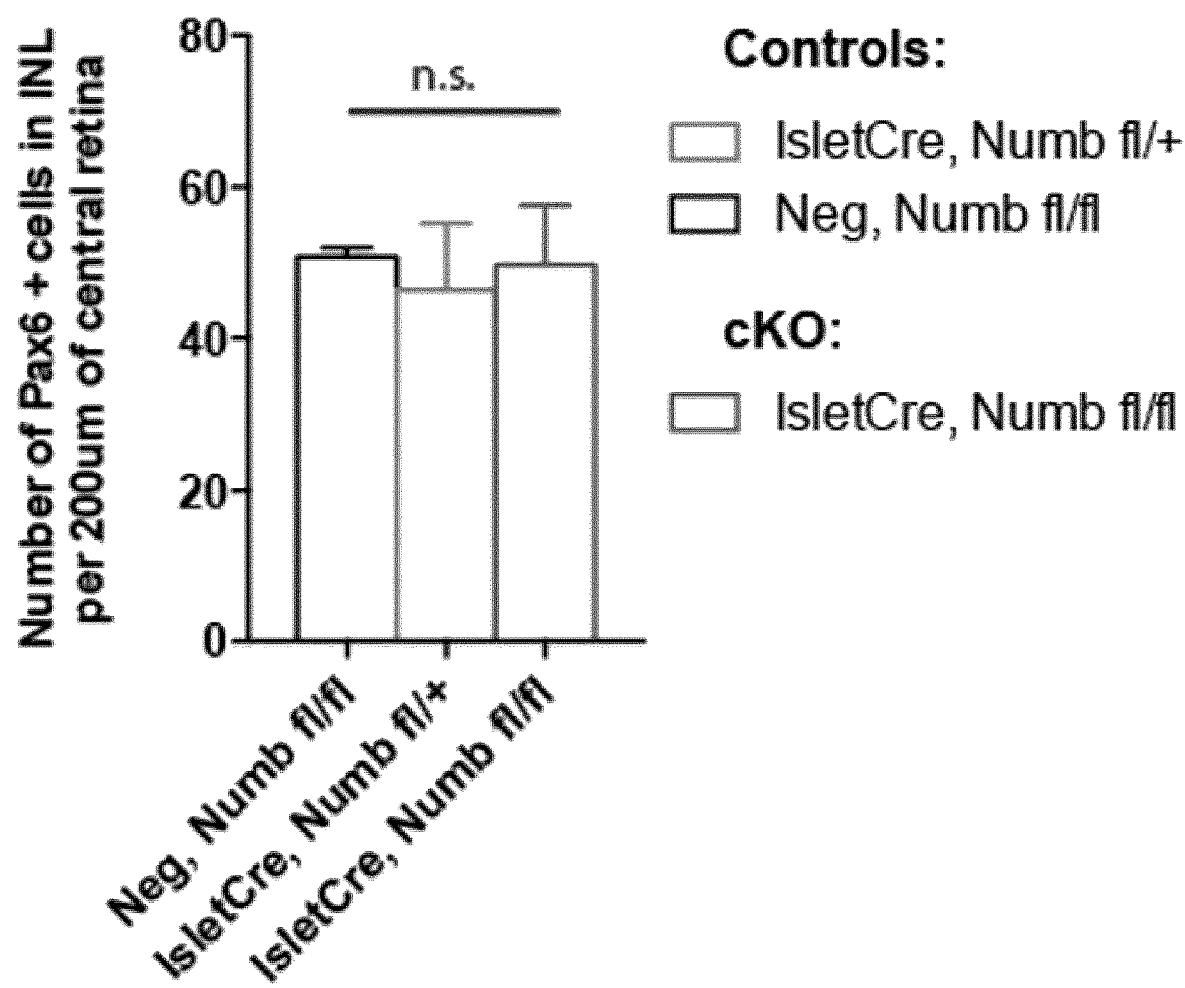
Figure 2J:
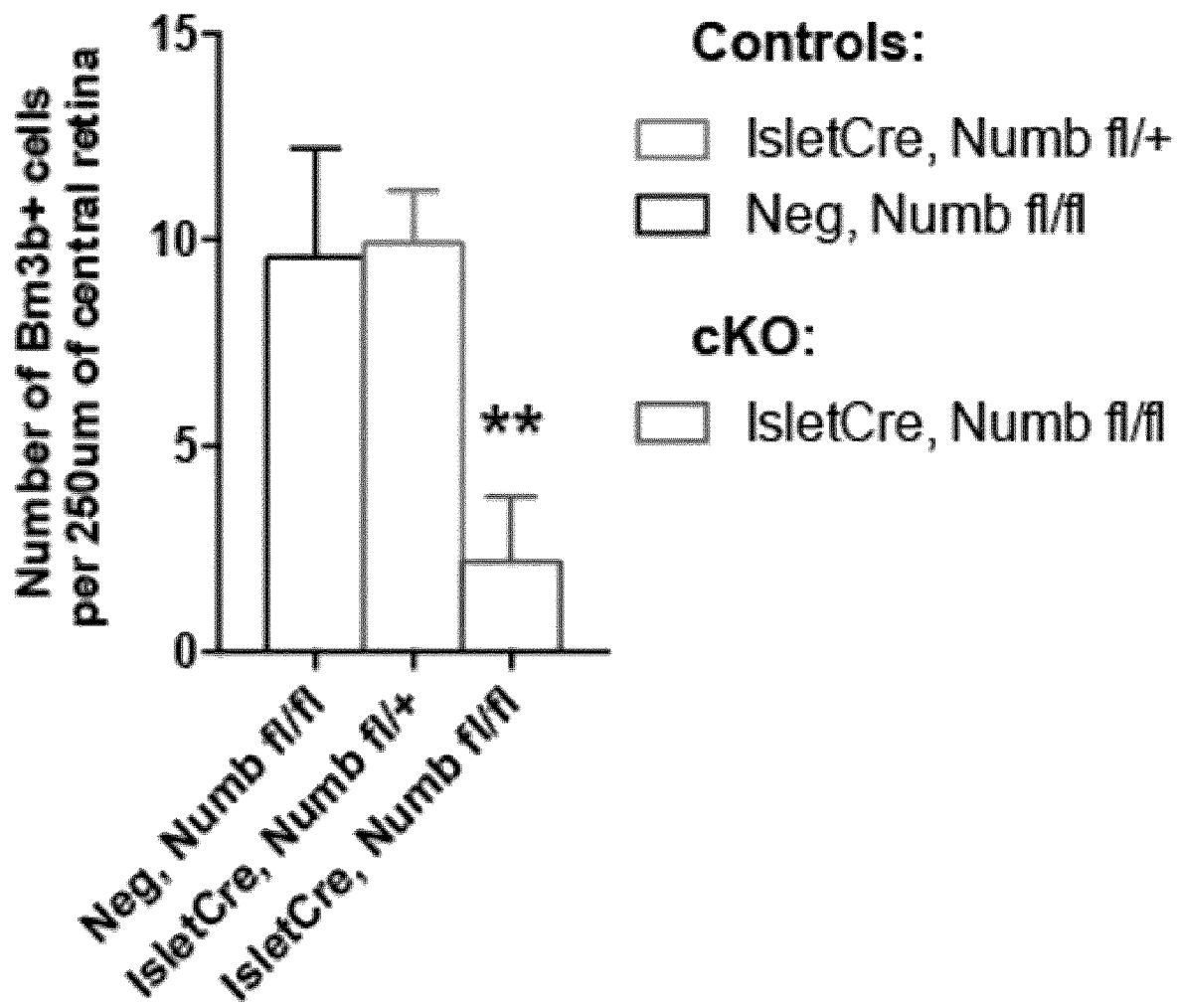
Figure 2K:
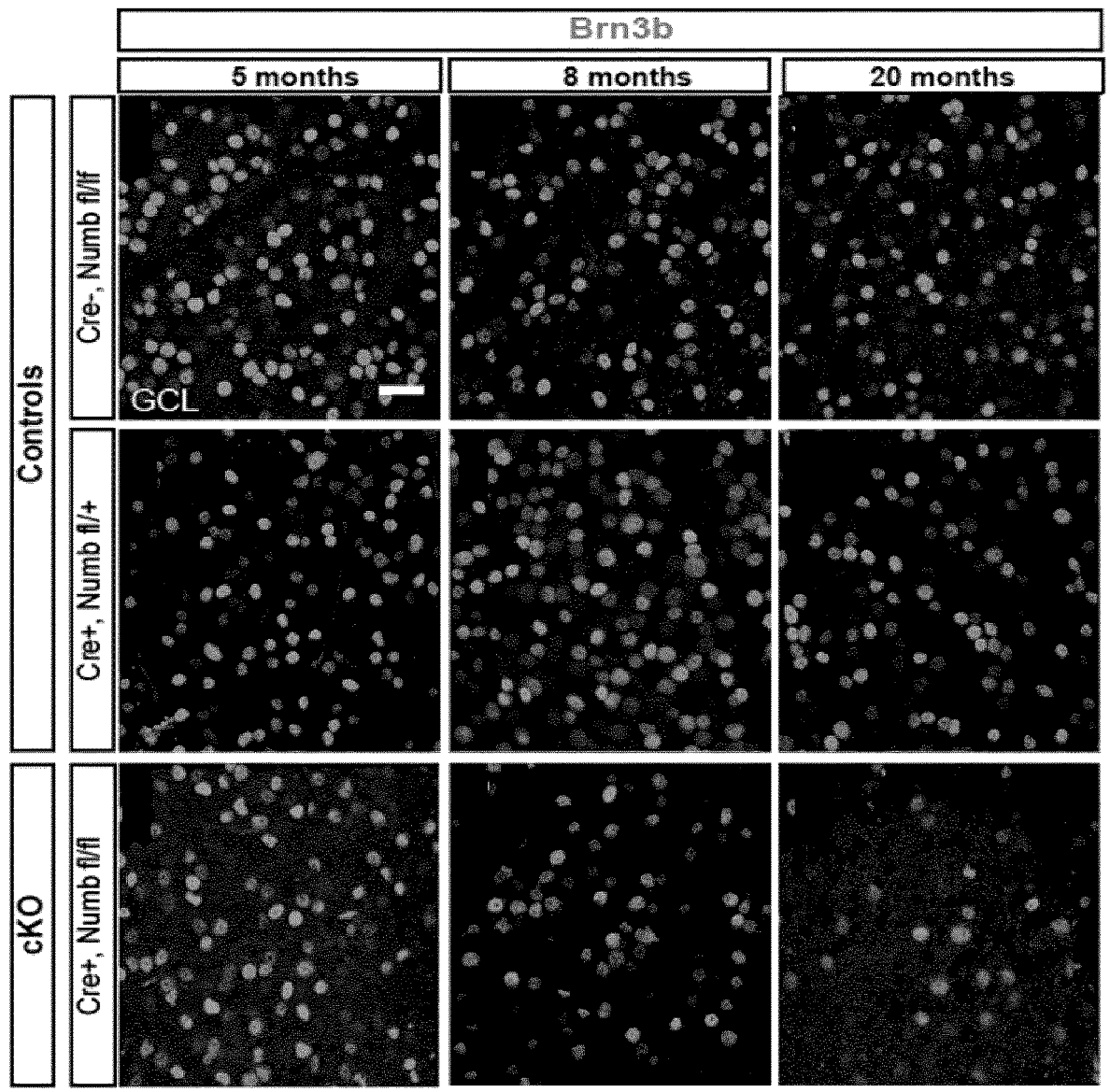
FIG. 2K. Immunostaining for Brn3b, was performed on retinal flat mounts at 5-month-old (FIG. 2K, left panels), at 8-months-old (FIG. 2K, middle panels) and 20-month-old (FIG. 2K, right panels) in controls (Cre−, Numb fl/fl; and Islet Cre+, Numb fl/+) and cKO (Islet Cre+; Numb fl/fl) mice. Images were taken in the ganglion cell layer (GCL).
Figure 2L:
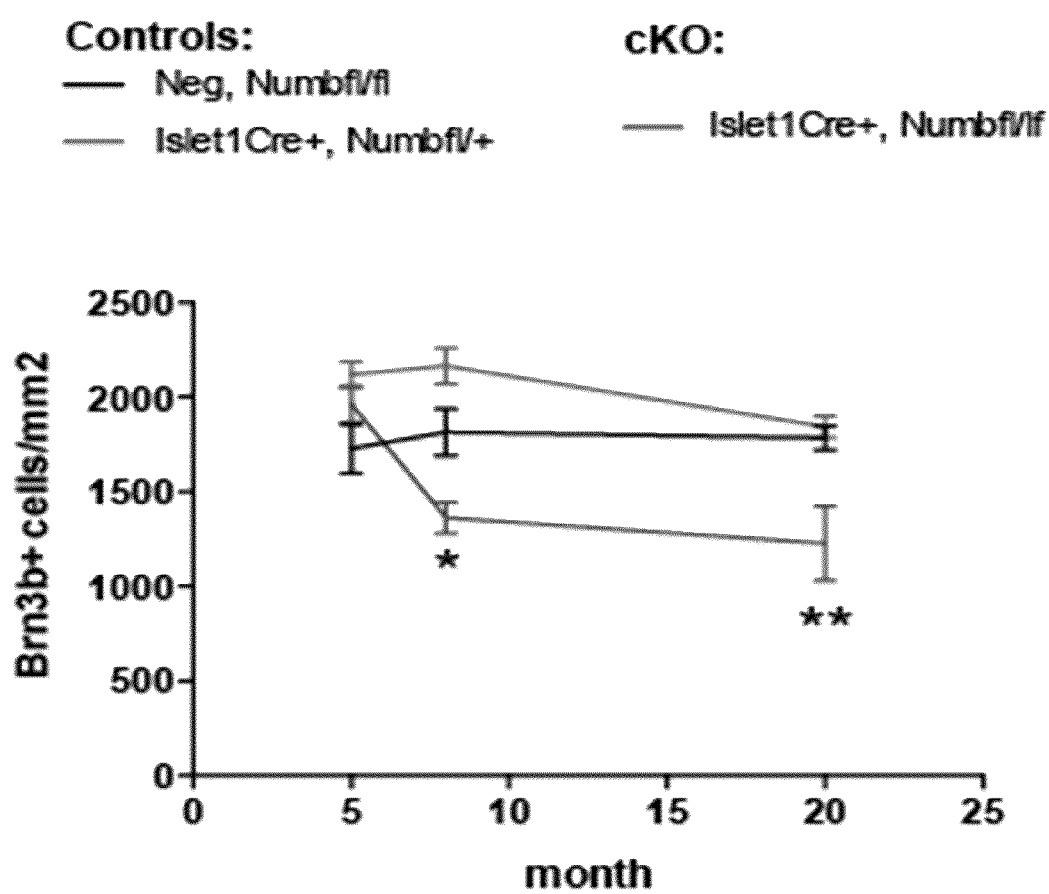
FIG. 2L. Quantification of the number of Brn3b+RGC per mm² in control and cKO mice at 5, 8 and 20 months old. A 50% loss of RGCs in 20-month-old mice was observed, indicating that Numb function is essential for long-term neuronal survival. Mean±SEM, n=5 animals/genotype/time point. Anova test n.s: not significant, * p≤0.05, **p≤0.01.

Thus, Numb is required to prevent neurodegeneration in stress conditions such as aging (FIGS. 2G and J-L). FIGS. 2G and J-L indeed show that absence of Numb in the cKO leads to neuronal cell loss in older animals only (20 month-old and 8-month old and not 5 month-old) therefore indicating that Numb protects neurons from age-induced neurodegeneration.

Figure 3A:
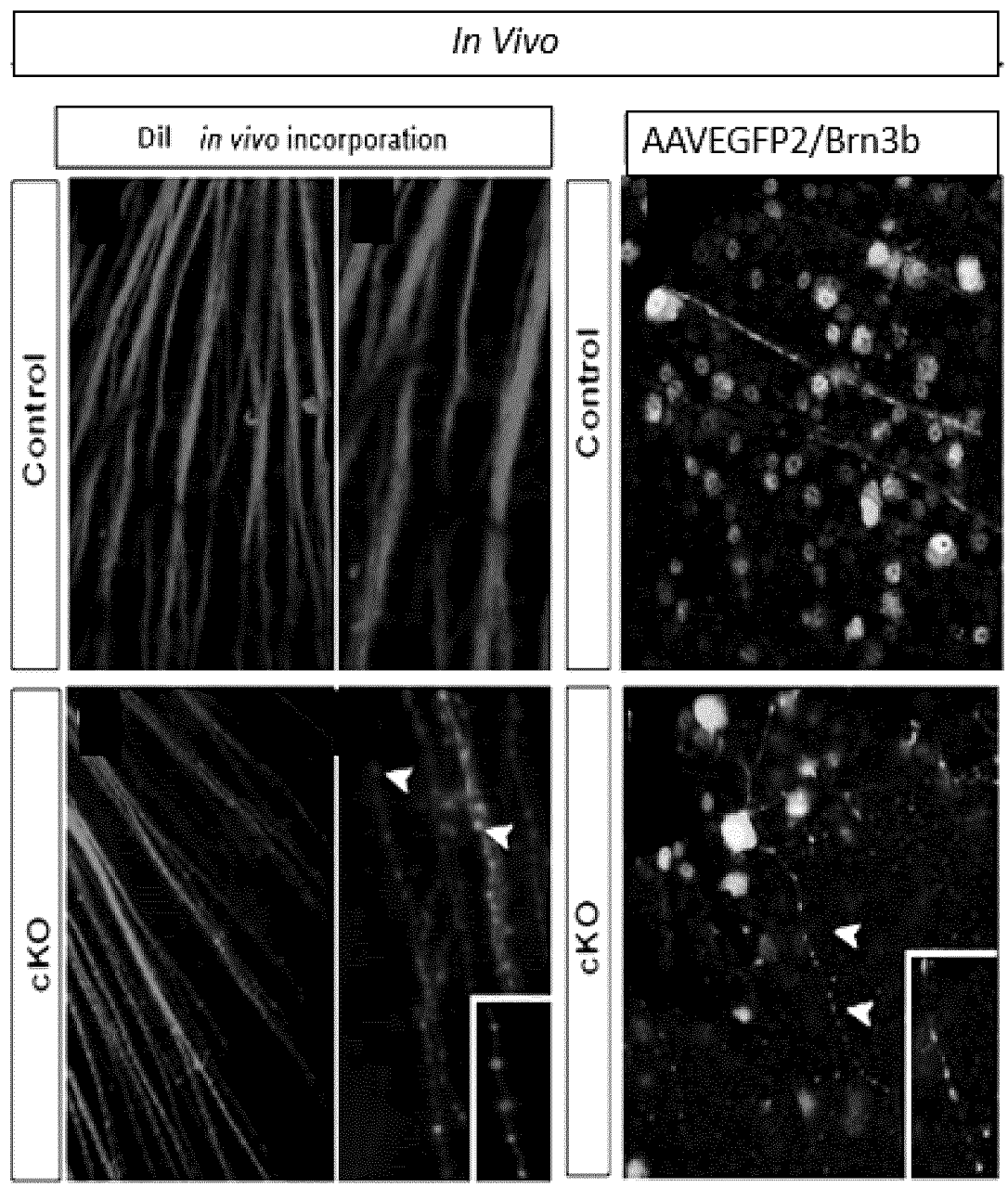
FIGS. 3A-G: Numb is essential to maintain axonal homeostasis in vivo and in culture.
Figure 3B:
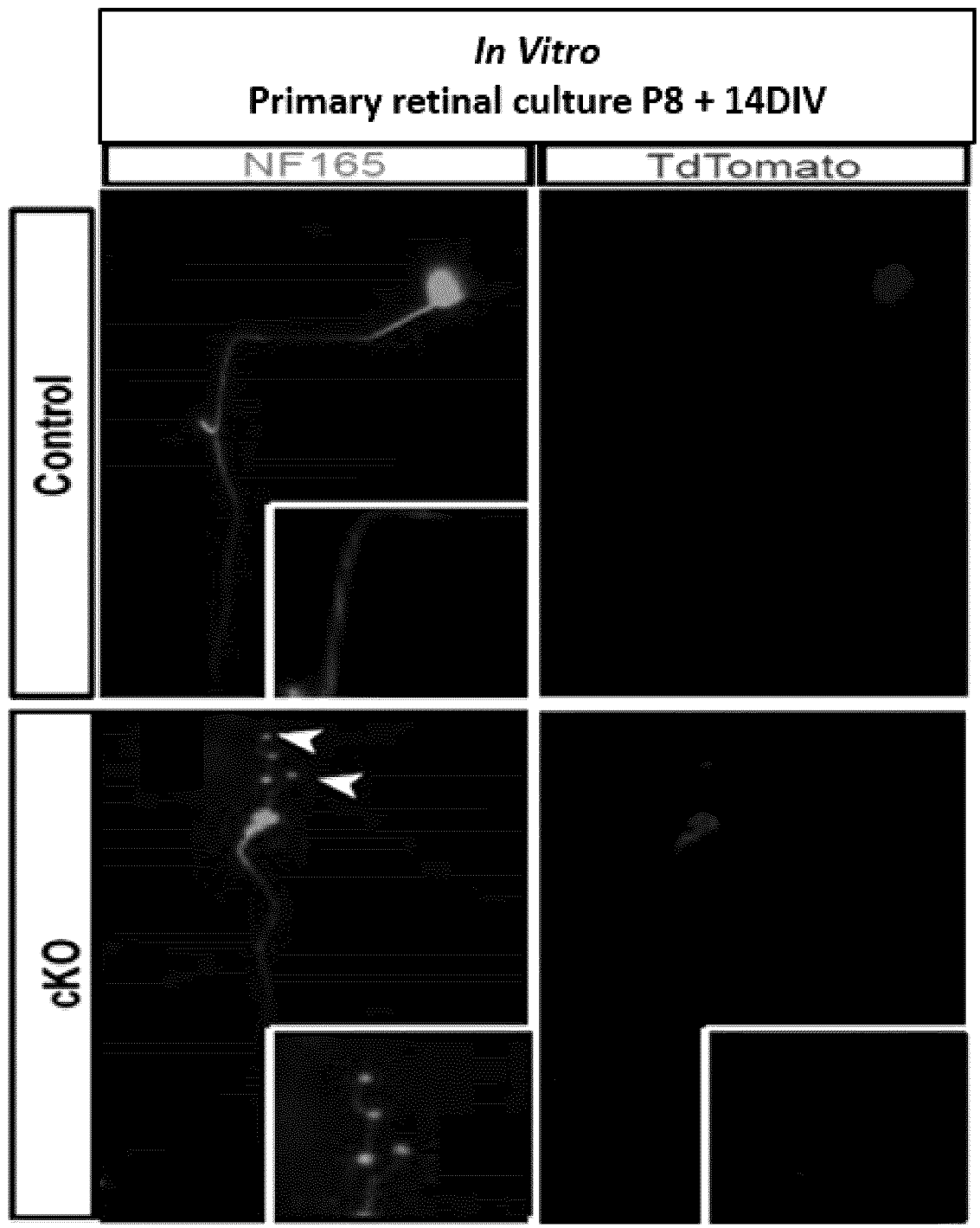
Figure 3C:
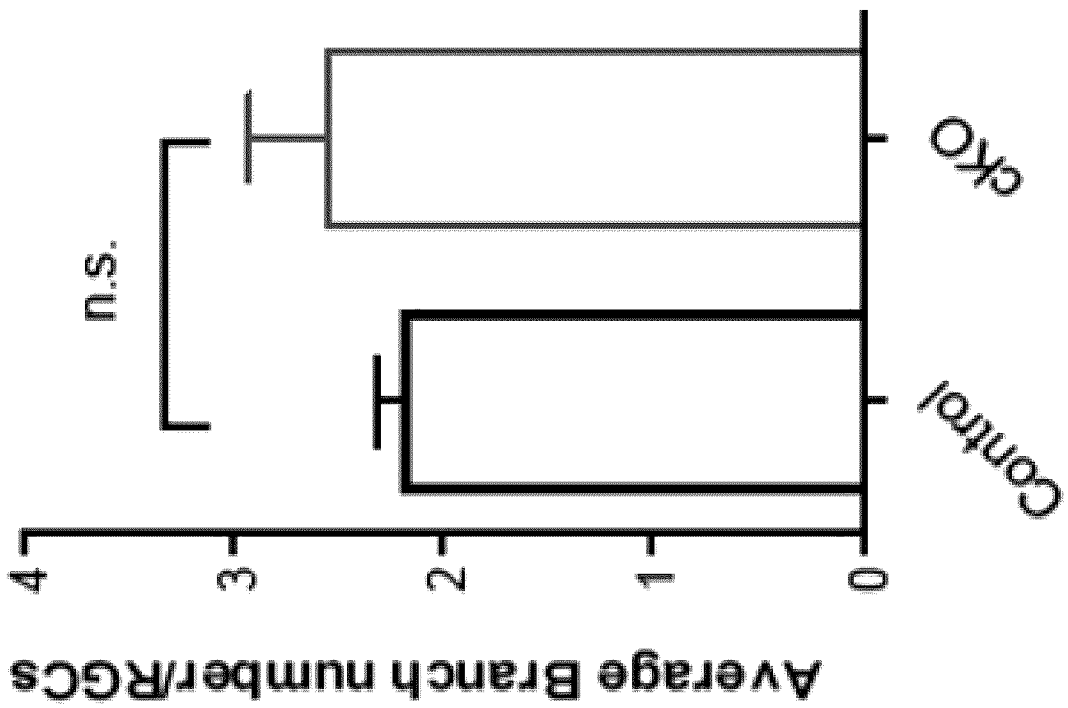
Figure 3D:
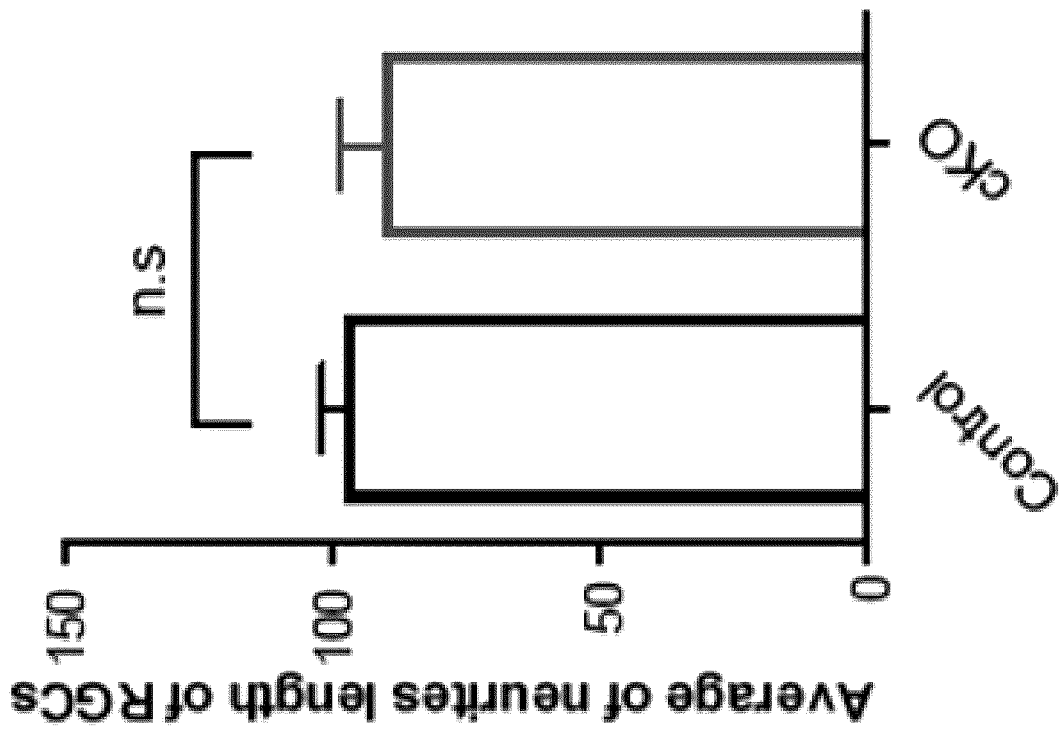
Figures 3E, 3F:
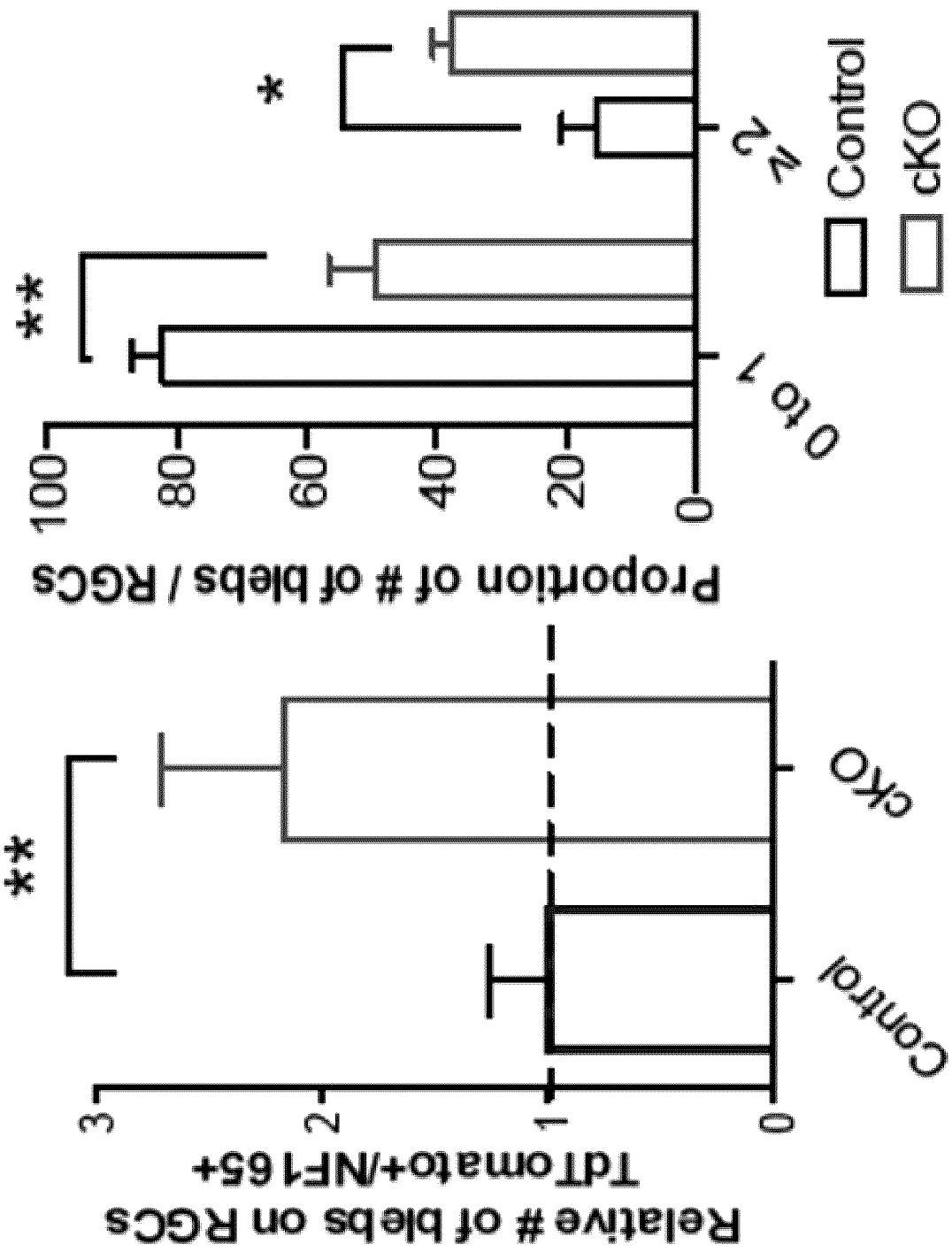
Figure 3G:
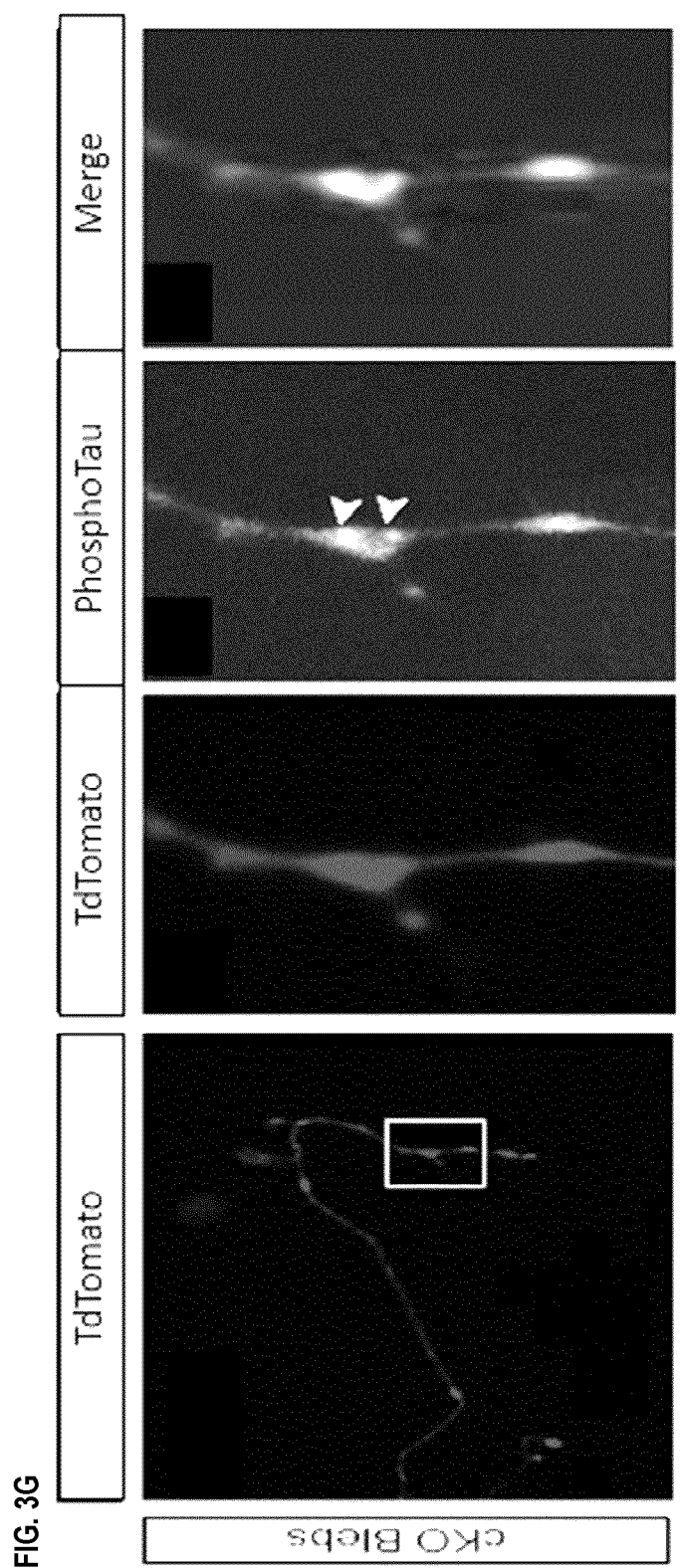

Importantly, before any cell loss could be detected, the inventors observed increased axonal blebbing in Numb cKO RGCs both in vitro and in vivo (FIGS. 3A-B (cKO: lower panels, arrows point to blebbing) and FIGS. 3E and F), but no change in neurite length (FIG. 3C) or branching (FIG. 3D), suggesting that altered axonal integrity might increase susceptibility to cellular stress. They also observed that the axonal blebs contained phosphorylated Tau (FIG. 3G), suggesting a connection between the loss of Numb and the formation of toxic forms of Tau.

Example 4: Tau Levels are Increased in Numb cKO Optic Nerves

Figure 4A:
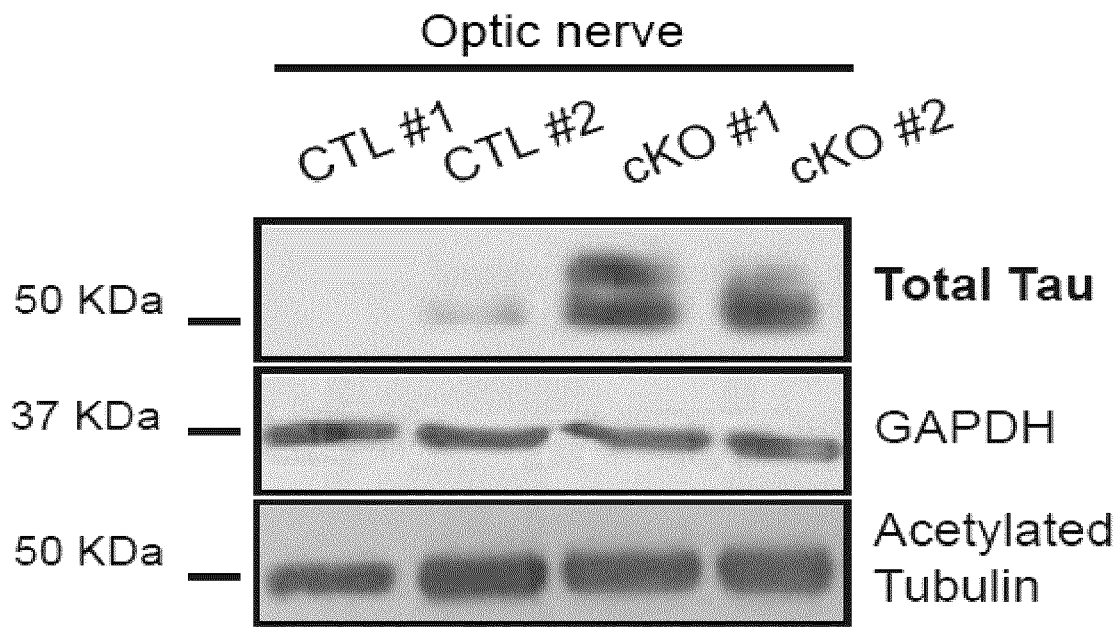
FIGS. 4A-G: Tau levels are increased in Numb cKO RGCs and Tau overexpression in RGCs phenocopies Numb inactivation.
Figure 4B:
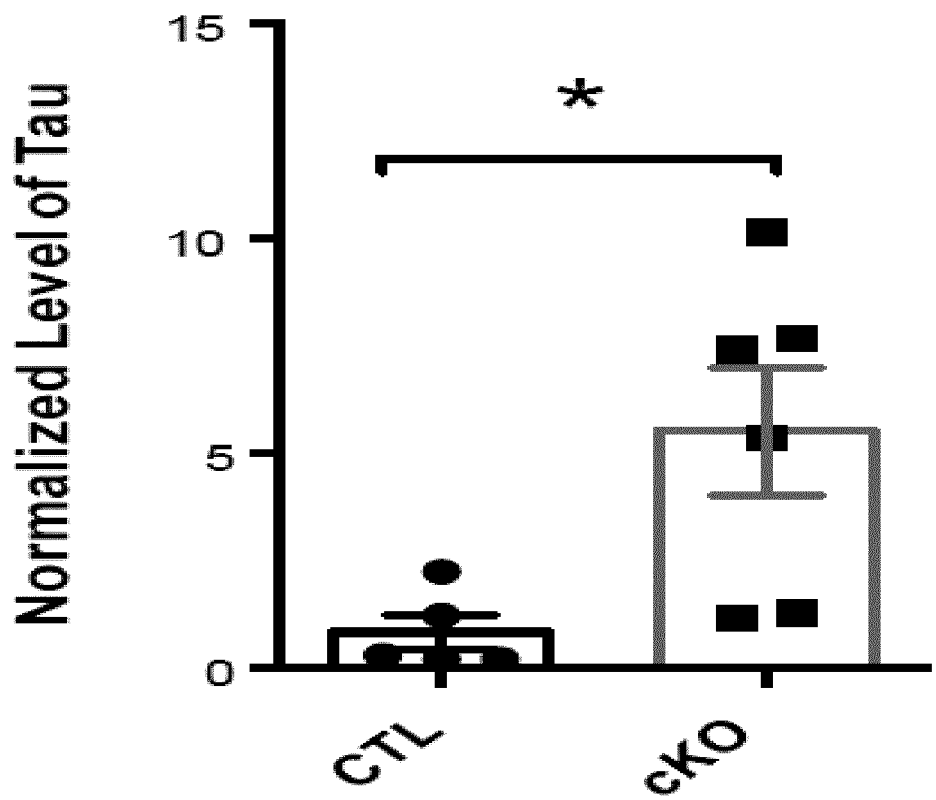
Figure 4C:
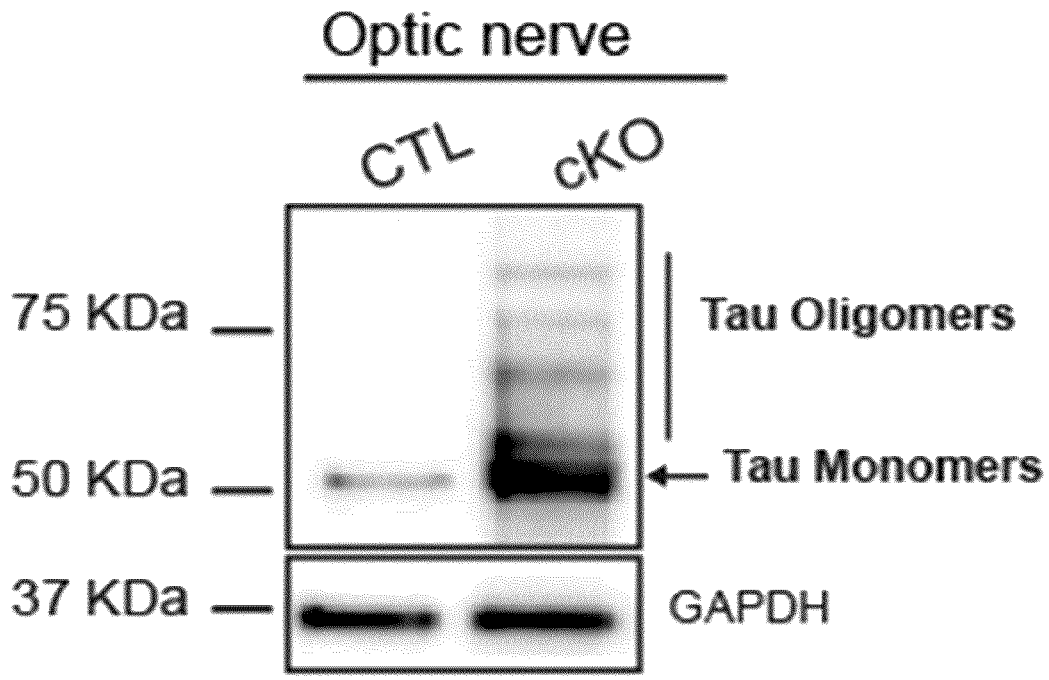
Figure 4D:
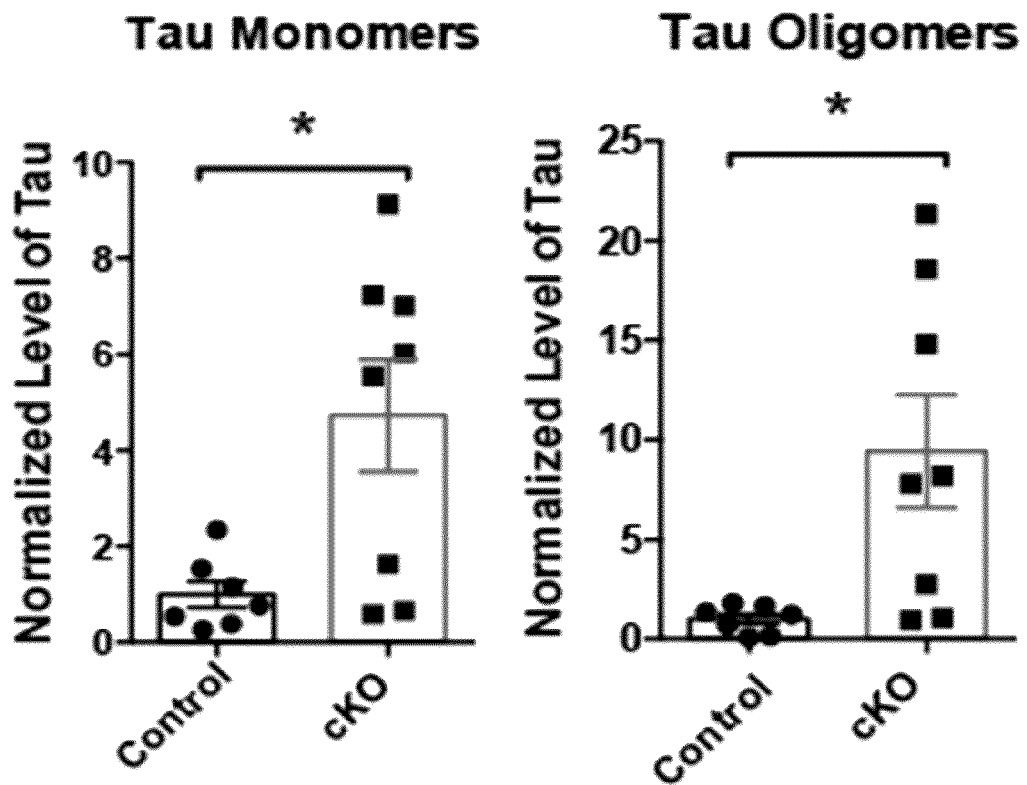

In total protein extracts of optic nerve samples (containing axons of RGCs) from control and cKO mice, the inventors found that the total levels of Tau were sharply increased in Numb cKO (FIGS. 4A-B). Similarly, the levels of oligomeric forms of Tau, which are toxic in neurons, were increased in Numb cKO optic nerves compared to controls (FIGS. 4C-D). These results indicate that Numb is required to maintain a proper balance of total and oligomeric Tau protein levels.

Figure 4E:
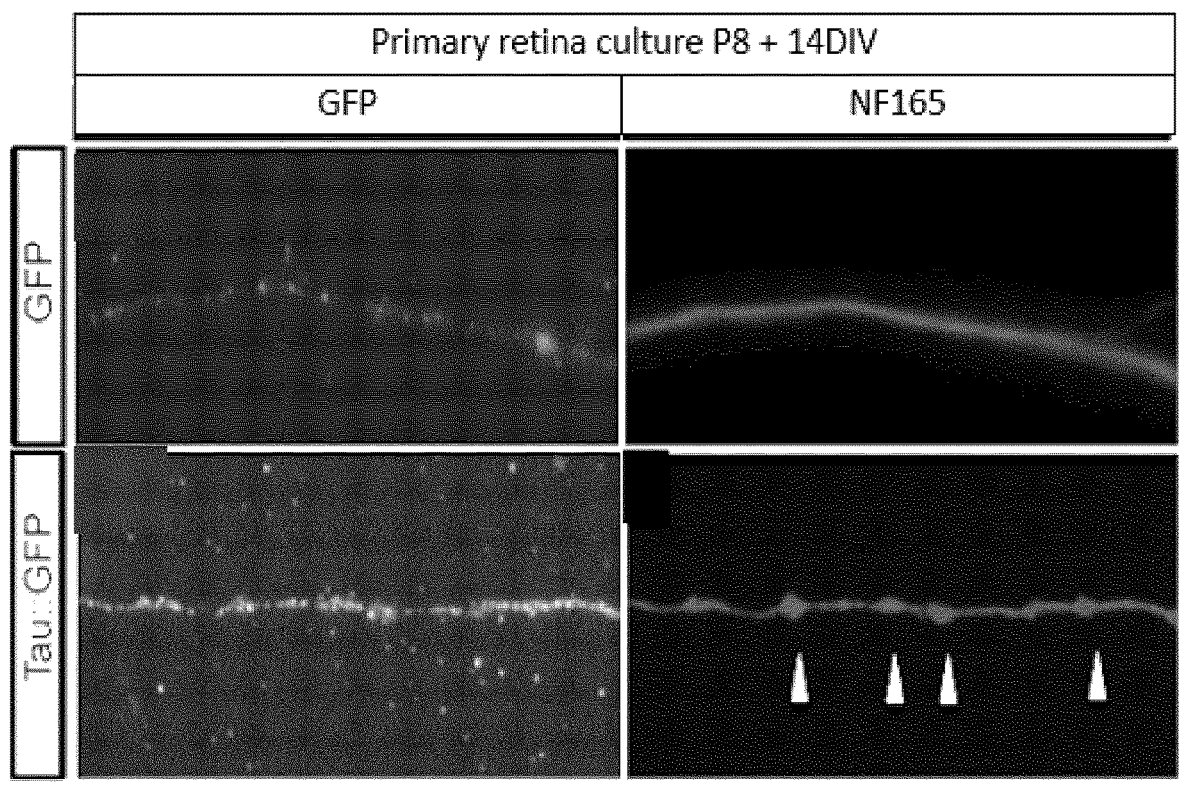
Figure 4F:
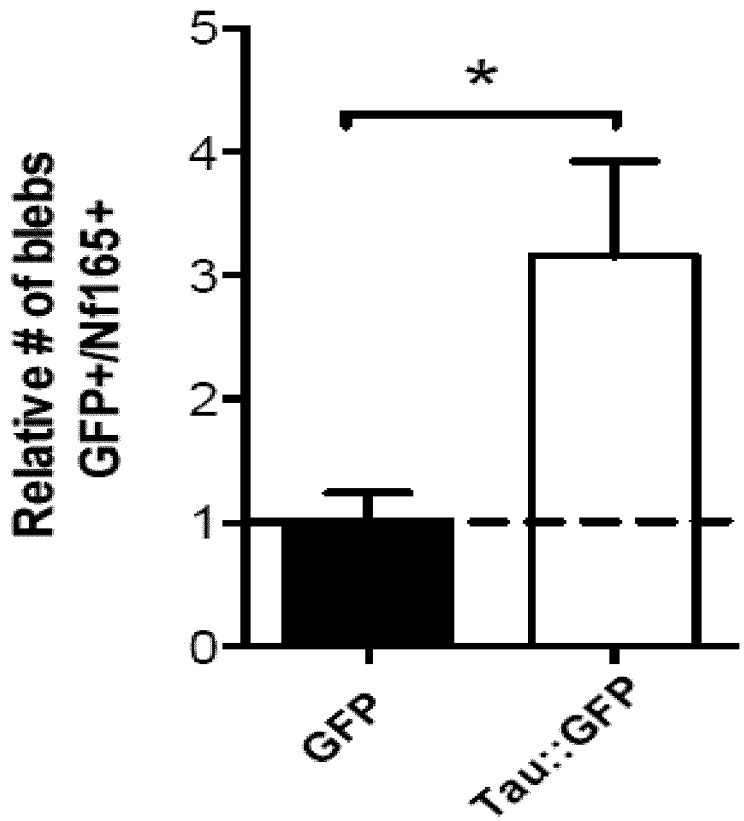
Figure 4G:
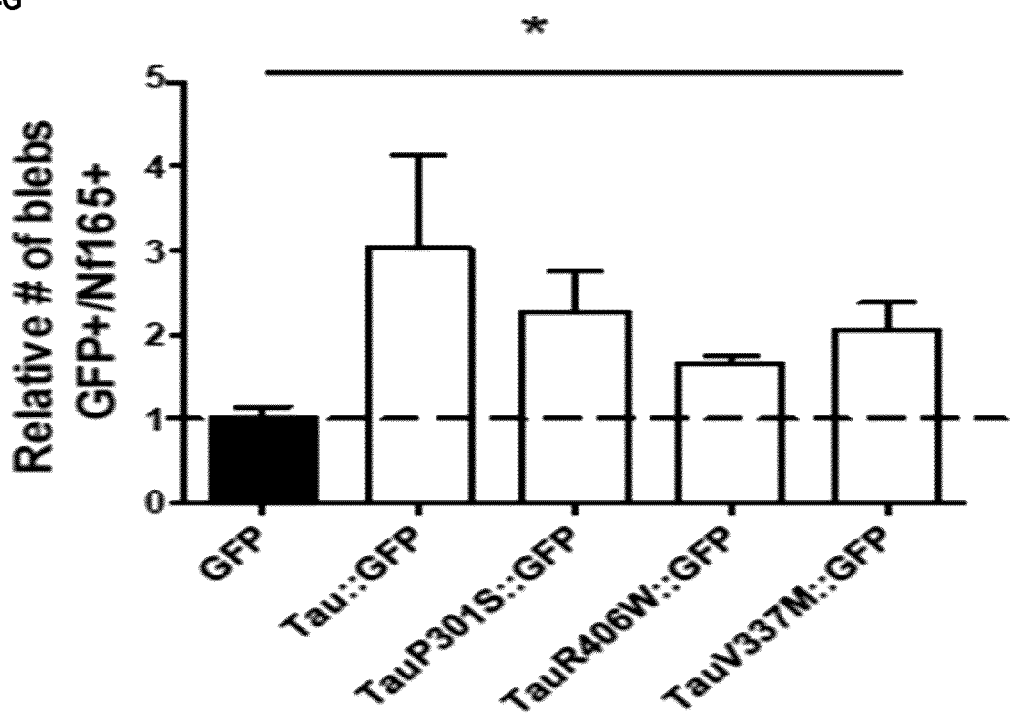

Example 5: Tau Overexpression in RGCs Leads to Axonal Blebbing, as Observed in the Numb cKO The inventors overexpressed Tau fused to GFP (Tau::GFP) (FIGS. 4E-F) or the various Tau mutants associated with tauopathies (TauP301S, TauR406W, TauV337M) (FIG. 4G) in primary mouse RGC cultures and found that they all lead to axonal blebbing (FIGS. 4E-G).

Example 6: Numb is Required to Prevent Neurodegeneration in Stress Conditions

N-methyl-D-aspartate (NMDA) receptors overactivation is linked to neurodegeneration/excitotoxicity. To study the susceptibility of neurons to excitotoxicity in the presence or absence of Numb, the inventors injected sublethal doses of NMDA or a control saline solution in the eyes of Numb cKO and control mice and studied RGC survival 3 days later. Whereas saline injections did not affect the number of RGCs, they found that NMDA injections led to a two-fold reduction of RGC numbers in Numb cKO mice compared to control (FIGS. 5A-C).

Figure 5A:
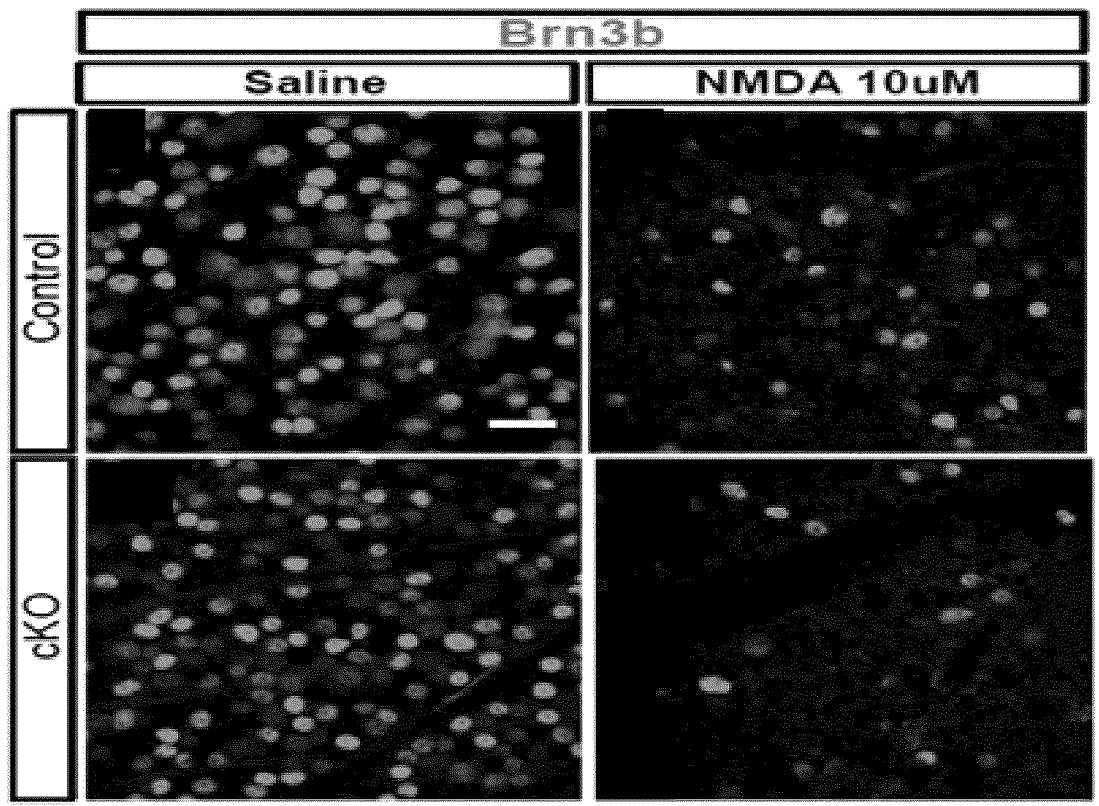
FIGS. 5A-C: Down regulation of Tau in Numb cKO RGCs rescues survival to control levels after NMDA-mediated excitotoxicity.
Figure 5B:
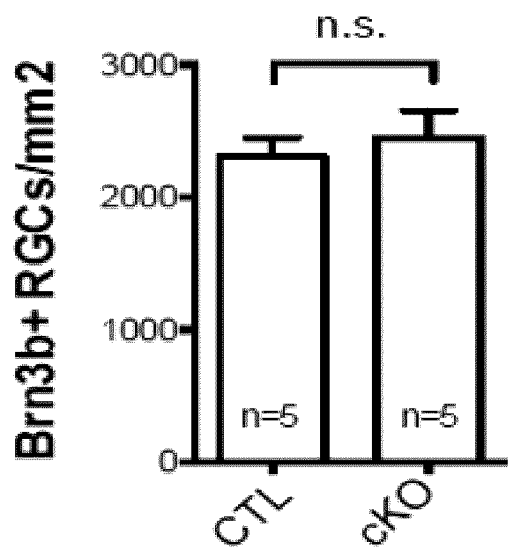
Figure 5C:
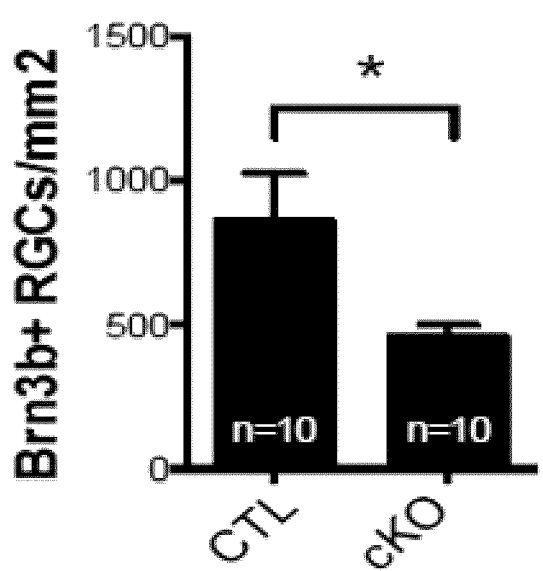

Thus, as indicated in Example 2 above, Numb is required to prevent neurodegeneration in stress conditions such as age-induced neurodegeneration (FIGS. 2G and J-L), and, as shown in this Example, such as excitotoxicity (FIGS. 5A-C).

Figure 5D:
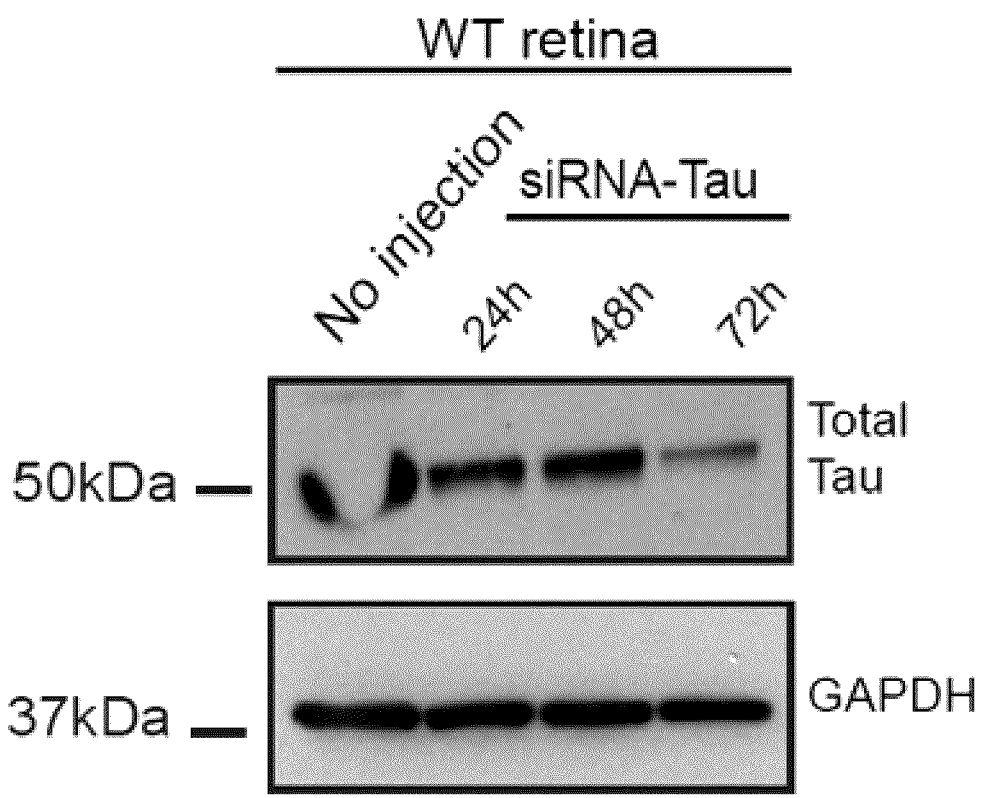
FIG. 5D. Analysis of Tau levels by western blot in retinal extract 24 h, 48 h or 72 h after injection of siRNA against Tau in the eye. Tau levels show a significant reduction after 72 h.
Figure 5E:
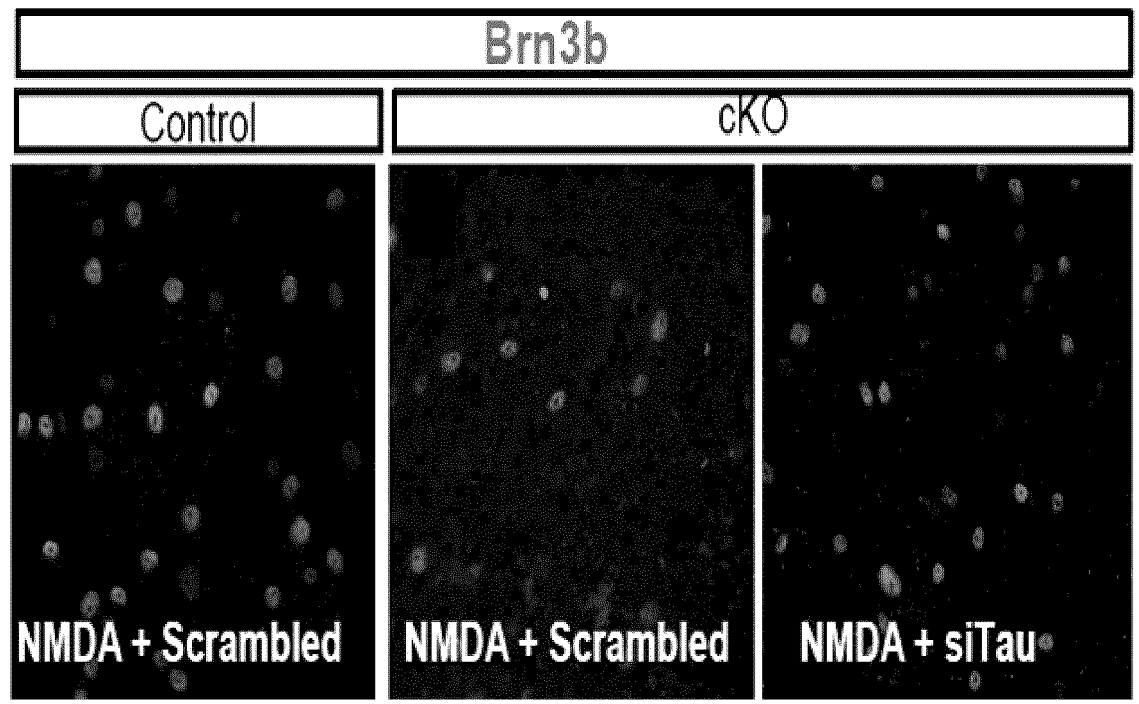
FIG. 5E. Immunostaining for Brn3b on retina flat mount 72 h (3 days) after injection of sublethal doses of NMDA (10 nM) in the eye with scramble siRNA (middle panel) or with siTAU (right panel) in 5-month-old control and cKO mice. Images were taken in the ganglion cell layer.
Figure 5F:
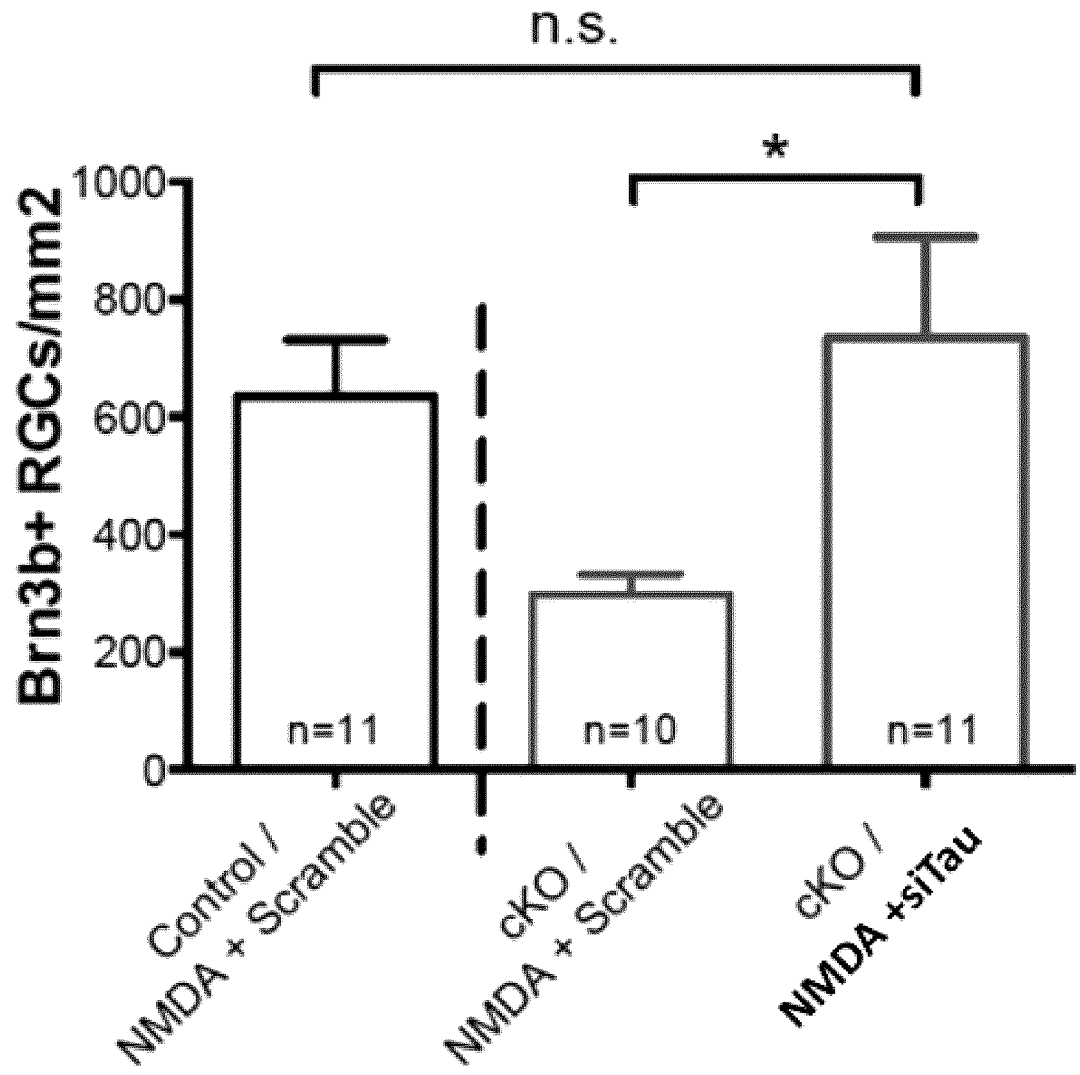
FIG. 5F. Quantification of number of Brn3b RGC per mm² in control and cKO mice 72 h after injection. Error bars represent SEM, n.s is not significant, * $p \leq 0.05$; Anova test.

To determine whether the elevated Tau levels in Numb cKO were responsible for the increased susceptibility to NMDA-mediated neurodegeneration, the inventors co-injected NMDA with an siRNA targeting Tau. They found that reducing Tau levels with the siRNA was sufficient to rescue RGC numbers to those of control-injected eyes (FIGS. 5D-F).

Example 7: Numb Interacts with Tau

Figure 6A:
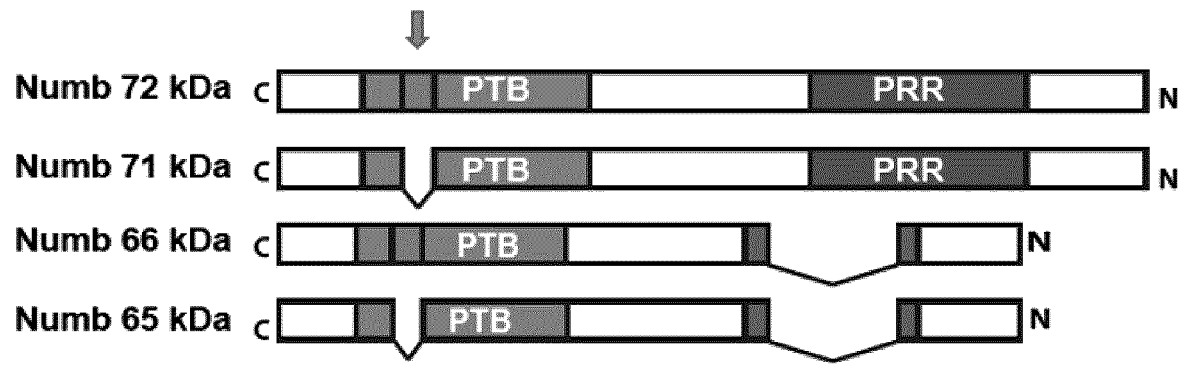
FIGS. 6A-I: Isoform Numb-72 interacts with Tau and regulates Tau level.
Figure 6B:
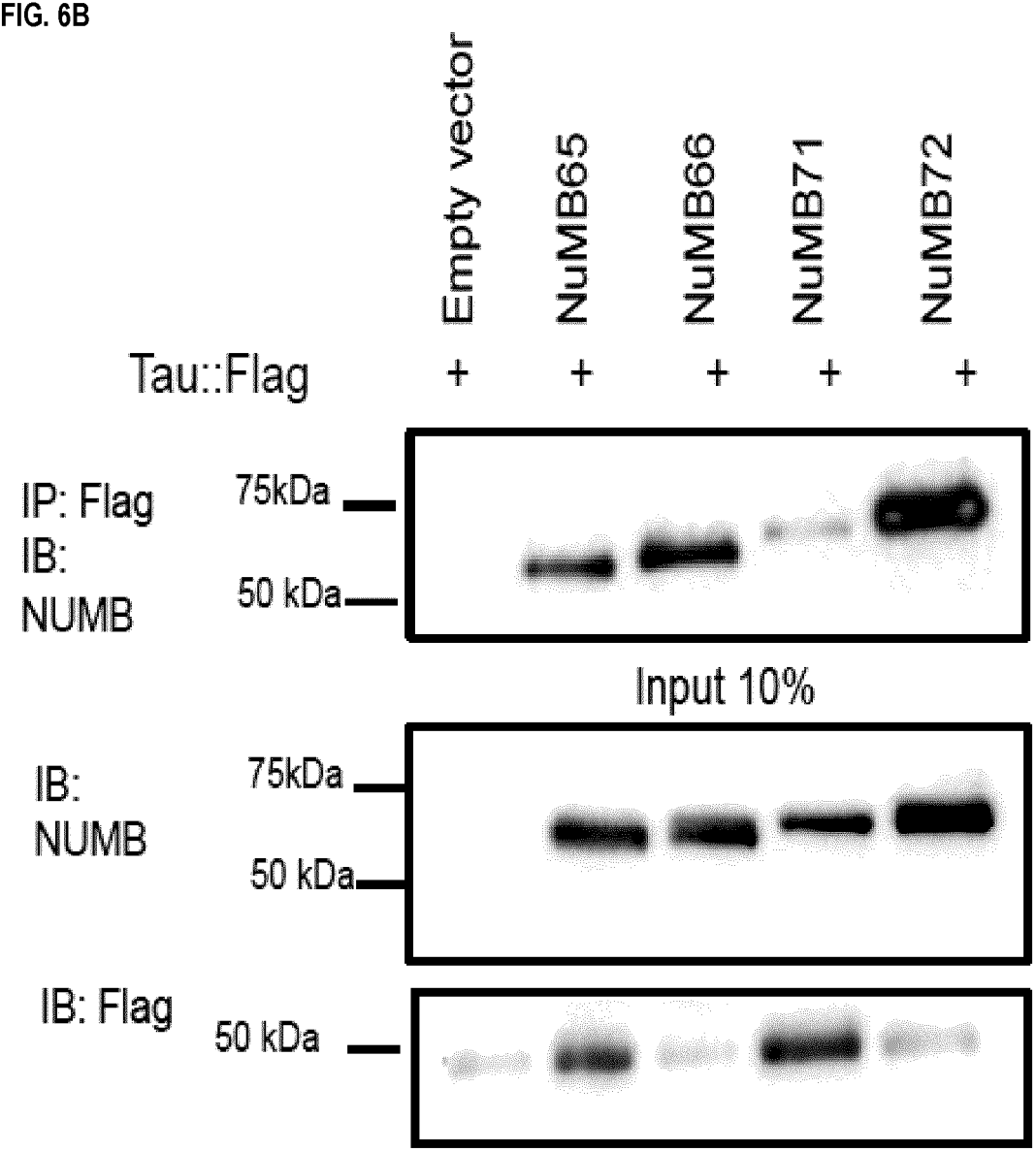

To study a possible physical interaction between Numb and Tau, the inventors expressed each isoform of Numb in HEK293T cells together with a flag-tagged version of Tau and 24 hours later they immunoprecipitated with a flag antibody and blotted for Numb. They found that all isoforms of Numb co-immunoprecipitated with Tau:Flag, showing that the proteins form a complex (FIGS. 6A-B).

Example 8: Numb Decreases Tau Levels in an Isoform-Specific Manner

Figure 6C:
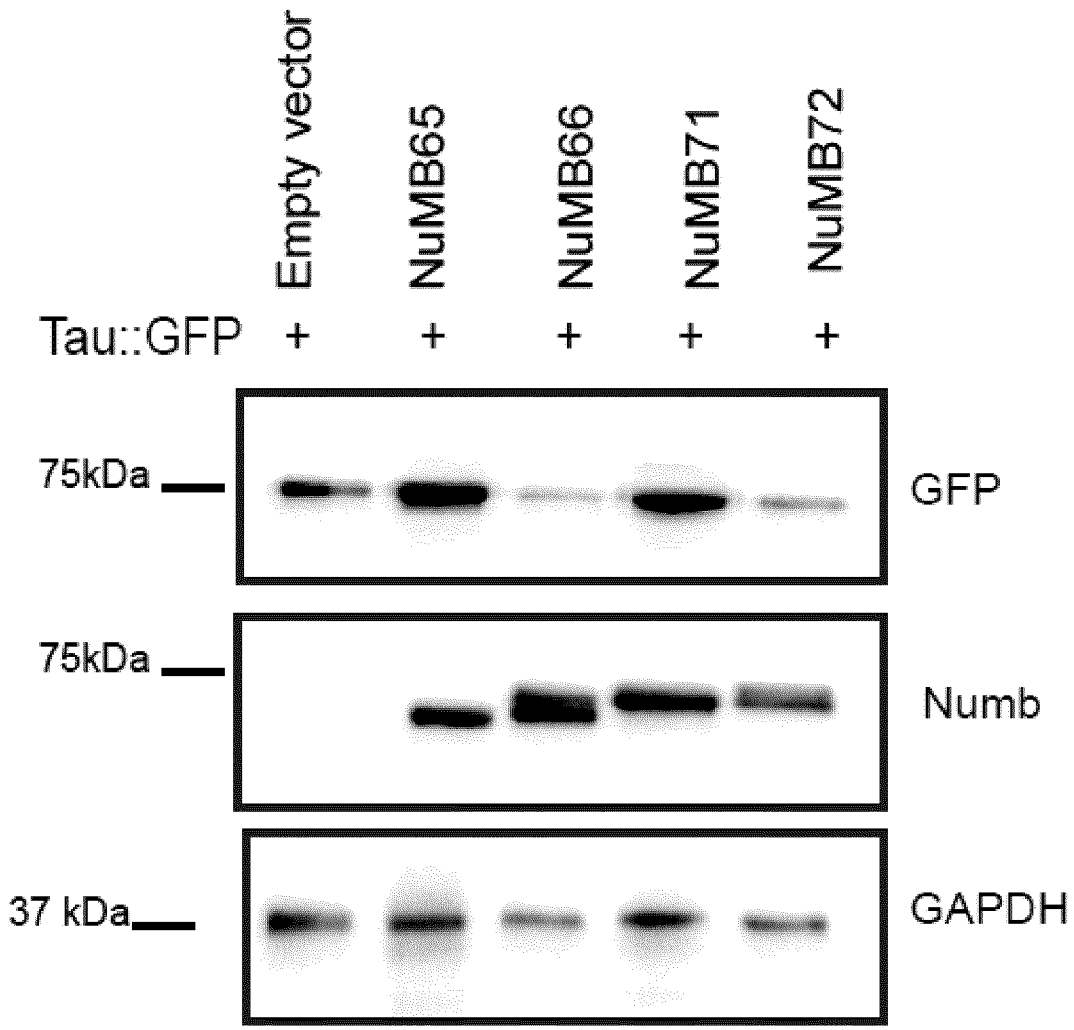

To determine whether increasing the levels of Numb could affect the levels of Tau, the inventors co-expressed all isoforms of Numb together with a Tau::Venus fusion protein in HEK293T cells and analyzed the levels of Tau::Venus by western blot 48 hours after transfection. While Numb-65 and Numb-71 did not affect Tau levels, Numb-72 and Numb-66 significantly reduced the levels of Tau in this assay (FIGS. 6B-C).

Figure 6D:
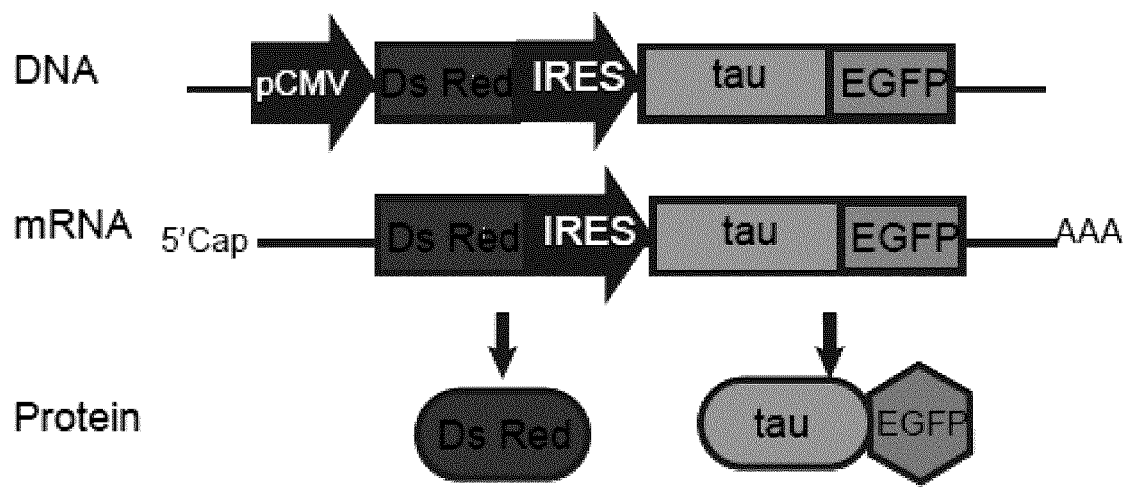
Figure 6E:
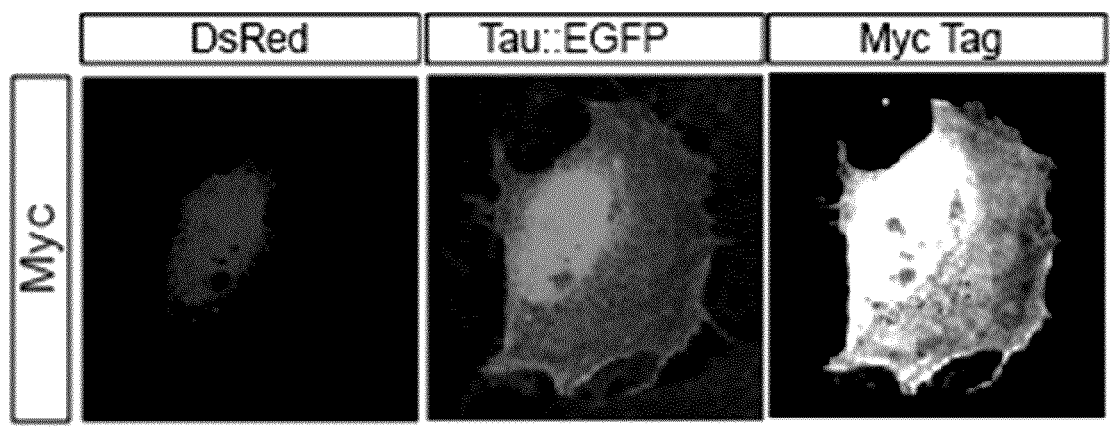
Figure 6F:
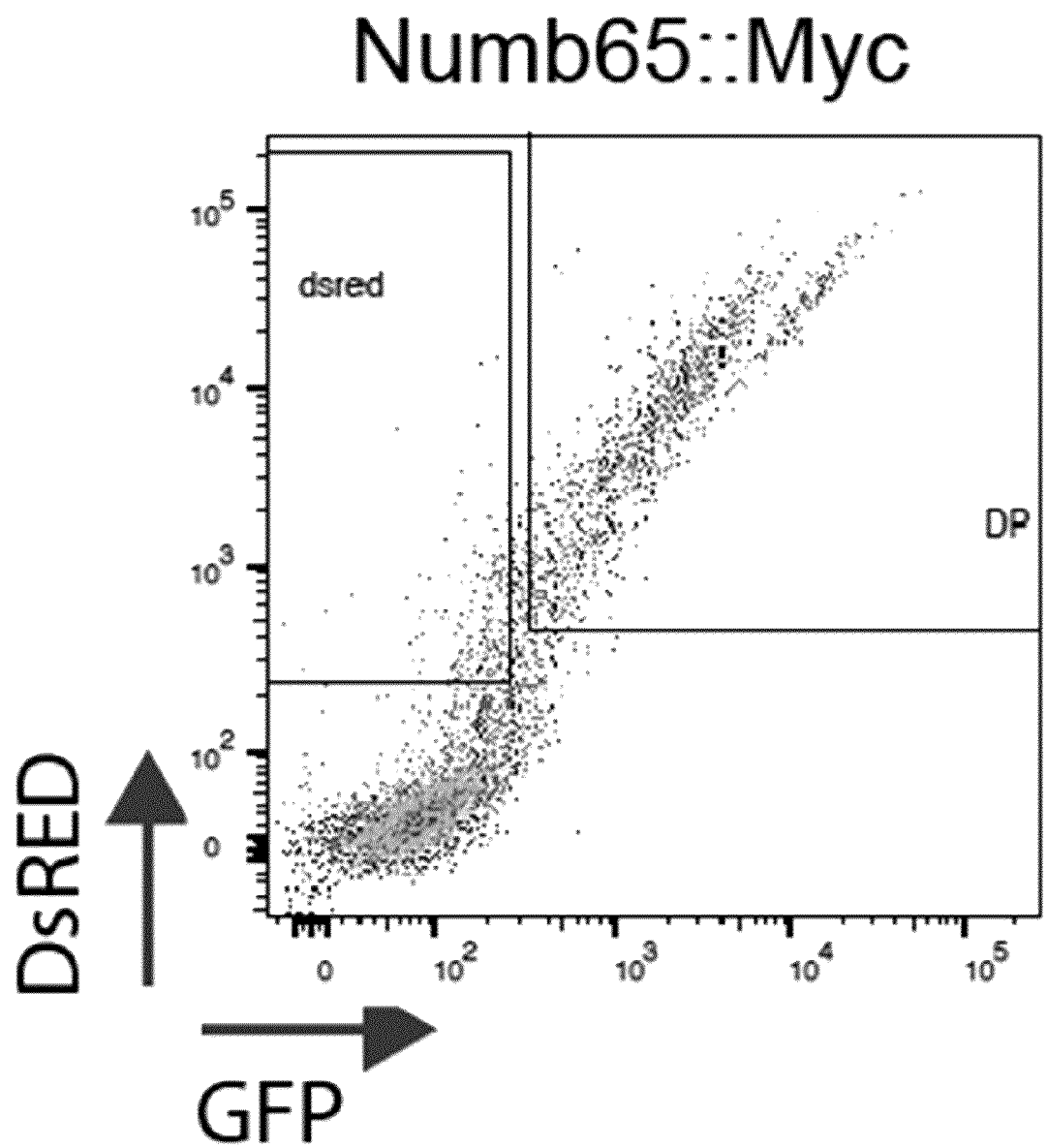
Figure 6G:
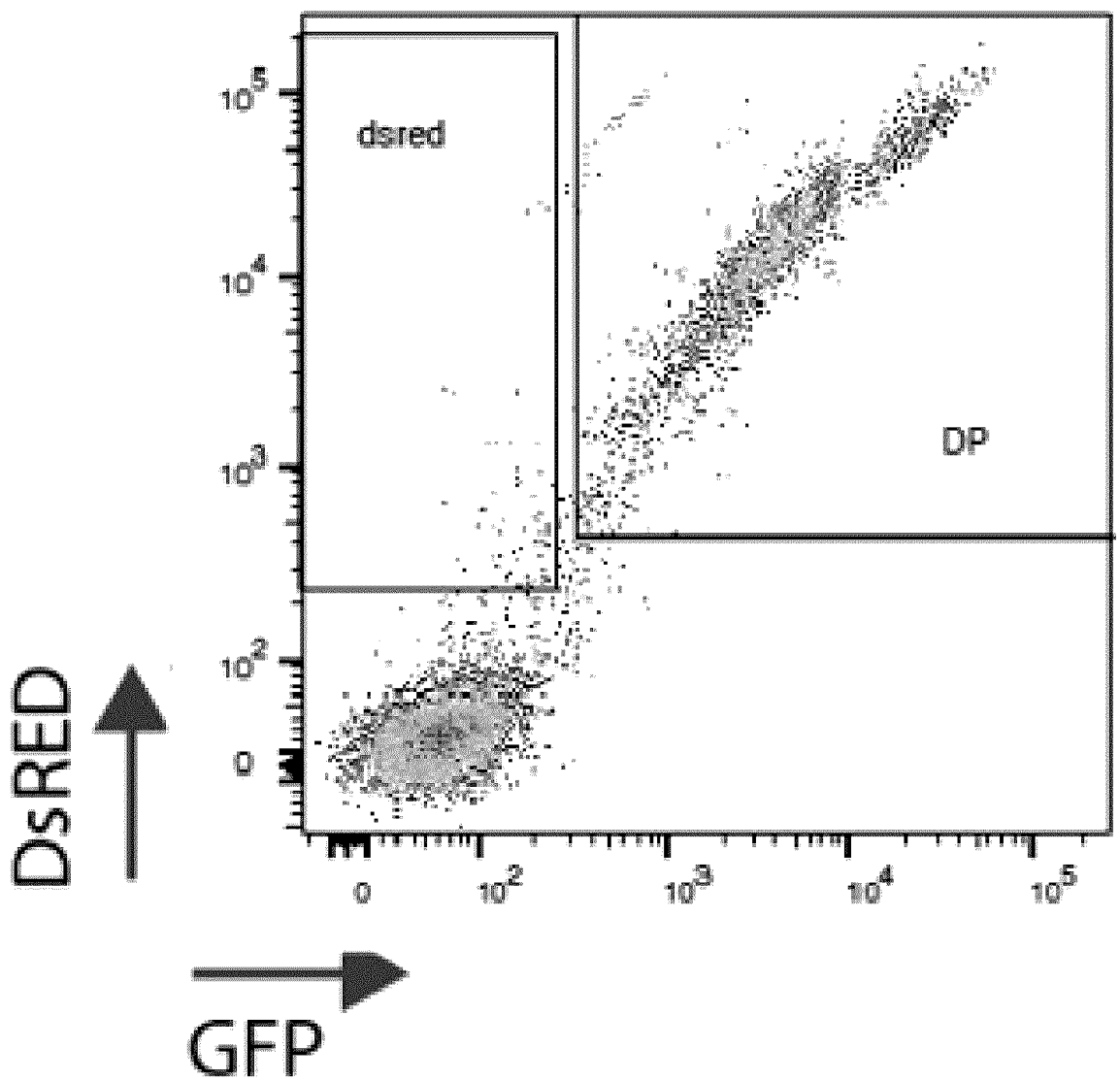
Figure 6H:
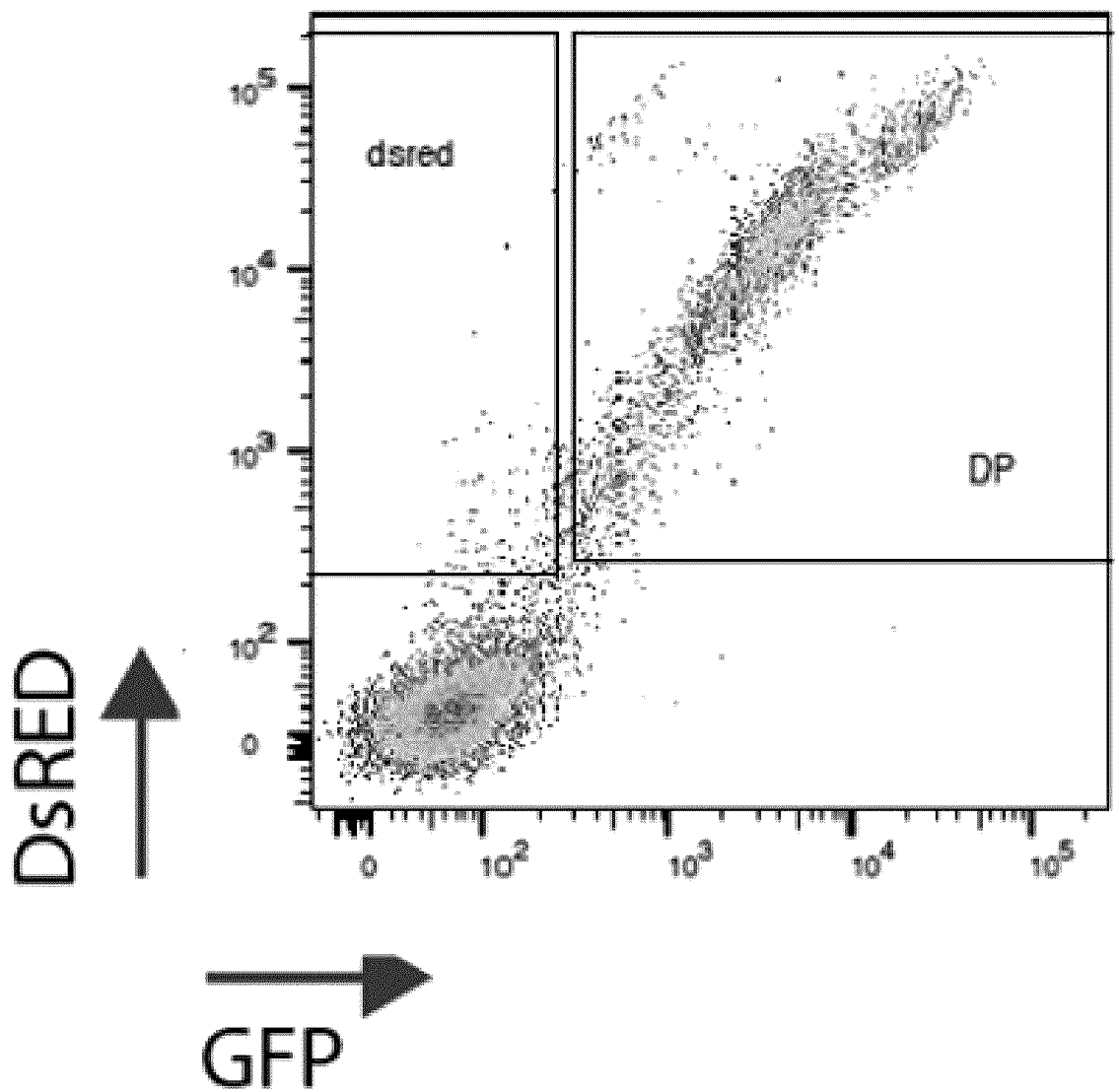
Figure 6I:
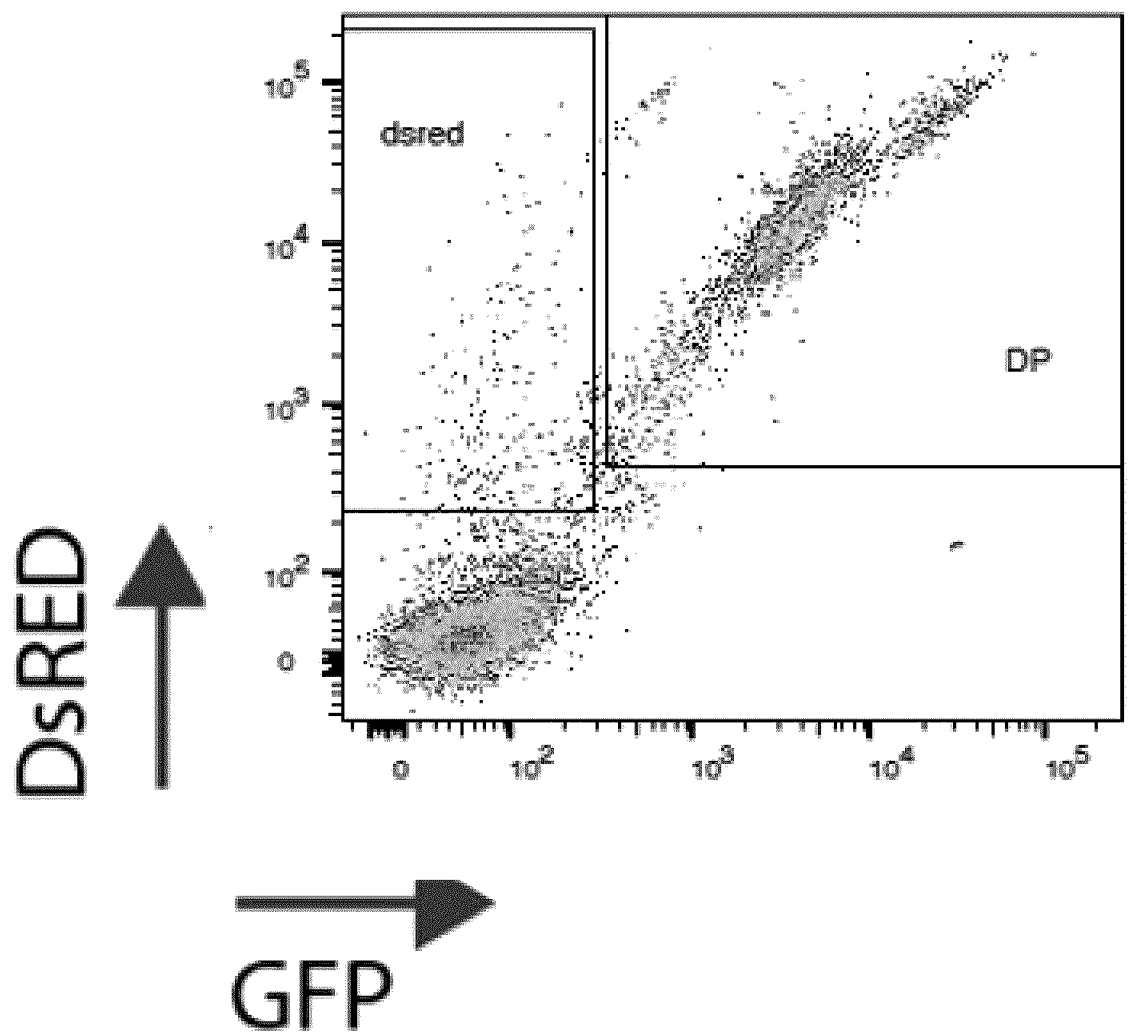
Figure 6J:
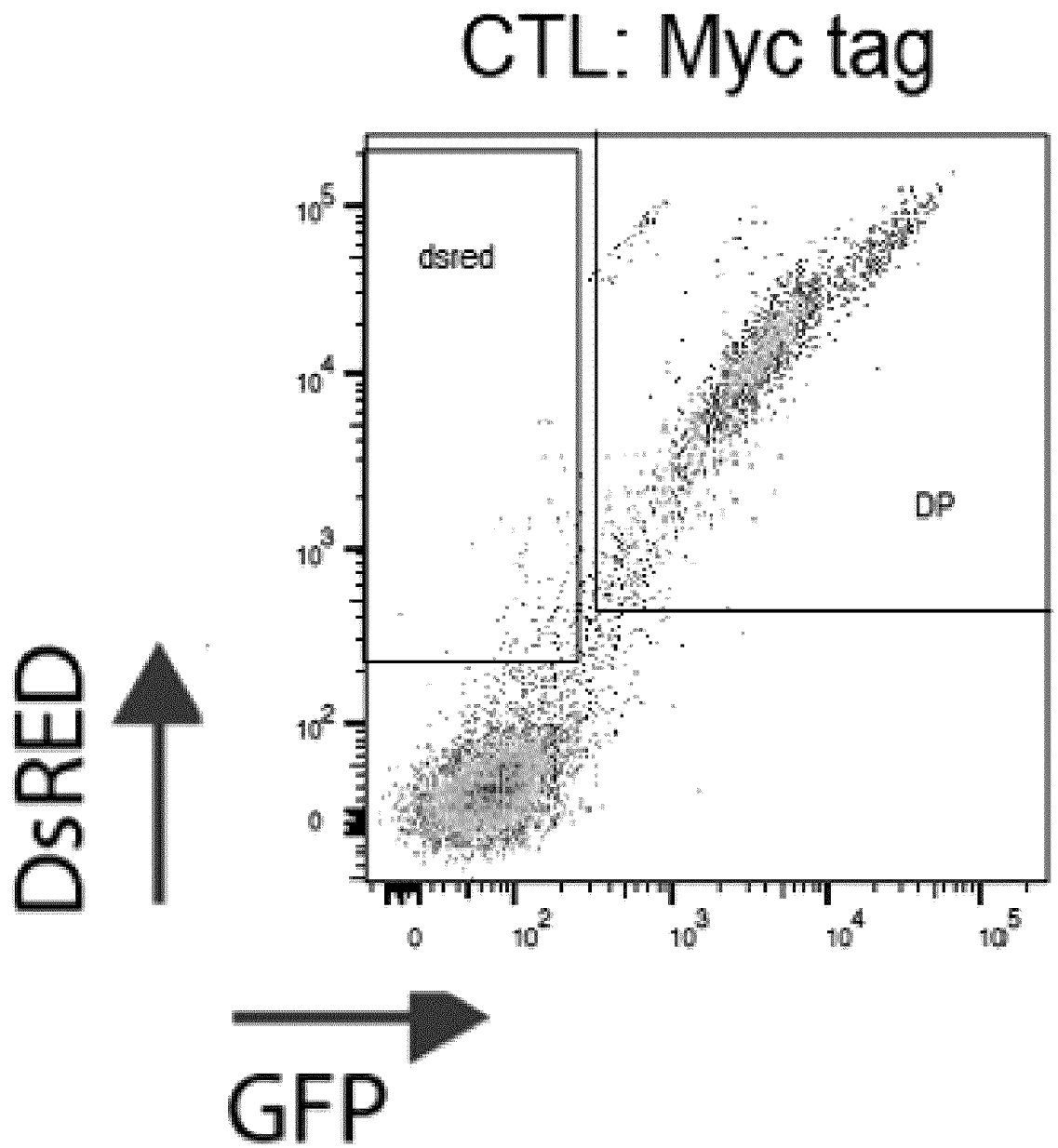
Figure 6K:
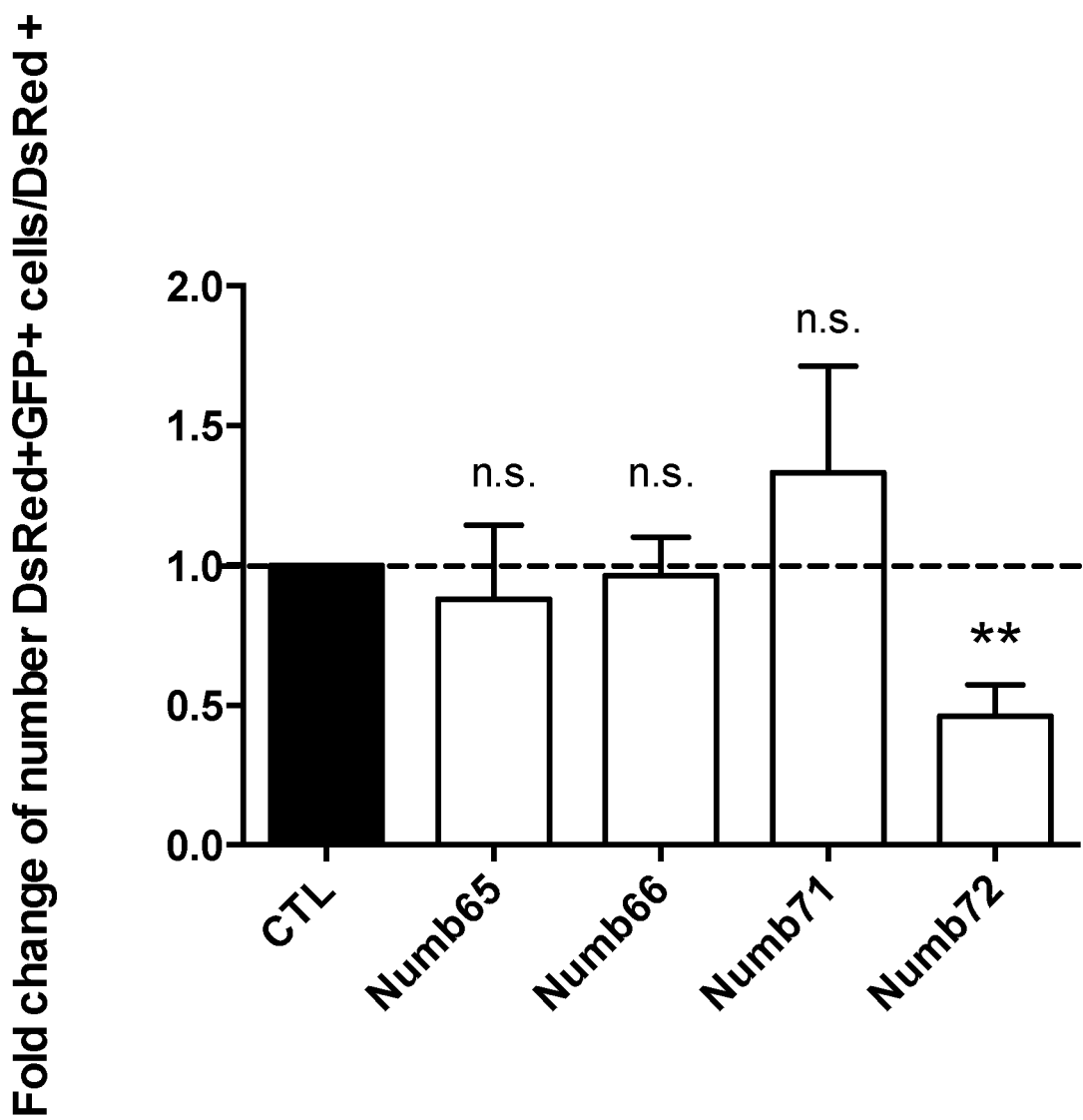
FIG. 6K Quantification represents fold change for 5 experiments, +/− SEM, **$p \leq 0.001$; n.s. non-significant Anova 1-way test.

Each Numb isoform was then transfected in a human-medulloblastoma-derived cell line (DAOY) expressing human Tau fused with GFP (Lasagna-Reeves et al., 2016). Additionally, this cell line expresses DsRed upstream of an internal ribosomal entry site (IRES), which is translated independently of the Tau-GFP protein, allowing to distinguish between effects of Numb on Tau protein levels from effects on transgene transcription (FIGS. 6D-E). Three days after transfection, the cells were collected and the levels of Tau-GFP over DsRed were analyzed by flow cytometry. Expression of Numb-72 increased the proportion of cells with low levels of Tau-GFP, compared to controls in this assay (FIGS. 6F-K). These results indicate that in this assay overexpression of Numb-72 reduces the levels of intracellular Tau in human cells.

Together, these results suggest that while Numb-72 is more consistent at doing so in multiple contexts and different cell lines than Numb-66, both Numb-66 and Numb-72 (which both have a long PTB) can reduce Tau levels.

Figure 7A:
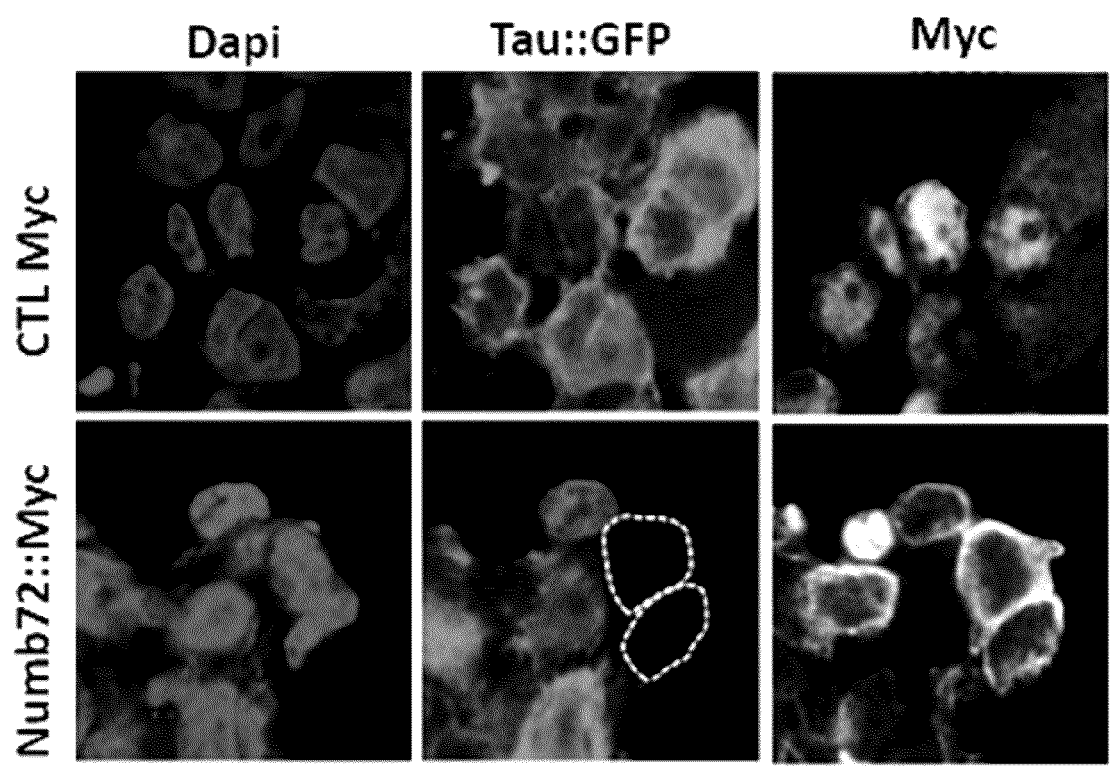
FIGS. 7A-B: Reduction of Tau levels by Numb72 does not appear to require the proteasome or lysosome pathways.
Figure 7B:
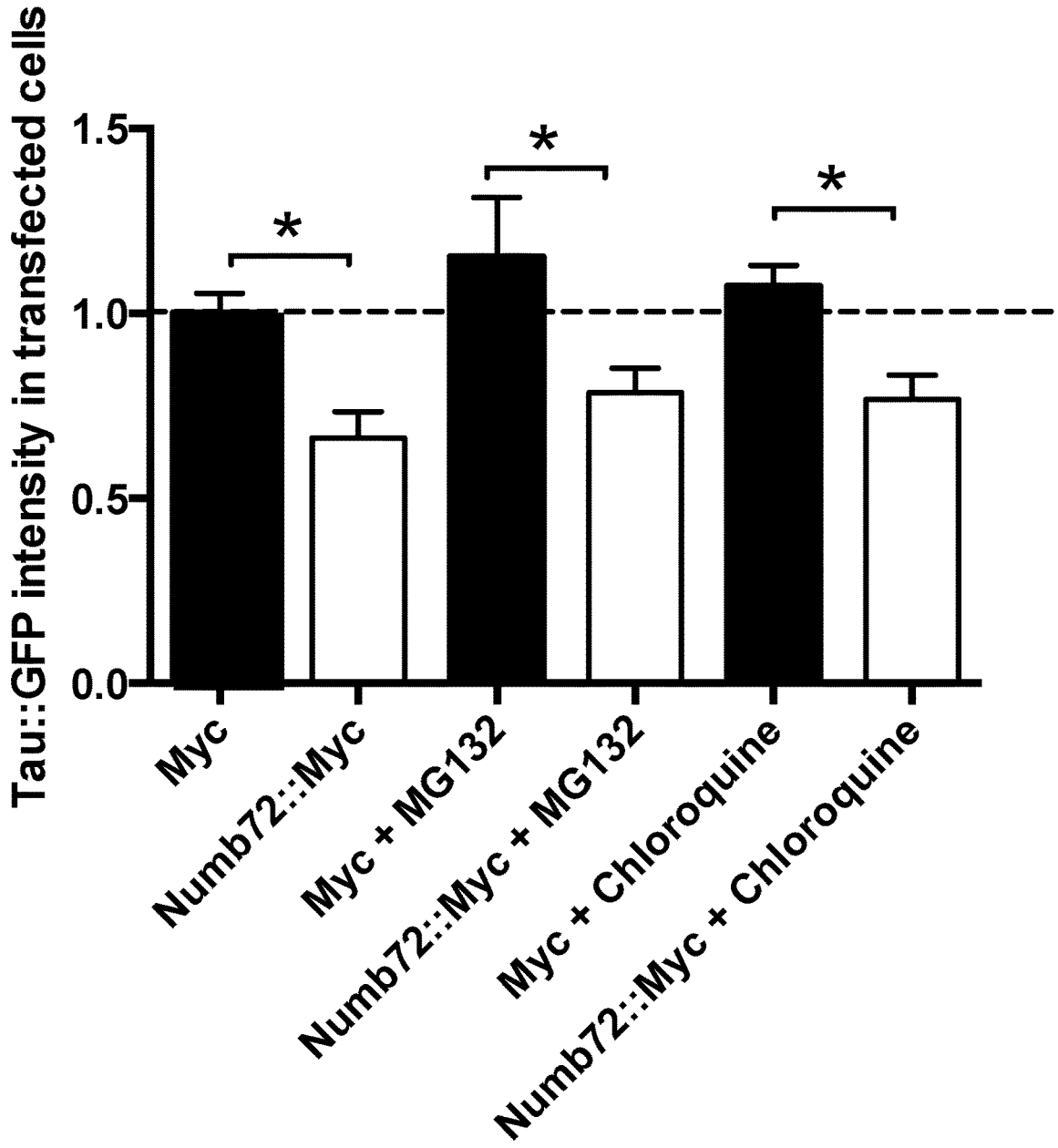

Example 9: Reduction of Tau Levels by Numb72 does not Appear to Require the Proteasome or Lysosome Pathways The potential role of the proteasome and of the lysosome on the ability of Numb to reduce Tau levels was assessed. A stable inducible cell line (HEK293) expressing a Tau::GFP fusion protein was transfected with Numb72 or a control empty vector. The intracellular Tau::GFP levels was compared when the cells were treated with a proteasome inhibitor (MG132), a lysosome inhibitor (Chloroquine) or a control (vehicle). Numb72 induced a decrease of Tau::GFP levels, and neither the proteasome inhibitor nor the lysosome inhibitor abolished the ability of Numb72 to reduce Tau::GFP levels, suggesting that the proteasome or lysosome activity is not required for Numb function. (FIGS. 7A-B).

Figure 8A:
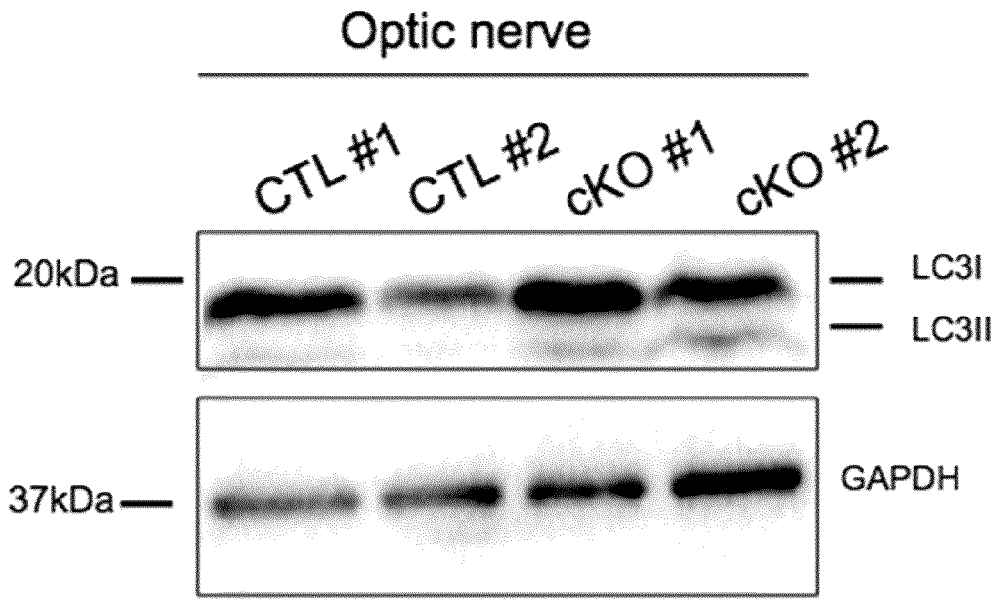
FIGS. 8A-B: Autophagy does not appear to be altered by Numb in optic nerves.
Figure 8B:
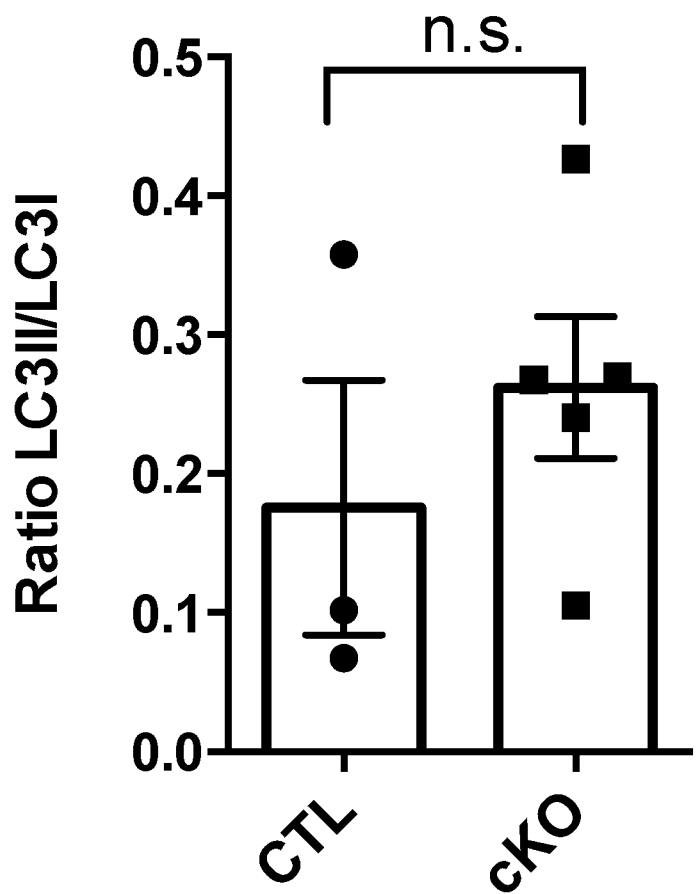

Example 10: Autophagy does not Appear to be Altered in Numb KO Mouse Optic Nerves The inventors sought to assess the impact of Numb on autophagy in optic nerves. To that effect, the level of an autophagy marker (LC3) was compared in optic nerve extracts from 5-month-old control mice versus that in cKO mice. A cytosolic form of LC3 (LC3-1) was conjugated to phosphatidylethanolamine to form LC3-phosphatidylethanolamine conjugate (LC3-11), and recruited to autophagosomal membranes. The ratio LC311/LC31 was then measured to evaluate autophagy. The ratio was unchanged between CTL and cKO, suggesting that the absence of Numb does not affect autophagy in this assay. (FIGS. 8A-B).

Figure 9A:
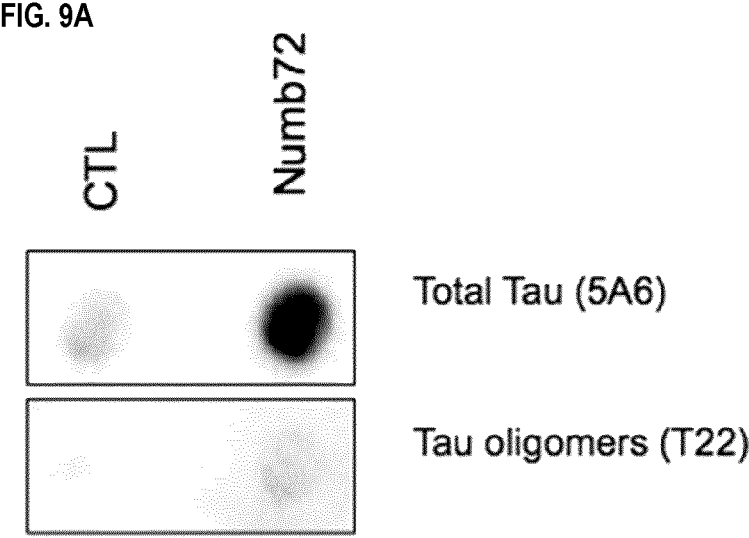
FIGS. 9A-B: Numb72 stimulates secretion of the monomeric form of Tau in the extracellular media in cell lines, but not oligomeric (toxic) Tau.
Figure 9B:
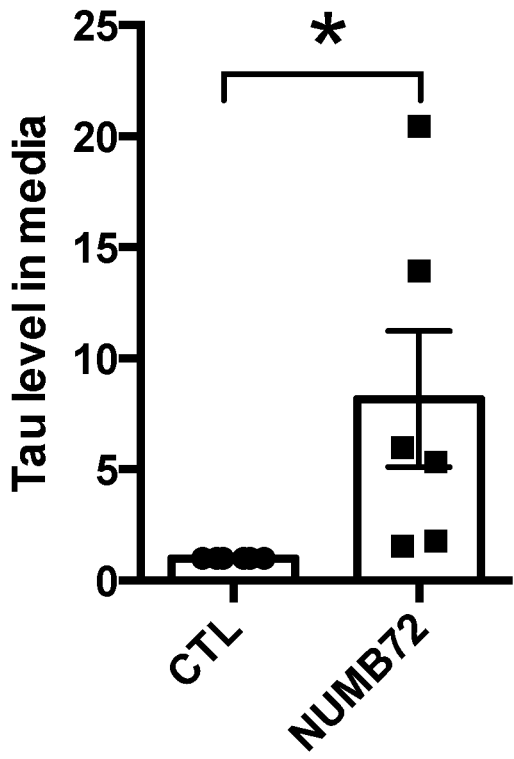
Figure 9C:
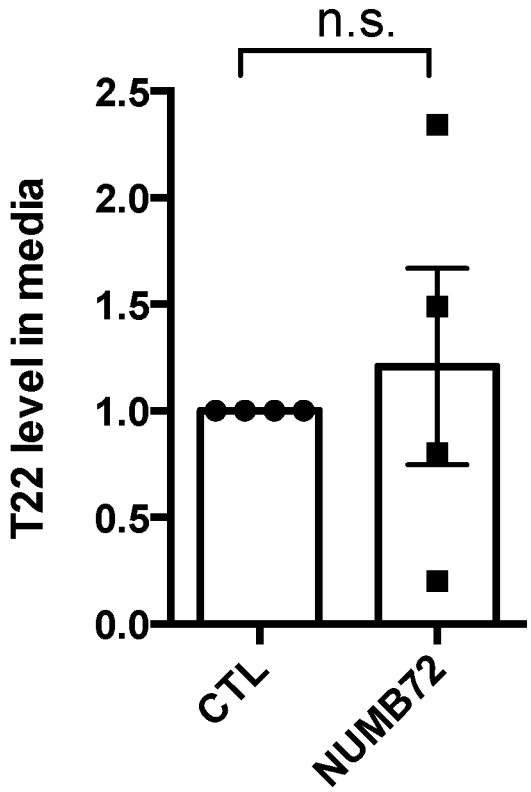

Example 11: Numb72 Stimulates Secretion of the Monomeric Form of Tau in the Extracellular Media in Cell Lines, but not Oligomeric (Toxic) Tau The impact of Numb on the secretion of monomeric and oligomeric Tau was assessed. A cell line (HEK293T) expressing Tau was transfected with either GFP (Control) or Numb72, and the monomeric Tau (5A6) and oligomeric Tau (T22) levels were assessed in the cell media by dot blot assay on the collected culture medium. FIGS. 9A-B show that Numb72 stimulates the secretion of monomeric Tau but not of toxic (oligomeric) Tau.

This data suggest that Numb regulates the amount of Tau monomer present in the cell by stimulating its secretion in the extracellular space. Decreasing the levels of Tau monomers in the cells could indirectly lead to reduced formation of the toxic Tau oligomers.

Figure 10A:
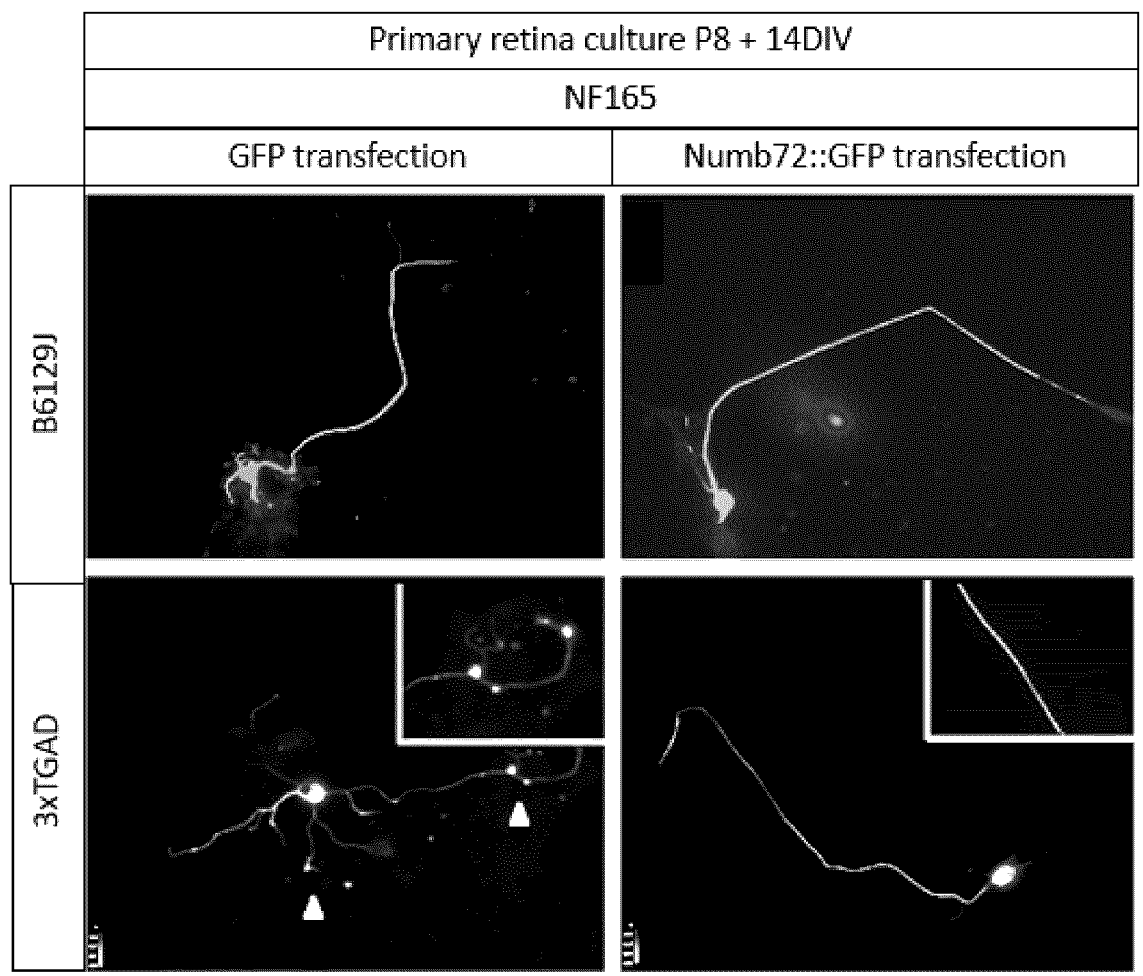
FIGS. 10A-H: Numb72 reduces blebbing in AD mouse model RGCs.
Figure 10B:
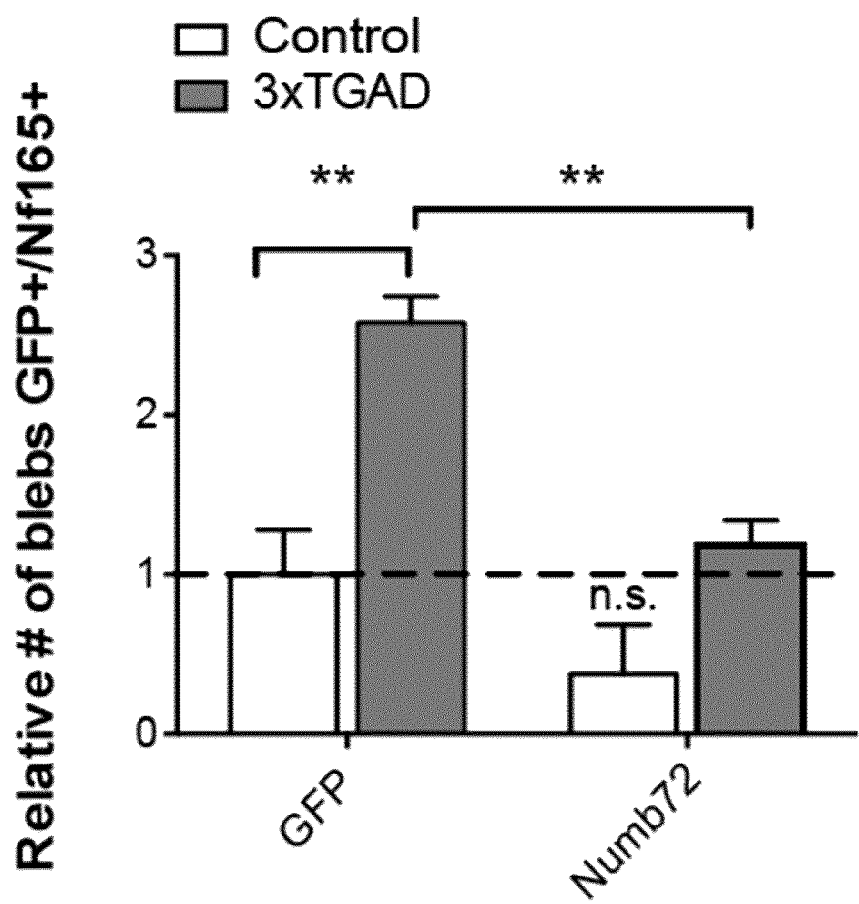
Figure 10C:
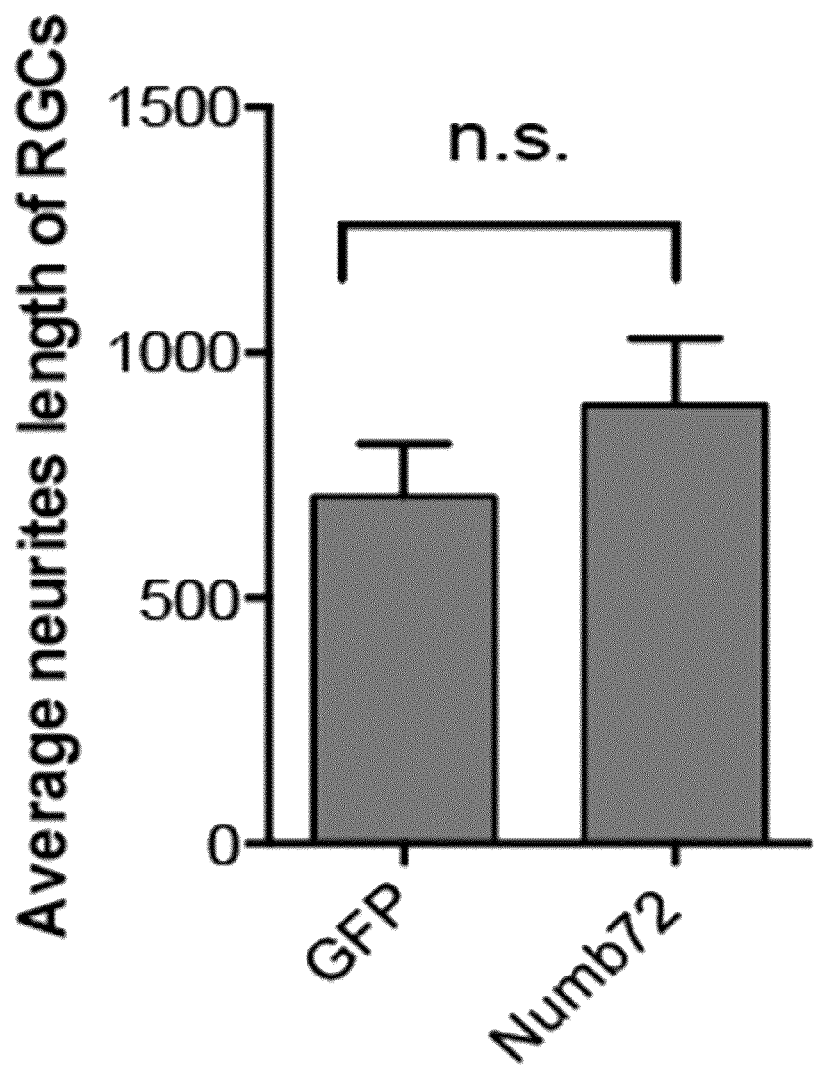
Figure 10D:
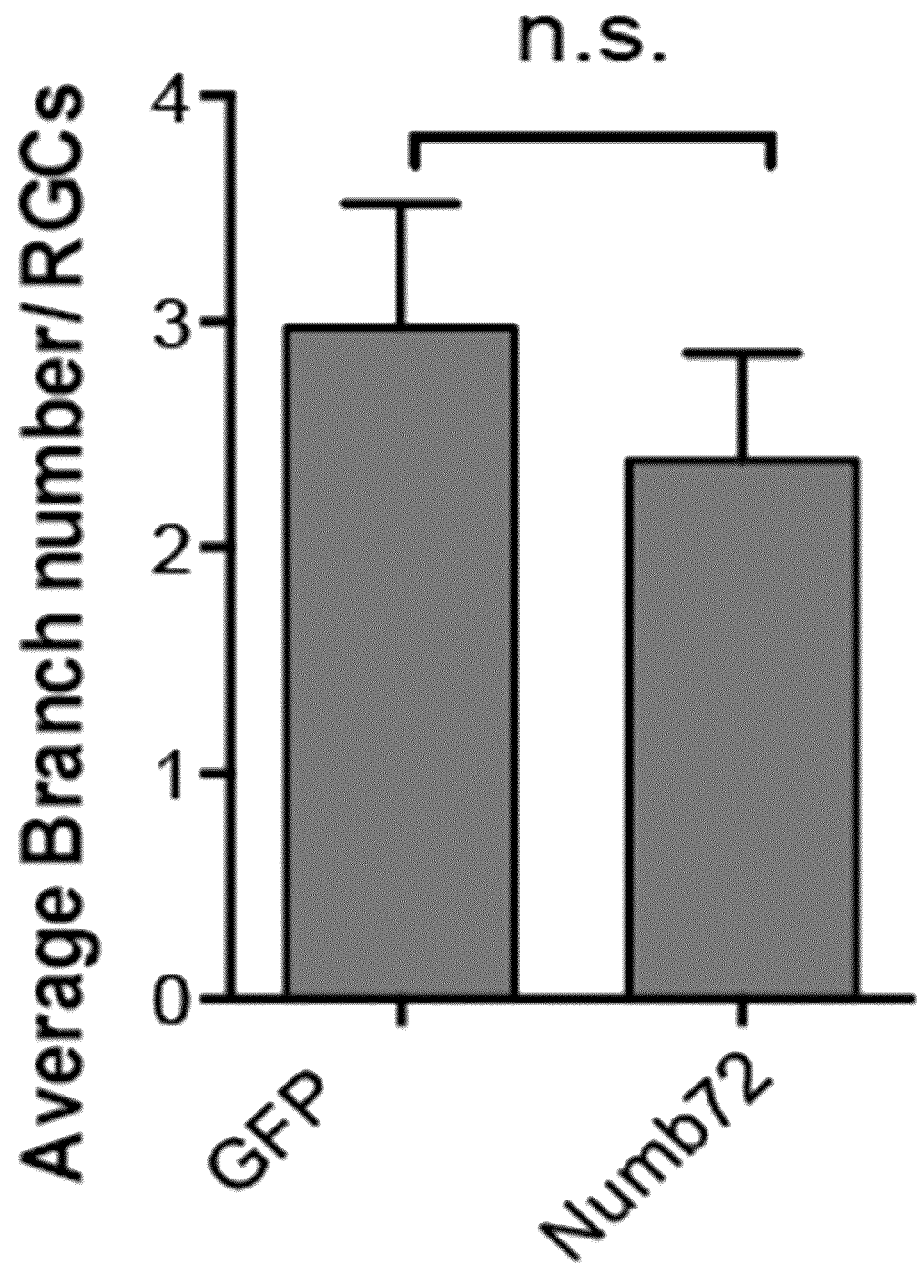
Figure 10E:
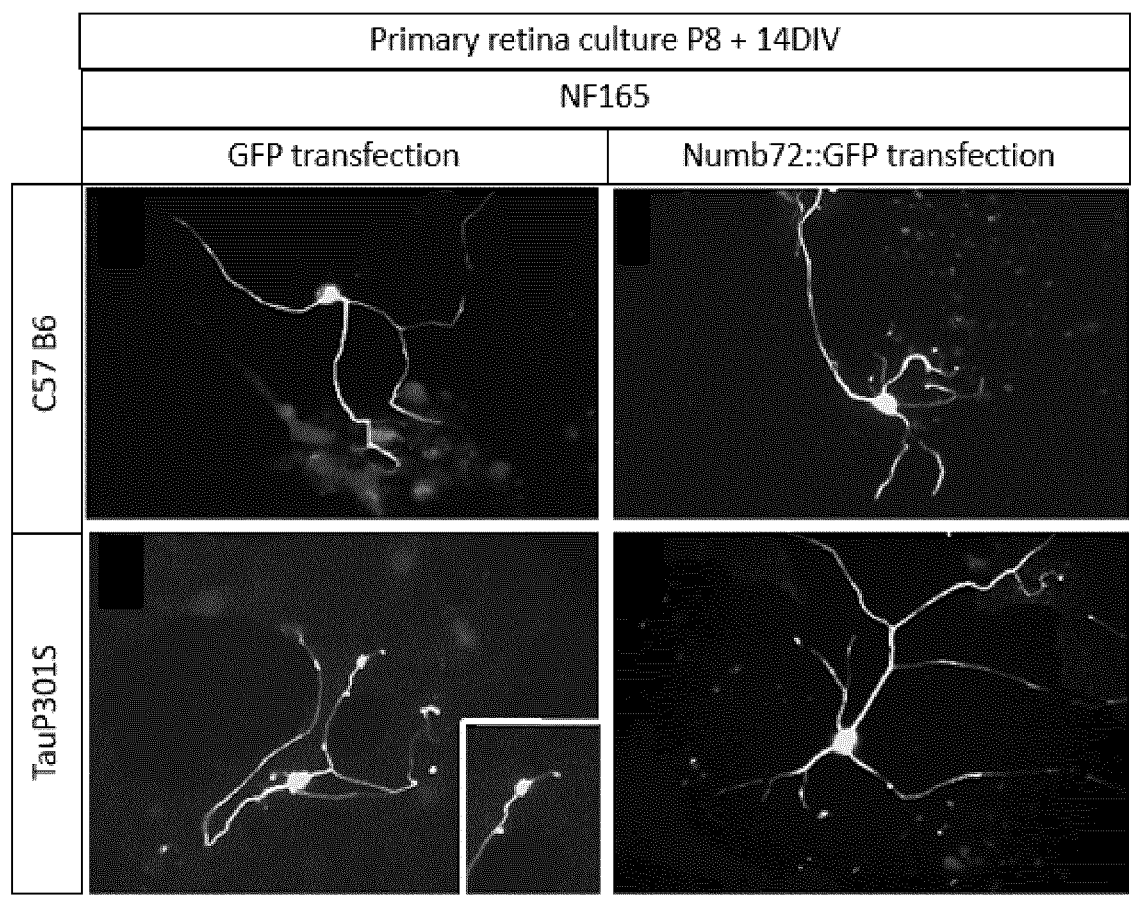
Figure 10F:
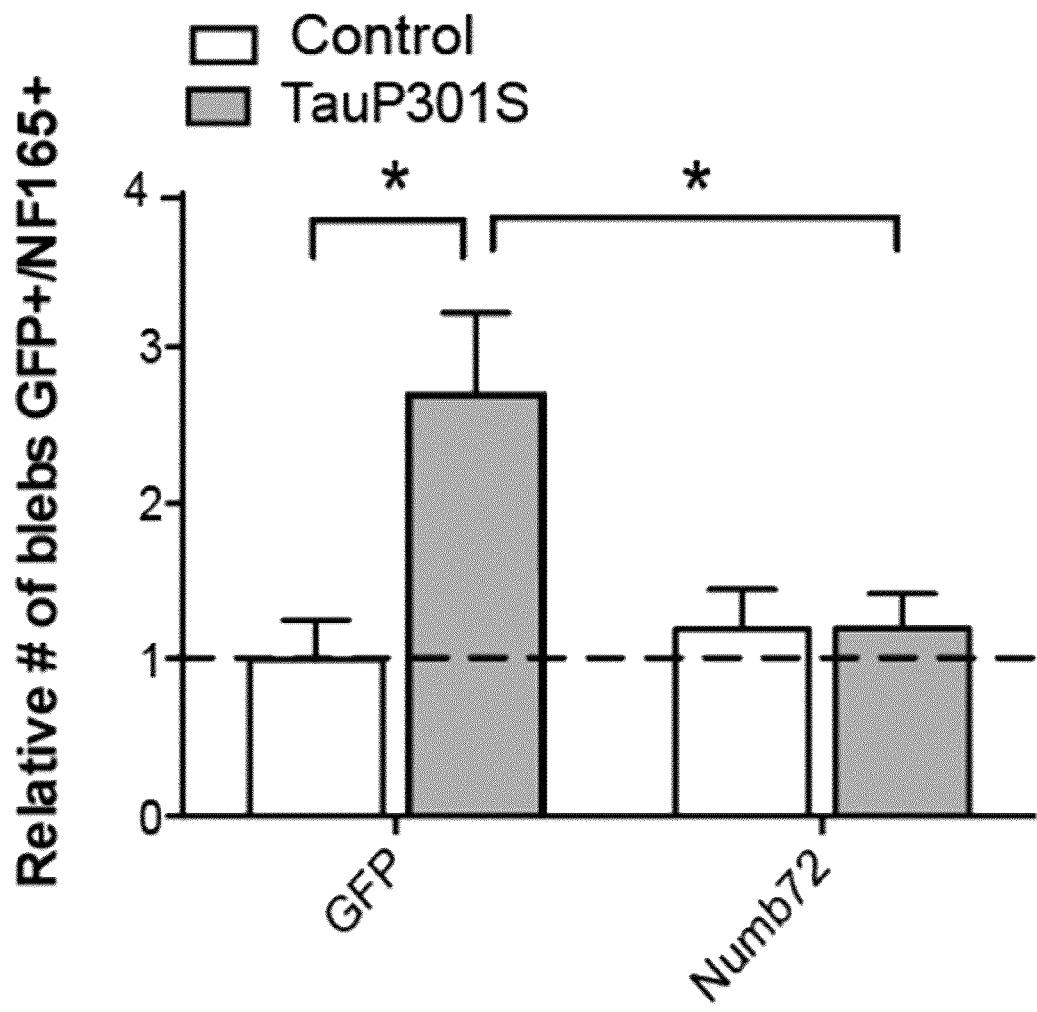
Figure 10G:
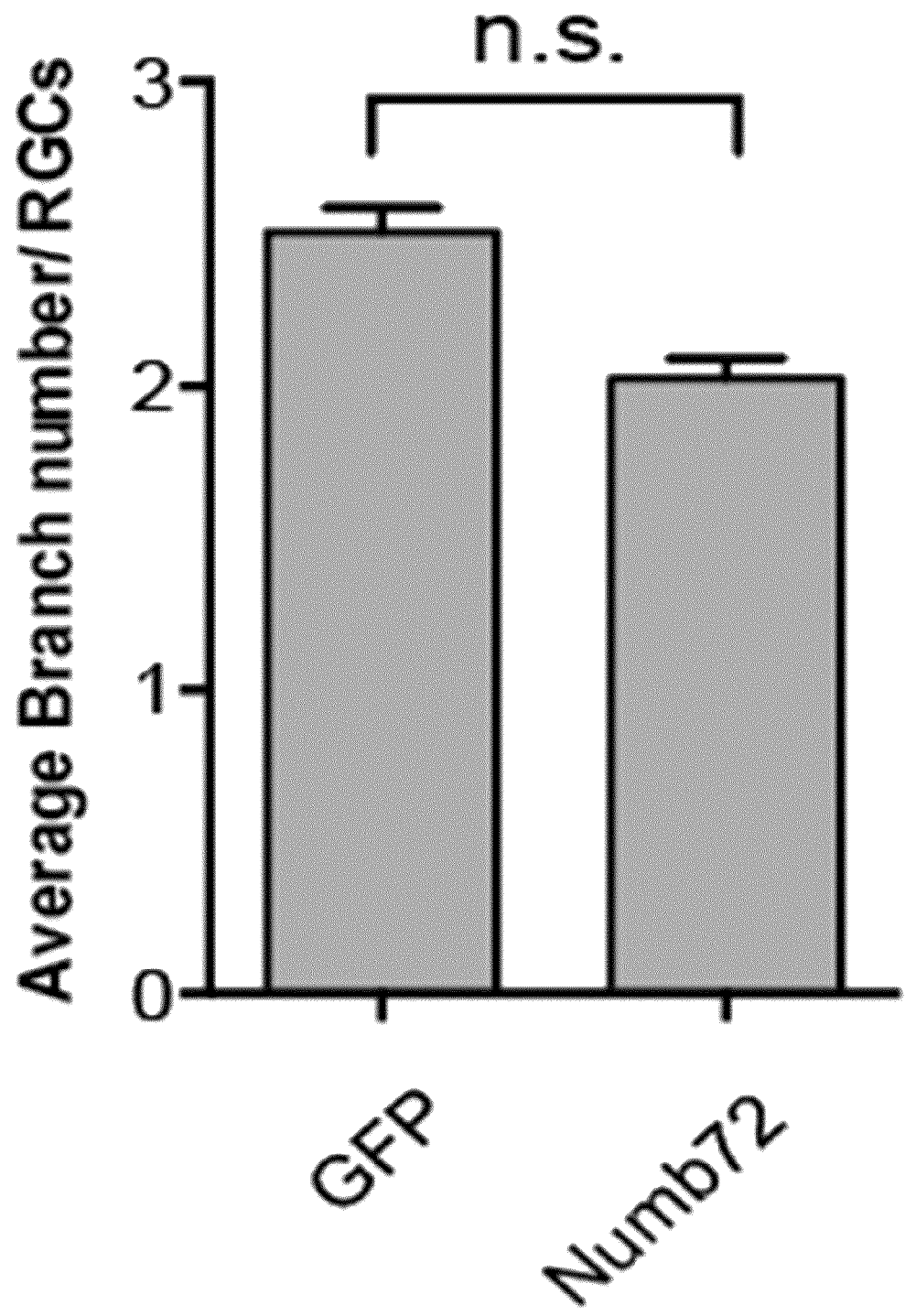
Figure 10H:
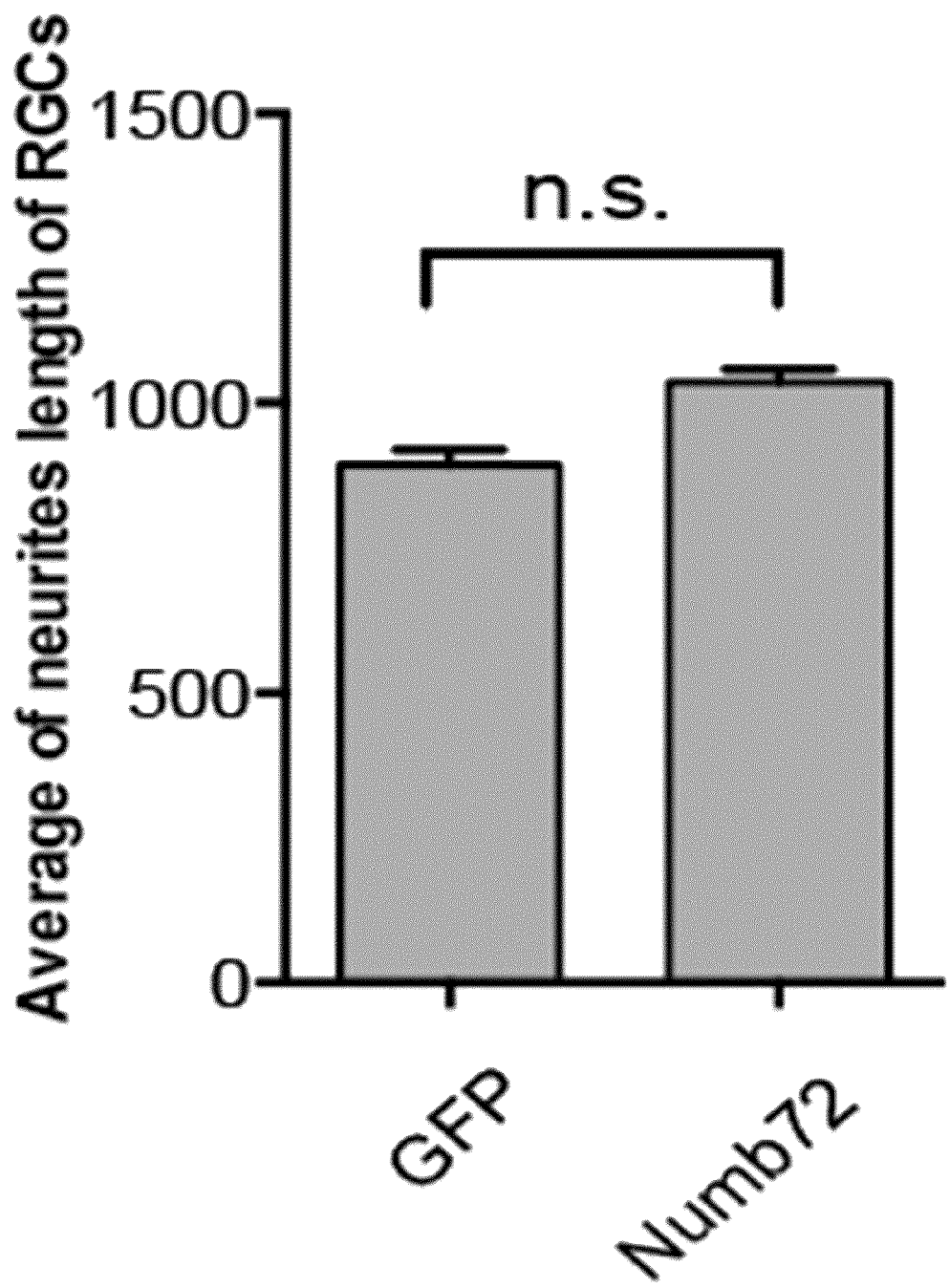

Example 12: Numb-72 Prevents the Accumulation of Axonal Blebs in Mouse Models of Tauopathy Such as Alzheimer's Disease To determine the neuroprotective effects of Numb-72, the inventors prepared primary RGC neuron cultures from control mice, triple transgenic mice (3×TGAD) expressing three mutations associated with familial Alzheimer's disease (APP Swedish, MAPT P301L, and PSEN1 M146V), or a P301S Tau mutant (model of tauopathy), and then expressed GFP or Numb-72 in these neurons by plasmid transfection. Two weeks later, the length of neurites, the number of branches, and the number of axonal blebs were counted. While neurite length (FIGS. 10C and G) and the number of branches (FIGS. 10D and H) was not changed in any condition, the inventors observed a significant increase in the number of axonal blebs in GFP-transfected neurons of the 3×TGAD (FIGS. 10A-B, GFP) and P301S mice (FIGS. 10E-F, GFP), but this number was reduced back to control levels upon expression of Numb-72 (FIGS. 10A-B and 10E-F, Numb72). These results indicate that expression of Numb-72 is neuroprotective in mouse models of AD and tauopathy in vitro.

Figure 11A:
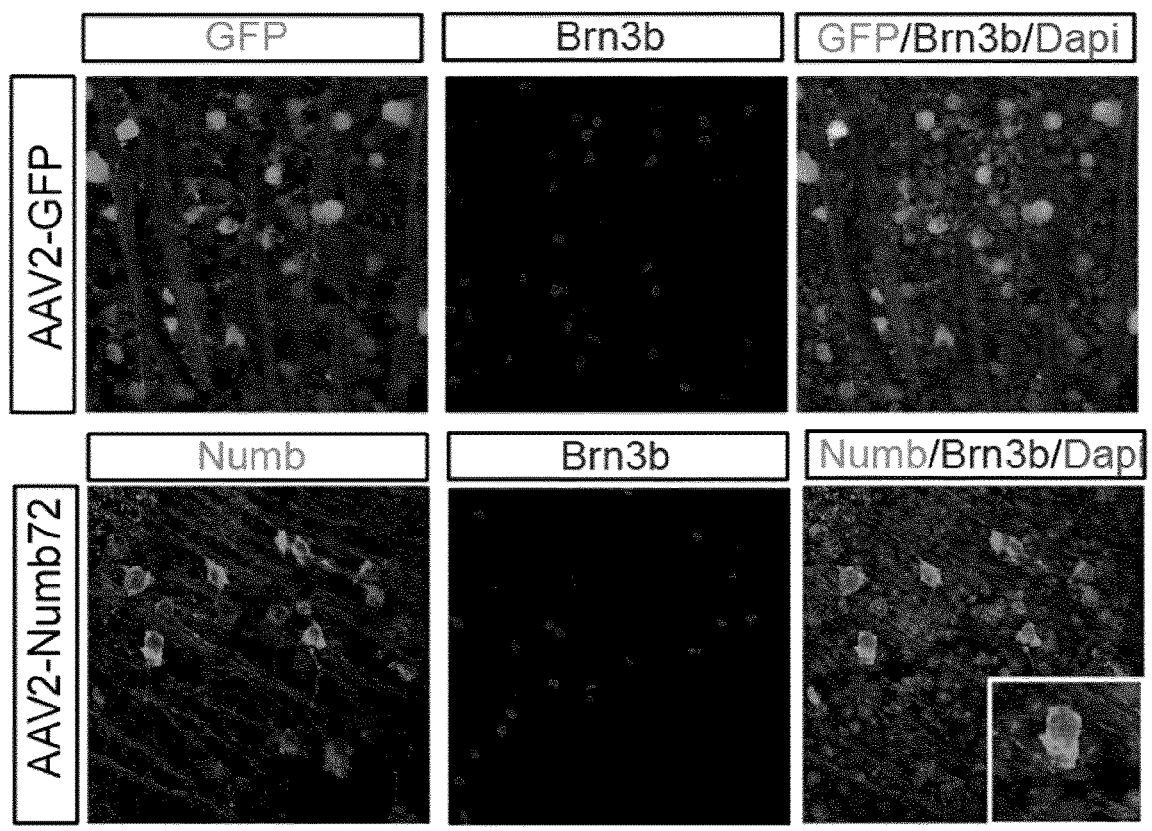
FIGS. 11A-C. Numb72 reduces RGC death in vivo in AD mouse model (3×TGAD).
Figure 11B:
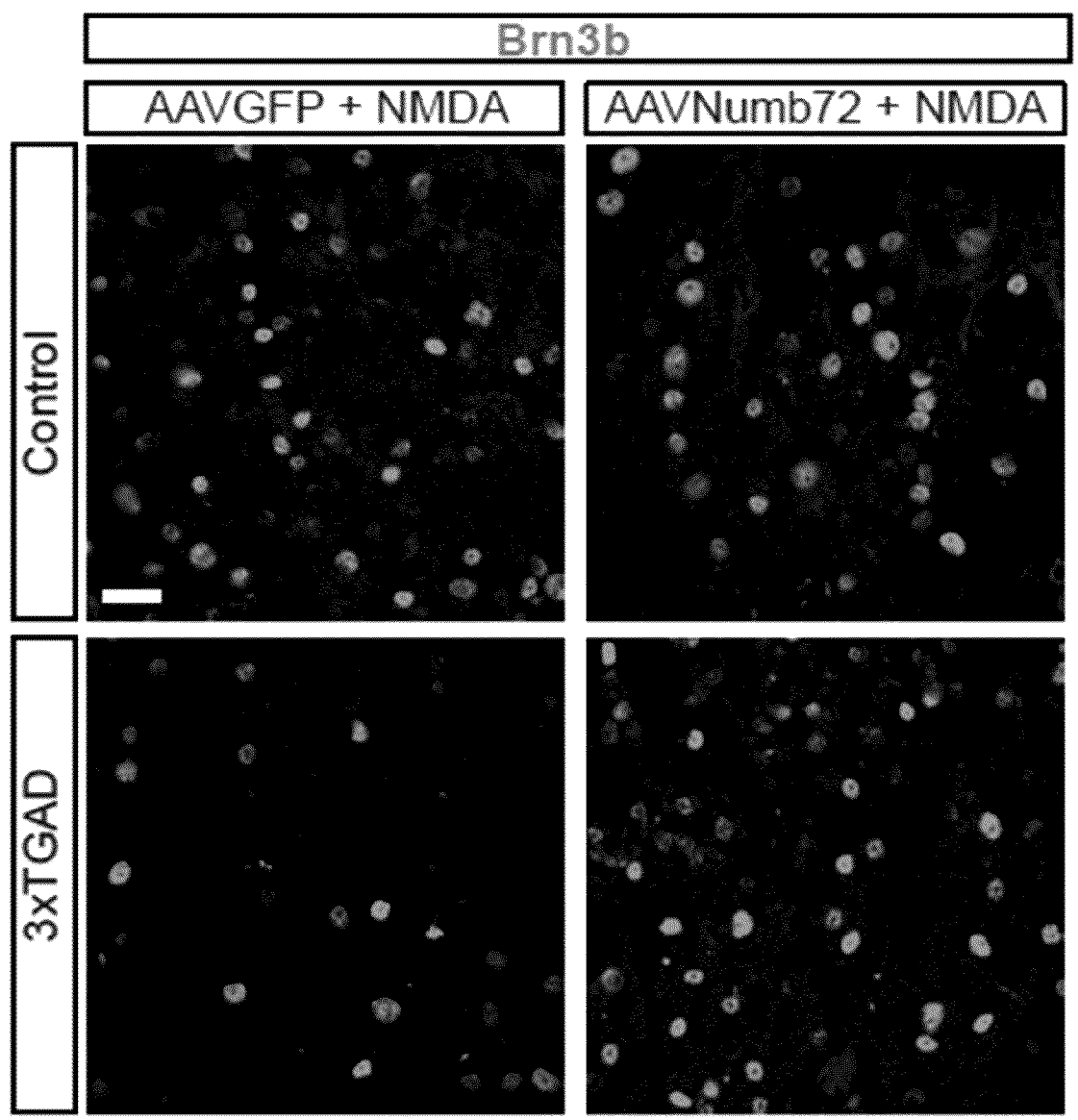
Figure 11C:
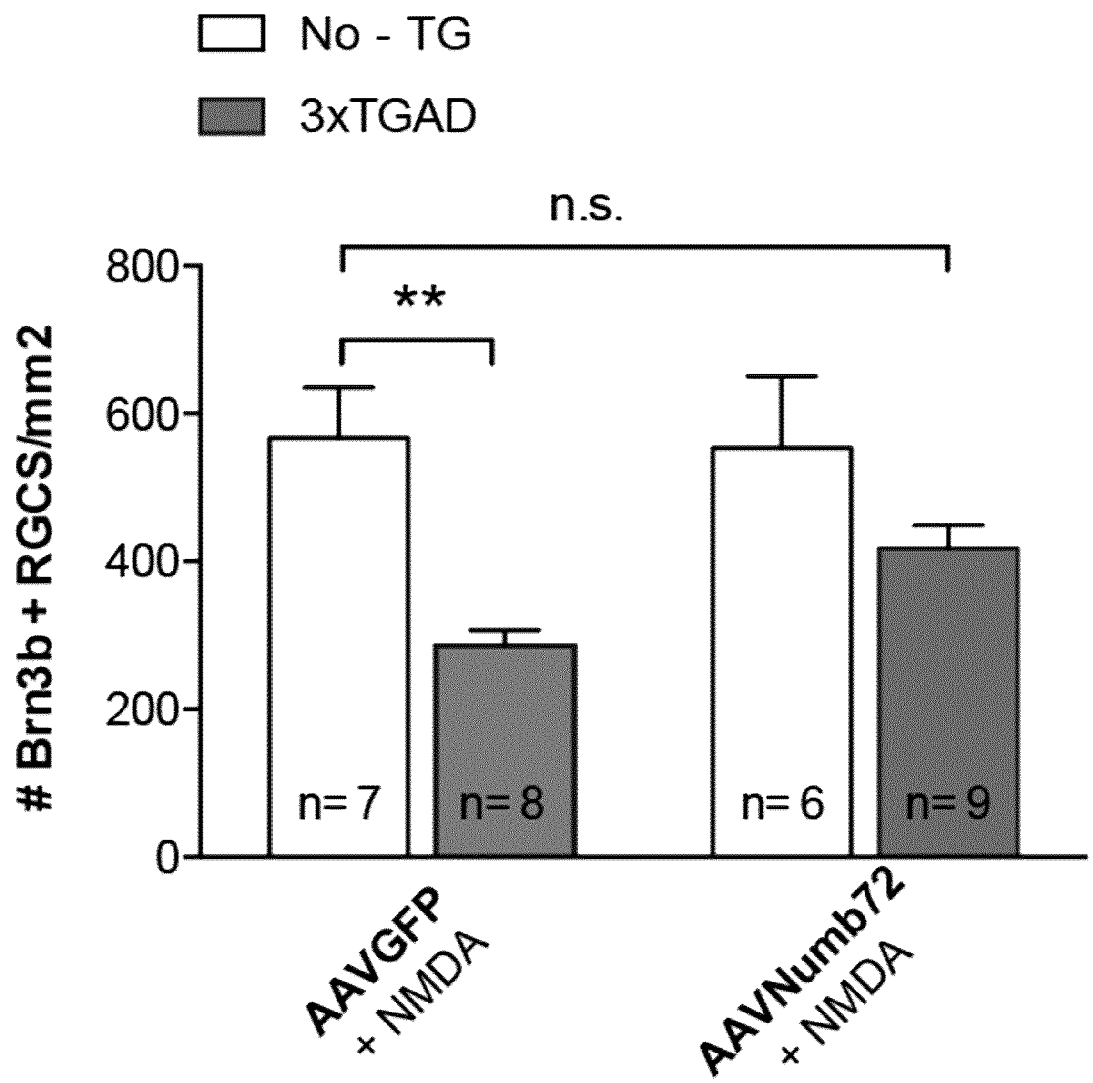
Figure 12A:
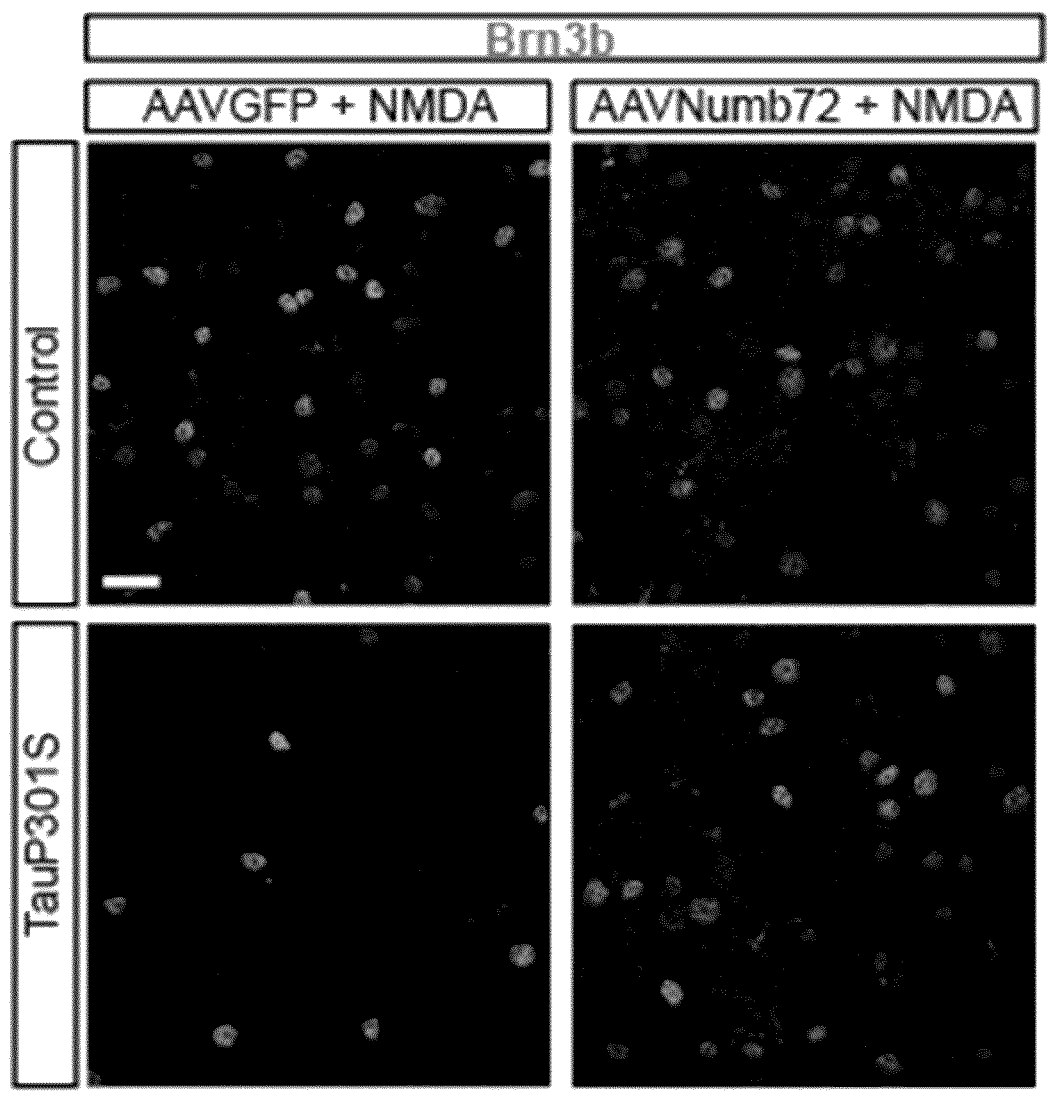
FIGS. 12A-B: Numb72 reduces RGCs cell death in vivo in tauopathy mouse model.
Figure 12B:
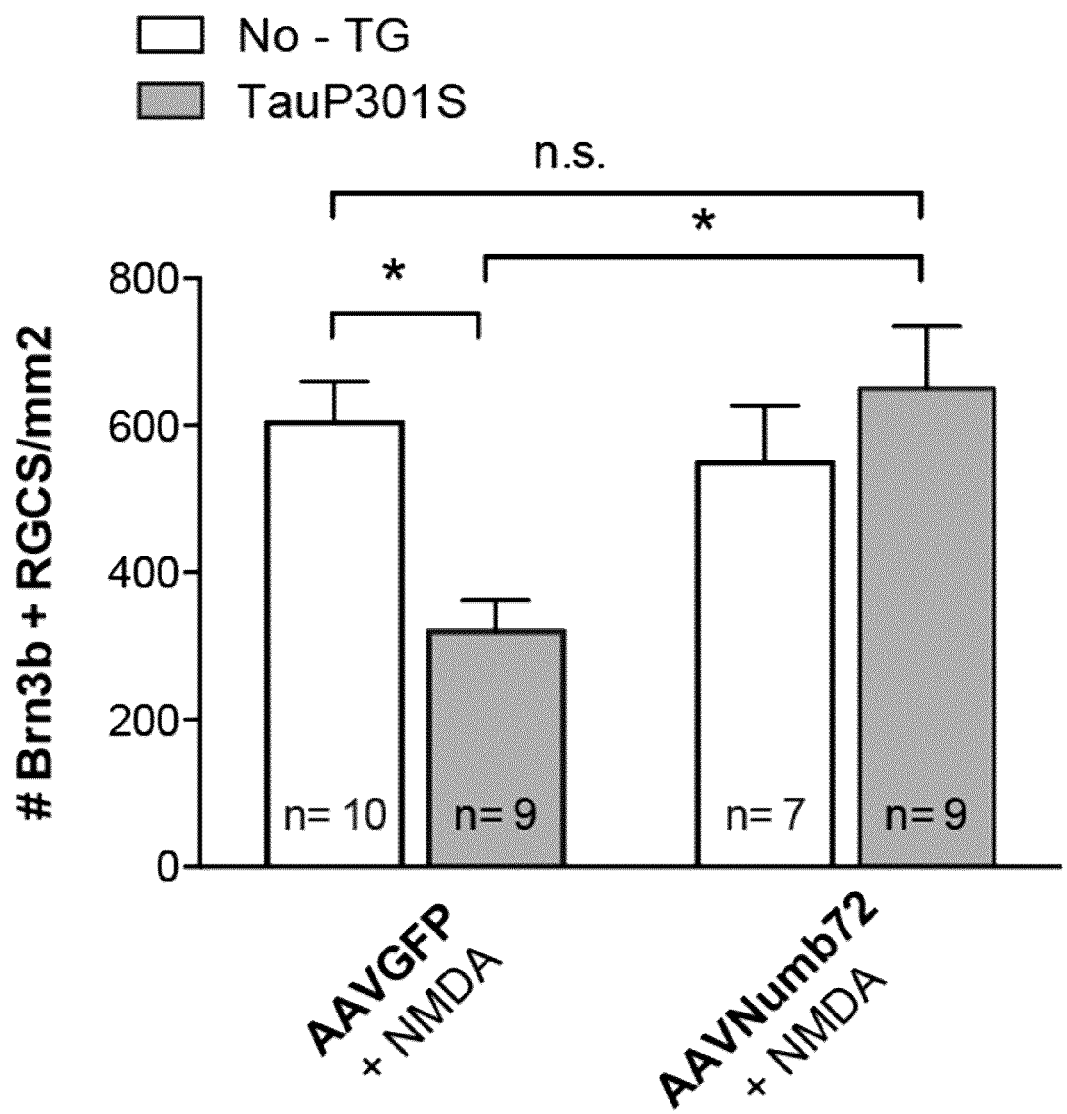

Example 13: Long PTB Numb Isoforms Prevents Axonal Blebbing and Neurons Loss In Vivo in Tauopathy Mouse Model To test neuroprotective activity of long PTB Numb-72 isoform in vivo, the inventors used an adeno-associated viral vector enhanced (AAV) vector to express a control protein (GFP (AAVGFP)) or the long PTB Numb-72 isoform (AAVNumb72) in neurons of 3×TGAD and TauP301S mice. The AAV serotype 2 vectors, which were shown to preferentially infect RGCs (Pang et al., 2008; Reid et al., 2017), were intravitreally injected in control, and 3×TGAD and TauP301S mice at 5 months of age. Since in this mouse model neurodegeneration is only detectable after 8 months, a low dose of NMDA was injected to accelerate neurodegeneration by causing excitotoxicity. Three days prior to sacrifice, all animals therefore received an intravitreal injection of sublethal doses of NMDA. RGC survival was assessed. Numb-72 expression reduced RGC death in 3×TGAD (FIGS. 11B-C) and TauP301S (FIGS. 12A-B) mice compared to control. These results show that expression of Numb-72 has neuroprotective effects on NMDA-mediated excitotoxicity in these animal models.

Figure 13A:
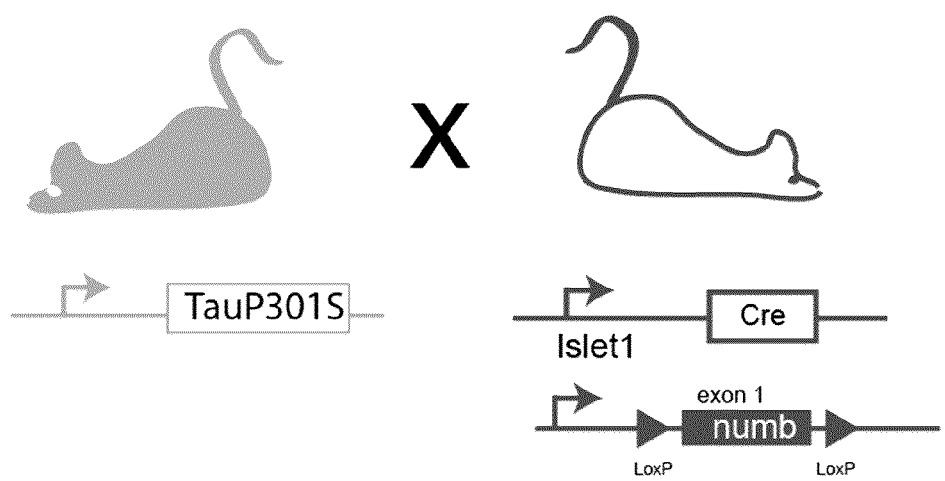
FIGS. 13A-B: The absence of Numb in TauP301S mouse increases RGC death.
Figure 13B:
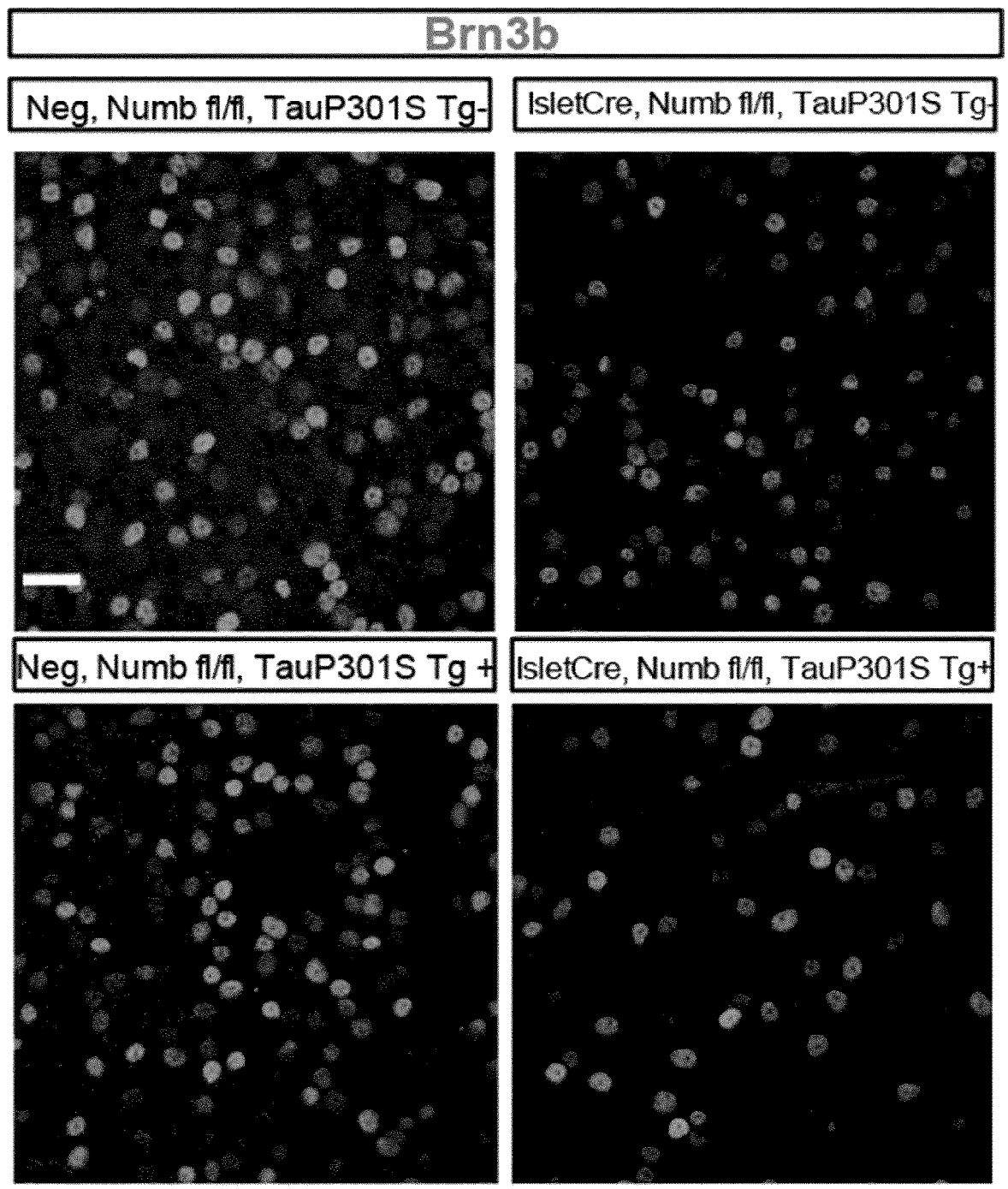
Figure 13C:
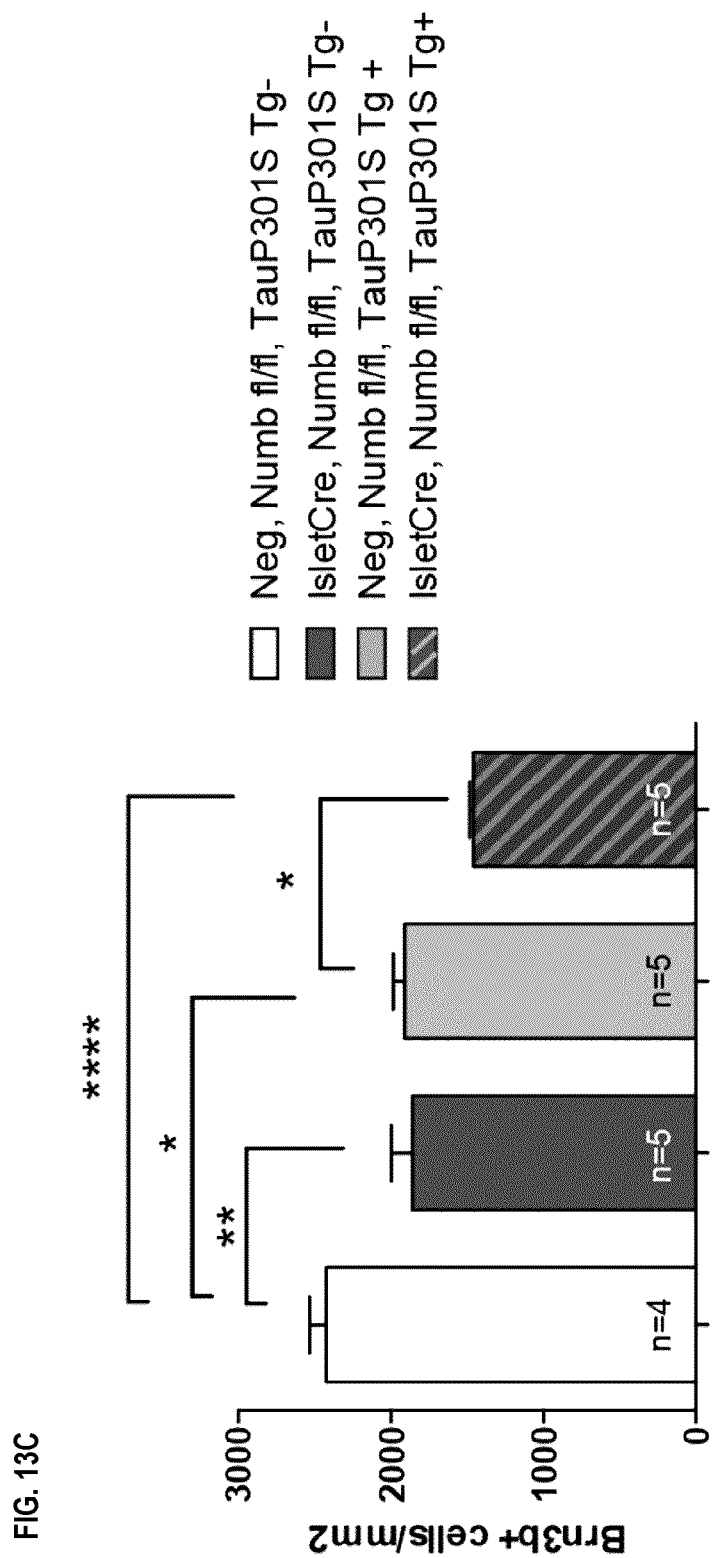
FIG. 13C: Quantification of the number of Brn3b+RGC per $mm^2$ in controls and cKO/Tg+ mice at 8 months old. The loss of Numb in a P301S transgenic Tau background leads to a significantly more important loss of RGCs than Tau transgenic alone or Numb cKO alone, supporting the idea that Numb has a protective effect on neuronal survival in this model. Mean±SEM, n=5 animals/genotype. Anova one-way test, * p≤0.05, p≤0.01, **p≤0.0001.

Example 14: Loss of Numb Accelerates Neurodegeneration in Mouse Model of Tauopathy The Tau P301S mouse models display neurodegeneration but only at late stages (9-12 months), suggesting that some other mechanisms allow for neuronal survival in this model for many months before the mutations cause neurons loss. To test whether Numb expressed in this disease mouse model is neuroprotective, the inventors crossed the Tau P301S with the Numb cKO mice (FIG. 13A). At 8-month-old a more severe phenotype was observed in the TauP301S model (IsletCre, Numb fl/fl, TauP301S Tg+) when Numb was deleted, suggesting that Numb loss accelerates neurodegeneration in this model (FIGS. 13B-C).

Figure 14A:
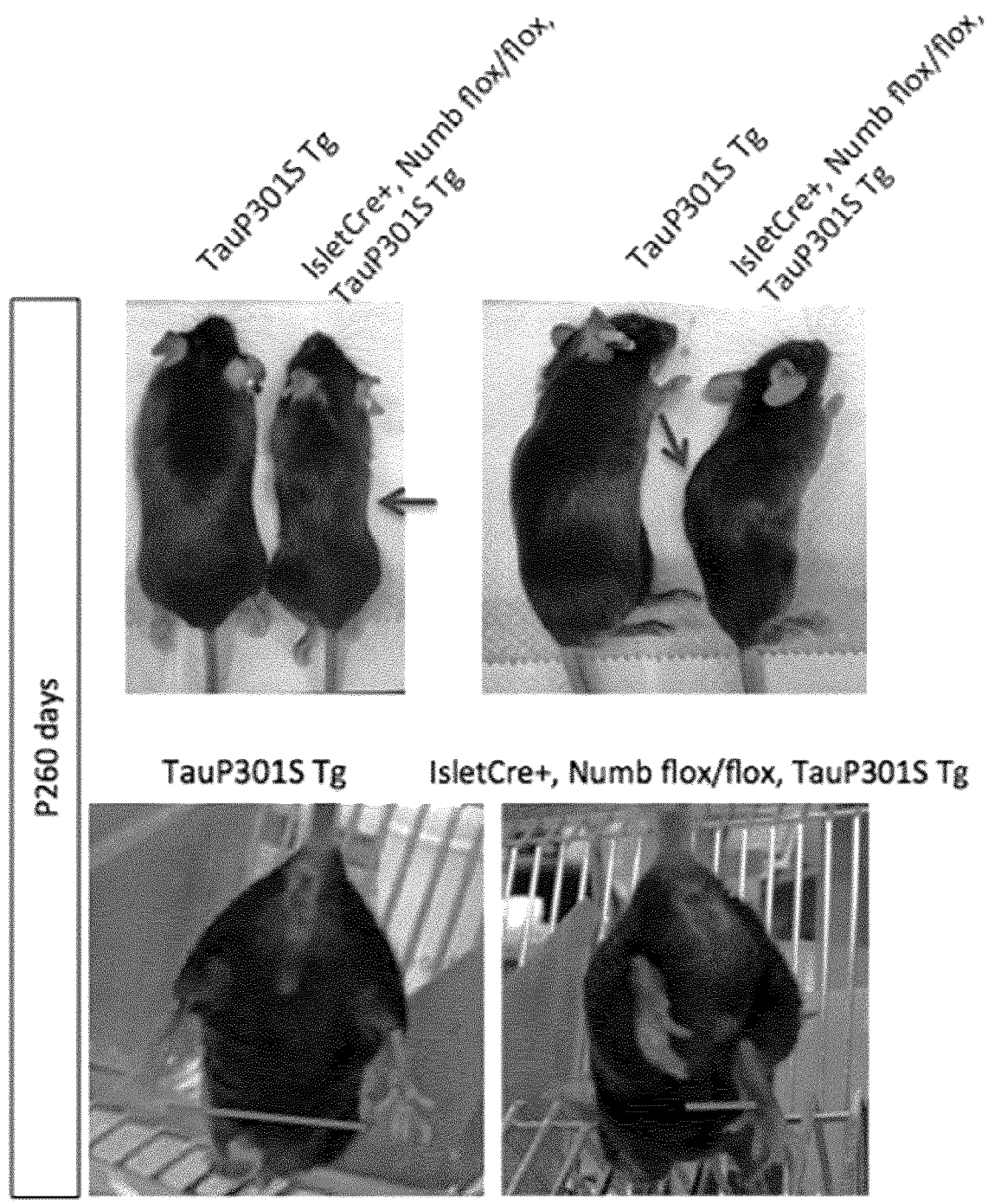
FIGS. 14A-B. The absence of Numb in TauP301S transgenic mice accelerates lumbar paralysis. Because Islet-1-Cre is active in motoneurons of the spinal cord, where Numb is also expressed, the impact of loss of Numb in these motoneurons on motor deficits was assessed in the Numb cKO/TauP301S double mutant mice.
Figure 14B:
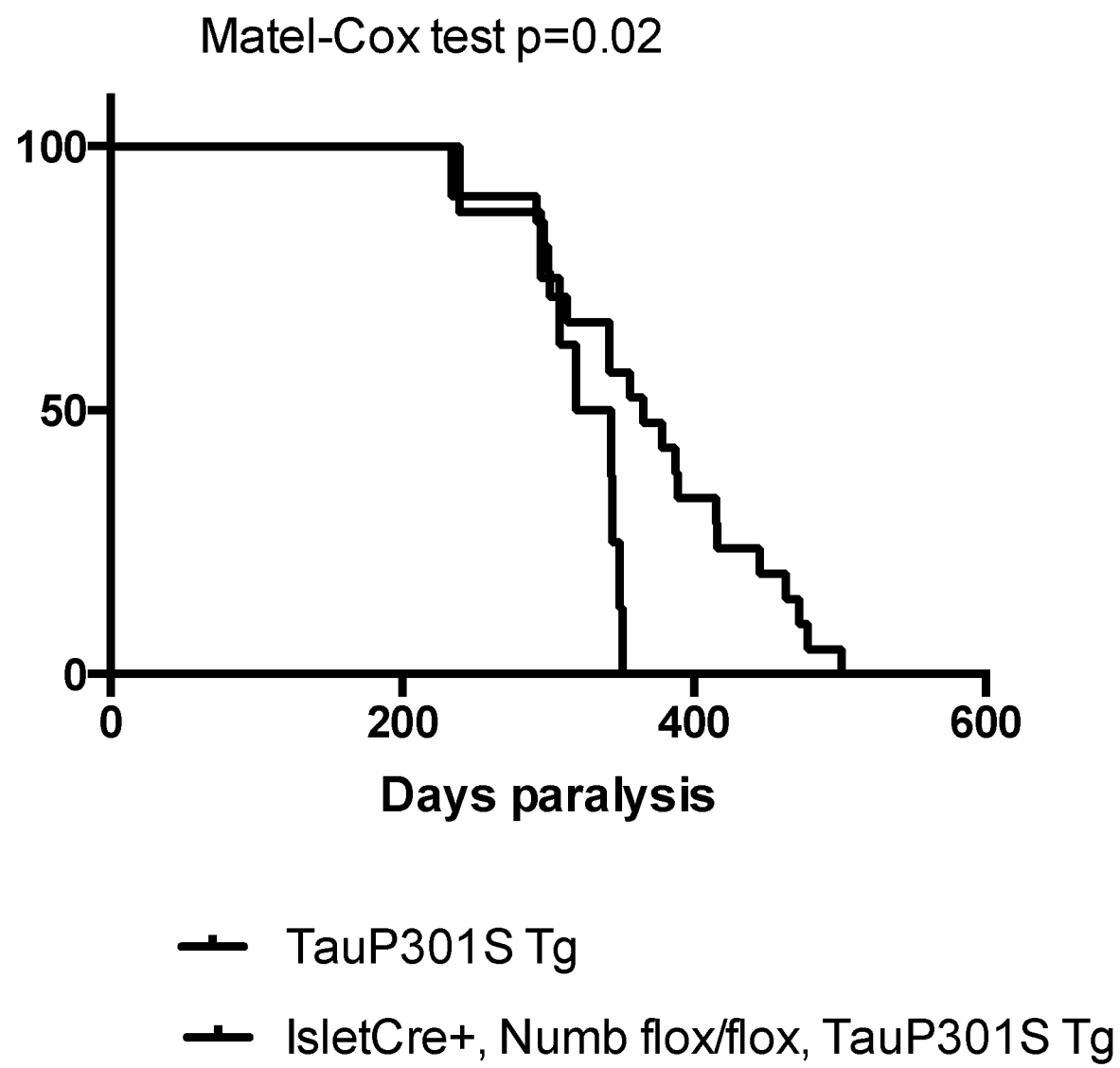

Example 15: The Absence of Numb in TauP301S Transgenic Mice Accelerates Lumbar Paralysis The inventors also observed an acceleration in motoneuron lumbar degeneration leading to posterior paralysis (motor deficit caused by degeneration of motor nerves) in the TauP301S mouse model when Numb was absent (FIGS. 14A-B). This effect also indicated the protective effect of Numb in neurodegeneration.

Example 16: Incidence of Numb-72 in Other Types of Neurons In Vivo

Figure 15A:
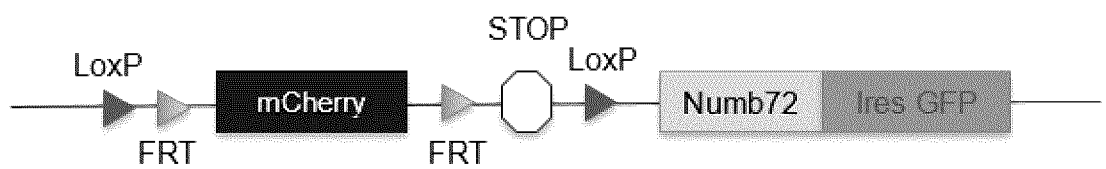
FIGS. 15A-B.
Figure 15B:
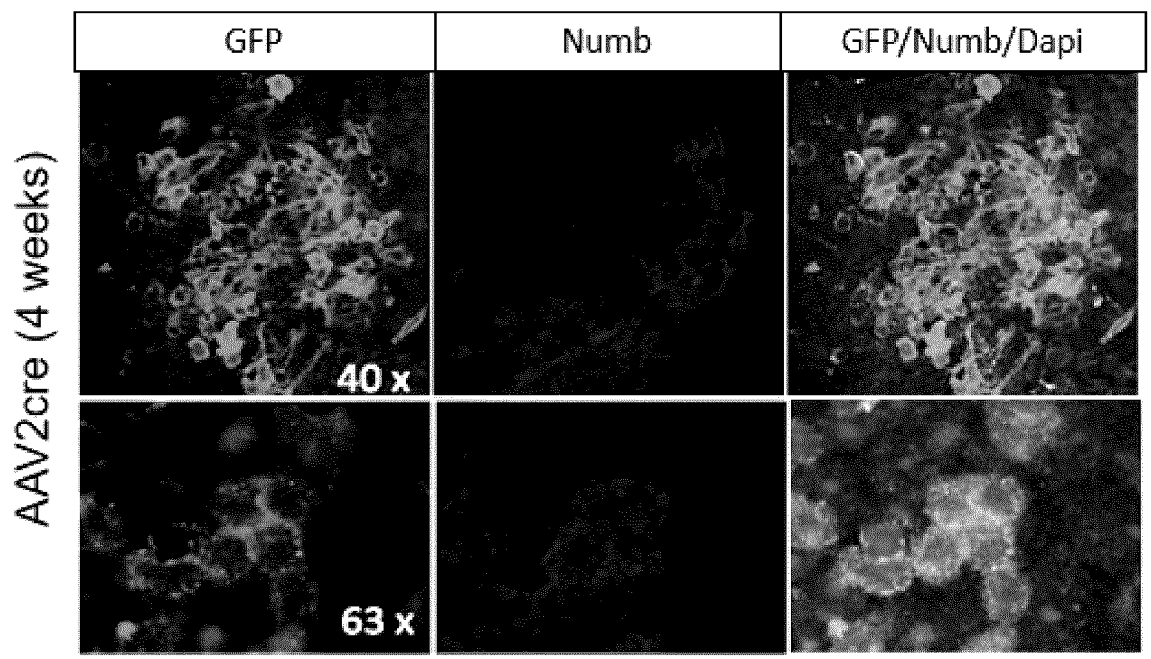

The inventors also designed and developed a transgenic inducible mouse line overexpressing the Numb-72 isoform in a Cre dependent manner (FIG. 15A-B). In this context, the incidence of Numb-72 will be analyzed in other types of neuron, in particular in the hippocampus where Tau tangles are abundant in AD by using a specific Cre to drive Numb-72 overexpression.

Example 17: Cell-Based Assay for Identifying Small Molecules that Increase the Levels of the Long PTB Numb Isoforms Isoform in Cells The inventors generate a stable cell line expressing a Numb mini-gene, in which the genomic fragment corresponding to a long PTB Numb isoform (e.g., Numb-72) exon 3, its upstream and downstream flanking introns, and constitutive exons 2 and 4 are inserted. The construct is built such that presence of exon 3 is revealed by a fluorescent reporter (producing a fusion protein), whereas the splicing out of exon 3 extinguishes fluorescence (e.g., reconstitution of a functional GFP fusion protein in the presence of exon 3). The cell-based assay is used to screen libraries of small molecules to identify those that promote the inclusion of exon 3 (long PTB). The cell-based assay is used for screening libraries of antisense oligonucleotides (ASOs), from 15-25 bases in length, derived from the genomic fragment corresponding to Numb exon 3, its upstream and downstream flanking introns.

Example 18: Demonstration that a Small Molecule or an ASO Promoting the Generation of the Long Numb Isoform is Neuroprotective In Vitro and In Vivo The small molecule(s) and/or ASOs identified in the screen assay above are tested for their neuroprotective effects on AD and tauopathy model neurons in culture and for their ability to reduce accumulation of Tau and prevent axonal blebbing. Molecules with positive effects are then be selected for in vivo studies in which they are injected systemically or directly in the eyes of animal models of AD and tauopathy.

The scope of the claims should not be limited by the preferred embodiments set forth in the examples but should be given the broadest interpretation consistent with the description as a whole.

REFERENCES

Bull, N. D., Guidi, A., Goedert, M., Martin, K. R., and Spillantini, M. G. (2012). Reduced axonal transport and increased excitotoxic retinal ganglion cell degeneration in mice transgenic for human mutant P301S tau. PLoS One 7, e34724.

Chen T et al (2012) The selective mGluR5 agonist CHPG protects against traumatic brain injury in vitro and in vivo via ERK and Akt pathway. Int J Mol Med 29(4): 630-6.

Chesser, A. S., Pritchard, S. M., and Johnson, G. V. (2013). Tau clearance mechanisms and their possible role in the pathogenesis of Alzheimer disease. Front Neurol 4, 122.

Chiasseu et al., (2016). Tau Accumulation, Altered Phosphorylation, and Missorting Promote Neurodegeneration in Glaucoma. J Neurosci. 2016 May 25; 36(21): 5785-98.

de Calignon, A., Polydoro, M., Suarez-Calvet, M., William, C., Adamowicz, D. H., Kopeikina, K. J., Pitstick, R., Sahara, N., Ashe, K. H., Carlson, G. A., et al. (2012). Propagation of tau pathology in a model of early Alzheimer's disease. Neuron 73, 685-697.

Dho, S. E., French, M. B., Woods, S. A., and McGlade, C. J. (1999). Characterization of four mammalian numb protein isoforms. Identification of cytoplasmic and membrane-associated variants of the phosphotyrosine binding domain. J Biol Chem 274, 33097-33104.

Flannery et al. (1997) Efficient photoreceptor-targeted gene expression in vivo by recombinant adeno-associated virus Proc Natl Acad Sci USA. 94(13): 6916-6921.

Frederiksen et al. (2012), Tau protein: a possible prognostic factor in optic neuritis and multiple sclerosis. Mult Scler. 2012 May; 18(5):592-9.

Gasparini, L., Crowther, R. A., Martin, K. R., Berg, N., Coleman, M., Goedert, M., and Spillantini, M. G. (2011). Tau inclusions in retinal ganglion cells of human P301S tau transgenic mice: effects on axonal viability. Neurobiol Aging 32, 419-433.

Guillozet, A. L., Weintraub, S., Mash, D. C., and Mesulam, M. M. (2003). Neurofibrillary tangles, amyloid, and memory in aging and mild cognitive impairment. Arch Neurol 60, 729-736.

Guo, L., Salt, T. E., Luong, V., Wood, N., Cheung, W., Maass, A., Ferrari, G., Russo-Marie, F., Sillito, A. M., Cheetham, M. E., et al. (2007). Targeting amyloid-beta in glaucoma treatment. Proc Natl Acad Sci USA 104, 13444-13449.

Gupta, N., Fong, J., Ang, L. C., and Yucel, Y. H. (2008). Retinal tau pathology in human glaucomas. Can J Ophthalmol 43, 53-60.

Ittner, L. M., Ke, Y. D., Delerue, F., Bi, M., Gladbach, A., van Eersel, J., Wolfing, H., Chieng, B. C., Christie, M. J., Napier, I. A., et al. (2010). Dendritic function of tau mediates amyloid-beta toxicity in Alzheimer's disease mouse models. Cell 142, 387-397.

Karaczyn, A., Bani-Yaghoub, M., Tremblay, R., Kubu, C., Cowling, R., Adams, T. L., Prudovsky, I., Spicer, D., Friesel, R., Vary, C., et al. (2010). Two novel human NUMB isoforms provide a potential link between development and cancer. Neural Dev 5, 31.

Kim et al., (2013) Rbfox3-regulated alternative splicing of Numb promotes neuronal differentiation during development. J. Cell Biol., 200 (4): 443.

Lasagna-Reeves, C. A., Castillo-Carranza, D. L., Sengupta, U., Sarmiento, J., Troncoso, J., Jackson, G. R., and Kayed, R. (2012). Identification of oligomers at early stages of tau aggregation in Alzheimer's disease. FASEB J 26, 1946-1959.

Lasagna-Reeves, C. A., de Haro, M., Hao, S., Park, J., Rousseaux, M. W., Al-Ramahi, I., Jafar-Nejad, P., Vilanova-Velez, L., See, L., De Maio, A., et al. (2016). Reduction of Nuak1 Decreases Tau and Reverses Phenotypes in a Tauopathy Mouse Model. Neuron 92, 407-418.

Matsuda T and Cepko C L., (2004) Electroporation and RNA interference in the rodent retina in vivo and in vitro. Proc Natl Acad Sci USA. January 6; 101(1):16-22. Epub 2003 Nov. 5. McKinnon, S. J. (2003). Glaucoma: ocular Alzheimer's disease? Front Biosci 8, s1140-1156.

Myeku, N., Clelland, C. L., Emrani, S., Kukushkin, N. V., Yu, W. H., Goldberg, A. L., and Duff, K. E. (2016). Tau-driven 26S proteasome impairment and cognitive dysfunction can be prevented early in disease by activating cAMP-PKA signaling. Nat Med 22, 46-53.

Ning, A., Cui, J., To, E., Ashe, K. H., and Matsubara, J. (2008). Amyloid-beta deposits lead to retinal degeneration in a mouse model of Alzheimer disease. Invest Ophthalmol Vis Sci 49, 5136-5143.

Oku et al. (2019). Tau Is Involved in Death of Retinal Ganglion Cells of Rats from Optic Nerve Crush. Invest Ophthalmol Vis Sci 60(6):2380-2387

Pang et al., (2008). Comparative analysis of in vivo and in vitro AAV vector transduction in the neonatal mouse retina: Effects of serotype and site of administration. Vision Research 48(3): 377-385.

Parnell, M., Guo, L., Abdi, M., and Cordeiro, M. F. (2012). Ocular manifestations of Alzheimer's disease in animal models. Int J Alzheimers Dis 2012, 786494.

Perez, S. E., Lumayag, S., Kovacs, B., Mufson, E. J., and Xu, S. (2009). Beta-amyloid deposition and functional impairment in the retina of the APPswe/PS1DeltaE9 transgenic mouse model of Alzheimer's disease. Invest Ophthalmol Vis Sci 50, 793-800.

Rajendran, D., Zhang, Y., Berry, D. M., and McGlade, C. J. (2016). Regulation of Numb isoform expression by activated ERK signaling. Oncogene 35, 5202-5213.

Reid et al., (2017) Improvement of Photoreceptor Targeting via Intravitreal Delivery in Mouse and Human Retina Using Combinatory rAAV2 Capsid Mutant Vectors. Invest Ophthalmol Vis Sci. 58(14): 6429-6439.

Roberson, E. D., Halabisky, B., Yoo, J. W., Yao, J., Chin, J., Yan, F., Wu, T., Hamto, P., Devidze, N., Yu, G. Q., et al. (2011). Amyloid-beta/Fyn-induced synaptic, network, and cognitive impairments depend on tau levels in multiple mouse models of Alzheimer's disease. J Neurosci 31, 700-711.

Roberson, E. D., Scearce-Levie, K., Palop, J. J., Yan, F., Cheng, I. H., Wu, T., Gerstein, H., Yu, G. Q., and Mucke, L. (2007). Reducing endogenous tau ameliorates amyloid beta-induced deficits in an Alzheimer's disease mouse model. Science 316, 750-754.

Sivak, J. M. (2013). The aging eye: common degenerative mechanisms between the Alzheimer's brain and retinal disease. Invest Ophthalmol Vis Sci 54, 871-880.

Srinivas et al. (2001). Cre reporter strains produced by targeted insertion of EYFP and ECFP into the ROSA26 locus. BMC Developmental Biology 1(4).

Wilson et al. (2007) Normal hemopoiesis and lymphopoiesis in the combined absence of numb and numblike. J Immunol. June 1; 178(11):6746-51.

Yang et al. (2016). A small molecule TrkB/TrkC neurotrophin receptor co-activator with distinctive effects on neuronal survival and process outgrowth. Neuropharmacology. 110(Pt A):343-361.

Yoshiyama, Y., Higuchi, M., Zhang, B., Huang, S. M., Iwata, N., Saido, T. C., Maeda, J., Suhara, T., Trojanowski, J. Q., and Lee, V. M. (2007). Synapse loss and microglial activation precede tangles in a P301S tauopathy mouse model. Neuron 53, 337-351.

Zhai et al. (2005). Honokiol-induced neurite outgrowth promotion depends on activation of extracellular signal-regulated kinases (ERK1/2). Eur J Pharmacol. 1; 516(2):112-7.

The invention claimed is:

1. A method of reducing neuronal microtubule binding protein Tau (Tau) levels, promoting neuronal Tau degradation and/or promoting neuronal survival, in a subject in need thereof comprising contacting the subject's neurons with therapeutically effective amount of a nucleic acid encoding Numb-72 in a gene delivery viral vector, whereby neural Tau levels is reduced in the presence of the nucleic acid, the neuronal Tau degradation is promoted and/or the neuronal survival is promoted as compared to in the absence thereof.

2. The method of claim 1, wherein the neurons are retinal neurons.

3. The method of claim 1, wherein the subject has a tauopathy or a Tau-associated optic neuropathy.

4. The method of claim 3, wherein the subject has a Tau-associated optic neuropathy.

5. The method of claim 1, wherein the viral vector is an adeno-associated vector (AAV).

6. The method of claim 5, wherein the AAV is of serotyp-2.

* * * * *

SEQUENCE LISTING

```
<160> NUMBER OF SEQ ID NOS: 30

<210> SEQ ID NO 1
<211> LENGTH: 651
<212> TYPE: PRT
<213> ORGANISM: homo sapiens

<400> SEQUENCE: 1

Met Asn Lys Leu Arg Gln Ser Phe Arg Arg Lys Lys Asp Val Tyr Val
1               5                   10                  15

Pro Glu Ala Ser Arg Pro His Gln Trp Gln Thr Asp Glu Glu Gly Val
            20                  25                  30

Arg Thr Gly Lys Cys Ser Phe Pro Val Lys Tyr Leu Gly His Val Glu
        35                  40                  45

Val Asp Glu Ser Arg Gly Met His Ile Cys Glu Asp Ala Val Lys Arg
    50                  55                  60

Leu Lys Ala Glu Arg Lys Phe Phe Lys Gly Phe Phe Gly Lys Thr Gly
65                  70                  75                  80

Lys Lys Ala Val Lys Ala Val Leu Trp Val Ser Ala Asp Gly Leu Arg
                85                  90                  95

Val Val Asp Glu Lys Thr Lys Asp Leu Ile Val Asp Gln Thr Ile Glu
            100                 105                 110

Lys Val Ser Phe Cys Ala Pro Asp Arg Asn Phe Asp Arg Ala Phe Ser
        115                 120                 125

Tyr Ile Cys Arg Asp Gly Thr Thr Arg Arg Trp Ile Cys His Cys Phe
    130                 135                 140
```

```
Met Ala Val Lys Asp Thr Gly Glu Arg Leu Ser His Ala Val Gly Cys
145                 150                 155                 160

Ala Phe Ala Ala Cys Leu Glu Arg Lys Gln Lys Arg Glu Lys Glu Cys
            165                 170                 175

Gly Val Thr Ala Thr Phe Asp Ala Ser Arg Thr Thr Phe Thr Arg Glu
        180                 185                 190

Gly Ser Phe Arg Val Thr Thr Ala Thr Glu Gln Ala Glu Arg Glu Glu
    195                 200                 205

Ile Met Lys Gln Met Gln Asp Ala Lys Lys Ala Glu Thr Asp Lys Ile
210                 215                 220

Val Val Gly Ser Ser Val Ala Pro Gly Asn Thr Ala Pro Ser Pro Ser
225                 230                 235                 240

Ser Pro Thr Ser Pro Thr Ser Asp Ala Thr Thr Ser Leu Glu Met Asn
                245                 250                 255

Asn Pro His Ala Ile Pro Arg Arg His Ala Pro Ile Glu Gln Leu Ala
            260                 265                 270

Arg Gln Gly Ser Phe Arg Gly Phe Pro Ala Leu Ser Gln Lys Met Ser
        275                 280                 285

Pro Phe Lys Arg Gln Leu Ser Leu Arg Ile Asn Glu Leu Pro Ser Thr
290                 295                 300

Met Gln Arg Lys Thr Asp Phe Pro Ile Lys Asn Ala Val Pro Glu Val
305                 310                 315                 320

Glu Gly Glu Ala Glu Ser Ile Ser Ser Leu Cys Ser Gln Ile Thr Asn
                325                 330                 335

Ala Phe Ser Thr Pro Glu Asp Pro Phe Ser Ser Ala Pro Met Thr Lys
            340                 345                 350

Pro Val Thr Val Val Ala Pro Gln Ser Pro Thr Phe Gln Ala Asn Gly
        355                 360                 365

Thr Asp Ser Ala Phe His Val Leu Ala Lys Pro Ala His Thr Ala Leu
    370                 375                 380

Ala Pro Val Ala Met Pro Val Arg Glu Thr Asn Pro Trp Ala His Ala
385                 390                 395                 400

Pro Asp Ala Ala Asn Lys Glu Ile Ala Ala Thr Cys Ser Gly Thr Glu
                405                 410                 415

Trp Gly Gln Ser Ser Gly Ala Ala Ser Pro Gly Leu Phe Gln Ala Gly
            420                 425                 430

His Arg Arg Thr Pro Ser Glu Ala Asp Arg Trp Leu Glu Glu Val Ser
        435                 440                 445

Lys Ser Val Arg Ala Gln Gln Pro Gln Ala Ser Ala Ala Pro Leu Gln
    450                 455                 460

Pro Val Leu Gln Pro Pro Pro Thr Ala Ile Ser Gln Pro Ala Ser
465                 470                 475                 480

Pro Phe Gln Gly Asn Ala Phe Leu Thr Ser Gln Pro Val Pro Val Gly
            485                 490                 495

Val Val Pro Ala Leu Gln Pro Ala Phe Val Pro Ala Gln Ser Tyr Pro
        500                 505                 510

Val Ala Asn Gly Met Pro Tyr Pro Ala Pro Asn Val Pro Val Val Gly
    515                 520                 525

Ile Thr Pro Ser Gln Met Val Ala Asn Val Phe Gly Thr Ala Gly His
530                 535                 540

Pro Gln Ala Ala His Pro His Gln Ser Pro Ser Leu Val Arg Gln Gln
545                 550                 555                 560
```

```
Thr Phe Pro His Tyr Glu Ala Ser Ser Ala Thr Thr Ser Pro Phe Phe
            565                 570                 575

Lys Pro Pro Ala Gln His Leu Asn Gly Ser Ala Ala Phe Asn Gly Val
        580                 585                 590

Asp Asp Gly Arg Leu Ala Ser Ala Asp Arg His Thr Glu Val Pro Thr
    595                 600                 605

Gly Thr Cys Pro Val Asp Pro Phe Glu Ala Gln Trp Ala Ala Leu Glu
    610                 615                 620

Asn Lys Ser Lys Gln Arg Thr Asn Pro Ser Pro Thr Asn Pro Phe Ser
625                 630                 635                 640

Ser Asp Leu Gln Lys Thr Phe Glu Ile Glu Leu
                645                 650

<210> SEQ ID NO 2
<211> LENGTH: 3647
<212> TYPE: DNA
<213> ORGANISM: homo sapiens

<400> SEQUENCE: 2
```

| | | | | | |
|---|---|---|---|---|---|
| gttgtcatgg | gggaggtggt | ggcgcttggt | ggccactggc | ggccgaggta | gaggcagtgg | 60 |
| cgcttgagtt | ggtcggggc | agcggcagat | ttgaggctta | agcaacttct | tccggggaag | 120 |
| agtgccagtg | cagccactgt | tacaattcaa | gatcttgatc | tatatccata | gattggaata | 180 |
| ttggtgggcc | agcaatcctc | agacgcctca | cttaggacaa | atgaggaaac | tgaggcttgg | 240 |
| tgaagttacg | aaacttgtcc | aaaatcacac | aacttgtaaa | gggcacagcc | aagattcaga | 300 |
| gccaggctgt | aaaaattaaa | atgaacaaat | tacggcaaag | ttttaggaga | aagaaggatg | 360 |
| tttatgttcc | agaggccagt | cgtccacatc | agtggcagac | agatgaagaa | ggcgttcgca | 420 |
| ccggaaaatg | tagcttcccg | gttaagtacc | ttggccatgt | agaagttgat | gaatcaagag | 480 |
| gaatgcacat | ctgtgaagat | gctgtaaaaa | gattgaaagc | tgaaaggaag | ttcttcaaag | 540 |
| gcttctttgg | aaaaactgga | agaaaagcag | ttaaagcagt | tctgtgggtc | tcagcagatg | 600 |
| gactcagagt | tgtggatgaa | aaaactaagg | acctcatagt | tgaccagacg | atagagaaag | 660 |
| tttcttttctg | tgccccagac | aggaactttg | atagagcctt | ttcttacata | tgccgtgatg | 720 |
| gcaccactcg | tcgctggatc | tgtcactgct | tcatggctgt | caaggacaca | ggtgaaaggt | 780 |
| tgagccatgc | agtaggctgt | gcttttgcag | cctgtttaga | gcgcaagcag | aagcgggaga | 840 |
| aggaatgtgg | agtgactgct | acttttgatg | ctagtcggac | cacttttaca | agagaaggat | 900 |
| cattccgtgt | cacaacagcc | actgaacaag | cagaaagaga | ggagatcatg | aaacaaatgc | 960 |
| aagatgccaa | gaaagctgaa | acagataaga | tagtcgttgg | ttcatcagtt | gcccctggca | 1020 |
| acactgcccc | atccccatcc | tctcccacct | ctcctacttc | tgatgccacg | acctctctgg | 1080 |
| agatgaacaa | tcctcatgcc | atcccacgcc | ggcatgctcc | aattgaacag | cttgctcgcc | 1140 |
| aaggctcttt | ccgaggtttt | cctgctctta | gccagaagat | gtcacccttt | aaacgccaac | 1200 |
| tatccctacg | catcaatgag | ttgccttcca | ctatgcagag | gaagactgat | ttccccatta | 1260 |
| aaaatgcagt | gccagaagta | gaaggggagg | cagagagcat | cagctccctg | tgctcacaga | 1320 |
| tcaccaatgc | cttcagcaca | cctgaggacc | ccttctcatc | tgctccgatg | accaaaccag | 1380 |
| tgacagtggt | ggcaccacaa | tctcctacct | tccaagctaa | tggcactgac | tcagccttcc | 1440 |
| atgtgcttgc | taagcagcc | catactgctc | tagcacccgt | agcaatgcct | gtgcgtgaaa | 1500 |
| ccaacccttg | ggcccatgcc | cctgatgctg | ctaacaagga | aattgcagcc | acatgttcgg | 1560 |
| ggaccgagtg | gggtcaatct | tctggtgctg | cctctccagg | tctcttccag | gccggtcata | 1620 |

-continued

```
gacgtactcc ctctgaggcc gaccgatggt tagaagaggt gtctaagagc gtccgggctc    1680
agcagcccca ggcctcagct gctcctctgc agccagttct ccagcctcct ccacccactg    1740
ccatctccca gccagcatca cctttccaag ggaatgcatt cctcacctct cagcctgtgc    1800
cagtgggtgt ggtcccagcc ctgcaaccag ccttttgtccc tgcccagtcc tatcctgtgg   1860
ccaatggaat gccctatcca gcccctaatg tgcctgtggt gggcatcact ccctcccaga    1920
tggtggccaa cgtatttggc actgcaggcc accctcaggc tgcccatccc catcagtcac    1980
ccagcctggt caggcagcag acattccctc actacgaggc aagcagtgct accaccagtc    2040
ccttctttaa gcctcctgct cagcacctca acggttctgc agctttcaat ggtgtagatg    2100
atggcaggtt ggcctcagca gacaggcata cagaggttcc tacaggcacc tgcccagtgg    2160
atccttttga agcccagtgg gctgcattag aaaataagtc caagcagcgt actaatccct    2220
cccctaccaa cccctttctcc agtgacttac agaagacgtt tgaaattgaa ctttaagcaa    2280
tcattatggc tatgtatctt gtccatacca gacaggggag aggggtagc ggtcaaagga     2340 gcaaaacaga ctttgtctcc tgattagtac tcttttcact aatcccaaag gtcccaagga    2400
acaagtccag gcccagagta ctgtgagggg tgattttgaa agacatggga aaaagcattc    2460
ctagagaaaa gctgccttgc aattaggcta agaagtcaa ggaaatgttg ctttctgtac     2520
tccctcttcc cttaccccct tacaaatctc tggcaacaga gaggcaaagt atctgaacaa    2580
gaatctatat tccaagcaca tttactgaaa tgtaaaacac aacaggaagc aaagcaatct    2640 cccttttgttt ttcaggccat tcacctgcct cctgtcagta gtggcctgta ttagagatca   2700
agaagagtgg tttgtgctca ggctggggaa cagagaggca cgctatgctg ccagaattcc    2760
caggagggca tatcagcaac tgcccagcag agctatattt tgggggagaa gttgagcttc    2820
cattttgagt aacagaataa atattatata tatcaaaagc caaaatctttt atttttatgc    2880 atttagaata ttttaaatag ttctcagata ttaagaagtt gtatgagttg taagtaatct    2940
tgccaaaggt aaagggcta gttgtaagaa attgtacata agattgattt atcattgatg     3000
cctactgaaa taaaaagagg aaaggctgga agctgcagac aggatcccta gcttgttttc    3060
tgtcagtcat tcattgtaag tagcacattg caacaacaat catgcttatg accaatacag    3120
tcactaggtt gtagttttttt ttaaataaag gaaaagcagt attgtcctgg ttttaaacct    3180
atgatggaat tctaatgtca ttatttaat ggaatcaatc gaaatatgct ctatagaaaa     3240
tatatctttt atatattgct gcagtttcct tatgttaatc ctttaacact aaggtaacat    3300
gacataatca taccatagaa gggaacacag gttaccatat tggtttgtaa tatgggtctt    3360
ggtgggtttt gttttatcct ttaaattttg ttcccatgag ttttgtgggg atgggattc     3420 tggttttatt agctttgtgt gtgtcctctt ccccaaaacc ccttttggt gagaacatcc      3480 ccttgacagt tgcagcctct tgacctcgga taacaataag agagctcatc tcattttac     3540 ttttgaacgt tggccttaca atcaaatgta agttatatat atttgtactg atgaaaattt    3600
ataatctgct ttaacaaaaa taaatgttca tggtagaagc tttaaa                   3647
```

<210> SEQ ID NO 3
<211> LENGTH: 603
<212> TYPE: PRT
<213> ORGANISM: homo sapiens

<400> SEQUENCE: 3

```
Met Asn Lys Leu Arg Gln Ser Phe Arg Arg Lys Lys Asp Val Tyr Val
1               5                   10                  15
```

```
Pro Glu Ala Ser Arg Pro His Gln Trp Gln Thr Asp Glu Glu Gly Val
            20                  25                  30

Arg Thr Gly Lys Cys Ser Phe Pro Val Lys Tyr Leu Gly His Val Glu
            35                  40                  45

Val Asp Glu Ser Arg Gly Met His Ile Cys Asp Ala Val Lys Arg
 50                      55                  60

Leu Lys Ala Glu Arg Lys Phe Phe Lys Gly Phe Phe Gly Lys Thr Gly
 65                      70                  75                  80

Lys Lys Ala Val Lys Ala Val Leu Trp Val Ser Ala Asp Gly Leu Arg
                 85                  90                  95

Val Val Asp Glu Lys Thr Lys Asp Leu Ile Val Asp Gln Thr Ile Glu
            100                 105                 110

Lys Val Ser Phe Cys Ala Pro Asp Arg Asn Phe Asp Arg Ala Phe Ser
            115                 120                 125

Tyr Ile Cys Arg Asp Gly Thr Thr Arg Arg Trp Ile Cys His Cys Phe
130                     135                 140

Met Ala Val Lys Asp Thr Gly Glu Arg Leu Ser His Ala Val Gly Cys
145                     150                 155                 160

Ala Phe Ala Ala Cys Leu Glu Arg Lys Gln Lys Arg Glu Lys Glu Cys
                165                 170                 175

Gly Val Thr Ala Thr Phe Asp Ala Ser Arg Thr Thr Phe Thr Arg Glu
            180                 185                 190

Gly Ser Phe Arg Val Thr Thr Ala Thr Glu Gln Ala Glu Arg Glu Glu
            195                 200                 205

Ile Met Lys Gln Met Gln Asp Ala Lys Lys Ala Glu Thr Asp Lys Ile
            210                 215                 220

Val Val Gly Ser Ser Val Ala Pro Gly Asn Thr Ala Pro Ser Pro Ser
225                     230                 235                 240

Ser Pro Thr Ser Pro Thr Ser Asp Ala Thr Thr Ser Leu Glu Met Asn
                245                 250                 255

Asn Pro His Ala Ile Pro Arg Arg His Ala Pro Ile Glu Gln Leu Ala
            260                 265                 270

Arg Gln Gly Ser Phe Arg Gly Phe Pro Ala Leu Ser Gln Lys Met Ser
            275                 280                 285

Pro Phe Lys Arg Gln Leu Ser Leu Arg Ile Asn Glu Leu Pro Ser Thr
            290                 295                 300

Met Gln Arg Lys Thr Asp Phe Pro Ile Lys Asn Ala Val Pro Glu Val
305                     310                 315                 320

Glu Gly Glu Ala Glu Ser Ile Ser Ser Leu Cys Ser Gln Ile Thr Asn
                325                 330                 335

Ala Phe Ser Thr Pro Glu Asp Pro Phe Ser Ser Ala Pro Met Thr Lys
            340                 345                 350

Pro Val Thr Val Val Ala Pro Gln Ser Pro Thr Phe Gln Gly Thr Glu
            355                 360                 365

Trp Gly Gln Ser Ser Gly Ala Ala Ser Pro Gly Leu Phe Gln Ala Gly
            370                 375                 380

His Arg Arg Thr Pro Ser Glu Ala Asp Arg Trp Leu Glu Glu Val Ser
385                     390                 395                 400

Lys Ser Val Arg Ala Gln Gln Pro Gln Ala Ser Ala Ala Pro Leu Gln
                405                 410                 415

Pro Val Leu Gln Pro Pro Pro Thr Ala Ile Ser Pro Ala Ser
            420                 425                 430
```

```
Pro Phe Gln Gly Asn Ala Phe Leu Thr Ser Gln Pro Val Pro Val Gly
            435                 440                 445
Val Val Pro Ala Leu Gln Pro Ala Phe Val Pro Ala Gln Ser Tyr Pro
450                 455                 460
Val Ala Asn Gly Met Pro Tyr Pro Ala Pro Asn Val Pro Val Val Gly
465                 470                 475                 480
Ile Thr Pro Ser Gln Met Val Ala Asn Val Phe Gly Thr Ala Gly His
                485                 490                 495
Pro Gln Ala Ala His Pro His Gln Ser Pro Leu Val Arg Gln Gln
                500                 505                 510
Thr Phe Pro His Tyr Glu Ala Ser Ser Ala Thr Thr Ser Pro Phe Phe
            515                 520                 525
Lys Pro Pro Ala Gln His Leu Asn Gly Ser Ala Ala Phe Asn Gly Val
530                 535                 540
Asp Asp Gly Arg Leu Ala Ser Ala Asp Arg His Thr Glu Val Pro Thr
545                 550                 555                 560
Gly Thr Cys Pro Val Asp Pro Phe Glu Ala Gln Trp Ala Ala Leu Glu
                565                 570                 575
Asn Lys Ser Lys Gln Arg Thr Asn Pro Ser Pro Thr Asn Pro Phe Ser
            580                 585                 590
Ser Asp Leu Gln Lys Thr Phe Glu Ile Glu Leu
            595                 600

<210> SEQ ID NO 4
<211> LENGTH: 161
<212> TYPE: PRT
<213> ORGANISM: homo sapiens

<400> SEQUENCE: 4

Arg Thr Gly Lys Cys Ser Phe Pro Val Lys Tyr Leu Gly His Val Glu
1               5                   10                  15
Val Asp Glu Ser Arg Gly Met His Ile Cys Glu Asp Ala Val Lys Arg
                20                  25                  30
Leu Lys Ala Glu Arg Lys Phe Phe Lys Gly Phe Phe Gly Lys Thr Gly
            35                  40                  45
Lys Lys Ala Val Lys Ala Val Leu Trp Val Ser Ala Asp Gly Leu Arg
50                  55                  60
Val Val Asp Glu Lys Thr Lys Asp Leu Ile Val Asp Gln Thr Ile Glu
65                  70                  75                  80
Lys Val Ser Phe Cys Ala Pro Asp Arg Asn Phe Asp Arg Ala Phe Ser
                85                  90                  95
Tyr Ile Cys Arg Asp Gly Thr Thr Arg Arg Trp Ile Cys His Cys Phe
                100                 105                 110
Met Ala Val Lys Asp Thr Gly Glu Arg Leu Ser His Ala Val Gly Cys
            115                 120                 125
Ala Phe Ala Ala Cys Leu Glu Arg Lys Gln Lys Arg Glu Lys Glu Cys
130                 135                 140
Gly Val Thr Ala Thr Phe Asp Ala Ser Arg Thr Thr Phe Thr Arg Glu
145                 150                 155                 160
Gly

<210> SEQ ID NO 5
<211> LENGTH: 3503
<212> TYPE: DNA
<213> ORGANISM: homo sapiens
```

```
<400> SEQUENCE: 5
gttgtcatgg gggaggtggt ggcgcttggt ggccactggc ggccgaggta gaggcagtgg        60
cgcttgagtt ggtcggggc agcggcagat ttgaggctta agcaacttct tccggggaag       120
agtgccagtg cagccactgt tacaattcaa gatcttgatc tatatccata gattggaata       180
ttggtgggcc agcaatcctc agacgcctca cttaggacaa atgaggaaac tgaggcttgg       240
tgaagttacg aaacttgtcc aaaatcacac aacttgtaaa gggcacagcc aagattcaga       300
gccaggctgt aaaattaaa atgaacaaat tacggcaaag ttttaggaga aagaaggatg       360
tttatgttcc agaggccagt cgtccacatc agtggcagac agatgaagaa ggcgttcgca       420
ccggaaaatg tagcttcccg gttaagtacc ttggccatgt agaagttgat gaatcaagag       480
gaatgcacat ctgtgaagat gctgtaaaaa gattgaaagc tgaaaggaag ttcttcaaag       540
gcttctttgg aaaaactgga agaaagcag ttaaagcagt tctgtgggtc tcagcagatg       600
gactcagagt tgtggatgaa aaactaagg acctcatagt tgaccagacg atagagaaag       660
tttctttctg tgcccagac aggaactttg atagagcctt ttcttacata tgccgtgatg       720
gcaccactcg tcgctggatc tgtcactgct tcatggctgt caaggacaca ggtgaaaggt       780
tgagccatgc agtaggctgt gcttttgcag cctgtttaga gcgcaagcag aagcgggaga       840
aggaatgtgg agtgactgct acttttgatg ctagtcggac cacttttaca agagaaggat       900
cattccgtgt cacaacagcc actgaacaag cagaaagaga ggagatcatg aaacaaatgc       960
aagatgccaa gaaagctgaa acagataaga tagtcgttgg ttcatcagtt gcccctggca      1020
acactgcccc atccccatcc tctcccacct ctcctacttc tgatgccacg acctctctgg      1080
agatgaacaa tcctcatgcc atcccacgcc ggcatgctcc aattgaacag cttgctcgcc      1140
aaggctcttt ccgaggtttt cctgctctta gccagaagat gtcacccttt aaacgccaac      1200
tatccctacg catcaatgag ttgccttcca ctatgcagag gaagactgat ttccccatta      1260
aaaatgcagt gccagaagta gaggggagg cagagagcat cagctccctg tgctcacaga      1320
tcaccaatgc cttcagcaca cctgaggacc ccttctcatc tgctccgatg accaaaccag      1380
tgacagtggt ggcaccacaa tctcctacct tccaagggac cgagtggggt caatcttctg      1440
gtgctgcctc tccaggtctc ttccaggccg gtcatagacg tactccctct gaggccgacc      1500
gatggttaga agaggtgtct aagagcgtcc gggctcagca gccccaggcc tcagctgctc      1560
ctctgcagcc agttctccag cctcctccac ccactgccat ctcccagcca gcatcacctt      1620
tccaagggaa tgcattcctc acctctcagc ctgtgccagt gggtgtggtc ccagccctgc      1680
aaccagcctt tgtccctgcc cagtcctatc ctgtggccaa tggaatgccc tatccagccc      1740
ctaatgtgcc tgtggtgggc atcactccct cccagatggt ggccaacgta tttggcactg      1800
caggccaccc tcaggctgcc catccccatc agtcacccag cctggtcagg cagcagacat      1860
tccctcacta cgaggcaagc agtgctacca ccagtccctt ctttaagcct cctgctcagc      1920
acctcaacgg ttctgcagct ttcaatggtg tagatgatgg caggttggcc tcagcagaca      1980
ggcatacaga ggttcctaca ggcacctgcc cagtggatcc ttttgaagcc cagtgggctg      2040
cattagaaaa taagtccaag cagcgtacta atccctcccc taccaaccct ttctccagtg      2100
acttacagaa gacgtttgaa attgaacttt aagcaatcat tatggctatg tatcttgtcc      2160
ataccagaca gggagcaggg ggtagcggtc aaaggagcaa aacagacttt gtctcctgat      2220
tagtactctt ttcactaatc ccaaaggtcc caaggaacaa gtccaggccc agagtactgt      2280 gagggggtgat tttgaaagac atgggaaaaa gcattcctag agaaaagctg ccttgcaatt      2340
```

```
aggctaaaga agtcaaggaa atgttgcttt ctgtactccc tcttccctta cccccttaca   2400
aatctctggc aacagagagg caaagtatct gaacaagaat ctatattcca agcacattta   2460
ctgaaatgta aaacacaaca ggaagcaaag caatctccct ttgtttttca ggccattcac   2520
ctgcctcctg tcagtagtgg cctgtattag agatcaagaa gagtggtttg tgctcaggct   2580
ggggaacaga gaggcacgct atgctgccag aattcccagg agggcatatc agcaactgcc   2640
cagcagagct atattttggg ggagaagttg agcttccatt ttgagtaaca gaataaaatat   2700
tatatatatc aaaagccaaa atctttattt ttatgcattt agaatatttt aaatagttct   2760
cagatattaa gaagttgtat gagttgtaag taatcttgcc aaaggtaaag gggctagttg   2820
taagaaattg tacataagat tgatttatca ttgatgccta ctgaaataaa agaggaaag   2880
gctggaagct gcagacagga tccctagctt gttttctgtc agtcattcat tgtaagtagc   2940
acattgcaac aacaatcatg cttatgacca atacagtcac taggttgtag tttttttaa   3000
ataaaggaaa agcagtattg tcctggtttt aaacctatga tggaattcta atgtcattat   3060
tttaatggaa tcaatcgaaa tatgctctat agagaatata tcttttatat attgctgcag   3120
tttccttatg ttaatccttt aacactaagg taacatgaca taatcatacc atagaaggga   3180
acacaggtta ccatattggt ttgtaatatg ggtcttggtg ggttttgttt tatcctttaa   3240
attttgttcc catgagtttt gtggggatgg ggattctggt tttattagct ttgtgtgtgt   3300
cctcttcccc caaaccccct tttggtgaga acatcccctt gacagttgca gcctcttgac   3360
ctcggataac aataagagag ctcatctcat ttttactttt gaacgttggc cttacaatca   3420
aatgtaagtt atatatattt gtactgatga aaatttataa tctgctttaa caaaaataaa   3480
tgttcatggt agaagctttt aaa                                           3503
```

<210> SEQ ID NO 6
<211> LENGTH: 640
<212> TYPE: PRT
<213> ORGANISM: homo sapiens

<400> SEQUENCE: 6

Met Asn Lys Leu Arg Gln Ser Phe Arg Arg Lys Lys Asp Val Tyr Val
1               5                   10                  15

Pro Glu Ala Ser Arg Pro His Gln Trp Gln Thr Asp Glu Glu Gly Val
                20                  25                  30

Arg Thr Gly Lys Cys Ser Phe Pro Val Lys Tyr Leu Gly His Val Glu
            35                  40                  45

Val Asp Glu Ser Arg Gly Met His Ile Cys Glu Asp Ala Val Lys Arg
        50                  55                  60

Leu Lys Ala Thr Gly Lys Lys Ala Val Lys Ala Val Leu Trp Val Ser
65                  70                  75                  80

Ala Asp Gly Leu Arg Val Val Asp Glu Lys Thr Lys Asp Leu Ile Val
                85                  90                  95

Asp Gln Thr Ile Glu Lys Val Ser Phe Cys Ala Pro Asp Arg Asn Phe
            100                 105                 110

Asp Arg Ala Phe Ser Tyr Ile Cys Arg Asp Gly Thr Thr Arg Arg Trp
        115                 120                 125

Ile Cys His Cys Phe Met Ala Val Lys Asp Thr Gly Glu Arg Leu Ser
    130                 135                 140

His Ala Val Gly Cys Ala Phe Ala Ala Cys Leu Glu Arg Lys Gln Lys
145                 150                 155                 160

```
Arg Glu Lys Glu Cys Gly Val Thr Ala Thr Phe Asp Ala Ser Arg Thr
            165                 170                 175
Thr Phe Thr Arg Glu Gly Ser Phe Arg Val Thr Thr Ala Thr Glu Gln
        180                 185                 190
Ala Glu Arg Glu Glu Ile Met Lys Gln Met Gln Asp Ala Lys Lys Ala
    195                 200                 205
Glu Thr Asp Lys Ile Val Val Gly Ser Ser Val Ala Pro Gly Asn Thr
210                 215                 220
Ala Pro Ser Pro Ser Pro Thr Ser Pro Thr Ser Asp Ala Thr Thr
225                 230                 235                 240
Ser Leu Glu Met Asn Asn Pro His Ala Ile Pro Arg Arg His Ala Pro
                245                 250                 255
Ile Glu Gln Leu Ala Arg Gln Gly Ser Phe Arg Gly Phe Pro Ala Leu
            260                 265                 270
Ser Gln Lys Met Ser Pro Phe Lys Arg Gln Leu Ser Leu Arg Ile Asn
        275                 280                 285
Glu Leu Pro Ser Thr Met Gln Arg Lys Thr Asp Phe Pro Ile Lys Asn
    290                 295                 300
Ala Val Pro Glu Val Glu Gly Glu Ala Glu Ser Ile Ser Ser Leu Cys
305                 310                 315                 320
Ser Gln Ile Thr Asn Ala Phe Ser Thr Pro Glu Asp Pro Phe Ser Ser
                325                 330                 335
Ala Pro Met Thr Lys Pro Val Thr Val Ala Pro Gln Ser Pro Thr
            340                 345                 350
Phe Gln Ala Asn Gly Thr Asp Ser Ala Phe His Val Leu Ala Lys Pro
        355                 360                 365
Ala His Thr Ala Leu Ala Pro Val Ala Met Pro Val Arg Glu Thr Asn
    370                 375                 380
Pro Trp Ala His Ala Pro Asp Ala Ala Asn Lys Glu Ile Ala Ala Thr
385                 390                 395                 400
Cys Ser Gly Thr Glu Trp Gly Gln Ser Ser Ala Ala Ser Pro Gly
                405                 410                 415
Leu Phe Gln Ala Gly His Arg Arg Thr Pro Ser Glu Ala Asp Arg Trp
            420                 425                 430
Leu Glu Glu Val Ser Lys Ser Val Arg Ala Gln Gln Pro Gln Ala Ser
        435                 440                 445
Ala Ala Pro Leu Gln Pro Val Leu Gln Pro Pro Pro Thr Ala Ile
    450                 455                 460
Ser Gln Pro Ala Ser Pro Phe Gln Gly Asn Ala Phe Leu Thr Ser Gln
465                 470                 475                 480
Pro Val Pro Val Gly Val Pro Ala Leu Gln Pro Ala Phe Val Pro
                485                 490                 495
Ala Gln Ser Tyr Pro Val Ala Asn Gly Met Pro Tyr Pro Ala Pro Asn
            500                 505                 510
Val Pro Val Val Gly Ile Thr Pro Ser Gln Met Val Ala Asn Val Phe
        515                 520                 525
Gly Thr Ala Gly His Pro Gln Ala Ala His Pro His Gln Ser Pro Ser
    530                 535                 540
Leu Val Arg Gln Gln Thr Phe Pro His Tyr Glu Ala Ser Ser Ala Thr
545                 550                 555                 560
Thr Ser Pro Phe Phe Lys Pro Pro Ala Gln His Leu Asn Gly Ser Ala
                565                 570                 575
Ala Phe Asn Gly Val Asp Asp Gly Arg Leu Ala Ser Ala Asp Arg His
```

```
                    580             585             590
Thr Glu Val Pro Thr Gly Thr Cys Pro Val Asp Pro Phe Glu Ala Gln
                595             600             605

Trp Ala Ala Leu Glu Asn Lys Ser Lys Gln Arg Thr Asn Pro Ser Pro
    610             615             620

Thr Asn Pro Phe Ser Ser Asp Leu Gln Lys Thr Phe Glu Ile Glu Leu
625             630             635             640

<210> SEQ ID NO 7
<211> LENGTH: 592
<212> TYPE: PRT
<213> ORGANISM: homo sapiens

<400> SEQUENCE: 7

Met Asn Lys Leu Arg Gln Ser Phe Arg Arg Lys Lys Asp Val Tyr Val
1               5                  10                  15

Pro Glu Ala Ser Arg Pro His Gln Trp Gln Thr Asp Glu Glu Gly Val
                20                  25                  30

Arg Thr Gly Lys Cys Ser Phe Pro Val Lys Tyr Leu Gly His Val Glu
            35                  40                  45

Val Asp Glu Ser Arg Gly Met His Ile Cys Glu Asp Ala Val Lys Arg
        50                  55                  60

Leu Lys Ala Thr Gly Lys Lys Ala Val Lys Ala Val Leu Trp Val Ser
65                  70                  75                  80

Ala Asp Gly Leu Arg Val Val Asp Glu Lys Thr Lys Asp Leu Ile Val
                85                  90                  95

Asp Gln Thr Ile Glu Lys Val Ser Phe Cys Ala Pro Asp Arg Asn Phe
            100                 105                 110

Asp Arg Ala Phe Ser Tyr Ile Cys Arg Asp Gly Thr Thr Arg Arg Trp
        115                 120                 125

Ile Cys His Cys Phe Met Ala Val Lys Asp Thr Gly Glu Arg Leu Ser
130                 135                 140

His Ala Val Gly Cys Ala Phe Ala Ala Cys Leu Glu Arg Lys Gln Lys
145                 150                 155                 160

Arg Glu Lys Glu Cys Gly Val Thr Ala Thr Phe Asp Ala Ser Arg Thr
                165                 170                 175

Thr Phe Thr Arg Glu Gly Ser Phe Arg Val Thr Thr Ala Thr Glu Gln
            180                 185                 190

Ala Glu Arg Glu Glu Ile Met Lys Gln Met Gln Asp Ala Lys Lys Ala
        195                 200                 205

Glu Thr Asp Lys Ile Val Val Gly Ser Ser Val Ala Pro Gly Asn Thr
    210                 215                 220

Ala Pro Ser Pro Ser Ser Pro Thr Ser Pro Thr Ser Asp Ala Thr Thr
225                 230                 235                 240

Ser Leu Glu Met Asn Asn Pro His Ala Ile Pro Arg Arg His Ala Pro
                245                 250                 255

Ile Glu Gln Leu Ala Arg Gln Gly Ser Phe Arg Gly Phe Pro Ala Leu
            260                 265                 270

Ser Gln Lys Met Ser Pro Phe Lys Arg Gln Leu Ser Leu Arg Ile Asn
        275                 280                 285

Glu Leu Pro Ser Thr Met Gln Arg Lys Thr Asp Phe Pro Ile Lys Asn
    290                 295                 300

Ala Val Pro Glu Val Glu Gly Glu Ala Glu Ser Ile Ser Ser Leu Cys
305                 310                 315                 320
```

-continued

```
Ser Gln Ile Thr Asn Ala Phe Ser Thr Pro Glu Asp Pro Phe Ser Ser
            325                 330                 335

Ala Pro Met Thr Lys Pro Val Thr Val Val Ala Pro Gln Ser Pro Thr
        340                 345                 350

Phe Gln Gly Thr Glu Trp Gly Gln Ser Ser Gly Ala Ala Ser Pro Gly
            355                 360                 365

Leu Phe Gln Ala Gly His Arg Arg Thr Pro Ser Glu Ala Asp Arg Trp
370                 375                 380

Leu Glu Glu Val Ser Lys Ser Val Arg Ala Gln Gln Pro Gln Ala Ser
385                 390                 395                 400

Ala Ala Pro Leu Gln Pro Val Leu Gln Pro Pro Pro Thr Ala Ile
                405                 410                 415

Ser Gln Pro Ala Ser Pro Phe Gln Gly Asn Ala Phe Leu Thr Ser Gln
                420                 425                 430

Pro Val Pro Val Gly Val Val Pro Ala Leu Gln Pro Ala Phe Val Pro
            435                 440                 445

Ala Gln Ser Tyr Pro Val Ala Asn Gly Met Pro Tyr Pro Ala Pro Asn
            450                 455                 460

Val Pro Val Val Gly Ile Thr Pro Ser Gln Met Val Ala Asn Val Phe
465                 470                 475                 480

Gly Thr Ala Gly His Pro Gln Ala Ala His Pro Gln Ser Pro Ser
                485                 490                 495

Leu Val Arg Gln Gln Thr Phe Pro His Tyr Glu Ala Ser Ser Ala Thr
                500                 505                 510

Thr Ser Pro Phe Phe Lys Pro Pro Ala Gln His Leu Asn Gly Ser Ala
            515                 520                 525

Ala Phe Asn Gly Val Asp Asp Gly Arg Leu Ala Ser Ala Asp Arg His
            530                 535                 540

Thr Glu Val Pro Thr Gly Thr Cys Pro Val Asp Pro Phe Glu Ala Gln
545                 550                 555                 560

Trp Ala Ala Leu Glu Asn Lys Ser Lys Gln Arg Thr Asn Pro Ser Pro
                565                 570                 575

Thr Asn Pro Phe Ser Ser Asp Leu Gln Lys Thr Phe Glu Ile Glu Leu
            580                 585                 590

<210> SEQ ID NO 8
<211> LENGTH: 456
<212> TYPE: PRT
<213> ORGANISM: homo sapiens

<400> SEQUENCE: 8

Met Asn Lys Leu Arg Gln Ser Phe Arg Arg Lys Lys Asp Val Tyr Val
1               5                   10                  15

Pro Glu Ala Ser Arg Pro His Gln Trp Gln Thr Asp Glu Glu Gly Val
                20                  25                  30

Arg Thr Gly Lys Cys Ser Phe Pro Val Lys Tyr Leu Gly His Val Glu
            35                  40                  45

Val Asp Glu Ser Arg Gly Met His Ile Cys Glu Asp Ala Val Lys Arg
        50                  55                  60

Leu Lys Ala Glu Arg Lys Phe Phe Lys Gly Phe Phe Lys Thr Gly
65                  70                  75                  80

Lys Lys Ala Val Lys Ala Val Leu Trp Val Ser Ala Asp Gly Leu Arg
                85                  90                  95

Val Val Asp Glu Lys Thr Lys Asp Leu Ile Val Asp Gln Thr Ile Glu
            100                 105                 110
```

```
Lys Val Ser Phe Cys Ala Pro Asp Arg Asn Phe Asp Arg Ala Phe Ser
            115                 120                 125

Tyr Ile Cys Arg Asp Gly Thr Thr Arg Arg Trp Ile Cys His Cys Phe
    130                 135                 140

Met Ala Val Lys Asp Thr Gly Glu Arg Leu Ser His Ala Val Gly Cys
145                 150                 155                 160

Ala Phe Ala Ala Cys Leu Glu Arg Lys Gln Lys Arg Glu Lys Glu Cys
                165                 170                 175

Gly Val Thr Ala Thr Phe Asp Ala Ser Arg Thr Thr Phe Thr Arg Glu
                180                 185                 190

Gly Ser Phe Arg Val Thr Thr Ala Thr Glu Gln Ala Glu Arg Glu Glu
            195                 200                 205

Ile Met Lys Gln Met Gln Asp Ala Lys Lys Gly Thr Glu Trp Gly Gln
            210                 215                 220

Ser Ser Gly Ala Ala Ser Pro Gly Leu Phe Gln Ala Gly His Arg Arg
225                 230                 235                 240

Thr Pro Ser Glu Ala Asp Arg Trp Leu Glu Glu Val Ser Lys Ser Val
                245                 250                 255

Arg Ala Gln Gln Pro Gln Ala Ser Ala Ala Pro Leu Gln Pro Val Leu
                260                 265                 270

Gln Pro Pro Pro Thr Ala Ile Ser Gln Pro Ala Ser Pro Phe Gln
            275                 280                 285

Gly Asn Ala Phe Leu Thr Ser Gln Pro Val Pro Val Gly Val Val Pro
            290                 295                 300

Ala Leu Gln Pro Ala Phe Val Pro Ala Gln Ser Tyr Pro Val Ala Asn
305                 310                 315                 320

Gly Met Pro Tyr Pro Ala Pro Asn Val Pro Val Val Gly Ile Thr Pro
                325                 330                 335

Ser Gln Met Val Ala Asn Val Phe Gly Thr Ala Gly His Pro Gln Ala
                340                 345                 350

Ala His Pro His Gln Ser Pro Ser Leu Val Arg Gln Gln Thr Phe Pro
            355                 360                 365

His Tyr Glu Ala Ser Ser Ala Thr Thr Ser Pro Phe Phe Lys Pro Pro
    370                 375                 380

Ala Gln His Leu Asn Gly Ser Ala Ala Phe Asn Gly Val Asp Asp Gly
385                 390                 395                 400

Arg Leu Ala Ser Ala Asp Arg His Thr Glu Val Pro Thr Gly Thr Cys
                405                 410                 415

Pro Val Asp Pro Phe Glu Ala Gln Trp Ala Ala Leu Glu Asn Lys Ser
                420                 425                 430

Lys Gln Arg Thr Asn Pro Ser Pro Thr Asn Pro Phe Ser Ser Asp Leu
            435                 440                 445

Gln Lys Thr Phe Glu Ile Glu Leu
    450                 455

<210> SEQ ID NO 9
<211> LENGTH: 445
<212> TYPE: PRT
<213> ORGANISM: homo sapiens

<400> SEQUENCE: 9

Met Asn Lys Leu Arg Gln Ser Phe Arg Arg Lys Lys Asp Val Tyr Val
1               5                   10                  15

Pro Glu Ala Ser Arg Pro His Gln Trp Gln Thr Asp Glu Glu Gly Val
```

```
            20                  25                  30
Arg Thr Gly Lys Cys Ser Phe Pro Val Lys Tyr Leu Gly His Val Glu
            35                  40                  45

Val Asp Glu Ser Arg Gly Met His Ile Cys Glu Asp Ala Val Lys Arg
 50                  55                  60

Leu Lys Ala Thr Gly Lys Lys Ala Val Lys Ala Val Leu Trp Val Ser
 65                  70                  75                  80

Ala Asp Gly Leu Arg Val Val Asp Glu Lys Thr Lys Asp Leu Ile Val
                 85                  90                  95

Asp Gln Thr Ile Glu Lys Val Ser Phe Cys Ala Pro Asp Arg Asn Phe
                100                 105                 110

Asp Arg Ala Phe Ser Tyr Ile Cys Arg Asp Gly Thr Thr Arg Arg Trp
                115                 120                 125

Ile Cys His Cys Phe Met Ala Val Lys Asp Thr Gly Glu Arg Leu Ser
                130                 135                 140

His Ala Val Gly Cys Ala Phe Ala Ala Cys Leu Glu Arg Lys Gln Lys
145                 150                 155                 160

Arg Glu Lys Glu Cys Gly Val Thr Ala Thr Phe Asp Ala Ser Arg Thr
                165                 170                 175

Thr Phe Thr Arg Glu Gly Ser Phe Arg Val Thr Ala Thr Glu Gln
                180                 185                 190

Ala Glu Arg Glu Glu Ile Met Lys Gln Met Gln Asp Ala Lys Lys Gly
                195                 200                 205

Thr Glu Trp Gly Gln Ser Ser Gly Ala Ala Ser Pro Gly Leu Phe Gln
                210                 215                 220

Ala Gly His Arg Arg Thr Pro Ser Glu Ala Asp Arg Trp Leu Glu Glu
225                 230                 235                 240

Val Ser Lys Ser Val Arg Ala Gln Gln Pro Gln Ala Ser Ala Ala Pro
                245                 250                 255

Leu Gln Pro Val Leu Gln Pro Pro Pro Thr Ala Ile Ser Gln Pro
                260                 265                 270

Ala Ser Pro Phe Gln Gly Asn Ala Phe Leu Thr Ser Gln Pro Val Pro
                275                 280                 285

Val Gly Val Val Pro Ala Leu Gln Pro Ala Phe Val Pro Ala Gln Ser
                290                 295                 300

Tyr Pro Val Ala Asn Gly Met Pro Tyr Pro Ala Pro Asn Val Pro Val
305                 310                 315                 320

Val Gly Ile Thr Pro Ser Gln Met Val Ala Asn Val Phe Gly Thr Ala
                325                 330                 335

Gly His Pro Gln Ala Ala His Pro His Gln Ser Pro Ser Leu Val Arg
                340                 345                 350

Gln Gln Thr Phe Pro His Tyr Glu Ala Ser Ser Ala Thr Thr Ser Pro
                355                 360                 365

Phe Phe Lys Pro Pro Ala Gln His Leu Asn Gly Ser Ala Ala Phe Asn
                370                 375                 380

Gly Val Asp Asp Gly Arg Leu Ala Ser Ala Asp Arg His Thr Glu Val
385                 390                 395                 400

Pro Thr Gly Thr Cys Pro Val Asp Pro Phe Glu Ala Gln Trp Ala Ala
                405                 410                 415

Leu Glu Asn Lys Ser Lys Gln Arg Thr Asn Pro Ser Pro Thr Asn Pro
                420                 425                 430

Phe Ser Ser Asp Leu Gln Lys Thr Phe Glu Ile Glu Leu
                435                 440                 445
```

```
<210> SEQ ID NO 10
<211> LENGTH: 651
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (68)..(78)
<223> OTHER INFORMATION: Xaa can be any naturally occurring amino acid
<220> FEATURE:
<221> NAME/KEY: misc_feature
<222> LOCATION: (219)..(413)
<223> OTHER INFORMATION: Xaa can be any naturally occurring amino acid

<400> SEQUENCE: 10

Met Asn Lys Leu Arg Gln Ser Phe Arg Arg Lys Lys Asp Val Tyr Val
1               5                   10                  15

Pro Glu Ala Ser Arg Pro His Gln Trp Gln Thr Asp Glu Glu Gly Val
            20                  25                  30

Arg Thr Gly Lys Cys Ser Phe Pro Val Lys Tyr Leu Gly His Val Glu
        35                  40                  45

Val Asp Glu Ser Arg Gly Met His Ile Cys Asp Ala Val Lys Arg
    50                  55                  60

Leu Lys Ala Xaa Xaa Xaa Xaa Xaa Xaa Xaa Xaa Xaa Thr Gly
65                  70                  75                  80

Lys Lys Ala Val Lys Ala Val Leu Trp Val Ser Ala Asp Gly Leu Arg
                85                  90                  95

Val Val Asp Glu Lys Thr Lys Asp Leu Ile Val Asp Gln Thr Ile Glu
            100                 105                 110

Lys Val Ser Phe Cys Ala Pro Asp Arg Asn Phe Asp Arg Ala Phe Ser
        115                 120                 125

Tyr Ile Cys Arg Asp Gly Thr Thr Arg Arg Trp Ile Cys His Cys Phe
    130                 135                 140

Met Ala Val Lys Asp Thr Gly Glu Arg Leu Ser His Ala Val Gly Cys
145                 150                 155                 160

Ala Phe Ala Ala Cys Leu Glu Arg Lys Gln Lys Arg Glu Lys Glu Cys
                165                 170                 175

Gly Val Thr Ala Thr Phe Asp Ala Ser Arg Thr Thr Phe Thr Arg Glu
            180                 185                 190

Gly Ser Phe Arg Val Thr Thr Ala Thr Glu Gln Ala Glu Arg Glu Glu
        195                 200                 205

Ile Met Lys Gln Met Gln Asp Ala Lys Lys Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320
```

```
        Xaa Xaa Xaa Xaa Xaa Xaa Xaa Xaa Xaa Xaa Xaa Xaa
                        325                 330                 335

Xaa Xaa Xaa Xaa Xaa Xaa Xaa Xaa Xaa Xaa Xaa Xaa
                    340                 345                 350

Xaa Xaa Xaa Xaa Xaa Xaa Xaa Xaa Xaa Xaa Xaa Xaa
                355                 360                 365

Xaa Xaa Xaa Xaa Xaa Xaa Xaa Xaa Xaa Xaa Xaa Xaa
                    370                 375                 380

Xaa Xaa Xaa Xaa Xaa Xaa Xaa Xaa Xaa Xaa Xaa Xaa
        385                 390                 395                 400

Xaa Xaa Xaa Xaa Xaa Xaa Xaa Xaa Xaa Xaa Xaa Gly Thr Glu
                        405                 410                 415

Trp Gly Gln Ser Ser Gly Ala Ala Ser Pro Gly Leu Phe Gln Ala Gly
                    420                 425                 430

His Arg Arg Thr Pro Ser Glu Ala Asp Arg Trp Leu Glu Glu Val Ser
                435                 440                 445

Lys Ser Val Arg Ala Gln Gln Pro Gln Ala Ser Ala Ala Pro Leu Gln
            450                 455                 460

Pro Val Leu Gln Pro Pro Pro Thr Ala Ile Ser Gln Pro Ala Ser
        465                 470                 475                 480

Pro Phe Gln Gly Asn Ala Phe Leu Thr Ser Gln Pro Val Pro Val Gly
                        485                 490                 495

Val Val Pro Ala Leu Gln Pro Ala Phe Val Pro Ala Gln Ser Tyr Pro
                    500                 505                 510

Val Ala Asn Gly Met Pro Tyr Pro Ala Pro Asn Val Pro Val Val Gly
                515                 520                 525

Ile Thr Pro Ser Gln Met Val Ala Asn Val Phe Gly Thr Ala Gly His
            530                 535                 540

Pro Gln Ala Ala His Pro His Gln Ser Pro Ser Leu Val Arg Gln Gln
        545                 550                 555                 560

Thr Phe Pro His Tyr Glu Ala Ser Ser Ala Thr Thr Ser Pro Phe Phe
                        565                 570                 575

Lys Pro Pro Ala Gln His Leu Asn Gly Ser Ala Ala Phe Asn Gly Val
                    580                 585                 590

Asp Asp Gly Arg Leu Ala Ser Ala Asp Arg His Thr Glu Val Pro Thr
                595                 600                 605

Gly Thr Cys Pro Val Asp Pro Phe Glu Ala Gln Trp Ala Ala Leu Glu
            610                 615                 620

Asn Lys Ser Lys Gln Arg Thr Asn Pro Ser Pro Thr Asn Pro Phe Ser
        625                 630                 635                 640

Ser Asp Leu Gln Lys Thr Phe Glu Ile Glu Leu
                        645                 650

<210> SEQ ID NO 11
<211> LENGTH: 651
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (366)..(413)
<223> OTHER INFORMATION: Xaa can be any naturally occurring amino acid

<400> SEQUENCE: 11

Met Asn Lys Leu Arg Gln Ser Phe Arg Arg Lys Lys Asp Val Tyr Val
1               5                   10                  15
```

```
Pro Glu Ala Ser Arg Pro His Gln Trp Gln Thr Asp Glu Glu Gly Val
             20                  25                  30

Arg Thr Gly Lys Cys Ser Phe Pro Val Lys Tyr Leu Gly His Val Glu
         35                  40                  45

Val Asp Glu Ser Arg Gly Met His Ile Cys Asp Ala Val Lys Arg
 50                  55                  60

Leu Lys Ala Glu Arg Lys Phe Phe Lys Gly Phe Gly Lys Thr Gly
 65                  70                  75                  80

Lys Lys Ala Val Lys Ala Val Leu Trp Val Ser Ala Asp Gly Leu Arg
             85                  90                  95

Val Val Asp Glu Lys Thr Lys Asp Leu Ile Val Asp Gln Thr Ile Glu
            100                 105                 110

Lys Val Ser Phe Cys Ala Pro Asp Arg Asn Phe Asp Arg Ala Phe Ser
            115                 120                 125

Tyr Ile Cys Arg Asp Gly Thr Thr Arg Arg Trp Ile Cys His Cys Phe
130                 135                 140

Met Ala Val Lys Asp Thr Gly Glu Arg Leu Ser His Ala Val Gly Cys
145                 150                 155                 160

Ala Phe Ala Ala Cys Leu Glu Arg Lys Gln Lys Arg Glu Lys Glu Cys
                165                 170                 175

Gly Val Thr Ala Thr Phe Asp Ala Ser Arg Thr Thr Phe Thr Arg Glu
            180                 185                 190

Gly Ser Phe Arg Val Thr Thr Ala Thr Glu Gln Ala Glu Arg Glu Glu
        195                 200                 205

Ile Met Lys Gln Met Gln Asp Ala Lys Lys Ala Glu Thr Asp Lys Ile
        210                 215                 220

Val Val Gly Ser Ser Val Ala Pro Gly Asn Thr Ala Pro Ser Pro Ser
225                 230                 235                 240

Ser Pro Thr Ser Pro Thr Ser Asp Ala Thr Thr Ser Leu Glu Met Asn
                245                 250                 255

Asn Pro His Ala Ile Pro Arg Arg His Ala Pro Ile Glu Gln Leu Ala
            260                 265                 270

Arg Gln Gly Ser Phe Arg Gly Phe Pro Ala Leu Ser Gln Lys Met Ser
        275                 280                 285

Pro Phe Lys Arg Gln Leu Ser Leu Arg Ile Asn Glu Leu Pro Ser Thr
    290                 295                 300

Met Gln Arg Lys Thr Asp Phe Pro Ile Lys Asn Ala Val Pro Glu Val
305                 310                 315                 320

Glu Gly Glu Ala Glu Ser Ile Ser Ser Leu Cys Ser Gln Ile Thr Asn
                325                 330                 335

Ala Phe Ser Thr Pro Glu Asp Pro Phe Ser Ser Ala Pro Met Thr Lys
            340                 345                 350

Pro Val Thr Val Val Ala Pro Gln Ser Pro Thr Phe Gln Xaa Xaa Xaa
        355                 360                 365

Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Gly Thr Glu
                405                 410                 415

Trp Gly Gln Ser Ser Gly Ala Ala Ser Pro Gly Leu Phe Gln Ala Gly
            420                 425                 430
```

-continued

His Arg Arg Thr Pro Ser Glu Ala Asp Arg Trp Leu Glu Glu Val Ser
            435                 440                 445

Lys Ser Val Arg Ala Gln Gln Pro Gln Ala Ser Ala Ala Pro Leu Gln
450                 455                 460

Pro Val Leu Gln Pro Pro Pro Thr Ala Ile Ser Gln Pro Ala Ser
465                 470                 475                 480

Pro Phe Gln Gly Asn Ala Phe Leu Thr Ser Gln Pro Val Pro Val Gly
            485                 490                 495

Val Val Pro Ala Leu Gln Pro Ala Phe Val Pro Ala Gln Ser Tyr Pro
                500                 505                 510

Val Ala Asn Gly Met Pro Tyr Pro Ala Pro Asn Val Pro Val Val Gly
            515                 520                 525

Ile Thr Pro Ser Gln Met Val Ala Asn Val Phe Gly Thr Ala Gly His
        530                 535                 540

Pro Gln Ala Ala His Pro His Gln Ser Pro Ser Leu Val Arg Gln Gln
545                 550                 555                 560

Thr Phe Pro His Tyr Glu Ala Ser Ser Ala Thr Thr Ser Pro Phe Phe
            565                 570                 575

Lys Pro Pro Ala Gln His Leu Asn Gly Ser Ala Ala Phe Asn Gly Val
                580                 585                 590

Asp Asp Gly Arg Leu Ala Ser Ala Asp Arg His Thr Glu Val Pro Thr
            595                 600                 605

Gly Thr Cys Pro Val Asp Pro Phe Glu Ala Gln Trp Ala Ala Leu Glu
        610                 615                 620

Asn Lys Ser Lys Gln Arg Thr Asn Pro Ser Pro Thr Asn Pro Phe Ser
625                 630                 635                 640

Ser Asp Leu Gln Lys Thr Phe Glu Ile Glu Leu
            645                 650

<210> SEQ ID NO 12
<211> LENGTH: 531
<212> TYPE: PRT
<213> ORGANISM: homo sapiens

<400> SEQUENCE: 12

Met Asp Gly Ile Val Pro Asp Ile Ala Val Gly Thr Lys Arg Gly Ser
1               5                   10                  15

Asp Glu Leu Phe Ser Thr Cys Val Thr Asn Gly Pro Phe Ile Met Ser
                20                  25                  30

Ser Asn Ser Ala Ser Ala Ala Asn Gly Asn Asp Ser Lys Lys Phe Lys
            35                  40                  45

Gly Asp Ser Arg Ser Ala Gly Val Pro Ser Arg Val Ile His Ile Arg
        50                  55                  60

Lys Leu Pro Ile Asp Val Thr Glu Gly Glu Val Ile Ser Leu Gly Leu
65                  70                  75                  80

Pro Phe Gly Lys Val Thr Asn Leu Leu Met Leu Lys Gly Lys Asn Gln
                85                  90                  95

Ala Phe Ile Glu Met Asn Thr Glu Glu Ala Ala Asn Thr Met Val Asn
            100                 105                 110

Tyr Tyr Thr Ser Val Thr Pro Val Leu Arg Gly Gln Pro Ile Tyr Ile
        115                 120                 125

Gln Phe Ser Asn His Lys Glu Leu Lys Thr Asp Ser Ser Pro Asn Gln
    130                 135                 140

Ala Arg Ala Gln Ala Ala Leu Gln Ala Val Asn Ser Val Gln Ser Gly
145                 150                 155                 160

Asn Leu Ala Leu Ala Ser Ala Ala Val Asp Ala Gly Met Ala
                165                 170                 175

Met Ala Gly Gln Ser Pro Val Leu Arg Ile Ile Val Glu Asn Leu Phe
            180                 185                 190

Tyr Pro Val Thr Leu Asp Val Leu His Gln Ile Phe Ser Lys Phe Gly
        195                 200                 205

Thr Val Leu Lys Ile Ile Thr Phe Thr Lys Asn Asn Gln Phe Gln Ala
    210                 215                 220

Leu Leu Gln Tyr Ala Asp Pro Val Ser Ala Gln His Ala Lys Leu Ser
225                 230                 235                 240

Leu Asp Gly Gln Asn Ile Tyr Asn Ala Cys Cys Thr Leu Arg Ile Asp
                245                 250                 255

Phe Ser Lys Leu Thr Ser Leu Asn Val Lys Tyr Asn Asn Asp Lys Ser
            260                 265                 270

Arg Asp Tyr Thr Arg Pro Asp Leu Pro Ser Gly Asp Ser Gln Pro Ser
        275                 280                 285

Leu Asp Gln Thr Met Ala Ala Phe Gly Leu Ser Val Pro Asn Val
    290                 295                 300

His Gly Ala Leu Ala Pro Leu Ala Ile Pro Ser Ala Ala Ala Ala
305                 310                 315                 320

Ala Ala Ala Gly Arg Ile Ala Ile Pro Gly Leu Ala Gly Ala Gly Asn
                325                 330                 335

Ser Val Leu Leu Val Ser Asn Leu Asn Pro Glu Arg Val Thr Pro Gln
            340                 345                 350

Ser Leu Phe Ile Leu Phe Gly Val Tyr Gly Asp Val Gln Arg Val Lys
        355                 360                 365

Ile Leu Phe Asn Lys Lys Glu Asn Ala Leu Val Gln Met Ala Asp Gly
    370                 375                 380

Asn Gln Ala Gln Leu Ala Met Ser His Leu Asn Gly His Lys Leu His
385                 390                 395                 400

Gly Lys Pro Ile Arg Ile Thr Leu Ser Lys His Gln Asn Val Gln Leu
                405                 410                 415

Pro Arg Glu Gly Gln Glu Asp Gln Gly Leu Thr Lys Asp Tyr Gly Asn
            420                 425                 430

Ser Pro Leu His Arg Phe Lys Lys Pro Gly Ser Lys Asn Phe Gln Asn
        435                 440                 445

Ile Phe Pro Pro Ser Ala Thr Leu His Leu Ser Asn Ile Pro Pro Ser
    450                 455                 460

Val Ser Glu Glu Asp Leu Lys Val Leu Phe Ser Ser Asn Gly Gly Val
465                 470                 475                 480

Val Lys Gly Phe Lys Phe Phe Gln Lys Asp Arg Lys Met Ala Leu Ile
                485                 490                 495

Gln Met Gly Ser Val Glu Glu Ala Val Gln Ala Leu Ile Asp Leu His
            500                 505                 510

Asn His Asp Leu Gly Glu Asn His His Leu Arg Val Ser Phe Ser Lys
        515                 520                 525

Ser Thr Ile
        530

<210> SEQ ID NO 13
<211> LENGTH: 550
<212> TYPE: PRT
<213> ORGANISM: homo sapiens

```
<400> SEQUENCE: 13

Met Asp Gly Ile Val Pro Asp Ile Ala Val Gly Thr Lys Arg Gly Ser
1               5                   10                  15

Asp Glu Leu Phe Ser Thr Cys Val Thr Asn Gly Pro Phe Ile Met Ser
            20                  25                  30

Ser Asn Ser Ala Ser Ala Ala Asn Gly Asn Asp Ser Lys Lys Phe Lys
        35                  40                  45

Gly Asp Ser Arg Ser Ala Gly Val Pro Ser Arg Val Ile His Ile Arg
50                  55                  60

Lys Leu Pro Ile Asp Val Thr Glu Gly Glu Val Ile Ser Leu Gly Leu
65                  70                  75                  80

Pro Phe Gly Lys Val Thr Asn Leu Leu Met Leu Lys Gly Lys Asn Gln
                85                  90                  95

Ala Phe Ile Glu Met Asn Thr Glu Ala Ala Asn Thr Met Val Asn
            100                 105                 110

Tyr Tyr Thr Ser Val Thr Pro Val Leu Arg Gly Gln Pro Ile Tyr Ile
            115                 120                 125

Gln Phe Ser Asn His Lys Glu Leu Lys Thr Asp Ser Ser Pro Asn Gln
    130                 135                 140

Ala Arg Ala Gln Ala Ala Leu Gln Ala Val Asn Ser Val Gln Ser Gly
145                 150                 155                 160

Asn Leu Ala Leu Ala Ala Ser Ala Ala Val Asp Ala Gly Met Ala
                165                 170                 175

Met Ala Gly Gln Ser Pro Val Leu Arg Ile Ile Val Glu Asn Leu Phe
            180                 185                 190

Tyr Pro Val Thr Leu Asp Val Leu His Gln Ile Phe Ser Lys Phe Gly
        195                 200                 205

Thr Val Leu Lys Ile Ile Thr Phe Thr Lys Asn Asn Gln Phe Gln Ala
210                 215                 220

Leu Leu Gln Tyr Ala Asp Pro Val Ser Ala Gln His Ala Lys Leu Ser
225                 230                 235                 240

Leu Asp Gly Gln Asn Ile Tyr Asn Ala Cys Cys Thr Leu Arg Ile Asp
                245                 250                 255

Phe Ser Lys Leu Thr Ser Leu Asn Val Lys Tyr Asn Asn Asp Lys Ser
            260                 265                 270

Arg Asp Tyr Thr Arg Pro Asp Leu Pro Ser Gly Asp Ser Gln Pro Ser
        275                 280                 285

Leu Asp Gln Thr Met Ala Ala Phe Ala Ser Pro Tyr Ala Gly Ala
290                 295                 300

Gly Phe Pro Pro Thr Phe Ala Ile Pro Gln Ala Ala Gly Leu Ser Val
305                 310                 315                 320

Pro Asn Val His Gly Ala Leu Ala Pro Leu Ala Ile Pro Ser Ala Ala
                325                 330                 335

Ala Ala Ala Ala Ala Gly Arg Ile Ala Ile Pro Gly Leu Ala Gly
            340                 345                 350

Ala Gly Asn Ser Val Leu Leu Val Ser Asn Leu Asn Pro Glu Arg Val
        355                 360                 365

Thr Pro Gln Ser Leu Phe Ile Leu Phe Gly Val Tyr Gly Asp Val Gln
    370                 375                 380

Arg Val Lys Ile Leu Phe Asn Lys Lys Glu Asn Ala Leu Val Gln Met
385                 390                 395                 400

Ala Asp Gly Asn Gln Ala Gln Leu Ala Met Ser His Leu Asn Gly His
                405                 410                 415
```

-continued

Lys Leu His Gly Lys Pro Ile Arg Ile Thr Leu Ser Lys His Gln Asn
            420                 425                 430

Val Gln Leu Pro Arg Glu Gly Gln Glu Asp Gln Gly Leu Thr Lys Asp
        435                 440                 445

Tyr Gly Asn Ser Pro Leu His Arg Phe Lys Pro Gly Ser Lys Asn
450                 455                 460

Phe Gln Asn Ile Phe Pro Pro Ser Ala Thr Leu His Leu Ser Asn Ile
465                 470                 475                 480

Pro Pro Ser Val Ser Glu Glu Asp Leu Lys Val Leu Phe Ser Ser Asn
                485                 490                 495

Gly Gly Val Val Lys Gly Phe Lys Phe Gln Lys Asp Arg Lys Met
                500                 505                 510

Ala Leu Ile Gln Met Gly Ser Val Glu Glu Ala Val Gln Ala Leu Ile
                515                 520                 525

Asp Leu His Asn His Asp Leu Gly Glu Asn His His Leu Arg Val Ser
        530                 535                 540

Phe Ser Lys Ser Thr Ile
545                 550

<210> SEQ ID NO 14
<211> LENGTH: 557
<212> TYPE: PRT
<213> ORGANISM: homo sapiens

<400> SEQUENCE: 14

Met Asp Gly Ile Val Pro Asp Ile Ala Val Gly Thr Lys Arg Gly Ser
1               5                   10                  15

Asp Glu Leu Phe Ser Thr Cys Val Thr Asn Gly Pro Phe Ile Met Ser
            20                  25                  30

Ser Asn Ser Ala Ser Ala Ala Asn Gly Asn Asp Ser Lys Lys Phe Lys
        35                  40                  45

Gly Asp Ser Arg Ser Ala Gly Val Pro Ser Arg Val Ile His Ile Arg
    50                  55                  60

Lys Leu Pro Ile Asp Val Thr Glu Gly Glu Val Ile Ser Leu Gly Leu
65                  70                  75                  80

Pro Phe Gly Lys Val Thr Asn Leu Leu Met Leu Lys Gly Lys Asn Gln
                85                  90                  95

Ala Phe Ile Glu Met Asn Thr Glu Glu Ala Ala Asn Thr Met Val Asn
                100                 105                 110

Tyr Tyr Thr Ser Val Thr Pro Val Leu Arg Gly Gln Pro Ile Tyr Ile
            115                 120                 125

Gln Phe Ser Asn His Lys Glu Leu Lys Thr Asp Ser Ser Pro Asn Gln
        130                 135                 140

Ala Arg Ala Gln Ala Ala Leu Gln Ala Val Asn Ser Val Gln Ser Gly
145                 150                 155                 160

Asn Leu Ala Leu Ala Ala Ser Ala Ala Val Asp Ala Gly Met Ala
                165                 170                 175

Met Ala Gly Gln Ser Pro Val Leu Arg Ile Ile Val Glu Asn Leu Phe
                180                 185                 190

Tyr Pro Val Thr Leu Asp Val Leu His Gln Ile Phe Ser Lys Phe Gly
            195                 200                 205

Thr Val Leu Lys Ile Ile Thr Phe Thr Lys Asn Asn Gln Phe Gln Ala
        210                 215                 220

Leu Leu Gln Tyr Ala Asp Pro Val Ser Ala Gln His Ala Lys Leu Ser

```
                225                 230                 235                 240
Leu Asp Gly Gln Asn Ile Tyr Asn Ala Cys Cys Thr Leu Arg Ile Asp
                245                 250                 255
Phe Ser Lys Leu Thr Ser Leu Asn Val Lys Tyr Asn Asn Asp Lys Ser
            260                 265                 270
Arg Asp Tyr Thr Arg Pro Asp Leu Pro Ser Gly Asp Ser Gln Pro Ser
        275                 280                 285
Leu Asp Gln Thr Met Ala Ala Phe Gly Ala Pro Gly Ile Ile Ser
    290                 295                 300
Ala Ser Pro Tyr Ala Gly Ala Gly Phe Pro Pro Thr Phe Ala Ile Pro
305                 310                 315                 320
Gln Ala Ala Gly Leu Ser Val Pro Asn Val His Gly Ala Leu Ala Pro
                325                 330                 335
Leu Ala Ile Pro Ser Ala Ala Ala Ala Ala Ala Ala Gly Arg Ile
                340                 345                 350
Ala Ile Pro Gly Leu Ala Gly Ala Gly Asn Ser Val Leu Leu Val Ser
            355                 360                 365
Asn Leu Asn Pro Glu Arg Val Thr Pro Gln Ser Leu Phe Ile Leu Phe
        370                 375                 380
Gly Val Tyr Gly Asp Val Gln Arg Val Lys Ile Leu Phe Asn Lys Lys
385                 390                 395                 400
Glu Asn Ala Leu Val Gln Met Ala Asp Gly Asn Gln Ala Gln Leu Ala
                405                 410                 415
Met Ser His Leu Asn Gly His Lys Leu His Gly Lys Pro Ile Arg Ile
                420                 425                 430
Thr Leu Ser Lys His Gln Asn Val Gln Leu Pro Arg Glu Gly Gln Glu
            435                 440                 445
Asp Gln Gly Leu Thr Lys Asp Tyr Gly Asn Ser Pro Leu His Arg Phe
        450                 455                 460
Lys Lys Pro Gly Ser Lys Asn Phe Gln Asn Ile Phe Pro Pro Ser Ala
465                 470                 475                 480
Thr Leu His Leu Ser Asn Ile Pro Pro Ser Val Ser Glu Glu Asp Leu
                485                 490                 495
Lys Val Leu Phe Ser Ser Asn Gly Gly Val Val Lys Gly Phe Lys Phe
                500                 505                 510
Phe Gln Lys Asp Arg Lys Met Ala Leu Ile Gln Met Gly Ser Val Glu
            515                 520                 525
Glu Ala Val Gln Ala Leu Ile Asp Leu His Asn His Asp Leu Gly Glu
        530                 535                 540
Asn His His Leu Arg Val Ser Phe Ser Lys Ser Thr Ile
545                 550                 555

<210> SEQ ID NO 15
<211> LENGTH: 248
<212> TYPE: PRT
<213> ORGANISM: homo sapiens

<400> SEQUENCE: 15

Met Ser Gly Gly Gly Val Ile Arg Gly Pro Ala Gly Asn Asn Asp Cys
1               5                   10                  15
Arg Ile Tyr Val Gly Asn Leu Pro Pro Asp Ile Arg Thr Lys Asp Ile
            20                  25                  30
Glu Asp Val Phe Tyr Lys Tyr Gly Ala Ile Arg Asp Ile Asp Leu Lys
        35                  40                  45
```

```
Asn Arg Arg Gly Gly Pro Pro Phe Ala Phe Val Glu Phe Glu Asp Pro
 50                  55                  60

Arg Asp Ala Glu Asp Ala Val Tyr Gly Arg Asp Gly Tyr Asp Tyr Asp
 65                  70                  75                  80

Gly Tyr Arg Leu Arg Val Glu Phe Pro Arg Ser Gly Arg Gly Thr Gly
                 85                  90                  95

Arg Gly Gly Gly Gly Gly Gly Gly Gly Ala Pro Arg Gly Arg Tyr
            100                 105                 110

Gly Pro Pro Ser Arg Arg Ser Glu Asn Arg Val Val Val Ser Gly Leu
            115                 120                 125

Pro Pro Ser Gly Ser Trp Gln Asp Leu Lys Asp His Met Arg Glu Ala
130                 135                 140

Gly Asp Val Cys Tyr Ala Asp Val Tyr Arg Asp Gly Thr Gly Val Val
145                 150                 155                 160

Glu Phe Val Arg Lys Glu Asp Met Thr Tyr Ala Val Arg Lys Leu Asp
                165                 170                 175

Asn Thr Lys Phe Arg Ser His Glu Gly Glu Thr Ala Tyr Ile Arg Val
            180                 185                 190

Lys Val Asp Gly Pro Arg Ser Pro Ser Tyr Gly Arg Ser Arg Ser Arg
            195                 200                 205

Ser Arg Ser Arg Ser Arg Ser Arg Ser Asn Ser Arg Ser Arg
210                 215                 220

Ser Tyr Ser Pro Arg Arg Ser Arg Gly Ser Pro Arg Tyr Ser Pro Arg
225                 230                 235                 240

His Ser Arg Ser Arg Ser Arg Thr
            245

<210> SEQ ID NO 16
<211> LENGTH: 292
<212> TYPE: PRT
<213> ORGANISM: homo sapiens

<400> SEQUENCE: 16

Met Ser Gly Gly Gly Val Ile Arg Gly Pro Ala Gly Asn Asn Asp Cys
1               5                   10                  15

Arg Ile Tyr Val Gly Asn Leu Pro Pro Asp Ile Arg Thr Lys Asp Ile
                 20                  25                  30

Glu Asp Val Phe Tyr Lys Tyr Gly Ala Ile Arg Asp Ile Asp Leu Lys
            35                  40                  45

Asn Arg Arg Gly Gly Pro Pro Phe Ala Phe Val Glu Phe Glu Asp Pro
 50                  55                  60

Arg Asp Ala Glu Asp Ala Val Tyr Gly Arg Asp Gly Tyr Asp Tyr Asp
 65                  70                  75                  80

Gly Tyr Arg Leu Arg Val Glu Phe Pro Arg Ser Gly Arg Gly Thr Gly
                 85                  90                  95

Arg Gly Gly Gly Gly Gly Gly Gly Gly Ala Pro Arg Gly Arg Tyr
            100                 105                 110

Gly Pro Pro Ser Arg Arg Ser Glu Asn Arg Val Val Val Ser Gly Leu
            115                 120                 125

Pro Pro Ser Gly Ser Trp Gln Asp Leu Lys Asp His Met Arg Glu Ala
130                 135                 140

Gly Asp Val Cys Tyr Ala Asp Val Tyr Arg Asp Gly Thr Gly Val Val
145                 150                 155                 160

Glu Phe Val Arg Lys Glu Asp Met Thr Tyr Ala Val Arg Lys Leu Asp
                165                 170                 175
```

Asn Thr Lys Phe Arg Ser His Glu Phe Cys Leu Ser Asn Arg Glu Lys
            180                 185                 190

Leu Pro Thr Ser Gly Leu Lys Leu Met Gly Pro Glu Val Gln Val Met
            195                 200                 205

Glu Asp Leu Asp Leu Glu Ala Val Val Val Ala Glu Ala Val Ala Glu
210                 215                 220

Ala Thr Ala Gly Val Ala Val Thr Pro Gln Gly Glu Ala Glu Asp His
225                 230                 235                 240

His Ala Ile Leu Pro Val Ile Ala Asp Leu Ala Leu Val His Lys Met
                245                 250                 255

Ile Gly Asp Thr Phe Cys Arg Thr His Val Val Tyr Ser Phe Pro Leu
            260                 265                 270

Phe Ser Thr Ile Phe Ser Phe Phe Asn Ser Asn Cys Phe Val Gln Asn
            275                 280                 285

Gly Leu Lys Cys
    290

<210> SEQ ID NO 17
<211> LENGTH: 201
<212> TYPE: PRT
<213> ORGANISM: homo sapiens

<400> SEQUENCE: 17

Met Ser Gly Gly Gly Val Ile Arg Gly Pro Ala Gly Asn Asn Asp Cys
1               5                   10                  15

Arg Ile Tyr Val Gly Asn Leu Pro Pro Asp Ile Arg Thr Lys Asp Ile
            20                  25                  30

Glu Asp Val Phe Tyr Lys Tyr Gly Ala Ile Arg Asp Ile Asp Leu Lys
        35                  40                  45

Asn Arg Arg Gly Gly Pro Pro Phe Ala Phe Val Glu Phe Glu Asp Pro
50                  55                  60

Arg Asp Ala Glu Asp Ala Val Tyr Gly Arg Asp Gly Tyr Asp Tyr Asp
65                  70                  75                  80

Gly Tyr Arg Leu Arg Val Glu Phe Pro Arg Ser Gly Arg Gly Thr Gly
                85                  90                  95

Arg Gly Gly Gly Gly Gly Gly Gly Ala Pro Arg Gly Arg Tyr
            100                 105                 110

Gly Pro Pro Ser Arg Arg Ser Glu Asn Arg Val Val Val Ser Gly Leu
        115                 120                 125

Pro Pro Ser Gly Ser Trp Gln Asp Leu Lys Asp His Met Arg Glu Ala
130                 135                 140

Gly Asp Val Cys Tyr Ala Asp Val Tyr Arg Asp Gly Thr Gly Val Val
145                 150                 155                 160

Glu Phe Val Arg Lys Glu Asp Met Thr Tyr Ala Val Arg Lys Leu Asp
                165                 170                 175

Asn Thr Lys Phe Arg Ser His Glu Val Gly Tyr Thr Arg Ile Leu Phe
            180                 185                 190

Phe Asp Gln Asn Trp Ile Gln Trp Ser
        195                 200

<210> SEQ ID NO 18
<211> LENGTH: 758
<212> TYPE: PRT
<213> ORGANISM: homo sapiens

<400> SEQUENCE: 18

```
Met Ala Glu Pro Arg Gln Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415
```

```
Pro Gly Ser Ser Asp Pro Leu Ile Gln Pro Ser Ser Pro Ala Val Cys
            420                 425                 430

Pro Glu Pro Pro Ser Ser Pro Lys Tyr Val Ser Val Thr Ser Arg
435                 440                 445

Thr Gly Ser Ser Gly Ala Lys Glu Met Lys Leu Lys Gly Ala Asp Gly
            450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
            515                 520                 525

Thr Pro Ser Leu Pro Thr Pro Pro Thr Arg Glu Pro Lys Lys Val Ala
            530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
            595                 600                 605

Gly Ser Lys Asp Asn Ile Lys His Val Pro Gly Gly Gly Ser Val Gln
610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
            675                 680                 685

Glu Thr His Lys Leu Thr Phe Arg Glu Asn Ala Lys Ala Lys Thr Asp
690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
            740                 745                 750

Leu Ala Lys Gln Gly Leu
            755

<210> SEQ ID NO 19
<211> LENGTH: 441
<212> TYPE: PRT
<213> ORGANISM: homo sapiens

<400> SEQUENCE: 19

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30
```

```
Gln Asp Gln Glu Gly Asp Thr Asp Ala Gly Leu Lys Glu Ser Pro Leu
         35                  40                  45

Gln Thr Pro Thr Glu Asp Gly Ser Glu Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440
```

<210> SEQ ID NO 20
<211> LENGTH: 383
<212> TYPE: PRT
<213> ORGANISM: homo sapiens

<400> SEQUENCE: 20

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

```
<210> SEQ ID NO 21
<211> LENGTH: 352
<212> TYPE: PRT
<213> ORGANISM: homo sapiens

<400> SEQUENCE: 21

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 22
<211> LENGTH: 412
<212> TYPE: PRT
```

<213> ORGANISM: homo sapiens

<400> SEQUENCE: 22

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
    370                 375                 380

Thr Gly Ser Ile Asp Met Val Asp Ser Pro Gln Leu Ala Thr Leu Ala
385                 390                 395                 400
```

Asp Glu Val Ser Ala Ser Leu Ala Lys Gln Gly Leu
                405                 410

<210> SEQ ID NO 23
<211> LENGTH: 776
<212> TYPE: PRT
<213> ORGANISM: homo sapiens

<400> SEQUENCE: 23

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys Tyr Val Ser Ser Val Thr Ser Arg
            435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Ala Thr Lys Gln Val Gln Arg Arg Pro Pro
            500                 505                 510

Pro Ala Gly Pro Arg Ser Glu Arg Gly Glu Pro Pro Lys Ser Gly Asp
    515                 520                 525

Arg Ser Gly Tyr Ser Ser Pro Gly Ser Pro Gly Thr Pro Gly Ser Arg
    530                 535                 540

Ser Arg Thr Pro Ser Leu Pro Thr Pro Pro Thr Arg Glu Pro Lys Lys
545                 550                 555                 560

Val Ala Val Val Arg Thr Pro Pro Lys Ser Pro Ser Ser Ala Lys Ser
                565                 570                 575

Arg Leu Gln Thr Ala Pro Val Pro Met Pro Asp Leu Lys Asn Val Lys
            580                 585                 590

Ser Lys Ile Gly Ser Thr Glu Asn Leu Lys His Gln Pro Gly Gly Gly
    595                 600                 605

Lys Val Gln Ile Ile Asn Lys Lys Leu Asp Leu Ser Asn Val Gln Ser
610                 615                 620

Lys Cys Gly Ser Lys Asp Asn Ile Lys His Val Pro Gly Gly Gly Ser
625                 630                 635                 640

Val Gln Ile Val Tyr Lys Pro Val Asp Leu Ser Lys Val Thr Ser Lys
                645                 650                 655

Cys Gly Ser Leu Gly Asn Ile His His Lys Pro Gly Gly Gly Gln Val
            660                 665                 670

Glu Val Lys Ser Glu Lys Leu Asp Phe Lys Asp Arg Val Gln Ser Lys
            675                 680                 685

Ile Gly Ser Leu Asp Asn Ile Thr His Val Pro Gly Gly Gly Asn Lys
    690                 695                 700

Lys Ile Glu Thr His Lys Leu Thr Phe Arg Glu Asn Ala Lys Ala Lys
705                 710                 715                 720

Thr Asp His Gly Ala Glu Ile Val Tyr Lys Ser Pro Val Val Ser Gly
                725                 730                 735

Asp Thr Ser Pro Arg His Leu Ser Asn Val Ser Ser Thr Gly Ser Ile
            740                 745                 750

Asp Met Val Asp Ser Pro Gln Leu Ala Thr Leu Ala Asp Glu Val Ser
        755                 760                 765

Ala Ser Leu Ala Lys Gln Gly Leu
    770                 775

```
<210> SEQ ID NO 24
<211> LENGTH: 381
<212> TYPE: PRT
<213> ORGANISM: homo sapiens

<400> SEQUENCE: 24

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
            260                 265                 270

Gly Gly Gly Gln Val Glu Val Lys Ser Glu Lys Leu Asp Phe Lys Asp
        275                 280                 285

Arg Val Gln Ser Lys Ile Gly Ser Leu Asp Asn Ile Thr His Val Pro
    290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
        355                 360                 365

Ala Asp Glu Val Ser Ala Ser Leu Ala Lys Gln Gly Leu
    370                 375                 380
```

<210> SEQ ID NO 25
<211> LENGTH: 410
<212> TYPE: PRT
<213> ORGANISM: homo sapiens

<400> SEQUENCE: 25

| | | | | | | | | | | | | | | |
|---|---|---|---|---|---|---|---|---|---|---|---|---|---|---|
| Met | Ala | Glu | Pro | Arg | Gln | Glu | Phe | Glu | Val | Met | Glu | Asp | His | Ala | Gly |
| 1 | | | | 5 | | | | | 10 | | | | | 15 | |
| Thr | Tyr | Gly | Leu | Gly | Asp | Arg | Lys | Asp | Gln | Gly | Gly | Tyr | Thr | Met | His |
| | | | 20 | | | | | 25 | | | | | 30 | | |
| Gln | Asp | Gln | Glu | Gly | Asp | Thr | Asp | Ala | Gly | Leu | Lys | Glu | Ser | Pro | Leu |
| | | 35 | | | | | 40 | | | | | 45 | | | |
| Gln | Thr | Pro | Thr | Glu | Asp | Gly | Ser | Glu | Glu | Pro | Gly | Ser | Glu | Thr | Ser |
| | 50 | | | | | 55 | | | | | 60 | | | | |
| Asp | Ala | Lys | Ser | Thr | Pro | Thr | Ala | Glu | Asp | Val | Thr | Ala | Pro | Leu | Val |
| 65 | | | | | 70 | | | | | 75 | | | | | 80 |
| Asp | Glu | Gly | Ala | Pro | Gly | Lys | Gln | Ala | Ala | Gln | Pro | His | Thr | Glu |
| | | | | 85 | | | | | 90 | | | | | 95 | |
| Ile | Pro | Glu | Gly | Thr | Thr | Ala | Glu | Glu | Ala | Gly | Ile | Gly | Asp | Thr | Pro |
| | | | | 100 | | | | | 105 | | | | | 110 | |
| Ser | Leu | Glu | Asp | Glu | Ala | Ala | Gly | His | Val | Thr | Gln | Ala | Arg | Met | Val |
| | | | 115 | | | | | 120 | | | | | 125 | | |
| Ser | Lys | Ser | Lys | Asp | Gly | Thr | Gly | Ser | Asp | Asp | Lys | Lys | Ala | Lys | Gly |
| | 130 | | | | | 135 | | | | | 140 | | | | |
| Ala | Asp | Gly | Lys | Thr | Lys | Ile | Ala | Thr | Pro | Arg | Gly | Ala | Ala | Pro | Pro |
| 145 | | | | | 150 | | | | | 155 | | | | | 160 |
| Gly | Gln | Lys | Gly | Gln | Ala | Asn | Ala | Thr | Arg | Ile | Pro | Ala | Lys | Thr | Pro |
| | | | | 165 | | | | | 170 | | | | | 175 | |
| Pro | Ala | Pro | Lys | Thr | Pro | Pro | Ser | Ser | Gly | Glu | Pro | Pro | Lys | Ser | Gly |
| | | | 180 | | | | | 185 | | | | | 190 | | |
| Asp | Arg | Ser | Gly | Tyr | Ser | Ser | Pro | Gly | Ser | Pro | Gly | Thr | Pro | Gly | Ser |
| | | 195 | | | | | 200 | | | | | 205 | | | |
| Arg | Ser | Arg | Thr | Pro | Ser | Leu | Pro | Thr | Pro | Pro | Thr | Arg | Glu | Pro | Lys |
| 210 | | | | | 215 | | | | | 220 | | | | | |
| Lys | Val | Ala | Val | Val | Arg | Thr | Pro | Pro | Lys | Ser | Pro | Ser | Ser | Ala | Lys |
| 225 | | | | | 230 | | | | | 235 | | | | | 240 |
| Ser | Arg | Leu | Gln | Thr | Ala | Pro | Val | Pro | Met | Pro | Asp | Leu | Lys | Asn | Val |
| | | | | 245 | | | | | 250 | | | | | 255 | |
| Lys | Ser | Lys | Ile | Gly | Ser | Thr | Glu | Asn | Leu | Lys | His | Gln | Pro | Gly | Gly |
| | | | 260 | | | | | 265 | | | | | 270 | | |
| Gly | Lys | Val | Gln | Ile | Val | Tyr | Lys | Pro | Val | Asp | Leu | Ser | Lys | Val | Thr |
| | | | 275 | | | | | 280 | | | | | 285 | | |
| Ser | Lys | Cys | Gly | Ser | Leu | Gly | Asn | Ile | His | His | Lys | Pro | Gly | Gly | Gly |
| | | 290 | | | | | 295 | | | | | 300 | | | |
| Gln | Val | Glu | Val | Lys | Ser | Glu | Lys | Leu | Asp | Phe | Lys | Asp | Arg | Val | Gln |
| 305 | | | | | 310 | | | | | 315 | | | | | 320 |
| Ser | Lys | Ile | Gly | Ser | Leu | Asp | Asn | Ile | Thr | His | Val | Pro | Gly | Gly | Gly |
| | | | | 325 | | | | | 330 | | | | | 335 | |
| Asn | Lys | Lys | Ile | Glu | Thr | His | Lys | Leu | Thr | Phe | Arg | Glu | Asn | Ala | Lys |
| | | | 340 | | | | | 345 | | | | | 350 | | |
| Ala | Lys | Thr | Asp | His | Gly | Ala | Glu | Ile | Val | Tyr | Lys | Ser | Pro | Val | Val |
| | | 355 | | | | | 360 | | | | | 365 | | | |
| Ser | Gly | Asp | Thr | Ser | Pro | Arg | His | Leu | Ser | Asn | Val | Ser | Ser | Thr | Gly |

```
            370                 375                 380
Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 26
<211> LENGTH: 364
<212> TYPE: PRT
<213> ORGANISM: homo sapiens

<400> SEQUENCE: 26

Met Val Lys Leu Phe Ile Gly Asn Leu Pro Arg Glu Ala Thr Glu Gln
 1               5                  10                  15

Glu Ile Arg Ser Leu Phe Glu Gln Tyr Gly Lys Val Leu Glu Cys Asp
            20                  25                  30

Ile Ile Lys Asn Tyr Gly Phe Val His Ile Glu Asp Lys Thr Ala Ala
        35                  40                  45

Glu Asp Ala Ile Arg Asn Leu His His Tyr Lys Leu His Gly Val Asn
    50                  55                  60

Ile Asn Val Glu Ala Ser Lys Asn Lys Ser Lys Thr Ser Thr Lys Leu
65                  70                  75                  80

His Val Gly Asn Ile Ser Pro Thr Cys Thr Asn Lys Glu Leu Arg Ala
                85                  90                  95

Lys Phe Glu Glu Tyr Gly Pro Val Ile Glu Cys Asp Ile Val Lys Asp
            100                 105                 110

Tyr Ala Phe Val His Met Glu Arg Ala Glu Asp Ala Val Glu Ala Ile
        115                 120                 125

Arg Gly Leu Asp Asn Thr Glu Phe Gln Gly Lys Arg Met His Val Gln
130                 135                 140

Leu Ser Thr Ser Arg Leu Arg Thr Ala Pro Gly Met Gly Asp Gln Ser
145                 150                 155                 160

Gly Cys Tyr Arg Cys Gly Lys Glu Gly His Trp Ser Lys Glu Cys Pro
                165                 170                 175

Ile Asp Arg Ser Gly Arg Val Ala Asp Leu Thr Glu Gln Tyr Asn Glu
            180                 185                 190

Gln Tyr Gly Ala Val Arg Thr Pro Tyr Thr Met Ser Tyr Gly Asp Ser
        195                 200                 205

Leu Tyr Tyr Asn Asn Ala Tyr Gly Ala Leu Asp Ala Tyr Tyr Lys Arg
    210                 215                 220

Cys Arg Ala Ala Arg Ser Tyr Glu Ala Val Ala Ala Ala Ala Ala Ser
225                 230                 235                 240

Val Tyr Asn Tyr Ala Glu Gln Thr Leu Ser Gln Leu Pro Gln Val Gln
                245                 250                 255

Asn Thr Ala Met Ala Ser His Leu Thr Ser Thr Ser Leu Asp Pro Tyr
            260                 265                 270

Asp Arg His Leu Leu Pro Thr Ser Gly Ala Ala Ala Thr Ala Ala Ala
        275                 280                 285

Ala Ala Ala Ala Ala Ala Ala Val Thr Ala Ala Ser Thr Ser Tyr Tyr
    290                 295                 300

Gly Arg Asp Arg Ser Pro Leu Arg Arg Ala Thr Ala Pro Val Pro Thr
305                 310                 315                 320

Val Gly Glu Gly Tyr Gly Tyr Gly His Glu Ser Glu Leu Ser Gln Ala
                325                 330                 335
```

```
Ser Ala Ala Ala Arg Asn Ser Leu Tyr Asp Met Ala Arg Tyr Glu Arg
                340                 345                 350

Glu Gln Tyr Ala Asp Arg Ala Arg Tyr Ser Ala Phe
        355                 360
```

<210> SEQ ID NO 27
<211> LENGTH: 177
<212> TYPE: PRT
<213> ORGANISM: homo sapiens

<400> SEQUENCE: 27

```
Met Val Lys Leu Phe Ile Gly Asn Leu Pro Arg Glu Ala Thr Glu Gln
1               5                   10                  15

Glu Ile Arg Ser Leu Phe Glu Gln Tyr Gly Lys Val Leu Glu Cys Asp
            20                  25                  30

Ile Ile Lys Asn Tyr Gly Phe Val His Ile Glu Asp Lys Thr Ala Ala
        35                  40                  45

Glu Asp Ala Ile Arg Asn Leu His His Tyr Lys Leu His Gly Val Asn
    50                  55                  60

Ile Asn Val Glu Ala Ser Lys Asn Lys Ser Lys Thr Ser Thr Lys Leu
65                  70                  75                  80

His Val Gly Asn Ile Ser Pro Thr Cys Thr Asn Lys Glu Leu Arg Ala
                85                  90                  95

Lys Phe Glu Glu Tyr Gly Pro Val Ile Glu Cys Asp Ile Val Lys Asp
            100                 105                 110

Tyr Ala Phe Val His Met Glu Arg Ala Glu Asp Ala Val Glu Ala Ile
        115                 120                 125

Arg Gly Leu Asp Asn Thr Glu Phe Gln Gly Glu Pro Pro Ser Leu Gly
    130                 135                 140

Arg Gly Leu Asn Thr Arg Leu Cys Ala Glu Asn Gly Trp Ile Ser Lys
145                 150                 155                 160

Arg Arg Gly Leu Val Lys Ile Thr Ala Val Gly Trp Leu Val Met Lys
                165                 170                 175

Lys
```

<210> SEQ ID NO 28
<211> LENGTH: 143
<212> TYPE: PRT
<213> ORGANISM: homo sapiens

<400> SEQUENCE: 28

```
Met Val Lys Leu Phe Ile Gly Asn Leu Pro Arg Glu Ala Thr Glu Gln
1               5                   10                  15

Glu Ile Arg Ser Leu Phe Glu Gln Tyr Gly Lys Val Leu Glu Cys Asp
            20                  25                  30

Ile Ile Lys Asn Tyr Gly Phe Val His Ile Glu Asp Lys Thr Ala Ala
        35                  40                  45

Glu Asp Ala Ile Arg Asn Leu His His Tyr Lys Leu His Gly Val Asn
    50                  55                  60

Ile Asn Val Glu Ala Ser Lys Asn Lys Ser Lys Thr Ser Thr Lys Leu
65                  70                  75                  80

His Val Gly Asn Ile Ser Pro Thr Cys Thr Asn Lys Glu Leu Arg Ala
                85                  90                  95

Lys Phe Glu Glu Tyr Gly Pro Val Ile Glu Cys Asp Ile Val Lys Asp
            100                 105                 110

Tyr Ala Phe Val His Met Glu Arg Ala Glu Asp Ala Val Glu Ala Ile
```

```
                115              120             125
Arg Gly Leu Asp Asn Thr Glu Phe Gln Gly Met Cys Val Gly
    130             135             140

<210> SEQ ID NO 29
<211> LENGTH: 173
<212> TYPE: PRT
<213> ORGANISM: homo sapiens

<400> SEQUENCE: 29

Met Val Lys Leu Phe Ile Gly Asn Leu Pro Arg Glu Ala Thr Glu Gln
1               5                   10                  15

Glu Ile Arg Ser Leu Phe Glu Gln Tyr Gly Lys Val Leu Glu Cys Asp
            20                  25                  30

Ile Ile Lys Asn Tyr Gly Phe Val His Ile Glu Asp Lys Thr Ala Ala
        35                  40                  45

Glu Asp Ala Ile Arg Asn Leu His His Tyr Lys Leu His Gly Val Asn
    50                  55                  60

Ile Asn Val Glu Ala Ser Lys Asn Lys Ser Lys Thr Ser Thr Lys Leu
65                  70                  75                  80

His Val Gly Asn Ile Ser Pro Thr Cys Thr Asn Lys Glu Leu Arg Ala
                85                  90                  95

Lys Phe Glu Glu Tyr Gly Pro Val Ile Glu Cys Asp Ile Val Lys Asp
            100                 105                 110

Tyr Ala Phe Val His Met Glu Arg Ala Glu Asp Ala Val Glu Ala Ile
        115                 120                 125

Arg Gly Leu Asp Asn Thr Glu Phe Gln Gly Lys Ile Thr Pro Val Thr
    130                 135                 140

Glu Gly Tyr Cys Cys Cys Asn Lys Gly His Thr Tyr Ile Phe Lys Asn
145                 150                 155                 160

Cys Asn Leu Ile Leu Glu Ser Arg Lys Ser Arg Arg Cys
                165                 170

<210> SEQ ID NO 30
<211> LENGTH: 11
<212> TYPE: PRT
<213> ORGANISM: homo sapiens

<400> SEQUENCE: 30

Glu Arg Lys Phe Phe Lys Gly Phe Phe Gly Lys
1               5                   10
```